United States Patent
Lee et al.

(10) Patent No.: US 10,468,609 B2
(45) Date of Patent: Nov. 5, 2019

(54) ORGANIC ELECTROLUMINESCENT MATERIALS AND DEVICES

(71) Applicant: Universal Display Corporation, Ewing, NJ (US)

(72) Inventors: Chi Hang Lee, Chaiwan (HK); Siu Tung Lam, Apleichau (HK); Raymond Kwong, Fo Tan (HK)

(73) Assignee: Universal Display Corporation, Ewing, NJ (US)

( * ) Notice: Subject to any disclaimer, the term of this patent is extended or adjusted under 35 U.S.C. 154(b) by 247 days.

(21) Appl. No.: 15/583,429

(22) Filed: May 1, 2017

(65) Prior Publication Data

US 2017/0352809 A1    Dec. 7, 2017

Related U.S. Application Data

(60) Provisional application No. 62/344,508, filed on Jun. 2, 2016.

(51) Int. Cl.
| | | |
|---|---|---|
| H01L 51/50 | (2006.01) | |
| H01L 51/00 | (2006.01) | |
| C09K 11/02 | (2006.01) | |
| C09K 11/06 | (2006.01) | |
| C07F 5/02 | (2006.01) | |

(52) U.S. Cl.
CPC .............. *H01L 51/008* (2013.01); *C07F 5/02* (2013.01); *C09K 11/025* (2013.01); *C09K 11/06* (2013.01); *C09K 2211/10* (2013.01); *C09K 2211/18* (2013.01); *H01L 51/0085* (2013.01); *H01L 51/5016* (2013.01); *H01L 51/5056* (2013.01); *H01L 51/5072* (2013.01); *H01L 51/5096* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Hashimoto et al. "Triplet-Energy Control of Polycyclic Aromatic Hydrocarbons by BN Replacement: Development of Ambipolar Host Materials for Phosphorescent Organic Light-Emitting Diodes" Chem. Mater. 2014, 26, 6265-6271. (Year: 2014).*

(Continued)

*Primary Examiner* — Robert S Loewe
(74) *Attorney, Agent, or Firm* — Duane Morris LLP

(57) ABSTRACT

New organic materials having polyaromatic structure containing boron and high triplet energy are disclosed. The high triplet energy materials are useful as host materials in PHOLEDs and improve device quantum efficiency and stability.

20 Claims, 2 Drawing Sheets

(56) References Cited

U.S. PATENT DOCUMENTS

| | | | |
|---|---|---|---|
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 9,318,710 | B2 * | 4/2016 | Kwong ............... H01L 51/0071 |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0076853 | A1 * | 4/2004 | Jarikov ............... C09K 11/06 428/690 |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008055 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Pakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2014/0005399 | A1 | 1/2014 | Hatakeyama et al. |
| 2014/0027723 | A1 * | 1/2014 | Kim ............... H01L 51/0058 257/40 |
| 2014/0061629 | A1 | 3/2014 | Murase et al. |
| 2015/0097162 | A1 | 4/2015 | Ono et al. |
| 2016/0248024 | A1 | 8/2016 | Shin et al. |
| 2016/0351811 | A1 | 12/2016 | Lam et al. |
| 2016/0351812 | A1 | 12/2016 | Lam et al. |

FOREIGN PATENT DOCUMENTS

| | | |
|---|---|---|
| EP | 2034538 | 3/2009 |
| EP | 2711408 | 3/2014 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007/029798 | 3/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2012/121398 | 9/2012 |
| WO | 2014042197 | 3/2014 |
| WO | 2015/053572 | 4/2015 |

OTHER PUBLICATIONS

Wang et al. "B2N2-Dibenzo[a,e]pentalenes: Effect of the BN Orientation Pattern on Antiaromaticity and Optoelectronic Properties" J. Am. Chem. Soc. 2015, 137, 7668-7671. (Year: 2015).*

Catlin et al. "Preparation and Reactions of o-(Cyanomethyl)benzeneboronic Acid" J. Org. Chem. 1969, 34, 1660-1663. (Year: 1969).*

Morgan et al. "Efficient synthetic methods for the installation of boron-nitrogen bonds in conjugated organic molecules" Dalton Trans. 2016, 45, 5920-5924. (Year: 2016).*

Adachi, Chihaya et al., "Organic Electroluminescent Device Having a Hole Conductor as an Emitting Layer," Appl. Phys. Lett., 55(15): 1489-1491 (1989).

(56) References Cited

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)indium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based On Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II Phosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Hatakeyama, T. et al. "Synthesis of BN-Fused Polycyclic Aromatics via Tandem Intramolecular Electrophilic Arene Borylation" J. Am. Chem. Soc., 2011, 133 (46), pp. 18614-18617.

(56) References Cited

OTHER PUBLICATIONS

Bosdet, Michael J.D. et al., "Blue Fluorescent 4a-Aza-4b-boraphenanthrenes" Org. Lett., 2007, 9 (7), pp. 1395-1398.
Wang, Jian et al., "Substituent Effects on Twisted Internal Charge Transfer Excited States of N-Borylated Carbazoles and (Diphenylamino)boranes" J. Phys. Chem. A, 2012, 116 (4), pp. 1151-1158.
Taniguchi, Takuhiro et al., "TICT fluorescence of N-borylated 2,5-diarylpyrroles: a gear like dual motion in the excited state" Dalton Trans., 2013,42, 620-624.
DeMott, Jessica C. et al, "Experimental and computational exploration of the dynamic behavior of (PNP)BF2, a boron compound supported by an amido/bis(phosphine) pincer ligand" Dalton Trans., 2011,40, 11562-11570.
Sachdev, H. et al., "Structural and Spectroscopic Properties of Aryl Substituted Aminoboranes as Model Compounds and Synthons for B/C/N Materials and New Fluorescent Systems" Z. anorg. allg. Chem., 635: 2112-2119.

\* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application Ser. No. 62/344,508, filed Jun. 2, 2016, the entire contents of which is incorporated herein by reference.

FIELD

The present invention relates to organic materials with polyaromatic structure containing boron and having high triplet energy that are useful as high triplet energy hosts in phosphorescent organic light emitting diode (PHOLED) devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted $Ir(ppy)_3$, which has the following structure:

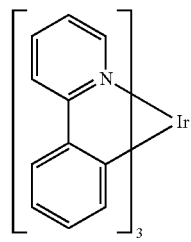

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" or "deposited over" a second layer, the first layer is disposed further away from substrate. There may be other layers between the first and second layer, unless it is specified that the first layer is "in contact with" the second layer. For example, a cathode may be described as "disposed over" or "deposited over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

New organic materials having polyaromatic structure and high triplet energy are disclosed. The high triplet energy materials are useful as host materials in PHOLEDs and improve device quantum efficiency and stability.

According to an aspect of the present disclosure, a compound having the structure of Formula I is disclosed, wherein $R^A$, $R^B$, and $R^C$ are each independently 5 or 6 membered aryl or heteroaryl rings;

wherein $R^1$, $R^2$, and $R^3$ each independently represent no substitutions or up to the maximum available substitutions;

wherein $R^1$, $R^2$, and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof;

wherein any $R^1$, $R^2$, and $R^3$ are optionally joined or fused to form a ring;

wherein $X^1$ is B, C, N, O, S, or Se;

wherein $X^2$-$X^7$ are independently B, C, or N;

wherein Y is B, N, or P;

wherein Z is BR, CRR', O, PR, S, or SiRR';

wherein $Y^1$ and $Y^2$ are each independently selected from the group consisting of carbon and nitrogen;

wherein R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof;

wherein R and R' is optionally bonded to at least one benzo or azabenzo ring to form fused rings;

wherein the dashed lines represent a metal M optionally coordinated to $R^B$ and $R^C$; and wherein when M is coordinated to $R^B$ and $R^C$, M replaces $R^2$ and $R^3$ that are on $Y^1$ and $Y^2$ respectively and bonds to $Y^1$ and $Y^2$.

According to another aspect, an OLED is disclosed where the OLED comprises an anode; a cathode; and an organic layer disposed between the anode and the cathode, wherein the organic layer comprises the compound having a structure of Formula I.

According to another aspect, a consumer product comprising an OLED is disclosed where the OLED comprises: an anode; a cathode; and an organic layer disposed between the anode and the cathode. The organic layer comprises the compound having a structure of Formula I.

According to another aspect, a formulation comprising a compound having a structure of Formula I is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
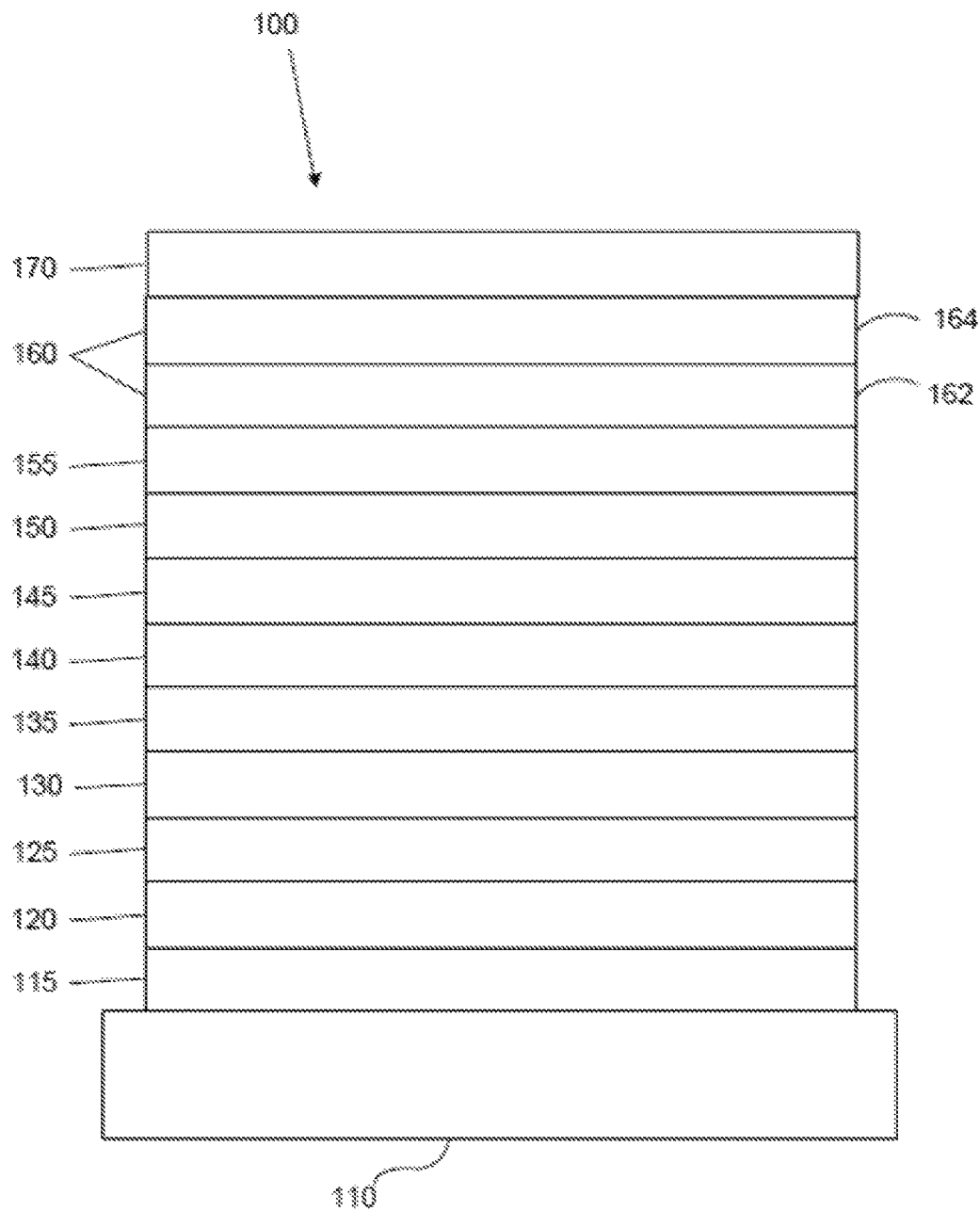
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
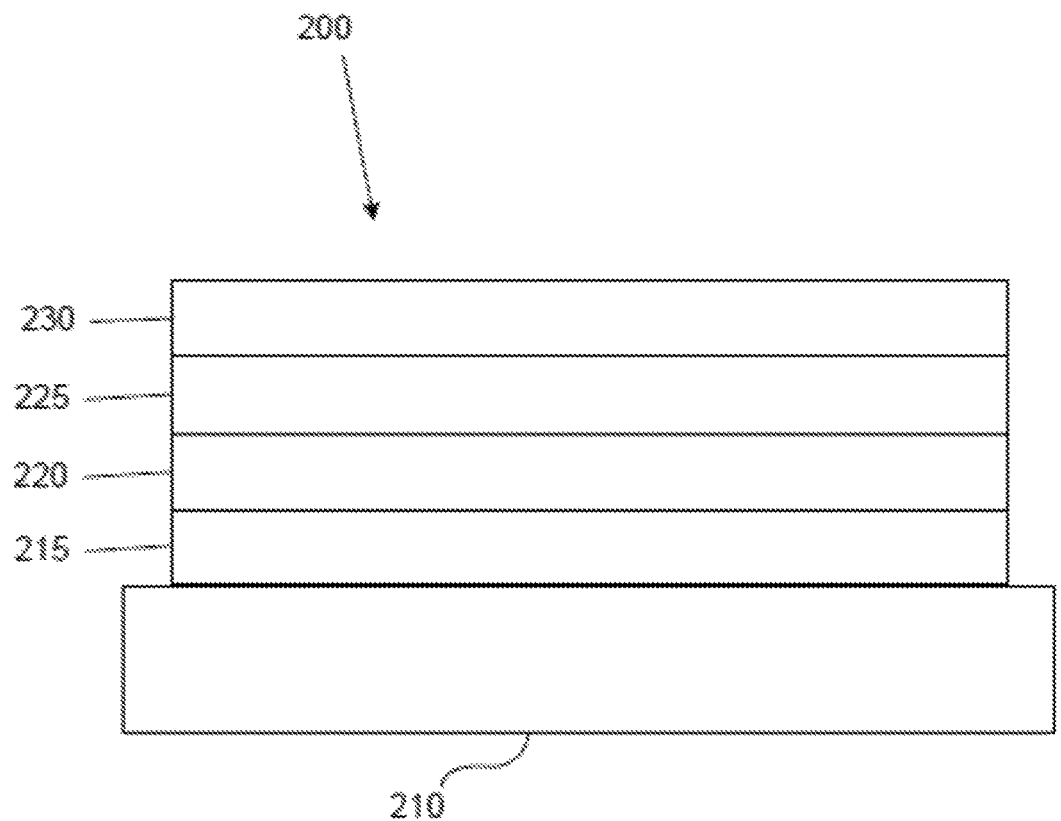
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both.

The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

OLEDs fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 to 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, azadibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the thermal population between the triplet states and the singlet excited states. Compounds that are capable of generating E-type delayed fluorescence are required to have very small singlet-triplet gaps. Thermal energy can activate the transition from the triplet state back to the singlet state. This type of delayed fluorescence is also known as thermally activated delayed fluorescence (TADF). A distinctive feature of TADF is that the delayed component increases as temperature rises due to the increased thermal energy. If the reverse intersystem crossing rate is fast enough to minimize the non-radiative decay from the triplet state, the fraction of back populated singlet excited states can potentially reach 75%. The total singlet fraction can be 100%, far exceeding the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

High triplet hosts are beneficial for providing good device efficiency for blue and green phosphorescent OLEDs. Inventors have found that boron containing hosts are beneficial since the Boron-heteroatom linkage may increase the triplet energy without losing the aromatic character which is important to the stabilization of charge.

According to an aspect of the present disclosure, a compound having a structure according to Formula I:

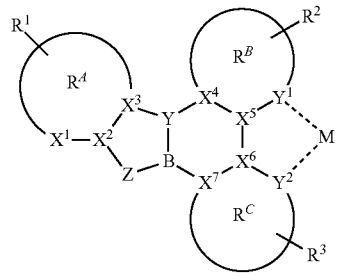

Formula I is disclosed, wherein $R^A$, $R^B$, and $R^C$ are each independently 5 or 6 membered aryl or heteroaryl rings;

wherein $R^1$, $R^2$, and $R^3$ each independently represent no substitutions or up to the maximum available substitutions;

wherein $R^1$, $R^2$, and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof;

wherein any $R^1$, $R^2$, and $R^3$ are optionally joined or fused to form a ring;

wherein $X^1$ is B, C, N, O, S, or Se;

wherein $X^2$-$X^7$ are independently B, C, or N;

wherein Y is B, N, or P;

wherein Z is BR, CRR', O, PR, S, or SiRR';

wherein $Y^1$ and $Y^2$ are each independently selected from the group consisting of carbon and nitrogen;

wherein R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof;

wherein R and R' is optionally bonded to at least one benzo or azabenzo ring to form fused rings;

wherein the dashed lines represent a metal M optionally coordinated to $R^B$ and $R^C$; and wherein when M is coordinated to $R^B$ and $R^C$, M replaces $R^2$ and $R^3$ that are on $Y^1$ and $Y^2$ respectively and bonds to $Y^1$ and $Y^2$.

In some embodiments of the compound, the compound has the formula:

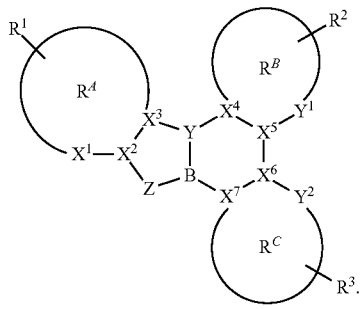

In some embodiments of the compound, the compound is a dimer. In some embodiments of the compound, at least one of $R^1$, $R^2$, and $R^3$ substituents are joined or fused to form a 5- or 6-membered ring, which can be further substituted. In some embodiments of the compound, $X^1$-$X^6$ are C, and $X^7$ is C or N.

In some embodiments of the compound, R and R' are independently aryl or heteroaryl. In some embodiments of the compound, R and R' are independently selected from the group consisting of phenyl, carbazole, azacarbazole, dibenzofuran, dibenzothiophene, dibenzoselenophene, azadibenzofuran, azadibenzothiophene, azadibenzoselenophene, triphenylene, azatriphenylene, and combinations thereof; and wherein R and R' are optionally further substituted by one or more substituent $X^B$ selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof; and $X^B$ is optionally bonded to at least one benzo or azabenzo ring to form a fused ring.

In some embodiments of the compound, the compound is selected from the group consisting of:

compound 1

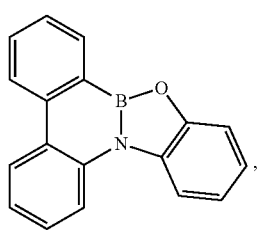

compound 2

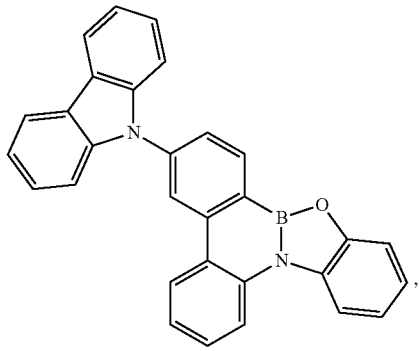

compound 3

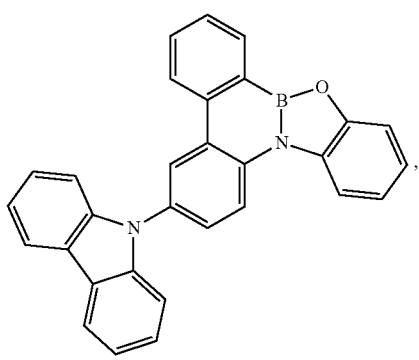

compound 4

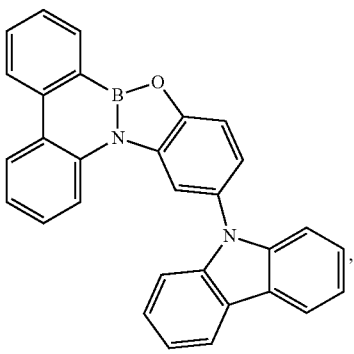

compound 4a

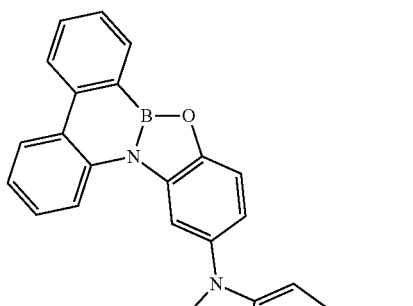

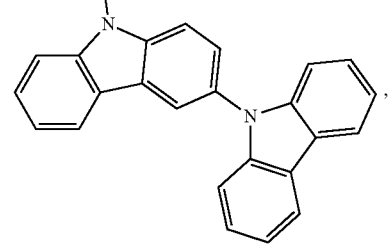

compound 5
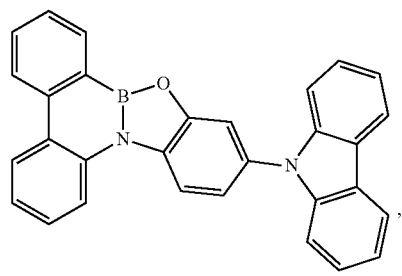
compound 6
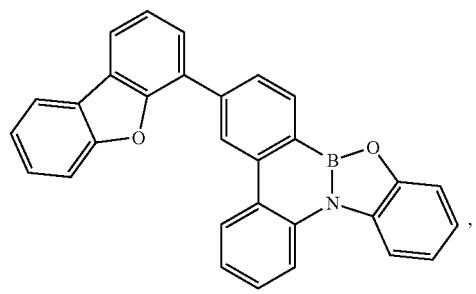
compound 7
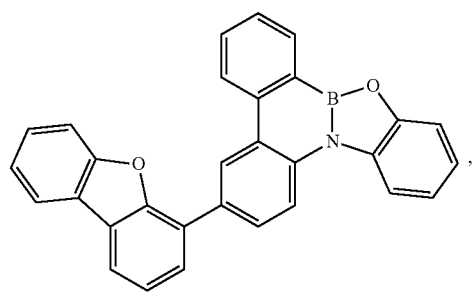
compound 8
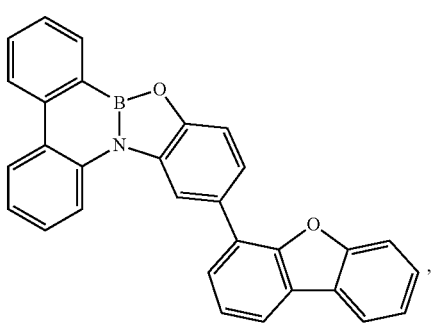
compound 9
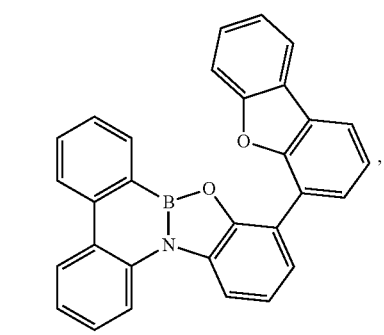
compound 10
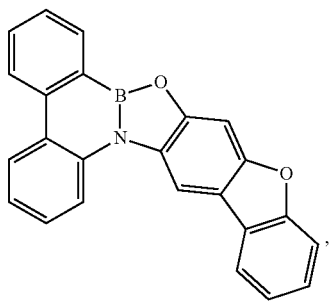
compound 11
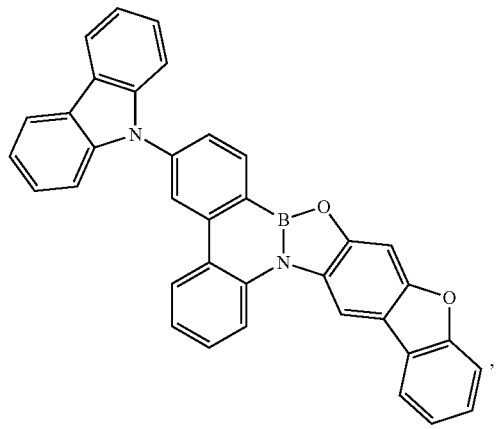
compound 12
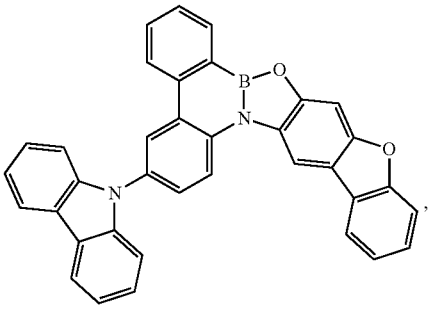
compound 13
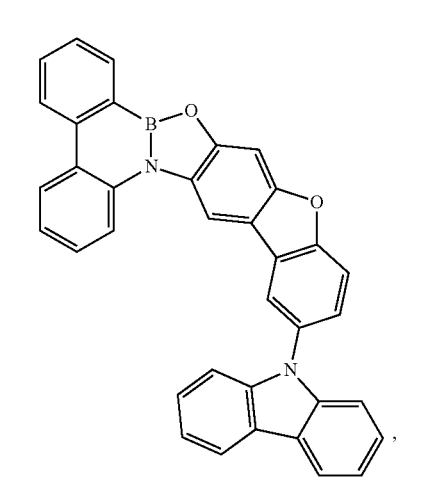

compound 14
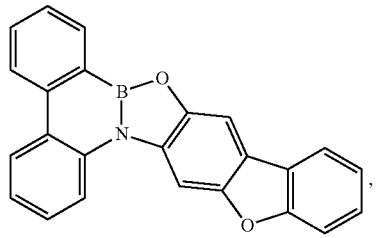
compound 15
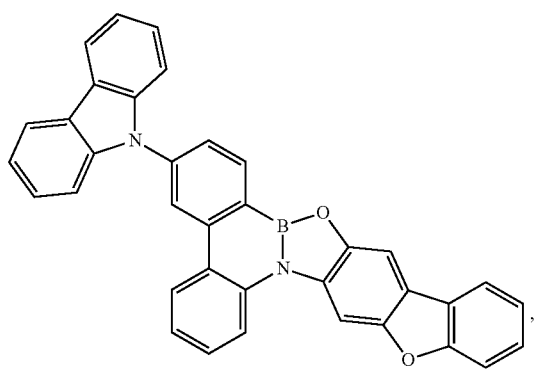
compound 16
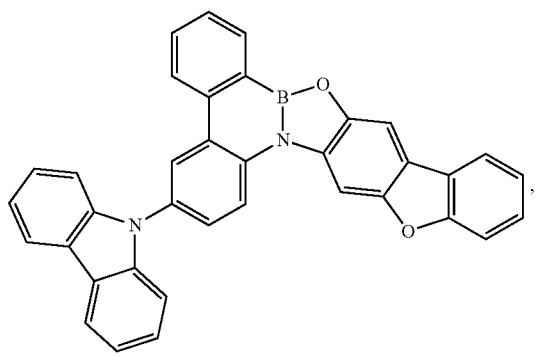
compound 17
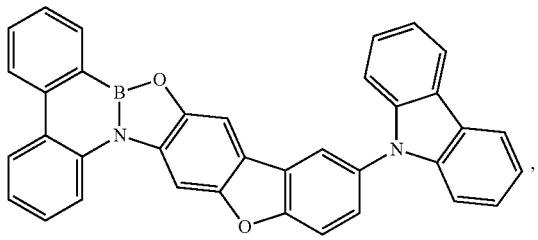
compound 18
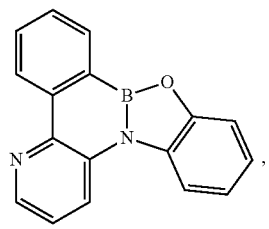
compound 19
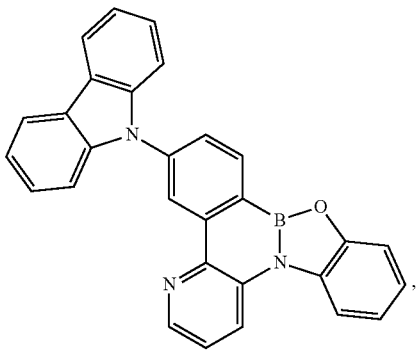
compound 20
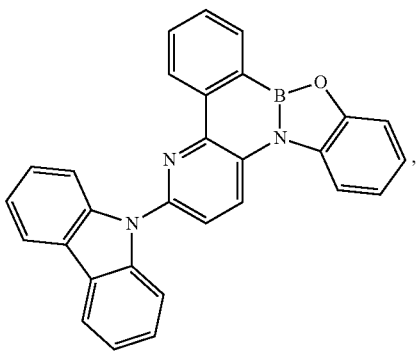
compound 21
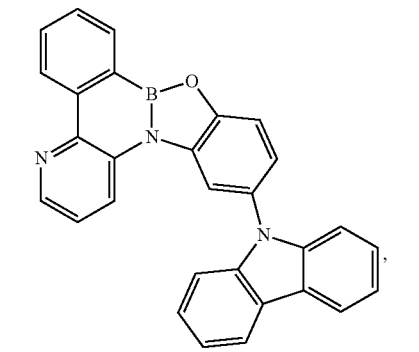
compound 22
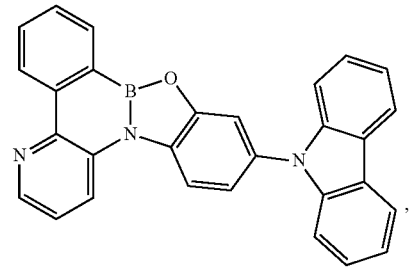
compound 23
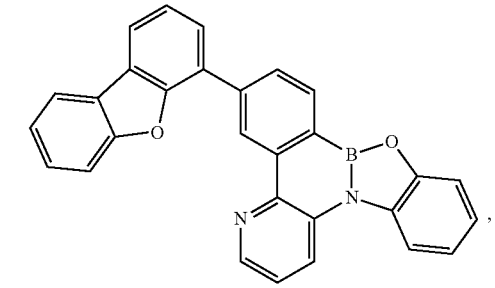

compound 24
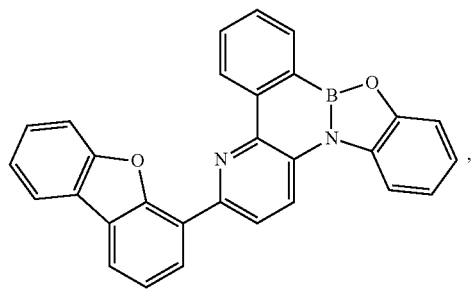
compound 25
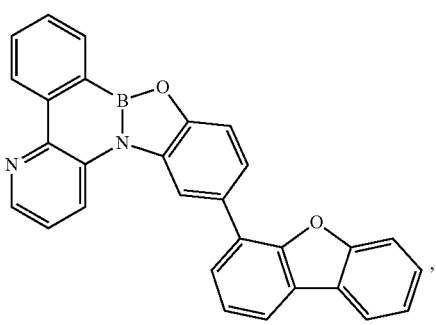
compound 26
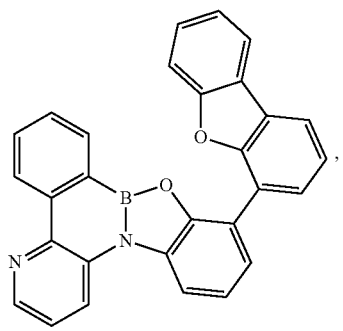
compound 27
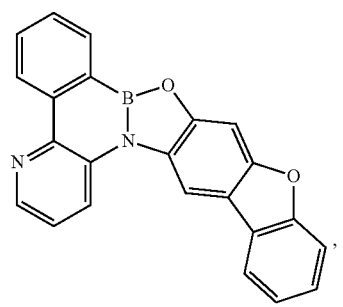
compound 28
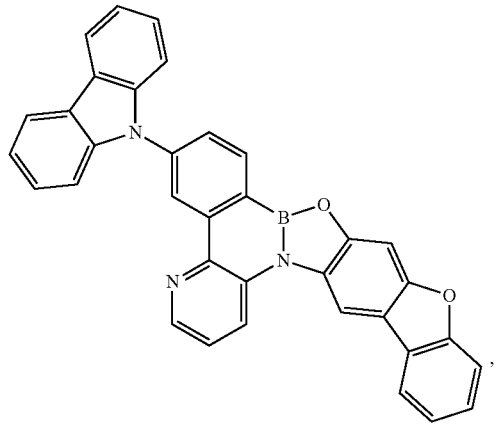
compound 29
compound 30
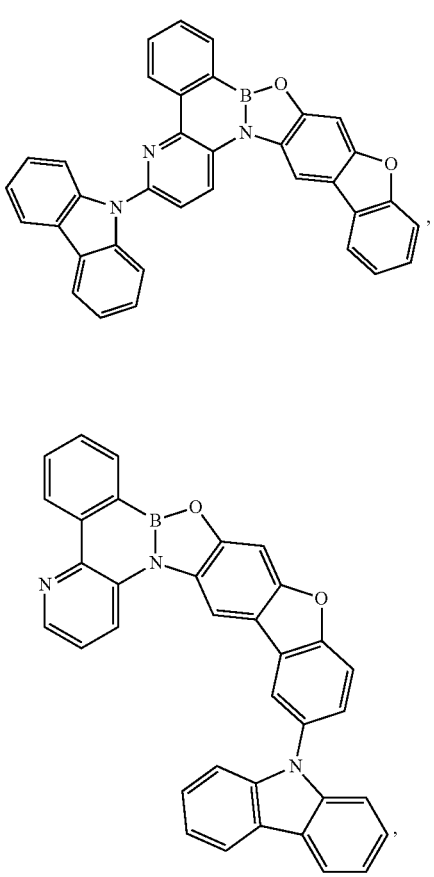
compound 31
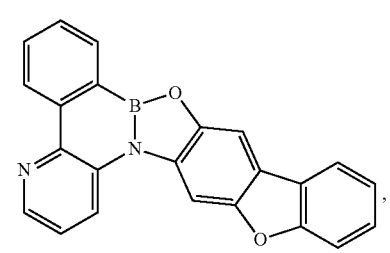

compound 32
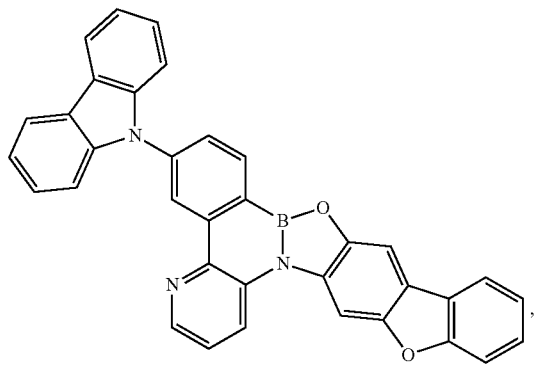
compound 33
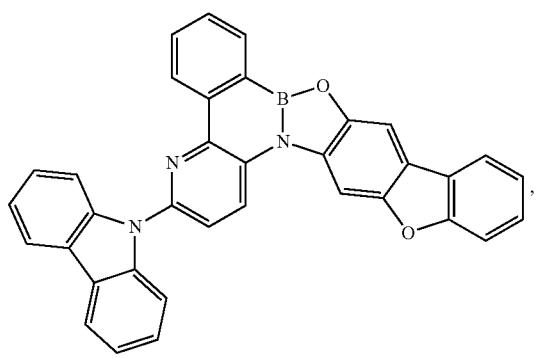
compound 34
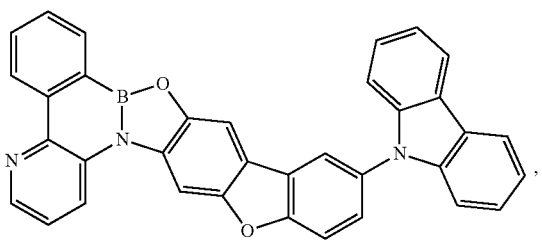
compound 35
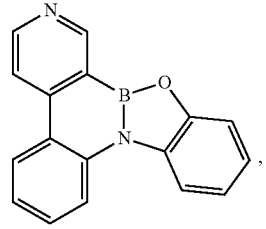
compound 36
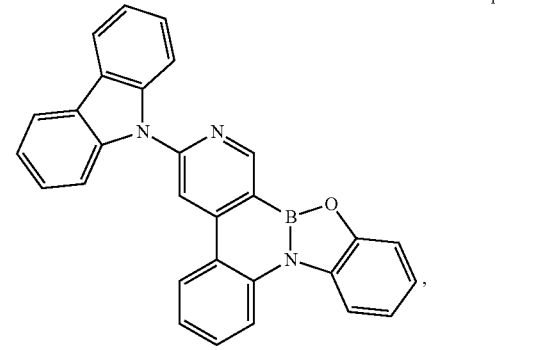
compound 37
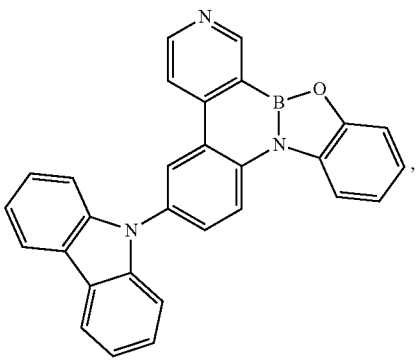
compound 38
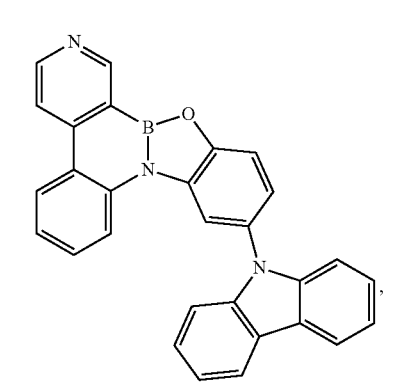
compound 39
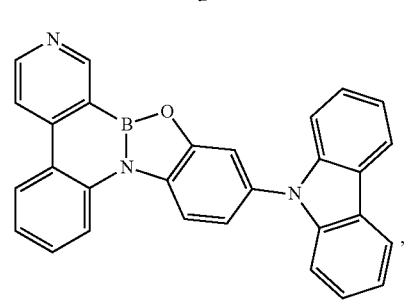
compound 40
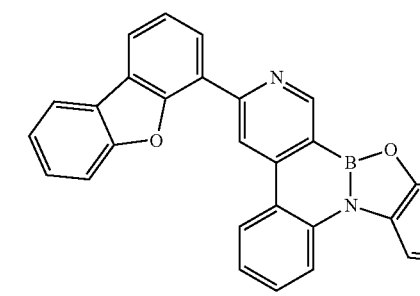
compound 41
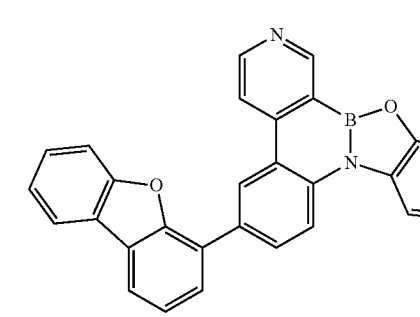

compound 42
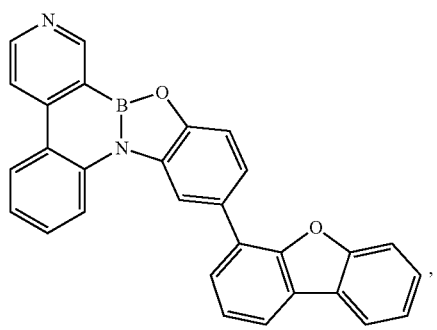
compound 43
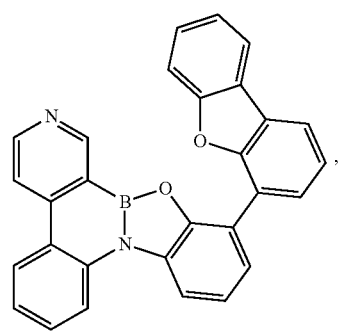
compound 44
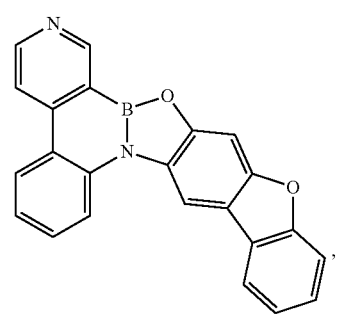
compound 45
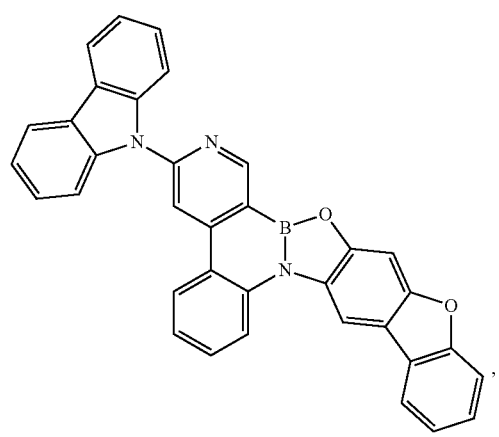
compound 46
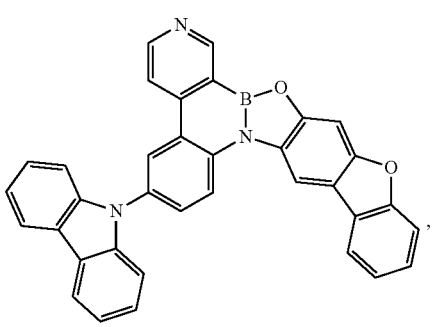
compound 47
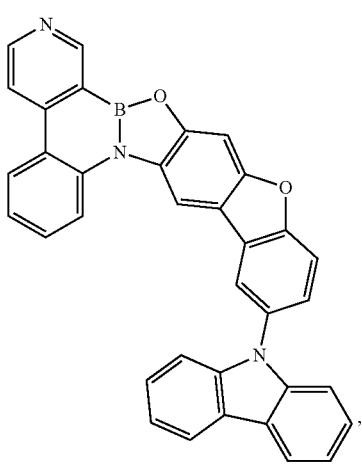
compound 48
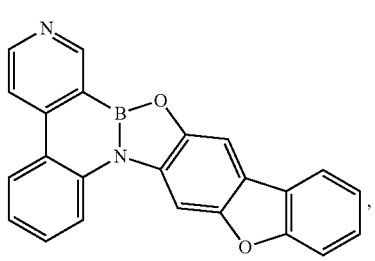
compound 49
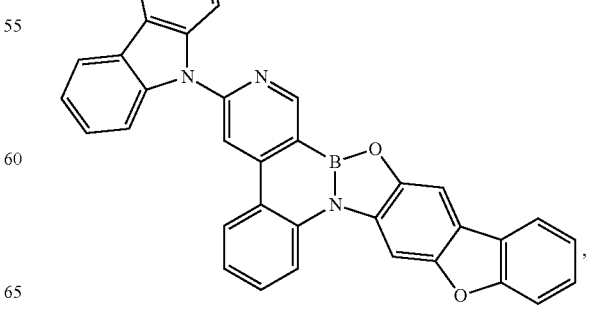

compound 50
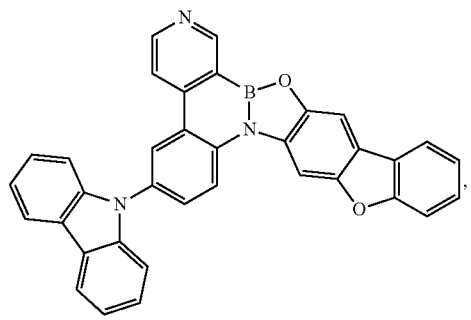
compound 51
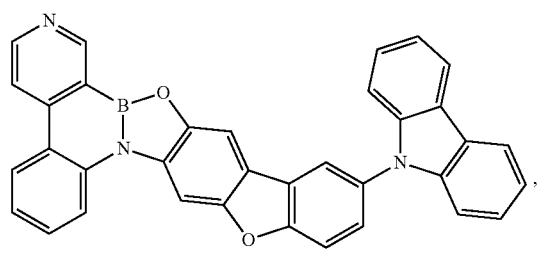
compound 52
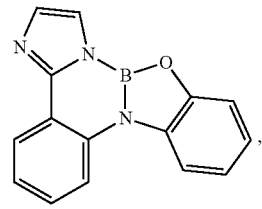
compound 53
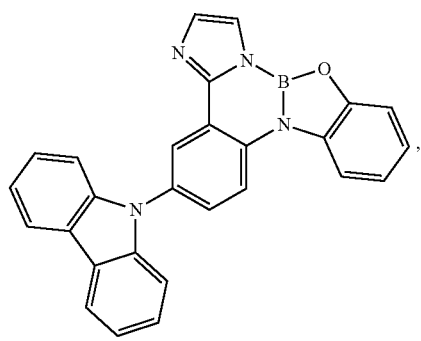
compound 54
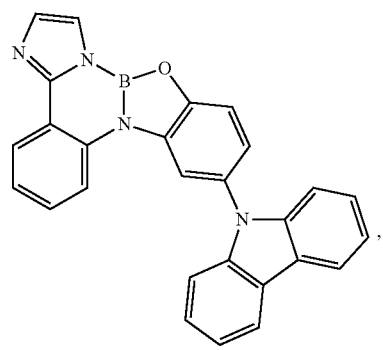
compound 55
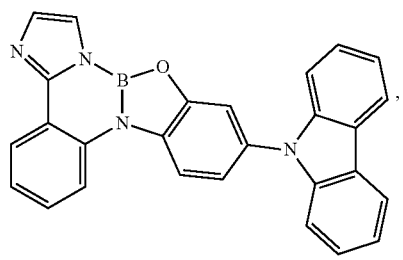
compound 56
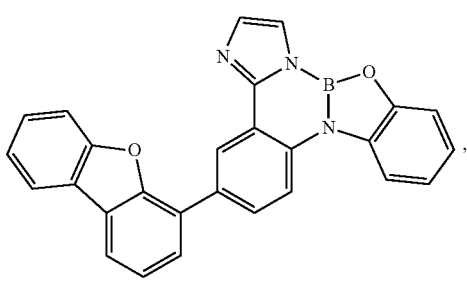
compound 57
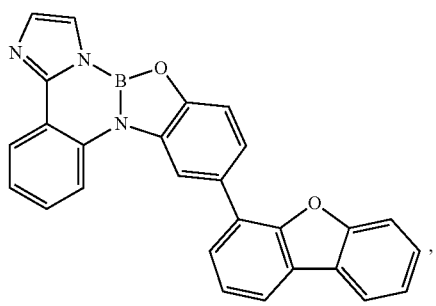
compound 58
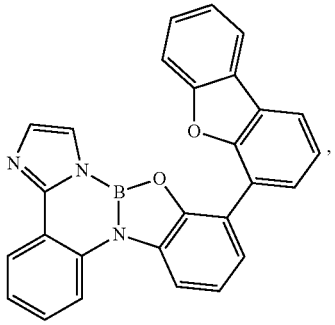
compound 59
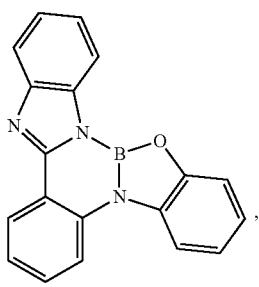

compound 60
compound 61
compound 62
compound 63
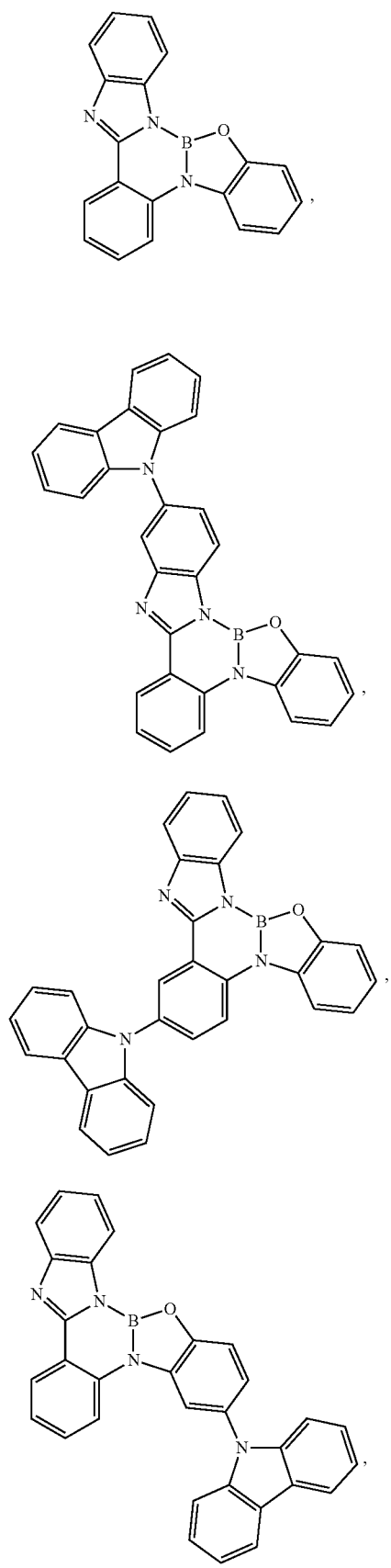
compound 64
compound 65
compound 66
compound 67
compound 68
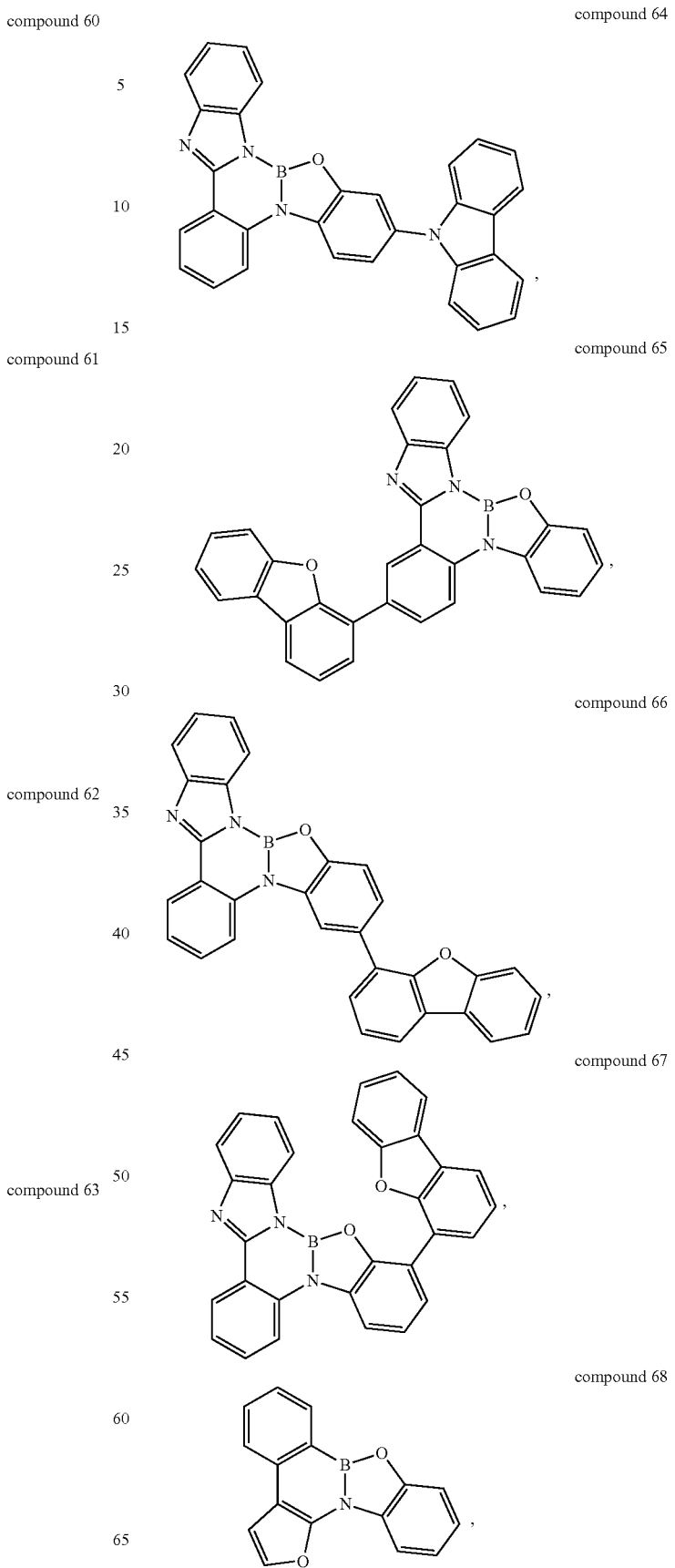

compound 69
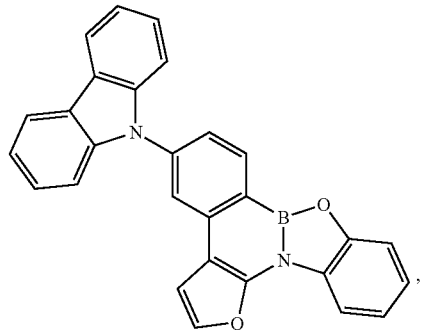
compound 70
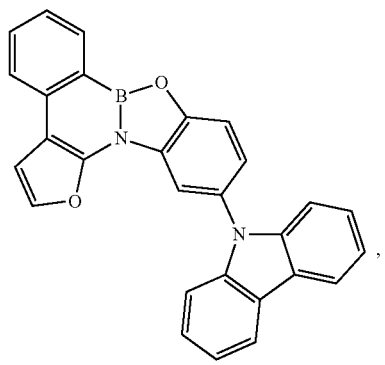
compound 71
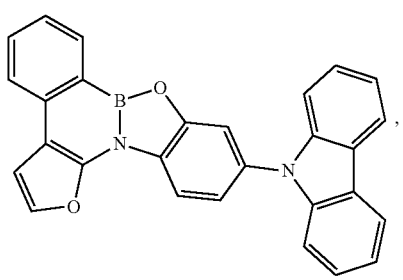
compound 72
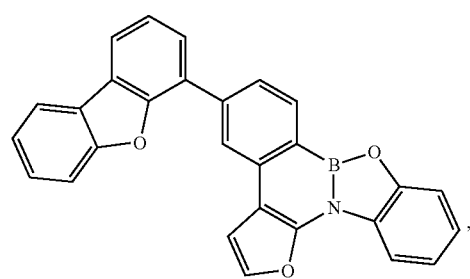
compound 73
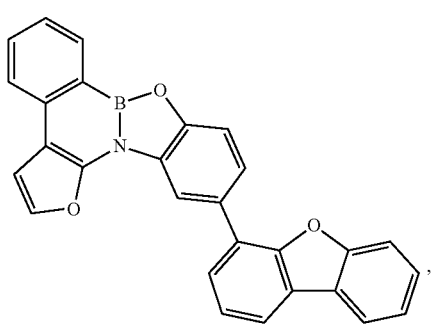
compound 74
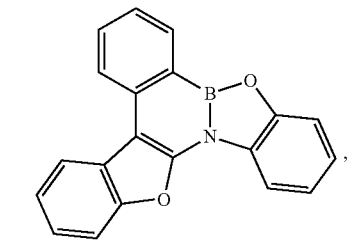
compound 75
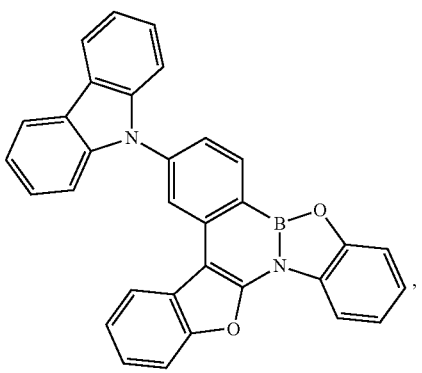
compound 76
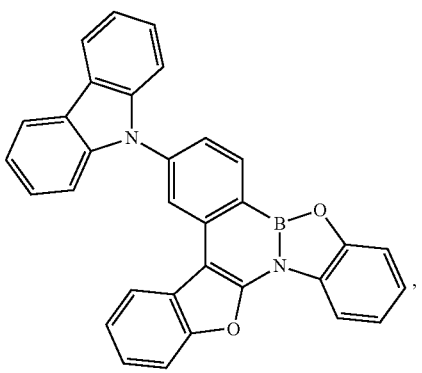
compound 77
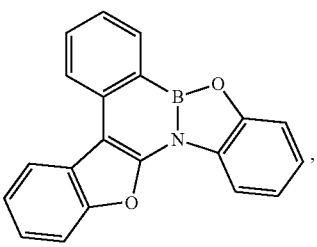
compound 78
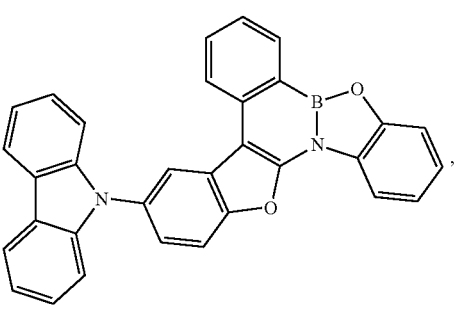

compound 79
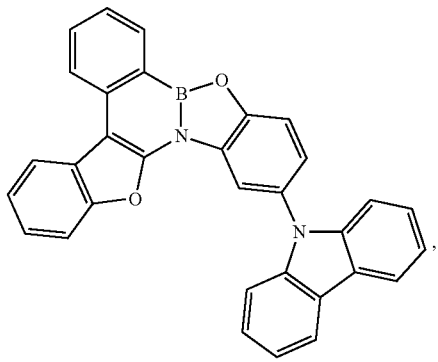
compound 80
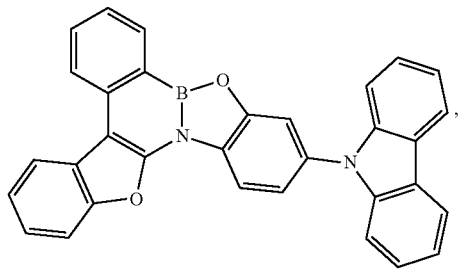
compound 81
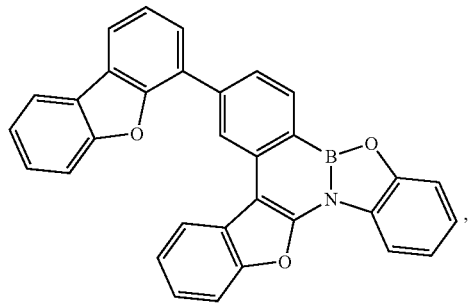
compound 82
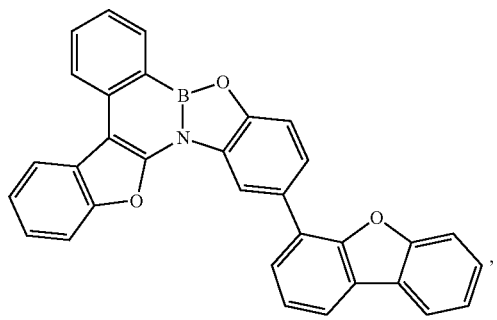
compound 83
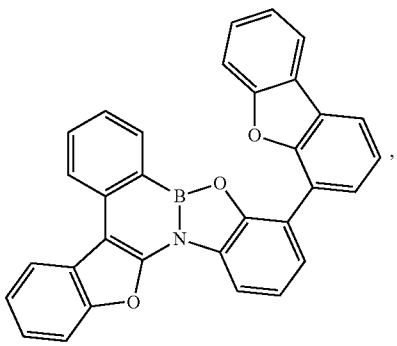
compound 84
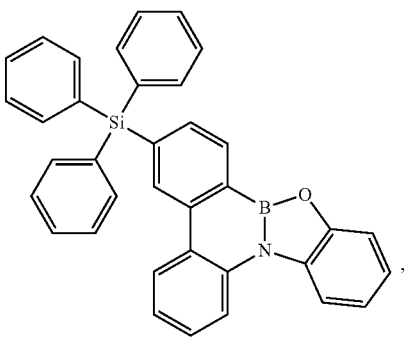
compound 85
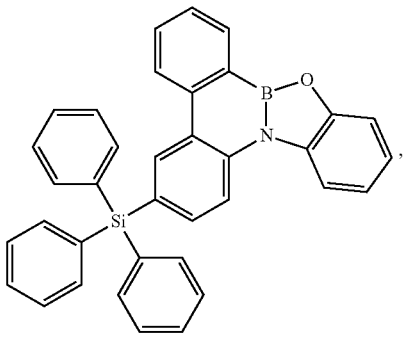
compound 86
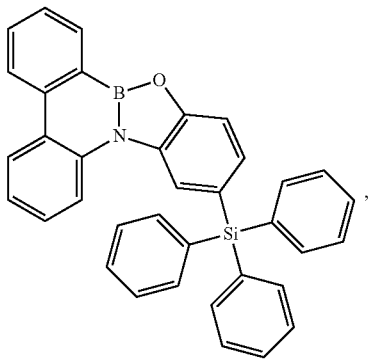

compound 87
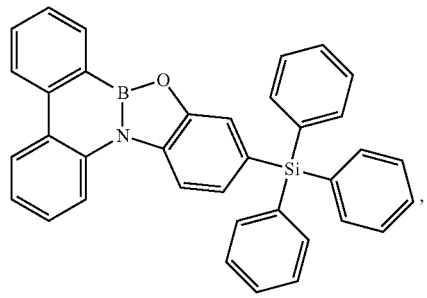
compound 88
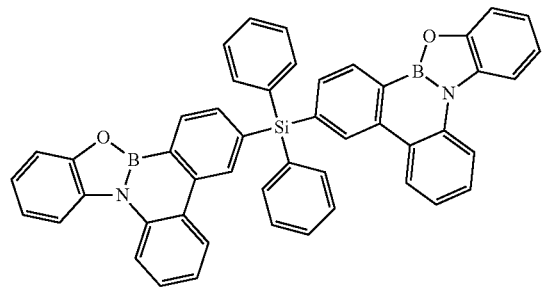
compound 89
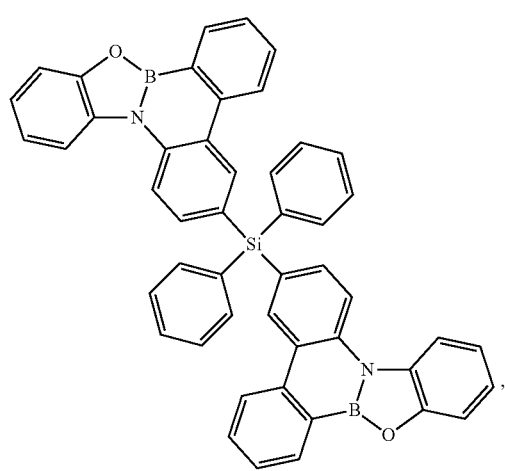
compound 90
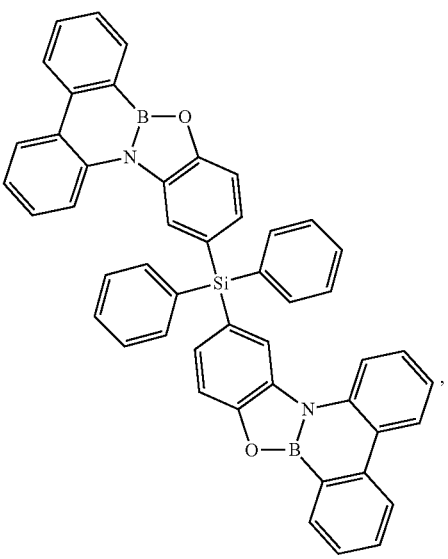
compound 91
compound 92
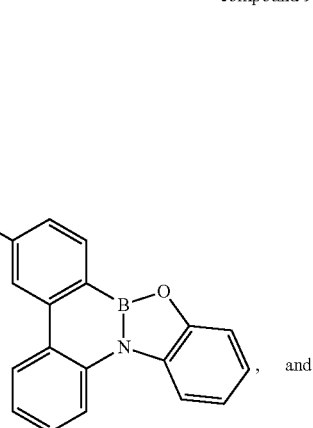
, and compound 93
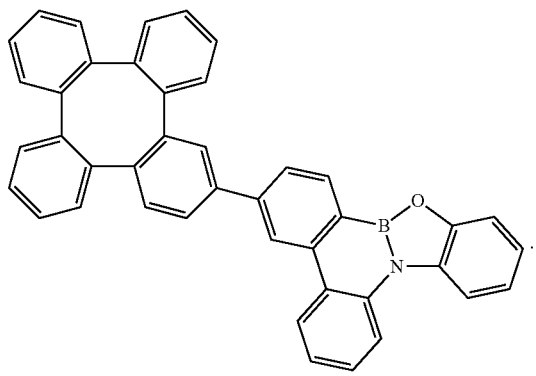
In some embodiments of the compound, $X^1$ is C or N, $R^A$ is aryl or heteroaryl and $R^A$ is connected to $X^1$ to form a fused ring.
In some embodiments of the compound, the compound is selected from the group consisting of:
compound 94
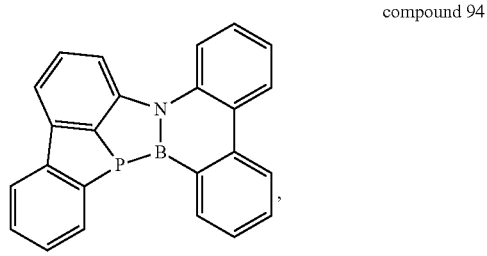
compound 95
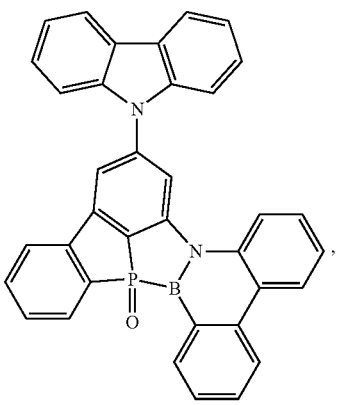
compound 96
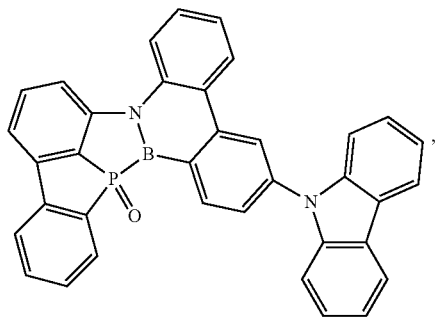
compound 97
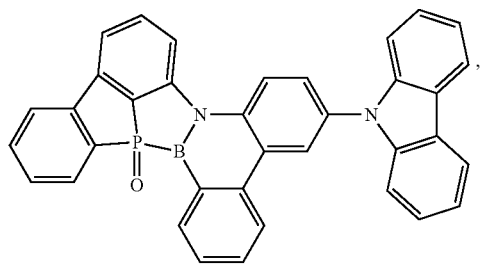
compound 98
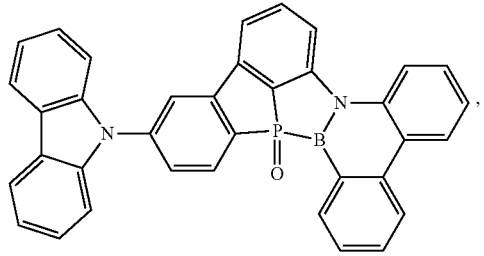
compound 99
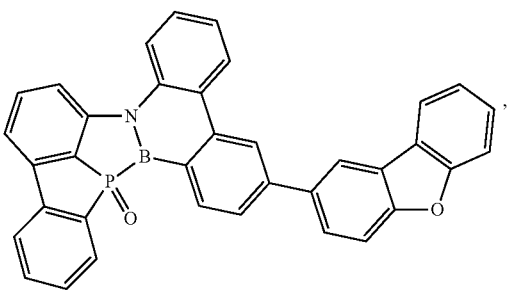
compound 100 compound 101
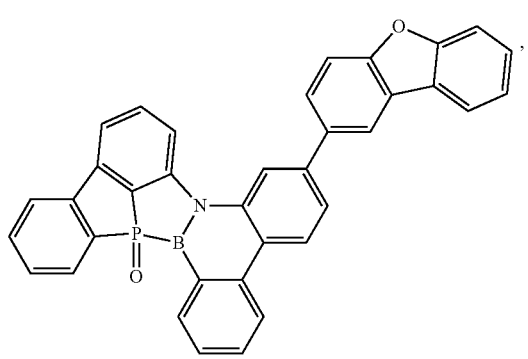
compound 102
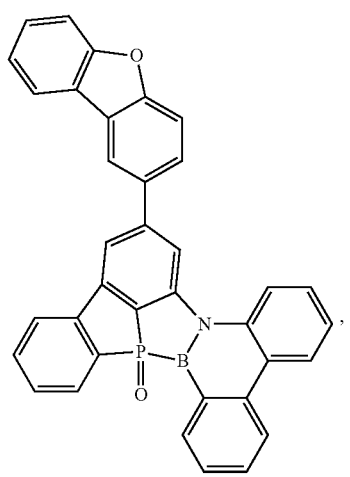
compound 103
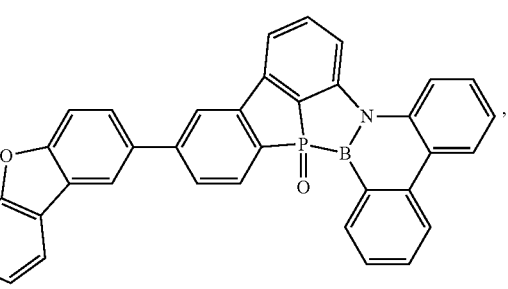
compound 104

compound 105
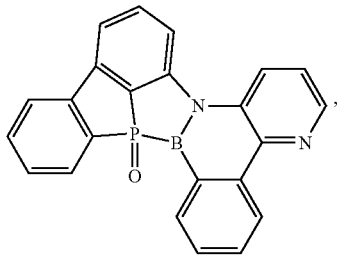
compound 106
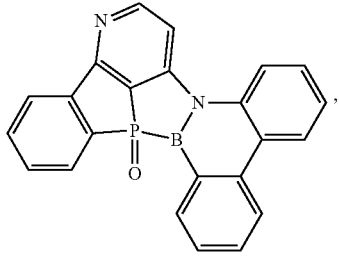
compound 107
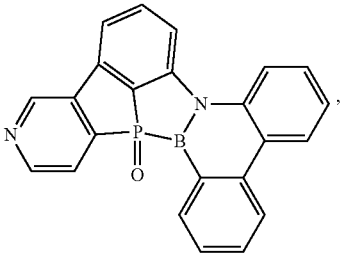
compound 108
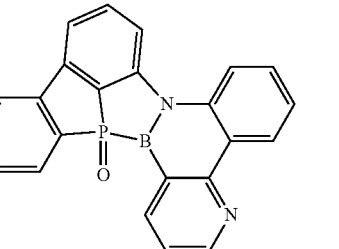
compound 109
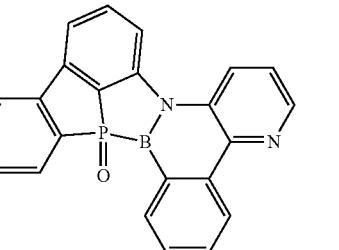

compound 110
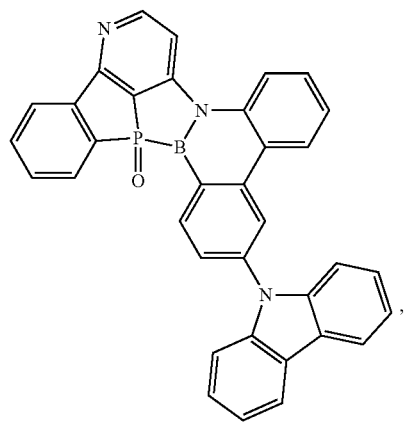
compound 111
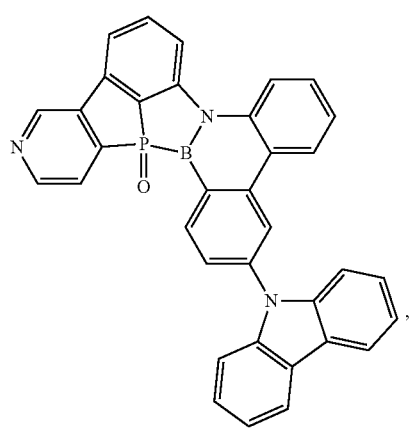
compound 112
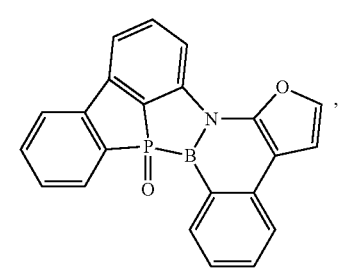
compound 113
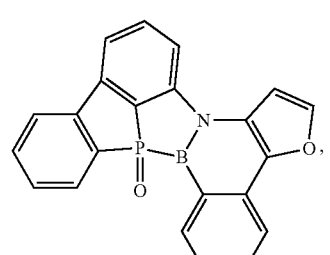
compound 114
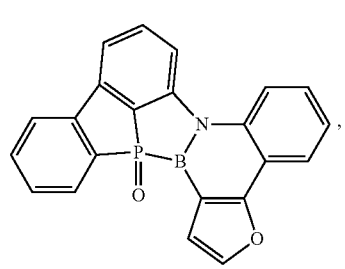
compound 115
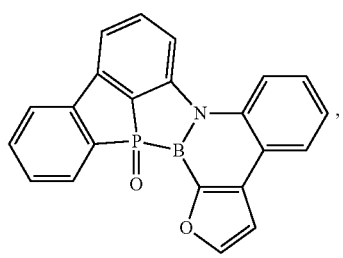
compound 116
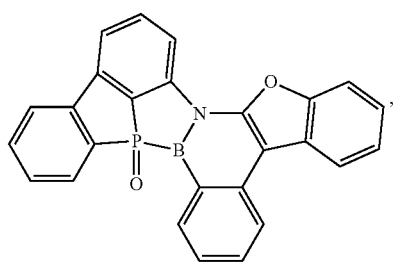
compound 117

compound 118

compound 119
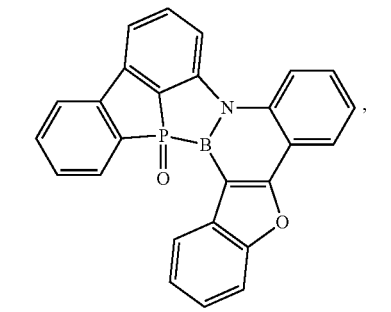

compound 120
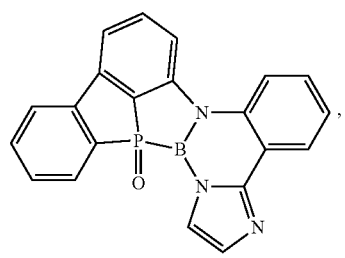
compound 121
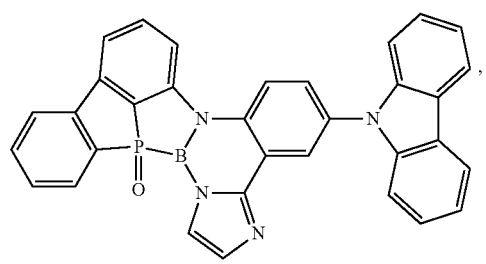
compound 122
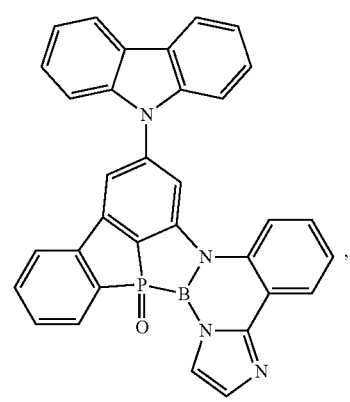
compound 123
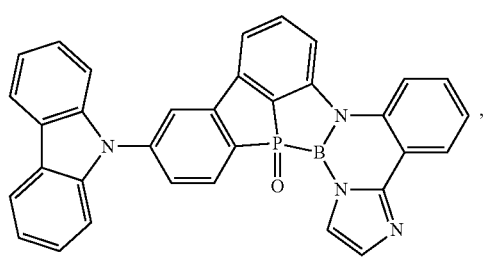
compound 124
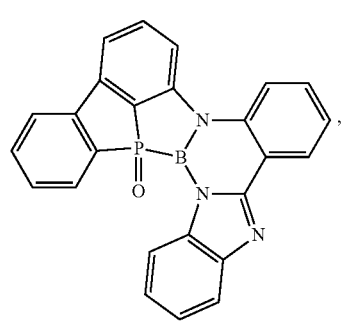
compound 125
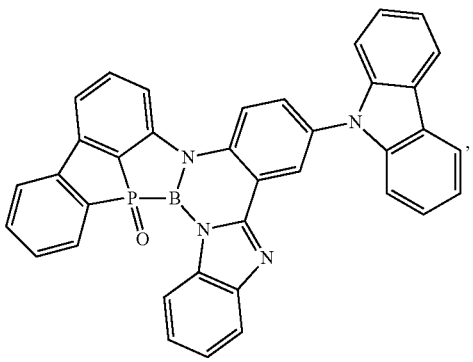
compound 126
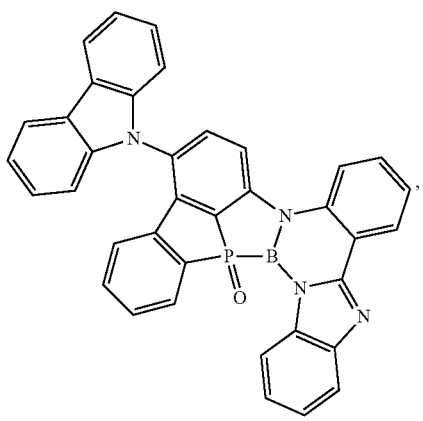
compound 127
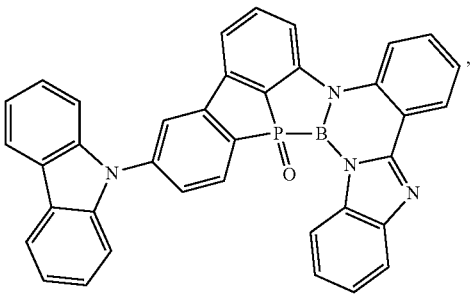

compound 128

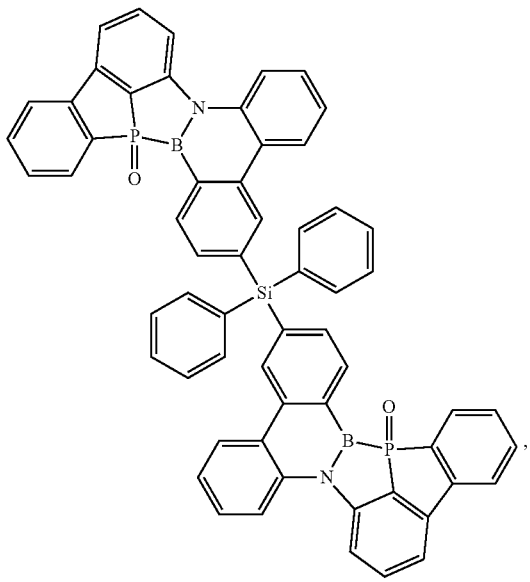

compound 129

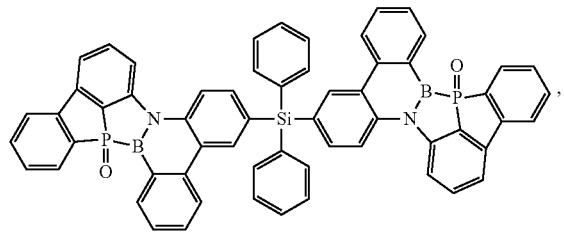

compound 130

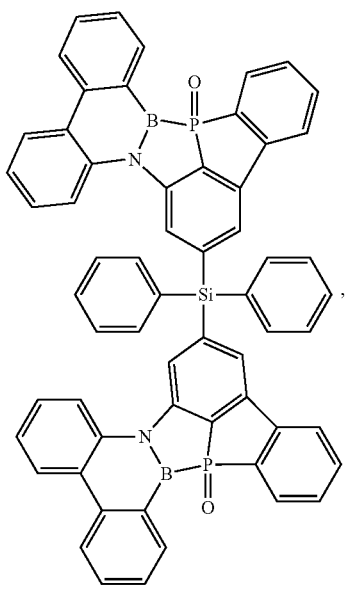

and compound 131

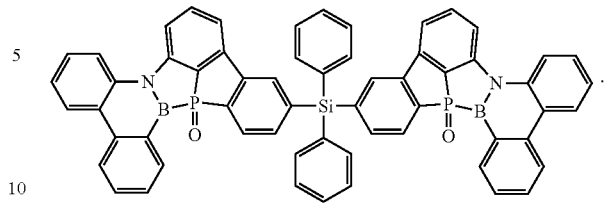

In some embodiments of the compound of Formula I, $R^A$ is an aryl ring. In some embodiments, $R^A$ is benzene.

In some embodiments of the compound of Formula I, $R^B$ is an aryl ring or a heteroaryl ring comprising one heteroatom selected from the group consisting of N, O, and S. In some embodiments of the compound, $R^B$ is selected from the group consisting of benzene, pyridine, furan, thiophene.

In some embodiments of the compound of Formula I, $R^C$ is an aryl ring or a heteroaryl ring comprising one or two nitrogen atoms. In some embodiments, $R^C$ is selected from the group consisting of benzene, pyridine, imidazole.

In some embodiments of the compound of Formula I, (a) at least one of $R^1$, $R^2$, and $R^3$ comprises a substituent selected from the group consisting of carbazole, azacarbazole, dibenzofuran, azadibenzofuran, dibenzothiophene, azadibenzothiophene, dibenzoselenophene, azadibenzoselenophene, triphenylene, azatriphenylene, diphenylsilyl, triphenylsilyl, and tetraphenylsilyl; (b) two of $R^1$, $R^2$, and $R^3$ form a fused benzo substituent on $R^A$, $R^B$, or $R^C$, respectively; or (c) both (a) and (b) are true.

In some embodiments of the compound of Formula I, at least one of $R^1$, $R^2$, and $R^3$ comprises a substituent selected from the group consisting of carbazole, azacarbazole, dibenzofuran, azadibenzofuran, dibenzothiophene, azadibenzothiophene, dibenzoselenophene, azadibenzoselenophene, triphenylene, azatriphenylene, diphenylsilyl, triphenylsilyl, and tetraphenylsilyl; and any remaining substituents from $R^1$, $R^2$, and $R^3$ are H.

In some embodiments of the compound of Formula I, one of $R^1$, $R^2$, and $R^3$ comprises a substituent selected from the group consisting of carbazole, azacarbazole, dibenzofuran, azadibenzofuran, dibenzothiophene, azadibenzothiophene, dibenzoselenophene, azadibenzoselenophene, triphenylene, azatriphenylene, diphenylsilyl, triphenylsilyl, and tetraphenylsilyl; and the remaining substituents from $R^1$, $R^2$, and $R^3$ are H.

In some embodiments of the compound of Formula I, $R^1$ comprises a substituent selected from the group consisting of carbazole, azacarbazole, dibenzofuran, azadibenzofuran, dibenzothiophene, azadibenzothiophene, dibenzoselenophene, azadibenzoselenophene, triphenylene, azatriphenylene, diphenylsilyl, triphenylsilyl, and tetraphenylsilyl; and the remaining substituents from $R^1$, $R^2$, and $R^3$ are H.

In some embodiments of the compound of Formula I, $R^2$ comprises a substituent selected from the group consisting of carbazole, azacarbazole, dibenzofuran, azadibenzofuran, dibenzothiophene, azadibenzothiophene, dibenzoselenophene, azadibenzoselenophene, triphenylene, azatriphenylene, diphenylsilyl, triphenylsilyl, and tetraphenylsilyl; and the remaining substituents $R^1$, $R^2$, and $R^3$ are H.

In some embodiments of the compound of Formula I, $R^3$ comprises a substituent selected from the group consisting of carbazole, azacarbazole, dibenzofuran, azadibenzofuran, dibenzothiophene, azadibenzothiophene, dibenzoselenophene, azadibenzoselenophene, triphenylene, azatriphenylene, diphenylsilyl, triphenylsilyl, and tetraphenylsilyl; and the remaining substituents from $R^1$, $R^2$, and $R^3$ are H.

In some embodiments of the compound of Formula I where M is coordinated to $R^B$ and $R^C$, M replaces $R^2$ and $R^3$ that are on $Y^1$ and $Y^2$ respectively and the compound has the formula:

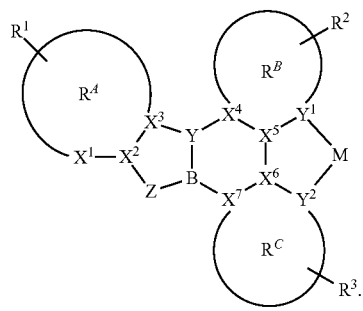

In some embodiments of the compound where M is coordinated to $R^B$ and $R^C$, M is selected from the group consisting of Ir, Rh, Re, Ru, Os, Pt, Au, and Cu. In some embodiments, M is Ir or Pt. In some embodiments, one of $Y^1$ and $Y^2$ is nitrogen, the other one of $Y^1$ and $Y^2$ is carbon. In some embodiments, one of $Y^1$ and $Y^2$ is neutral carbene carbon, the other one of $Y^1$ and $Y^2$ is anionic carbon.

In some embodiments of the compound of Formula I where M is coordinated to $R^B$ and $R^C$ the compound is homoleptic. In some embodiments of Formula I where M is coordinated to $R^B$ and $R^C$, the compound is heteroleptic.

In some embodiments of the compound of Formula I wherein M is coordinated to $R^B$ and $R^C$, the compound is selected from the group consisting of:

Compound M1

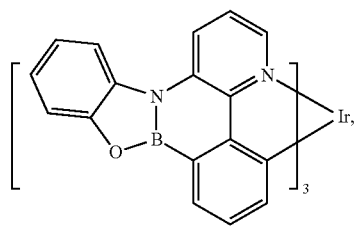

Compound M2

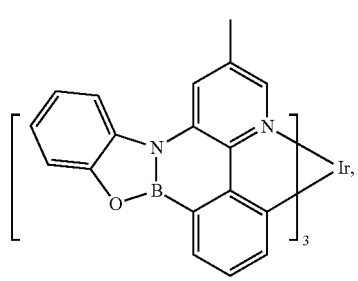

Compound M3

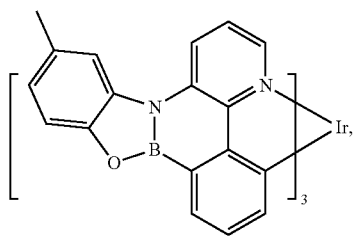

Compound M4

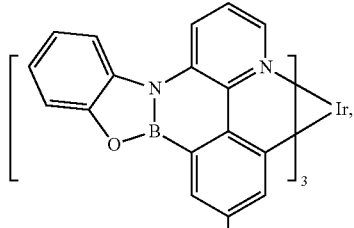

Compound M5

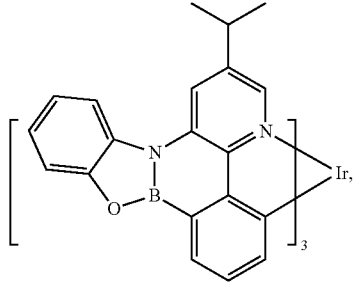

Compound M6

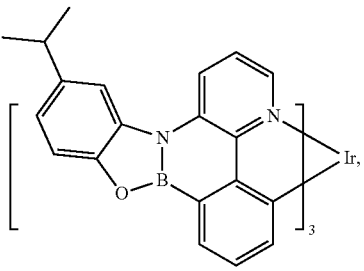

Compound M7

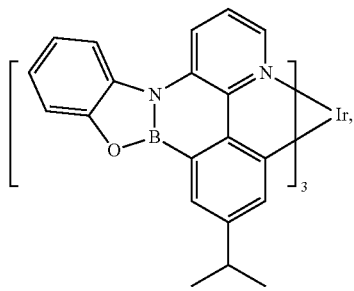

Compound M8

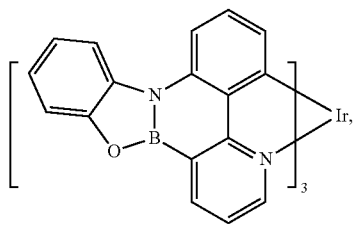

Compound M9
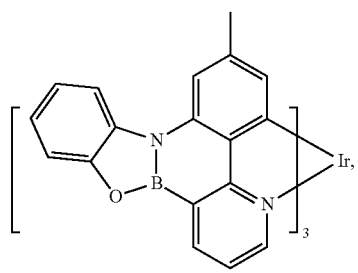
Compound M10
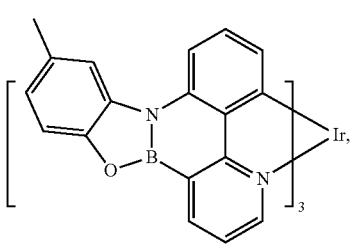
Compound M11
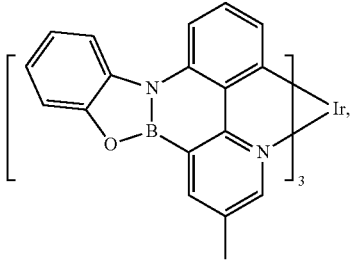
Compound M12
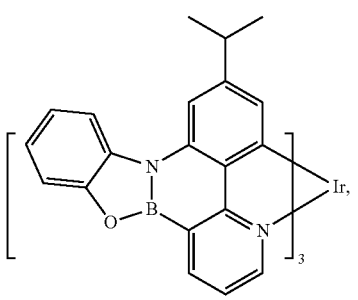
Compound M13
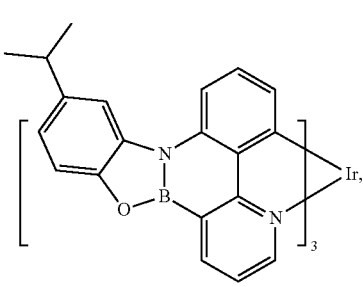
Compound M14
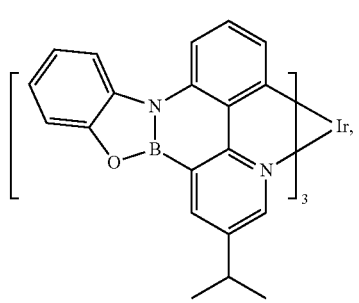
Compound M15
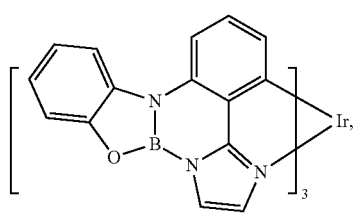
Compound M16
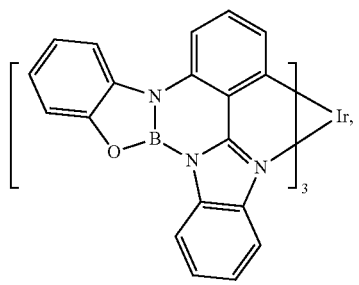
Compound M17
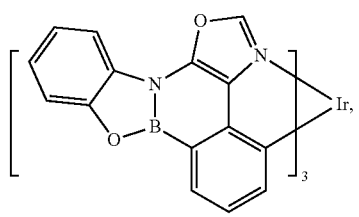
Compound M18
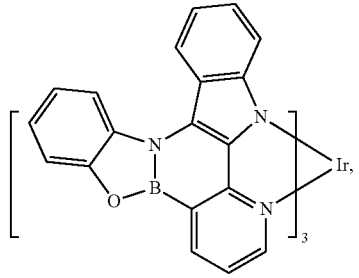
Compound M19
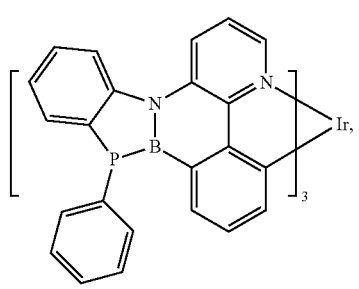

Compound M20
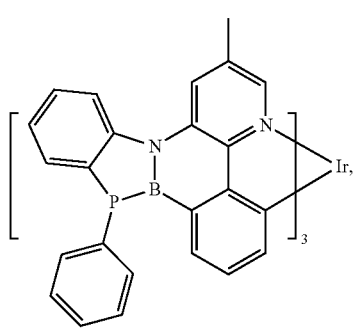
Compound M21
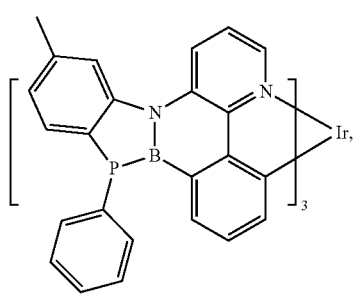
Compound M22
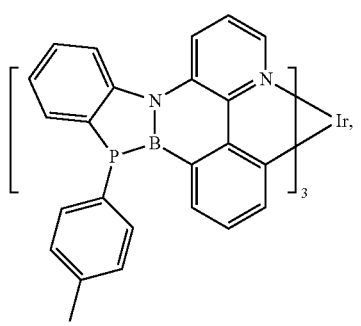
Compound M23
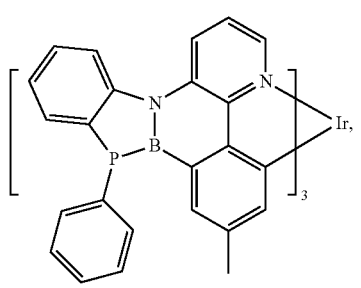
Compound M24
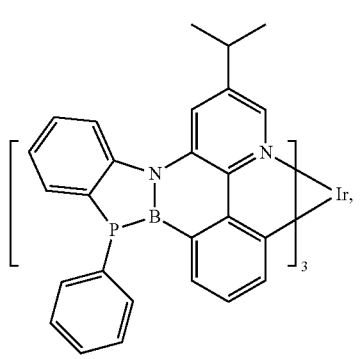
Compound M25
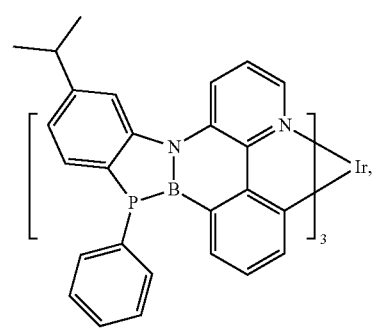
Compound M26
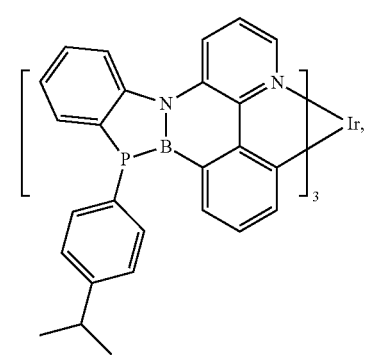
Compound M27
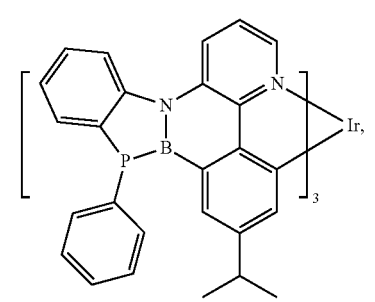
Compound M28
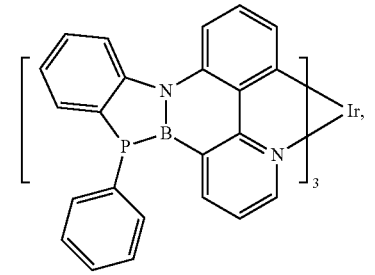
Compound M29
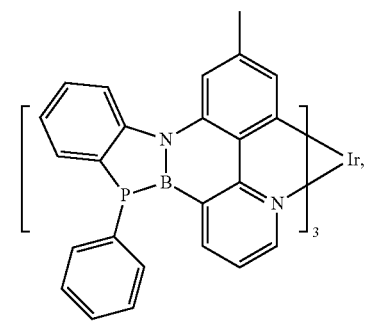

Compound M30
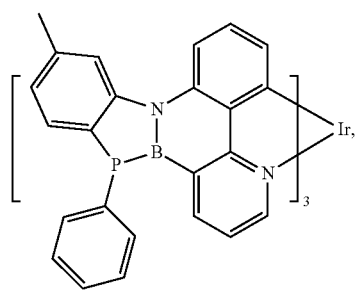
Compound M31
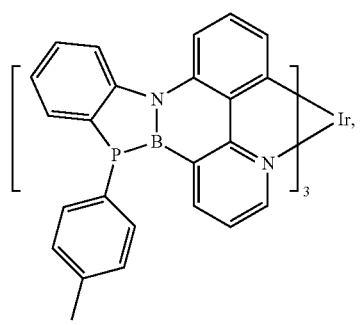
Compound M32
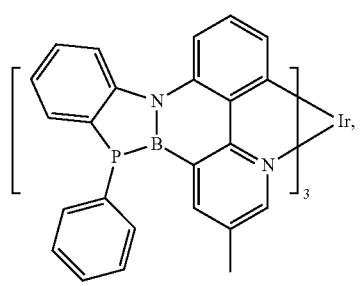
Compound M33
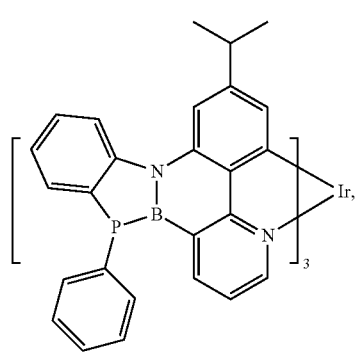
Compound M34
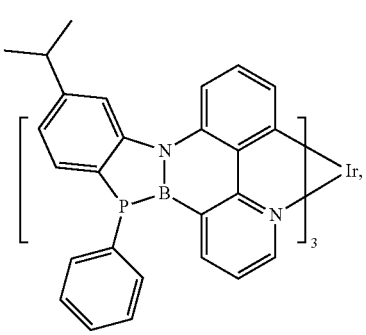
Compound M35
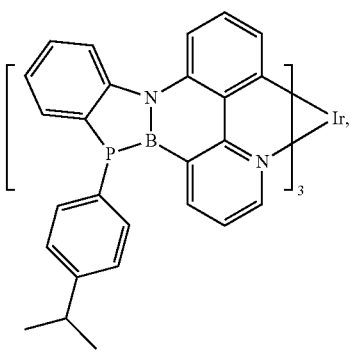
Compound M36
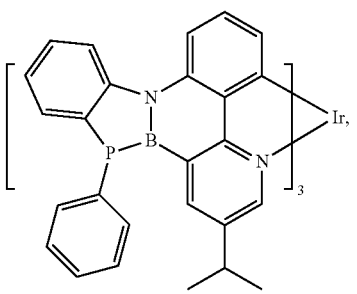
Compound M37
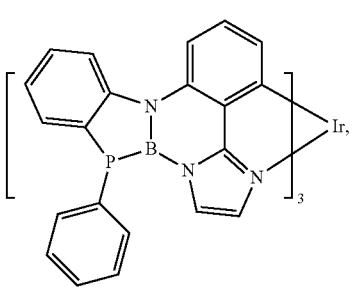
Compound M38
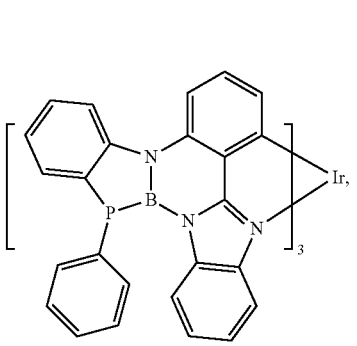
Compound M39
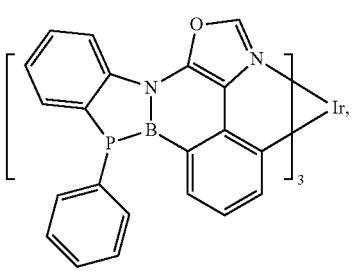

Compound M40
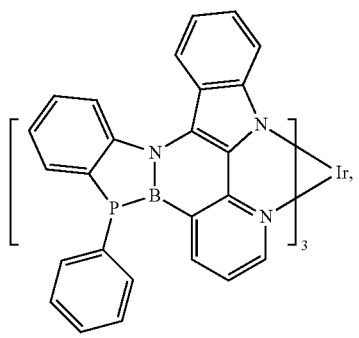
Compound M41
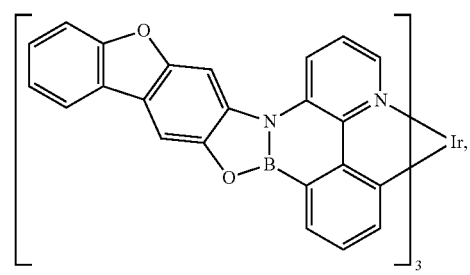
Compound M42
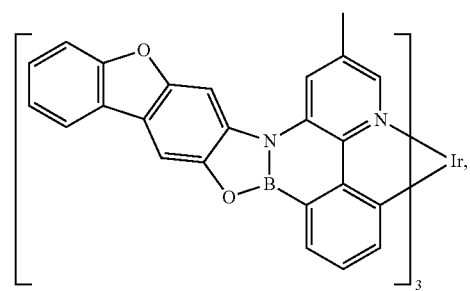
Compound M43
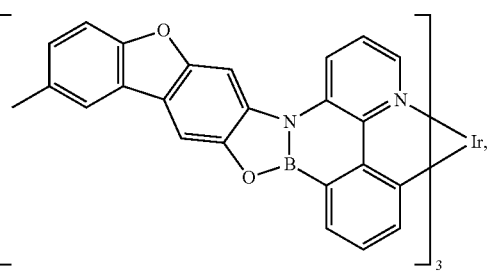
Compound M44
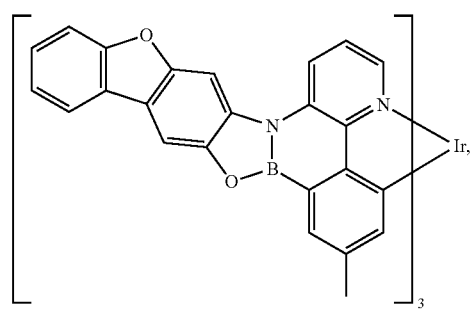
Compound M45
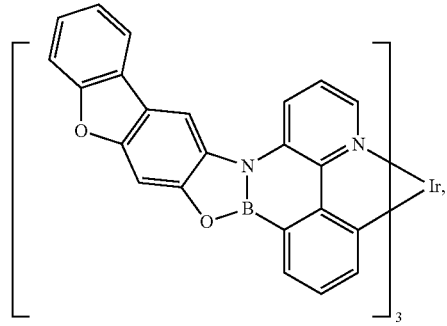
Compound M46
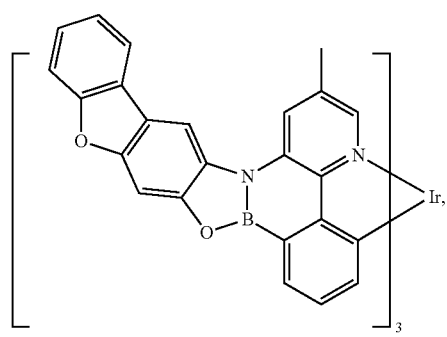
Compound M47
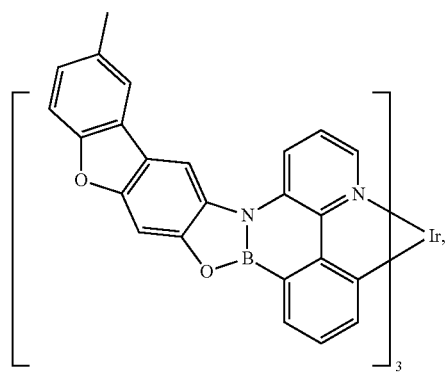
Compound M48
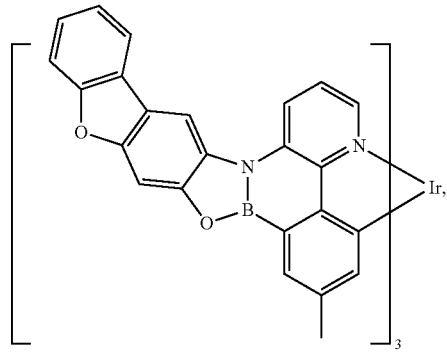

Compound M49
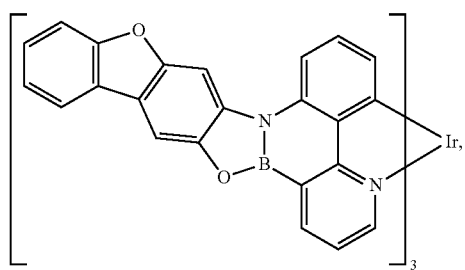
Compound M50
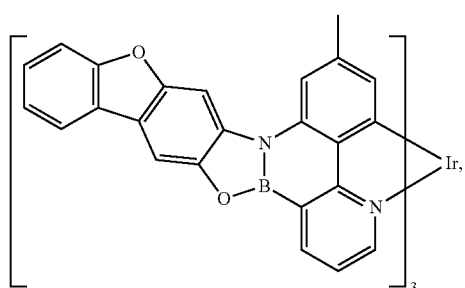
Compound M51
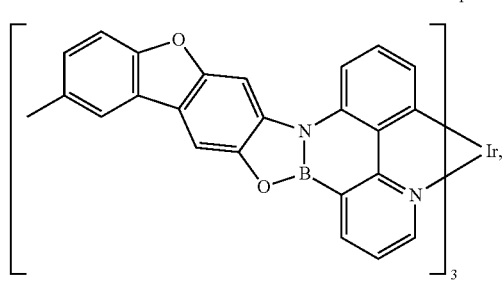
Compound M52
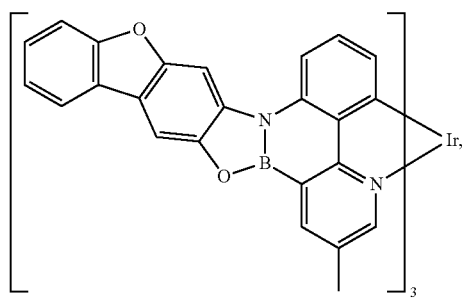
Compound M53
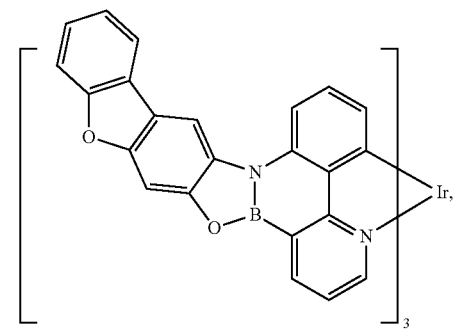
Compound M54
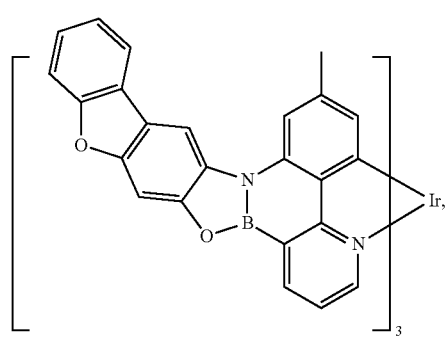
Compound M55
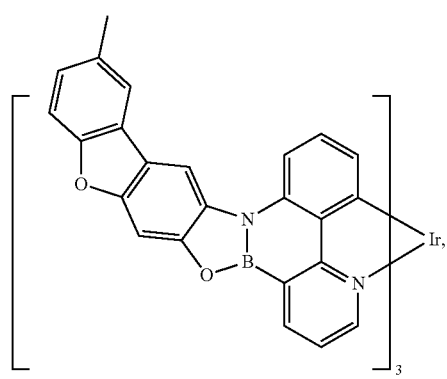
Compound M56
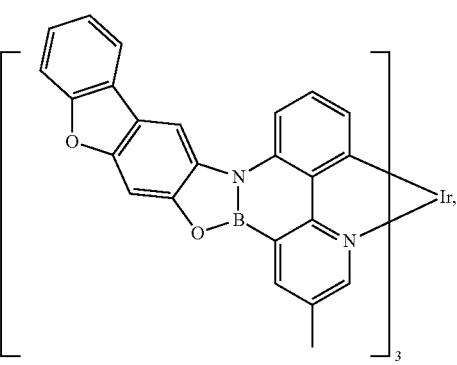
Compound M57
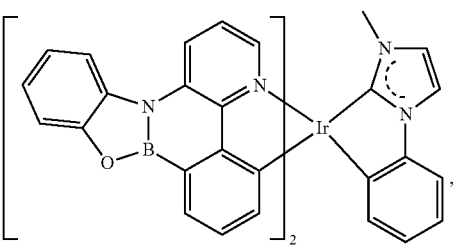

-continued
Compound M58
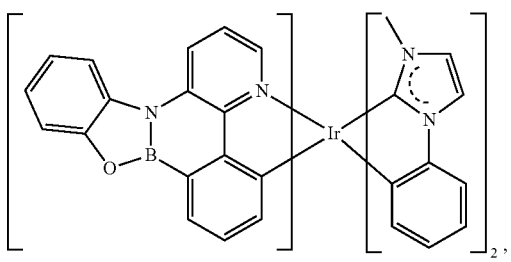
Compound M59
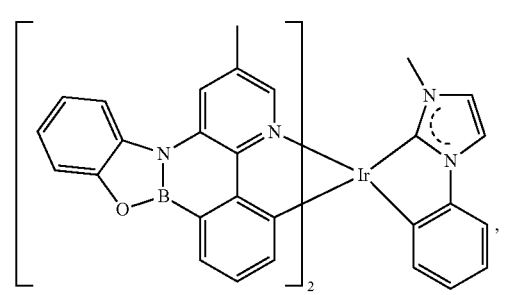
Compound M60
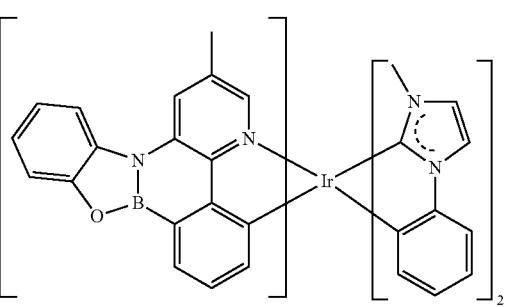
Compound M61
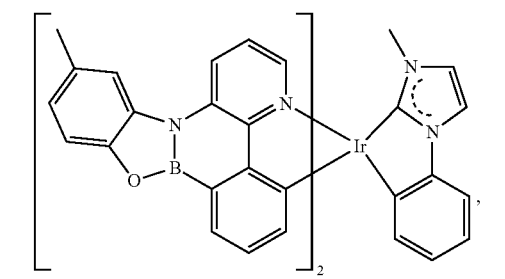
Compound M62
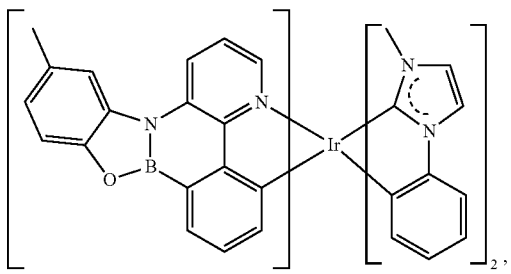
-continued
Compound M63
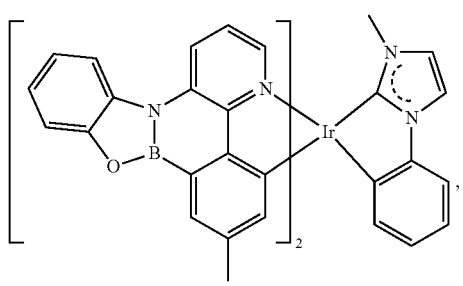
Compound M64
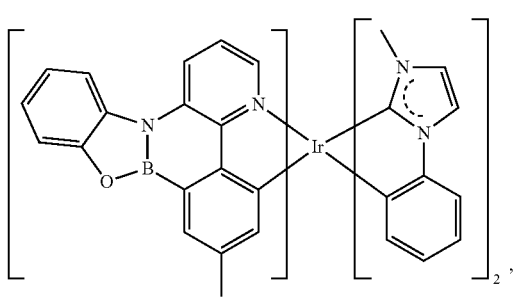
Compound M65
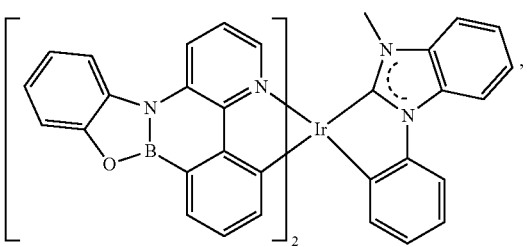
Compound M66
Compound M67
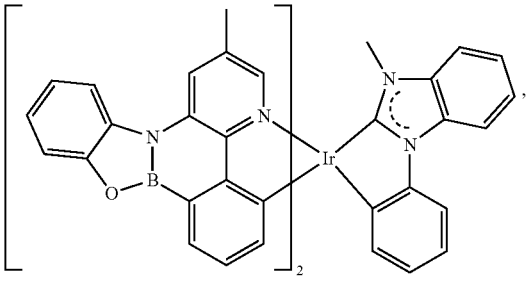

Compound M68
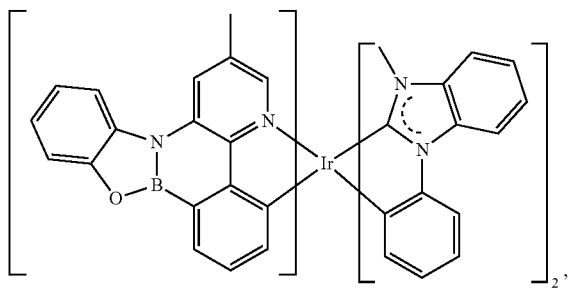
Compound M69
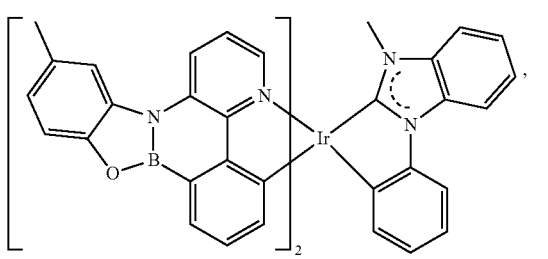
Compound M70
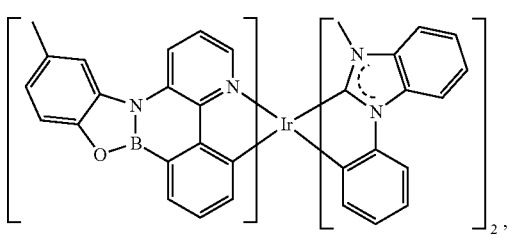
Compound M71
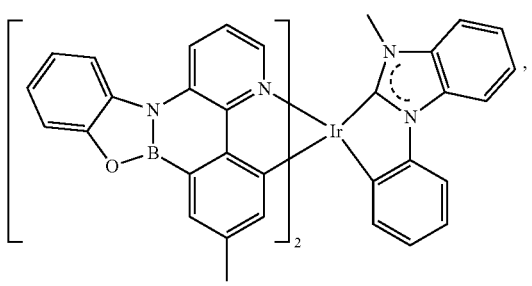
Compound M72
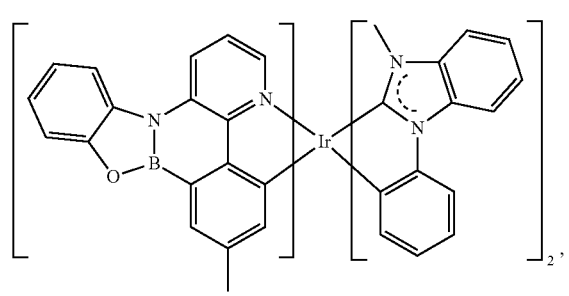
Compound M73
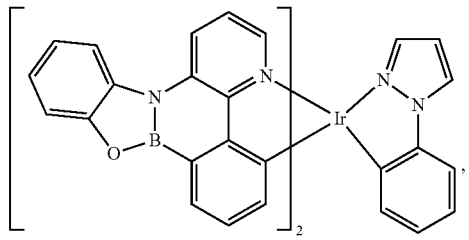
Compound M74
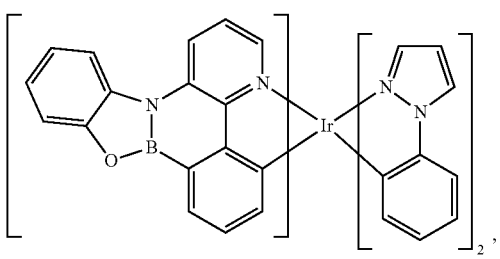
Compound M75
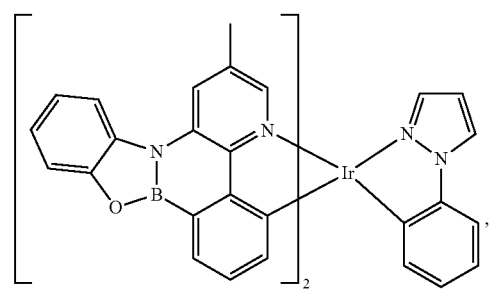
Compound M76
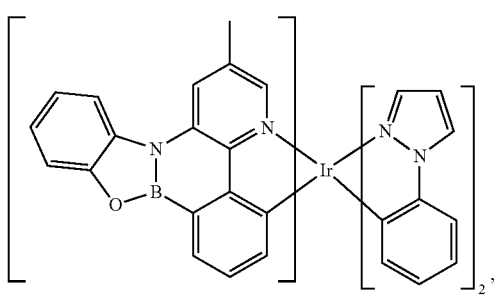
Compound M77
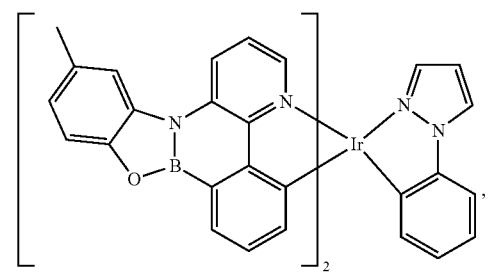

Compound M78
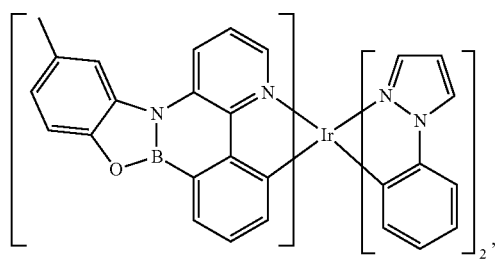
Compound M83
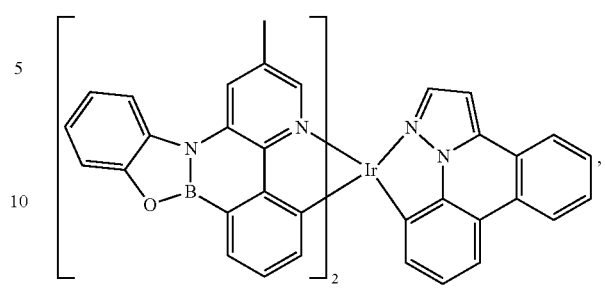
Compound M79
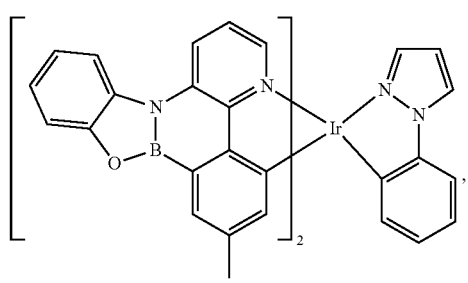
Compound M84
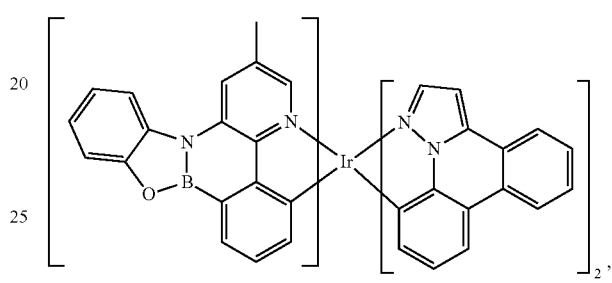
Compound M80
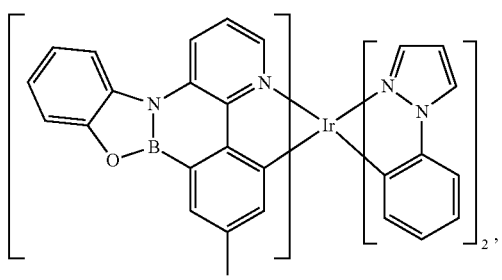
Compound M85
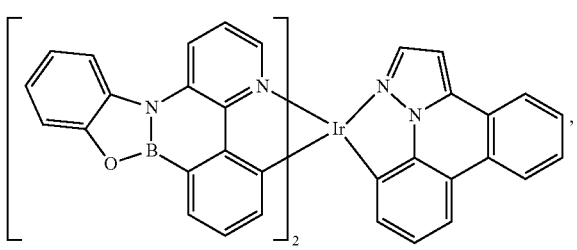
Compound M81
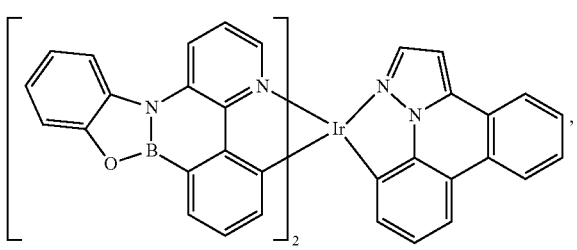
Compound M86
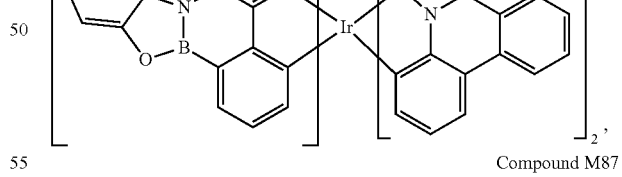
Compound M82
Compound M87
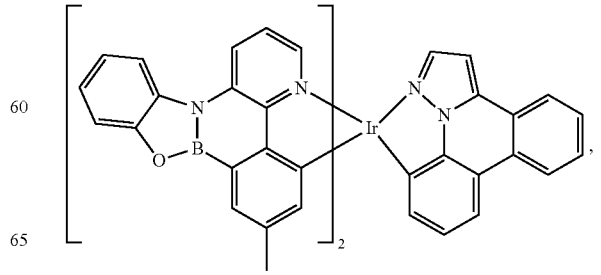

Compound M88
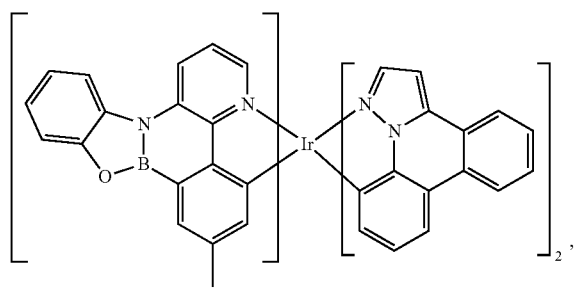
Compound M89
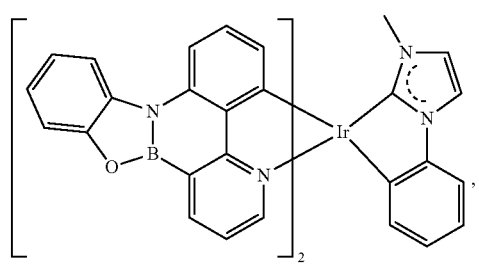
Compound M90
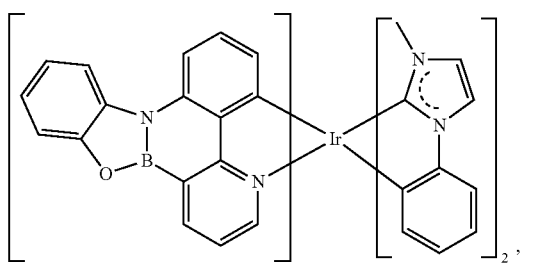
Compound M91
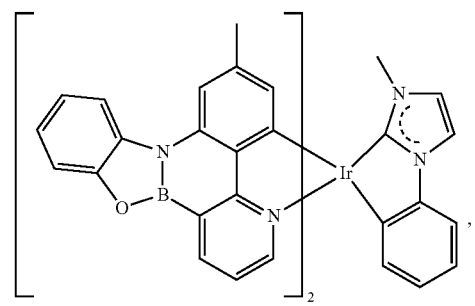
Compound M92
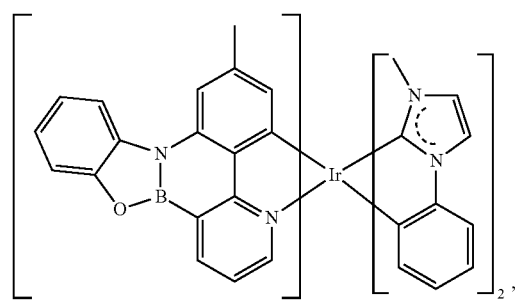
Compound M93
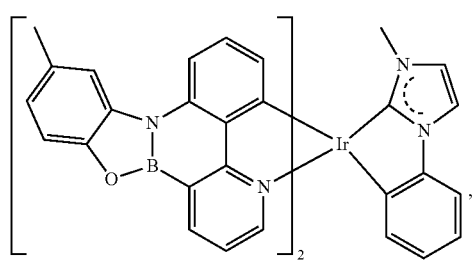
Compound M94
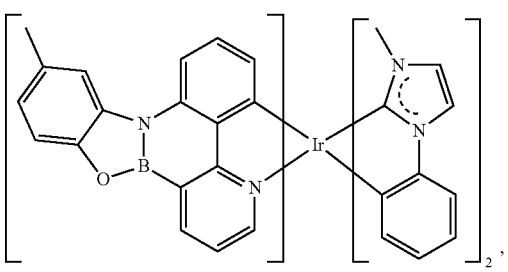
Compound M95
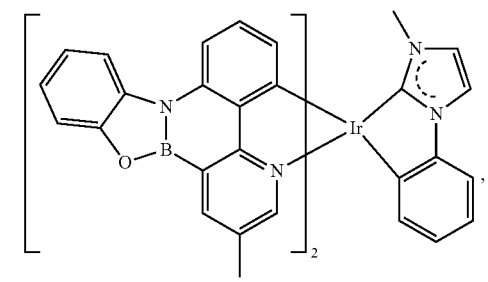
Compound M96
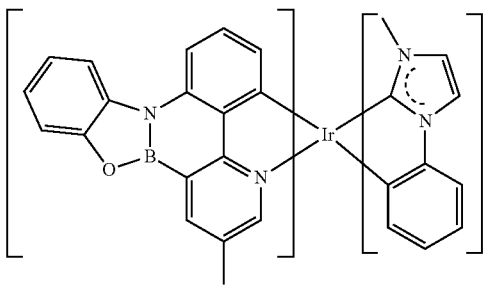
Compound M97

Compound M98
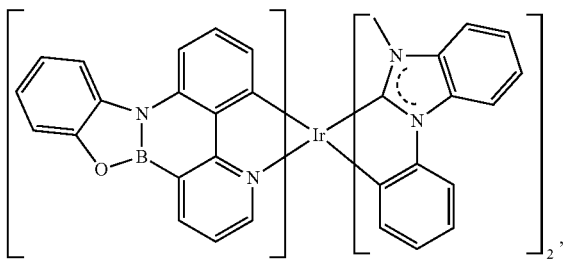
Compound M99
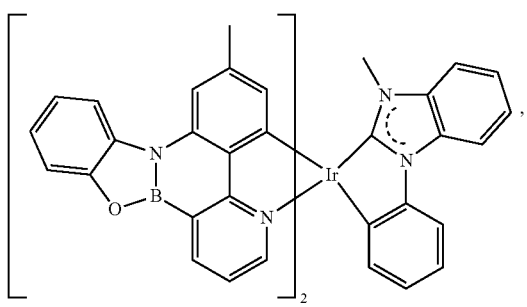
Compound M100
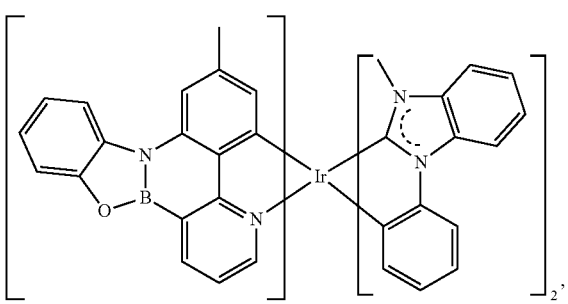
Compound M101
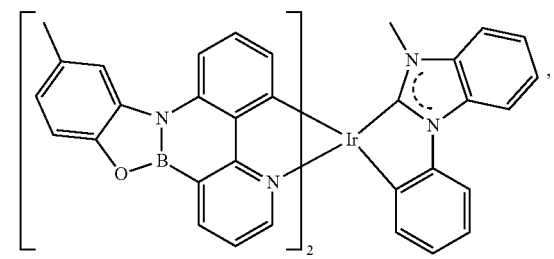
Compound M102
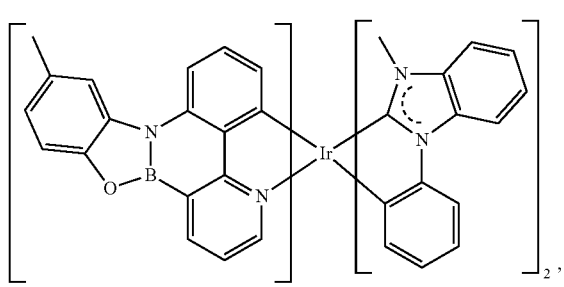
Compound M103
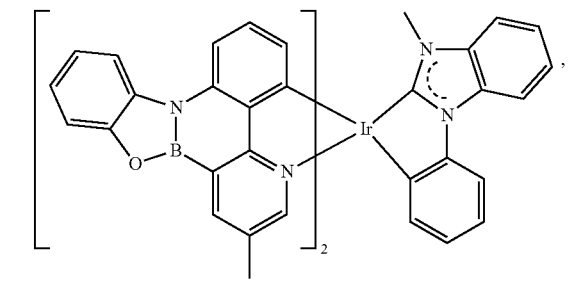
Compound M104
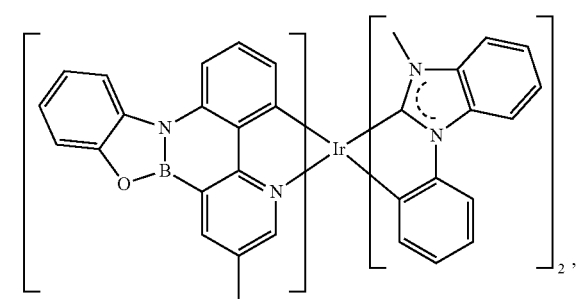
Compound M105
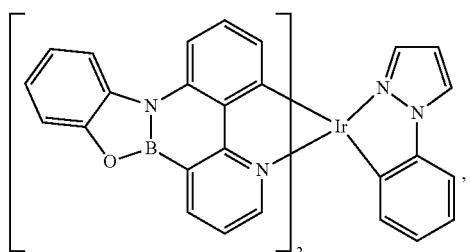
Compound M106
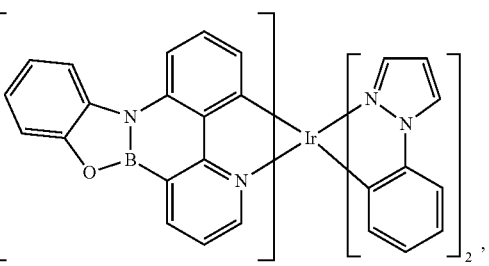
Compound M107
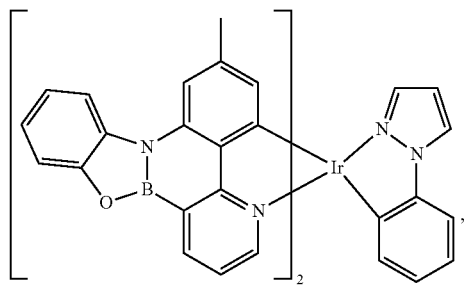

Compound M108
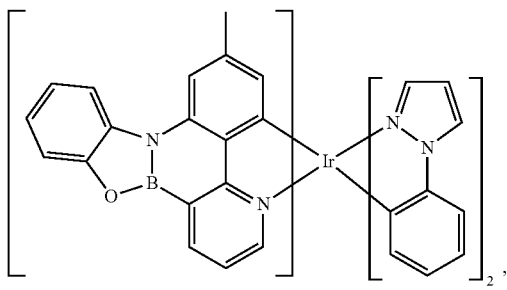
Compound M109
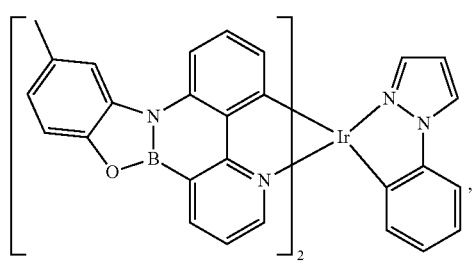
Compound M110
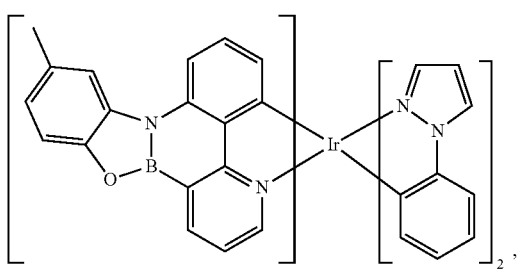
Compound M111
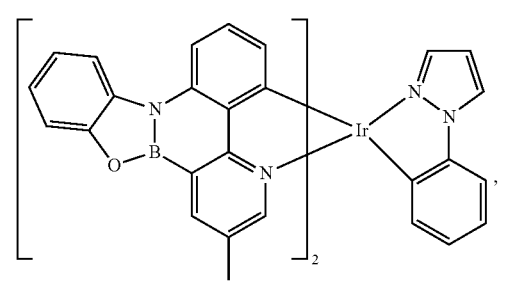
Compound M112
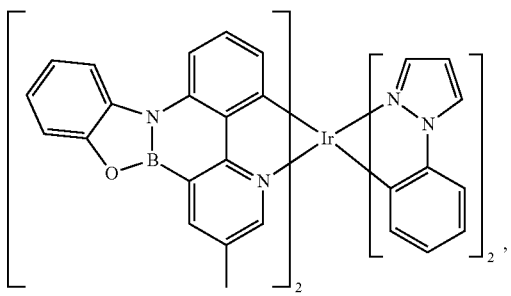
Compound M113
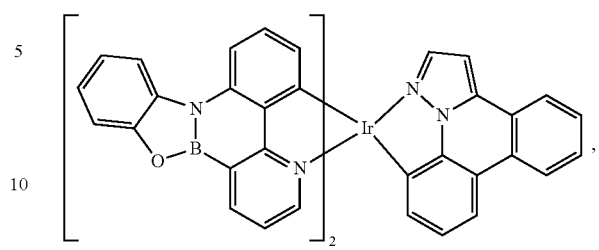
Compound M114
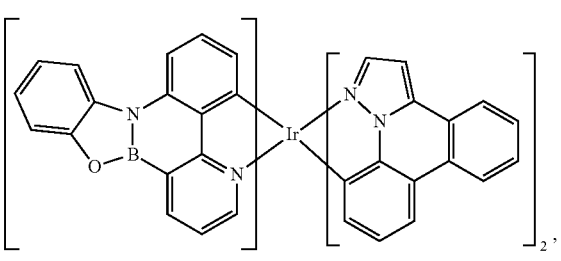
Compound M115
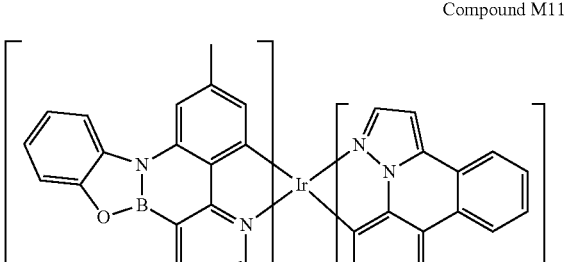
Compound M116
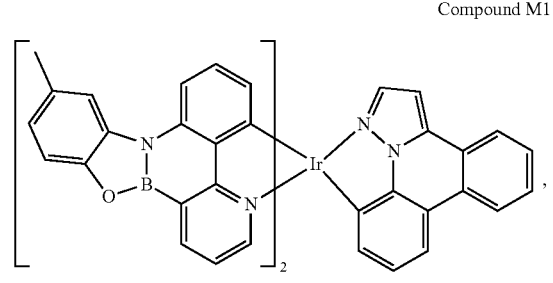
Compound M117

Compound M118
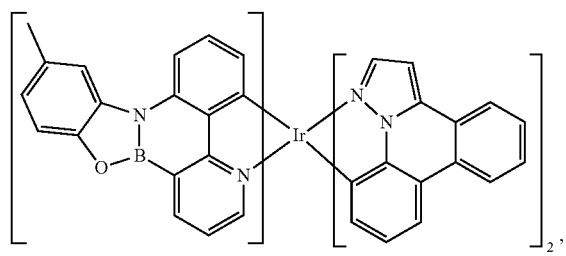
Compound M119
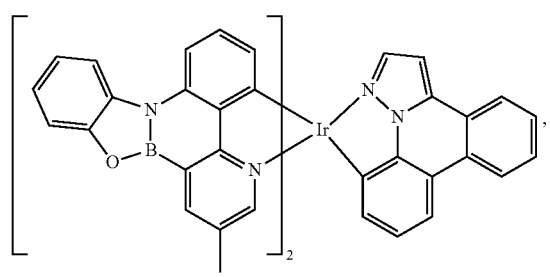
Compound M120
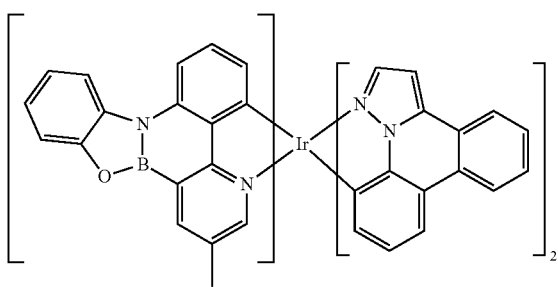
Compound M121
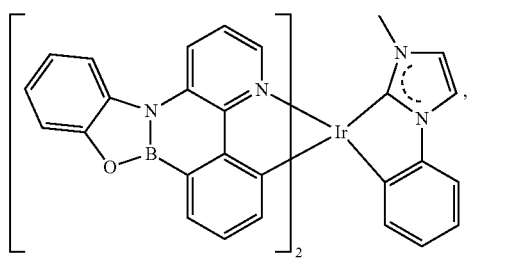
Compound M122
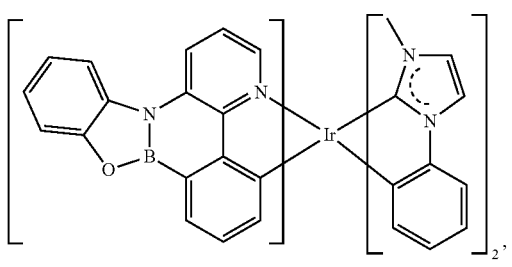
Compound M123
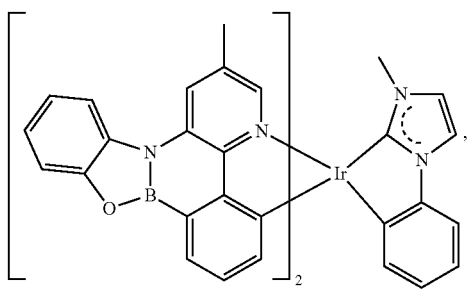
Compound M124
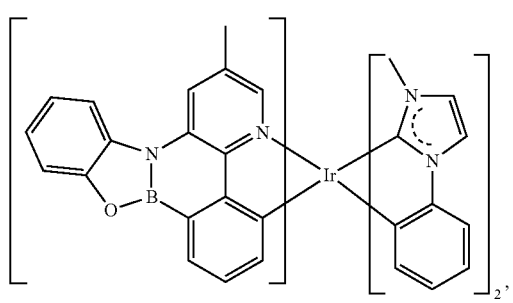
Compound M125
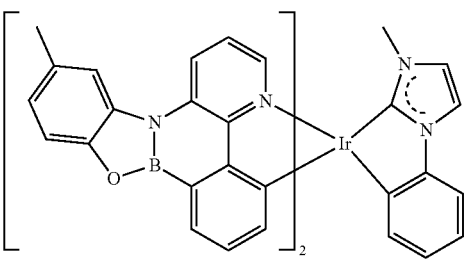
Compound M126
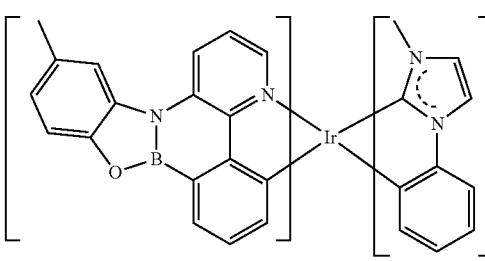
Compound M127
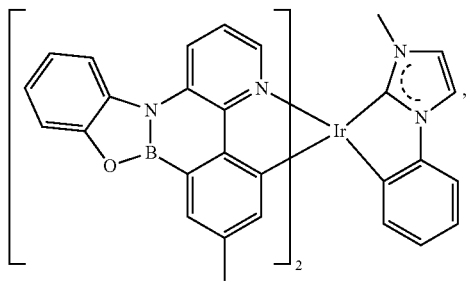

Compound M128
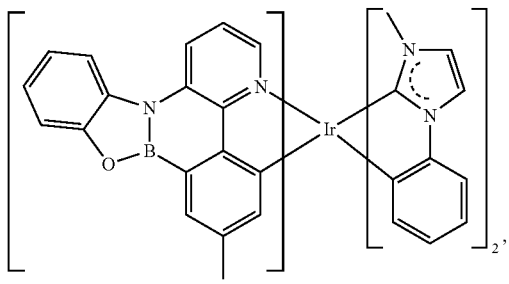
Compound M133
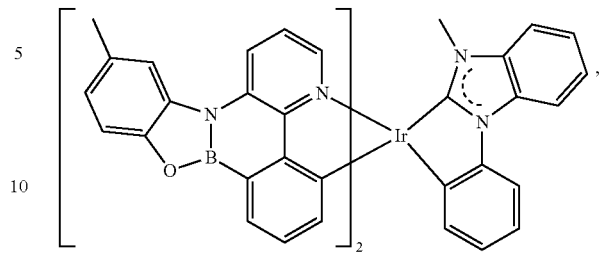
Compound M129
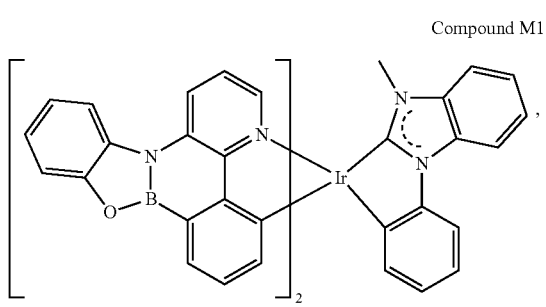
Compound M134
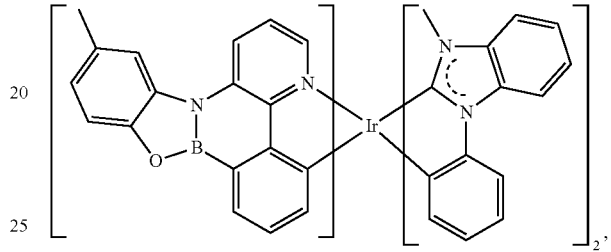
Compound M130
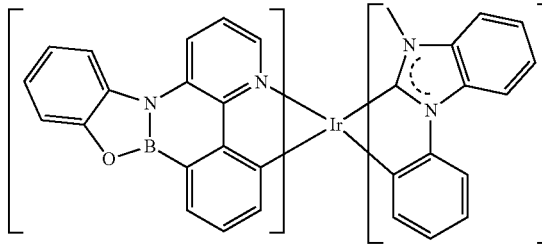
Compound M135
Compound M131
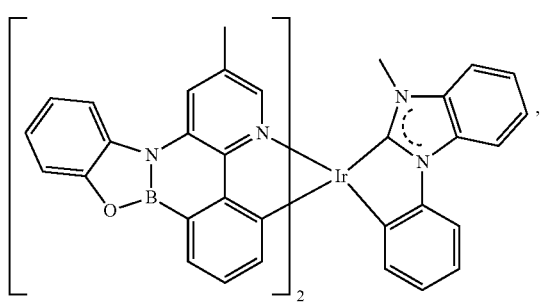
Compound M136
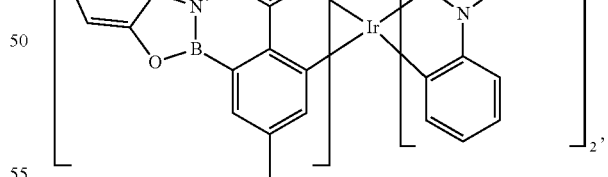
Compound M132
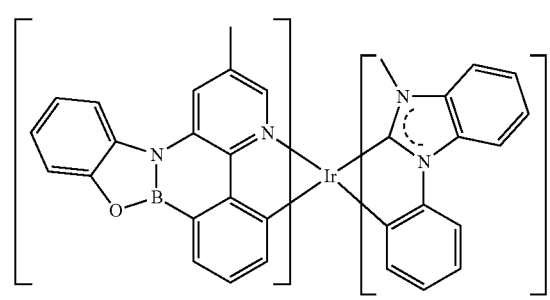
Compound M137
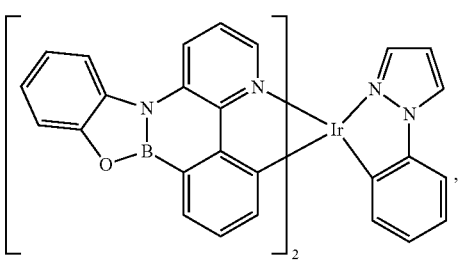

Compound M138
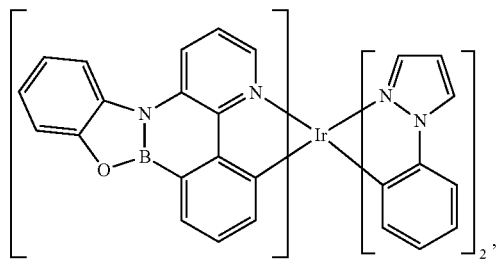
Compound M139
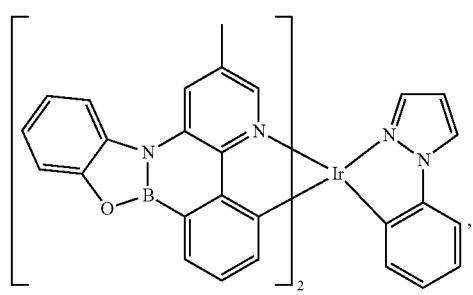
Compound M140
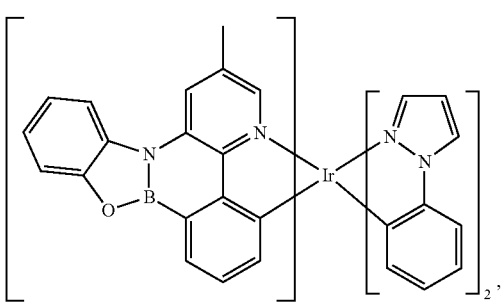
Compound M141
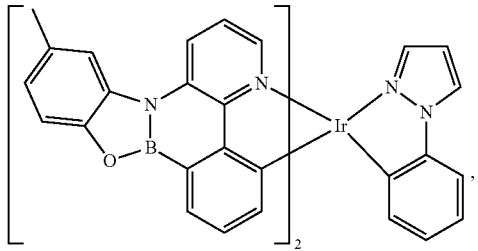
Compound M142
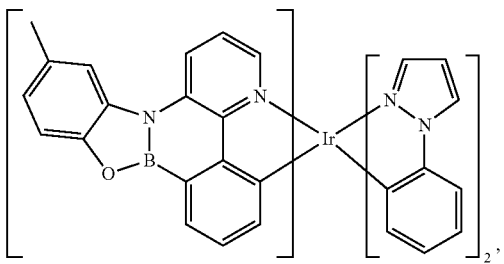
Compound M143
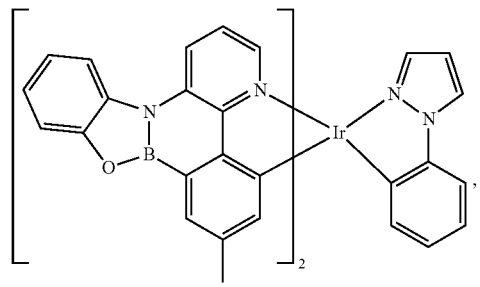
Compound M144
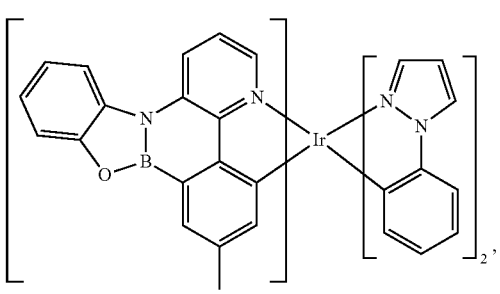
Compound M145
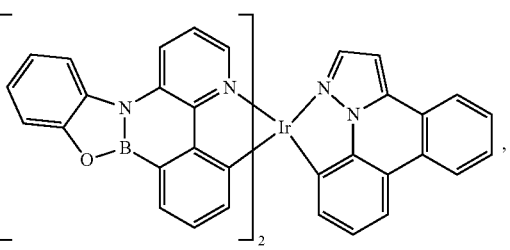
Compound M146
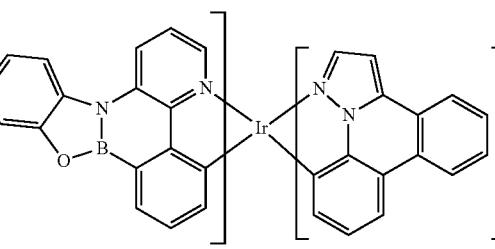
Compound M147
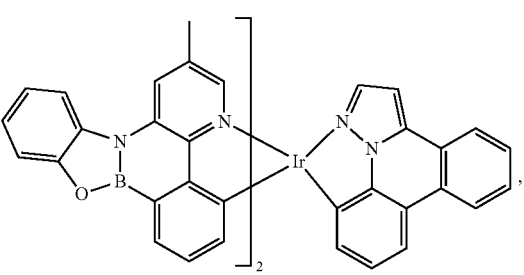

Compound M148
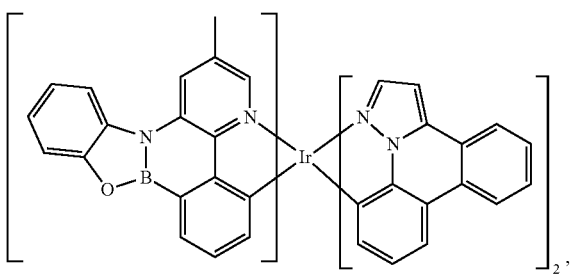
Compound M149
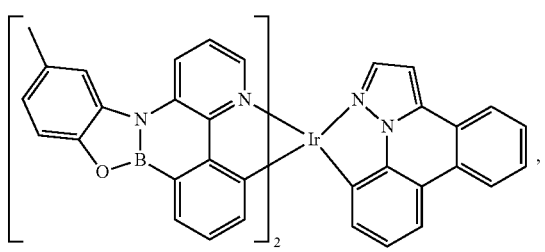
Compound M150
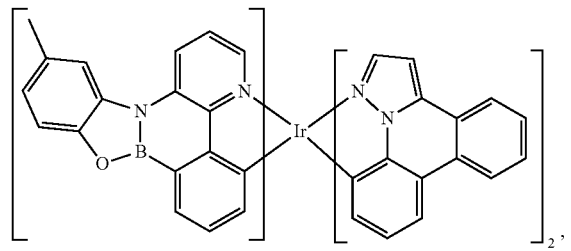
Compound M151
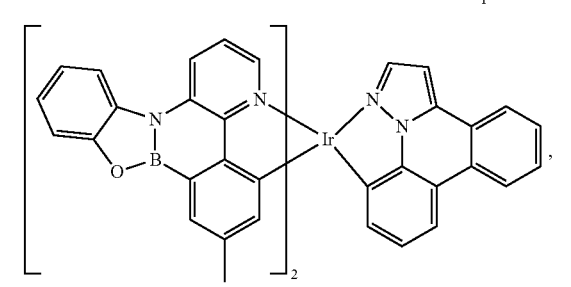
Compound M152
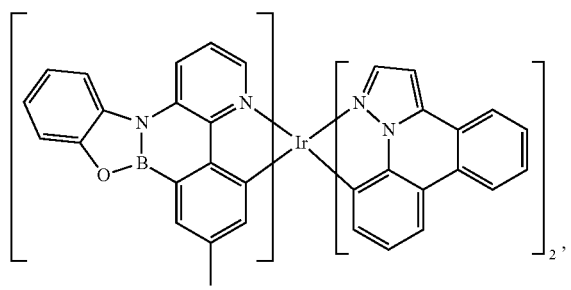
Compound M153
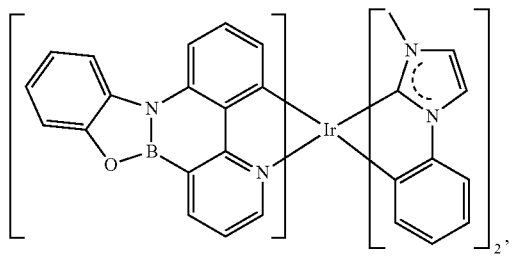
Compound M154
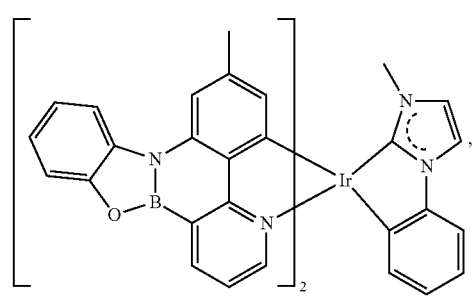
Compound M155
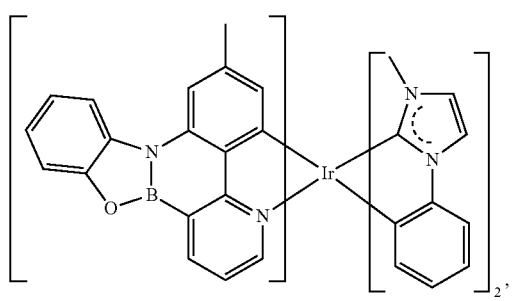
Compound M156
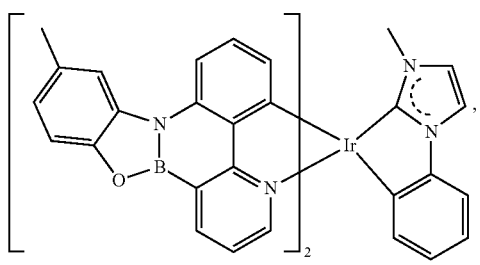
Compound M157

Compound M158
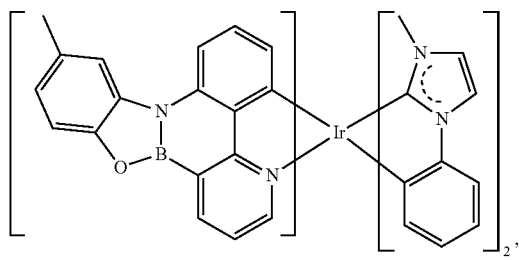
Compound M159
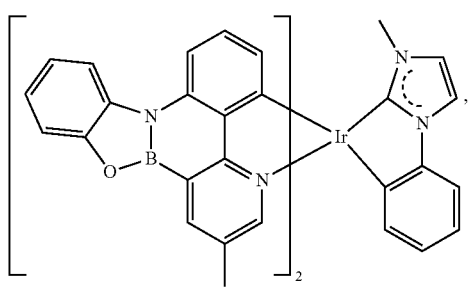
Compound M160
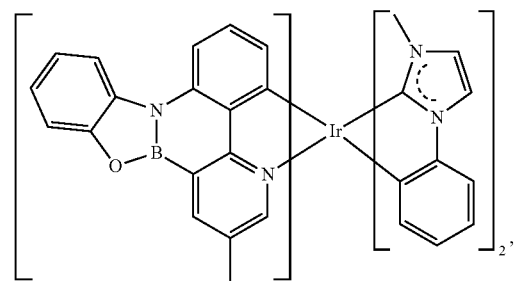
Compound M161
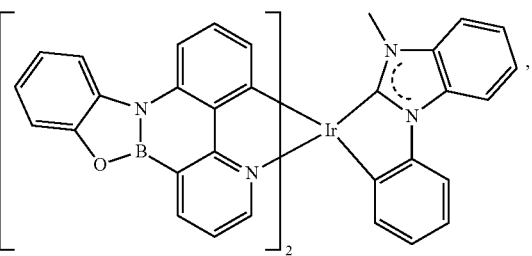
Compound M162
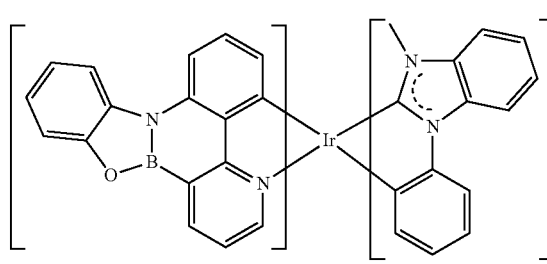
Compound M163
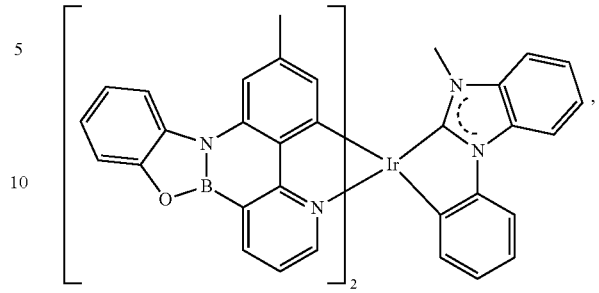
Compound M164
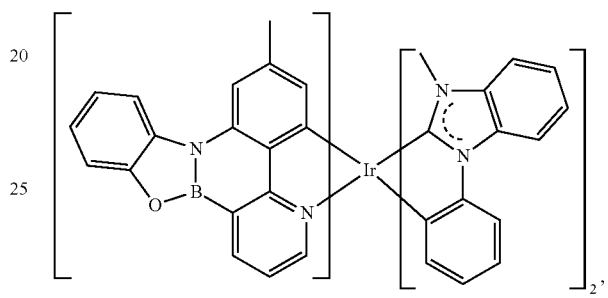
Compound M165
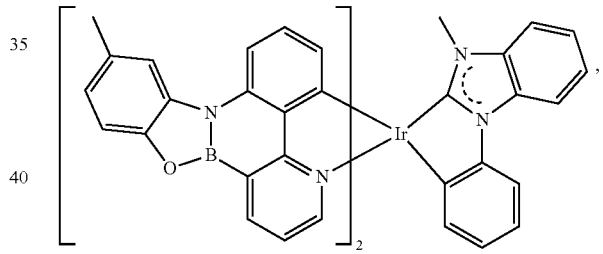
Compound M166
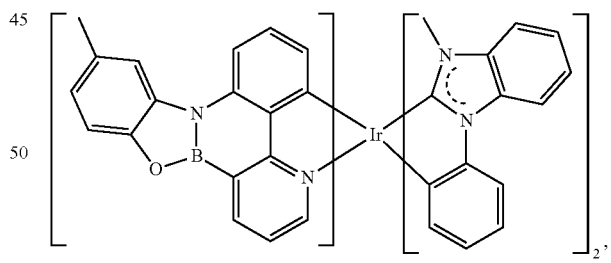
Compound M167
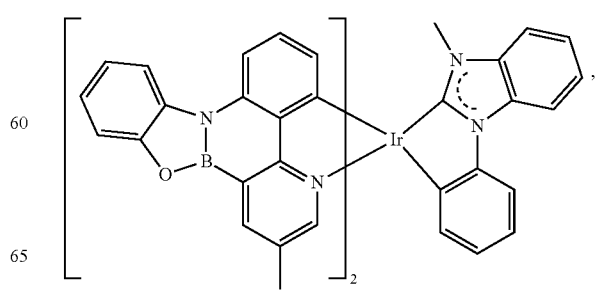

Compound M168
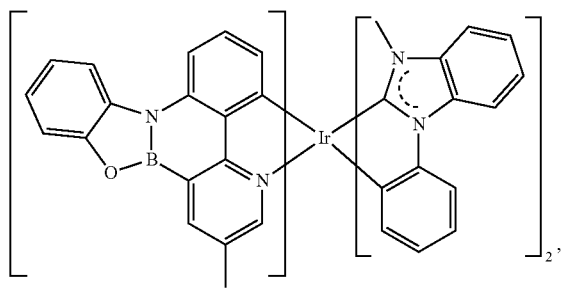
Compound M169
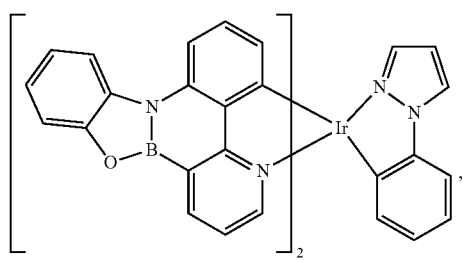
Compound M170
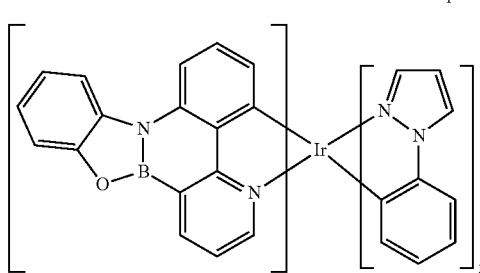
Compound M171
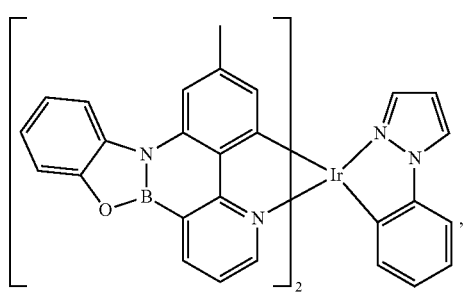
Compound M172
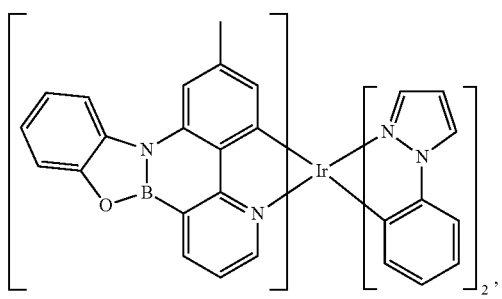
Compound M173
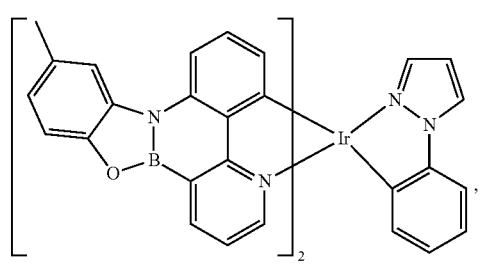
Compound M174
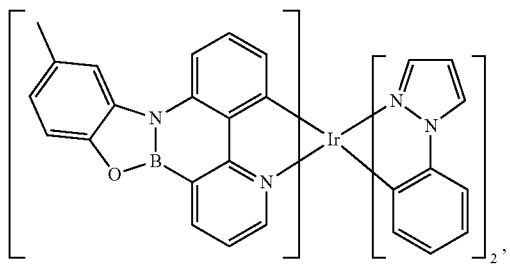
Compound M175
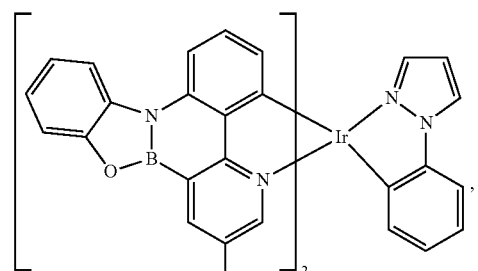
Compound M176
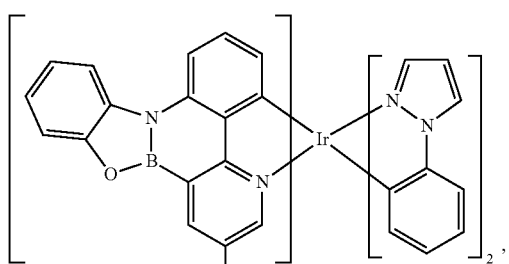
Compound M177
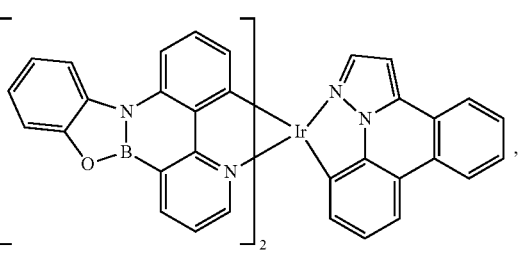

Compound M178
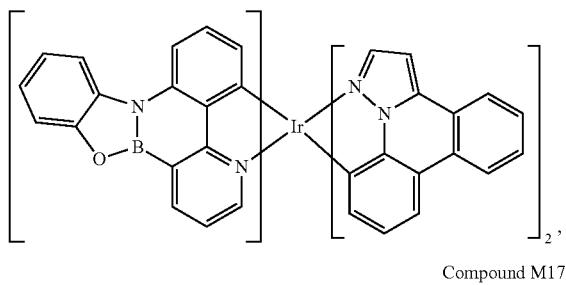
Compound M183
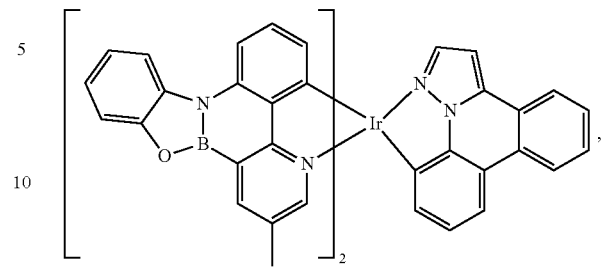
Compound M179
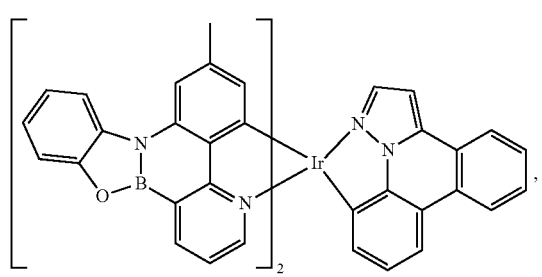
Compound M184
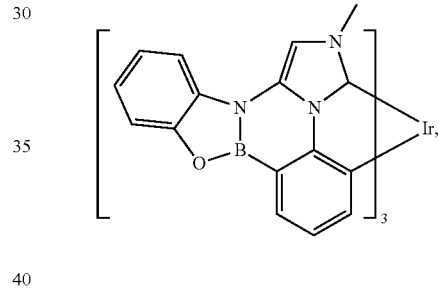
Compound M180
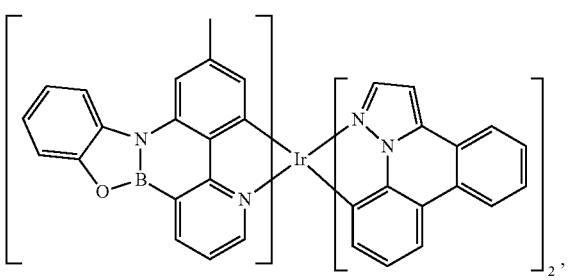
Compound M185
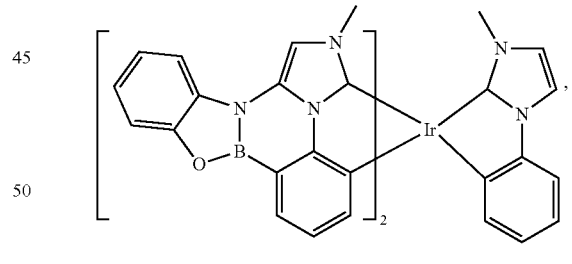
Compound M181
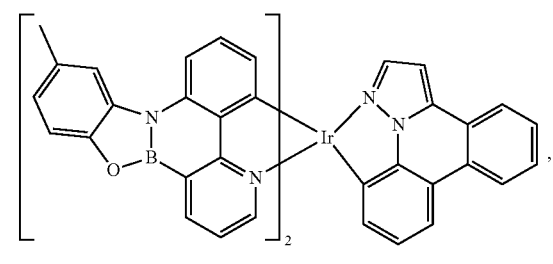
Compound M186
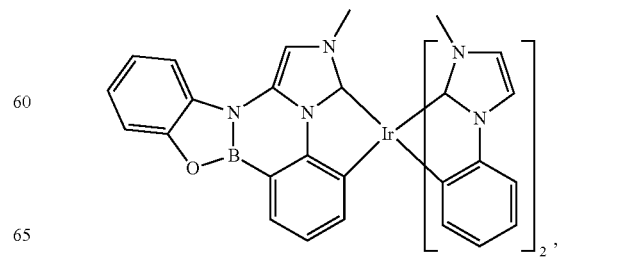
Compound M182
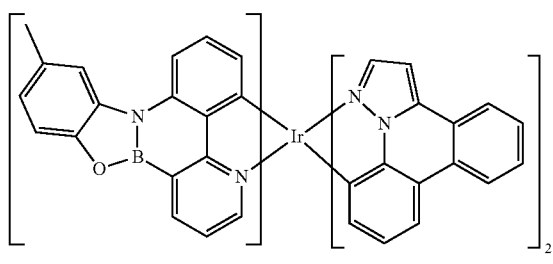
Compound M187

-continued

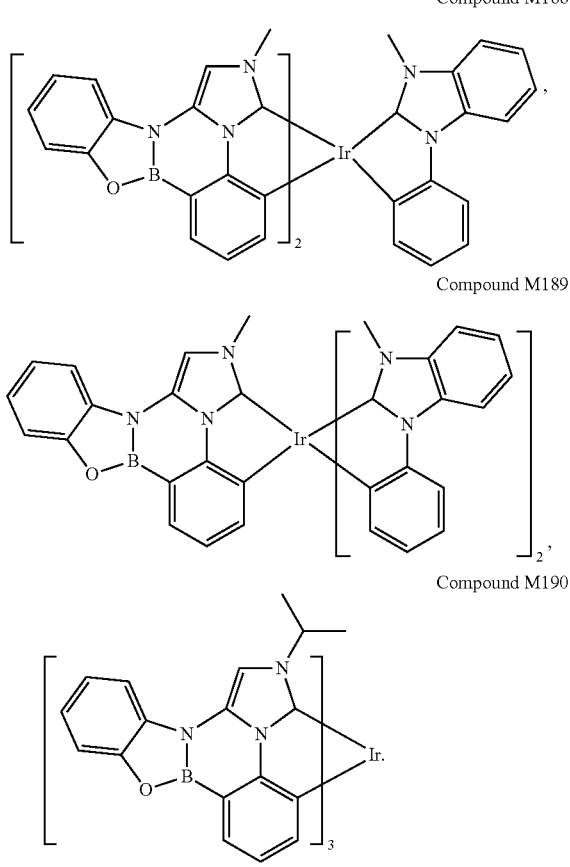

Compound M188

Compound M189

Compound M190

According to another aspect of the present disclosure, an OLED is disclosed where the OLED comprises: an anode; a cathode; and an organic layer disposed between the anode and the cathode. The organic layer comprises a compound having a structure of Formula I:

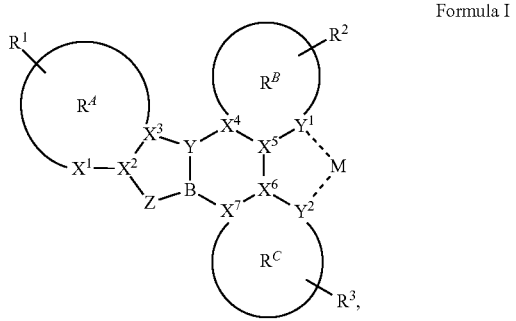

Formula I wherein $R^A$, $R^B$, and $R^C$ are each independently 5 or 6 membered aryl or heteroaryl rings;

wherein $R^1$, $R^2$, and $R^3$ each independently represent no substitutions or up to the maximum available substitutions;

wherein $R^1$, $R^2$, and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof;

wherein any $R^1$, $R^2$, and $R^3$ are optionally joined or fused to form a ring; wherein $X^1$ is B, C, N, O, S or Se;

wherein $X^2$-$X^7$ are independently B, C or N;

wherein Y is independently B, N or P;

wherein Z is independently BR, CRR', O, PR, S, SiRR';

wherein $Y^1$ and $Y^2$ are each independently selected from the group consisting of carbon and nitrogen;

wherein R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof;

wherein R and R' is optionally bonded to at least one benzo or azabenzo ring to form fused rings;

wherein the dashed lines represent a metal M optionally coordinated to $R^B$ and $R^C$; and wherein when M is coordinated to $R^B$ and $R^C$, M replaces $R^2$ and $R^3$ on $Y^1$ and $Y^2$ respectively and bonds to $Y^1$ and $Y^2$.

In some embodiments of the OLED, the compound is a dimer.

In some embodiments of the OLED, at least one of $R^1$, $R^2$, and $R^3$ substituents are joined or fused to form a 5- or 6-membered ring, which can be further substituted.

In some embodiments of the OLED, $X^1$-$X^6$ are C, and $X^7$ is C or N.

In some embodiments of the OLED, R and R' are independently aryl or heteroaryl. In some embodiments, R and R' are independently selected from the group consisting of phenyl, carbazole, azacarbazole, dibenzofuran, dibenzothiophene, dibenzoselenophene, azadibenzofuran, azadibenzothiophene, azadibenzoselenophene, triphenylene, azatriphenylene, and combinations thereof, and R and R' are optionally further substituted by one or more substituent $X^B$ selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof, and $X^B$ is optionally bonded to at least one benzo or azabenzo ring to form a fused ring.

In some embodiments of the OLED, the compound is selected from the group consisting of compound 1 through compound 93.

In some embodiments of the OLED, X1 is C or N, $R^A$ is aryl or heteroaryl and $R^A$ is connected to X1 to form a fused ring.

In some embodiments of the OLED, the compound is selected from the group consisting of compound 94 through compound 131.

In some embodiments of the OLED, the organic layer is an emissive layer and the compound of Formula I is a host. In some embodiments, the organic layer further comprises a phosphorescent emissive dopant.

In some embodiments, the phosphorescent emissive dopant is a transition metal complex having at least one ligand or part of the ligand if the ligand is more than bidentate, selected from the group consisting of:

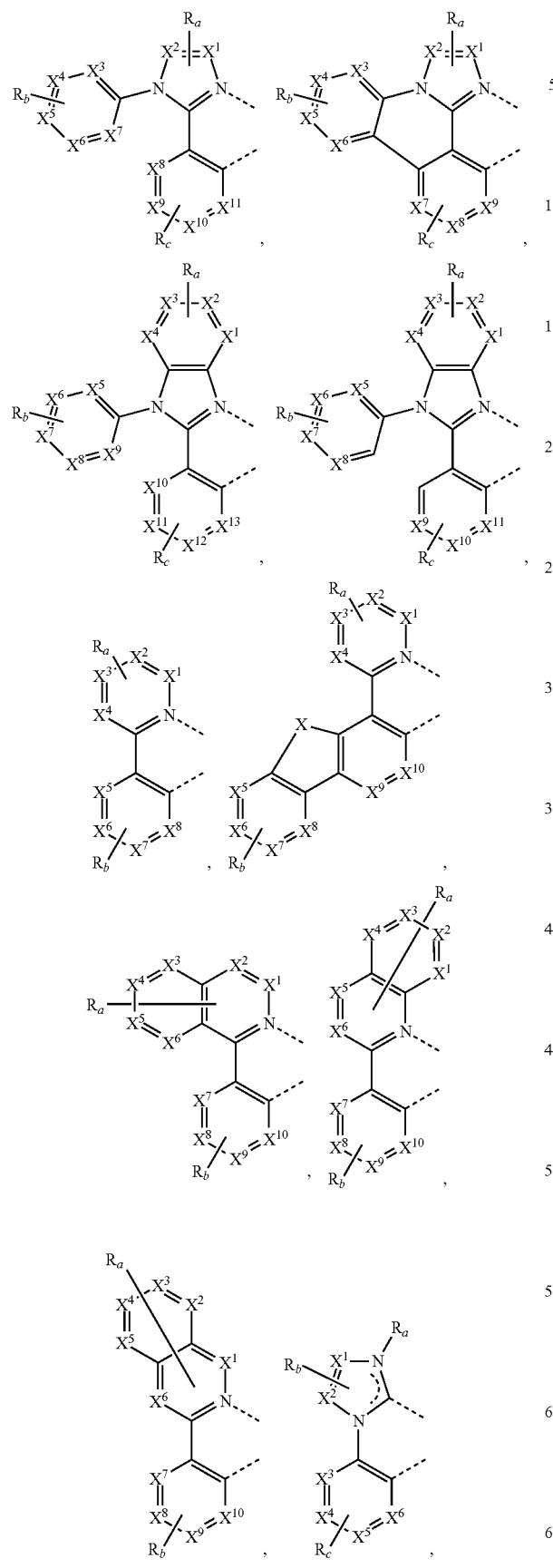
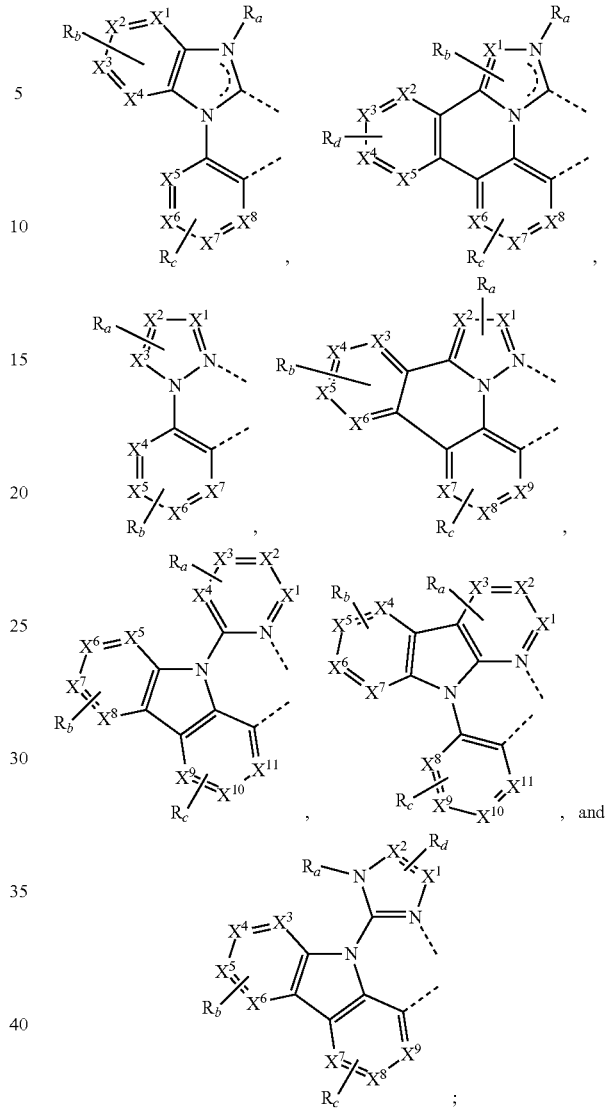

wherein each $X^1$ to $X^{13}$ are independently selected from the group consisting of carbon and nitrogen; wherein X is selected from the group consisting of BR', NR', PR', O, S, Se, C=O, S=O, SO$_2$, CR'R", SiR'R", and GeR'R"; wherein R' and R" are optionally fused or joined to form a ring; wherein each $R_a$, $R_b$, $R_c$, and $R_d$ may represent from mono substitution to the possible maximum number of substitution, or no substitution; wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent substituents of $R_a$, $R_b$, $R_c$, and $R_d$ are optionally fused or joined to form a ring or form a multidentate ligand.

In some embodiments of the OLED, the organic layer is a charge carrier blocking layer and the compound having Formula I is a charge carrier blocking material in the organic layer.

In some embodiments of the OLED, the organic layer is a charge carrier transporting layer and the compound having Formula I is a charge carrier transporting material in the organic layer.

In some embodiments of the OLED, when M in the compound is coordinated to $R^B$ and $R^C$, M is selected from the group consisting of Ir, Rh, Re, Ru, Os, Pt, Au, and Cu. In some embodiments, when M is coordinated to $R^B$ and $R^C$, M is Ir or Pt.

In some embodiments of the OLED, when M is coordinated to $R^B$ and $R^C$, one of $Y^1$ and $Y^2$ is nitrogen, the other one of $Y^1$ and $Y^2$ is carbon. In some embodiments, when M is coordinated to $R^B$ and $R^C$, one of $Y^1$ and $Y^2$ is neutral carbene carbon, the other one of $Y^1$ and $Y^2$ is anionic carbon.

In some embodiments of the OLED, when M is coordinated to $R^B$ and $R^C$, the compound is homoleptic. In some embodiments, when M is coordinated to $R^B$ and $R^C$, the compound is heteroleptic.

In some embodiments of the OLED, when M is coordinated to $R^B$ and $R^C$, the compound is selected from the group consisting of compound M1 through compound M190.

According to another aspect, a formulation comprising the compound having Formula I is also disclosed.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

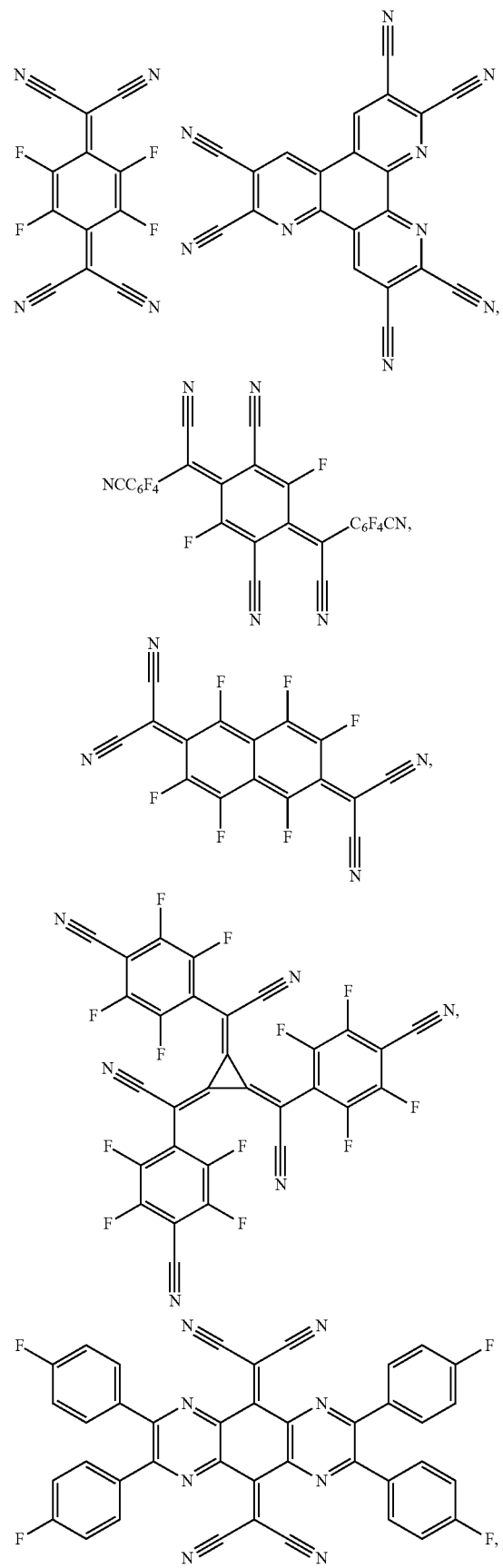

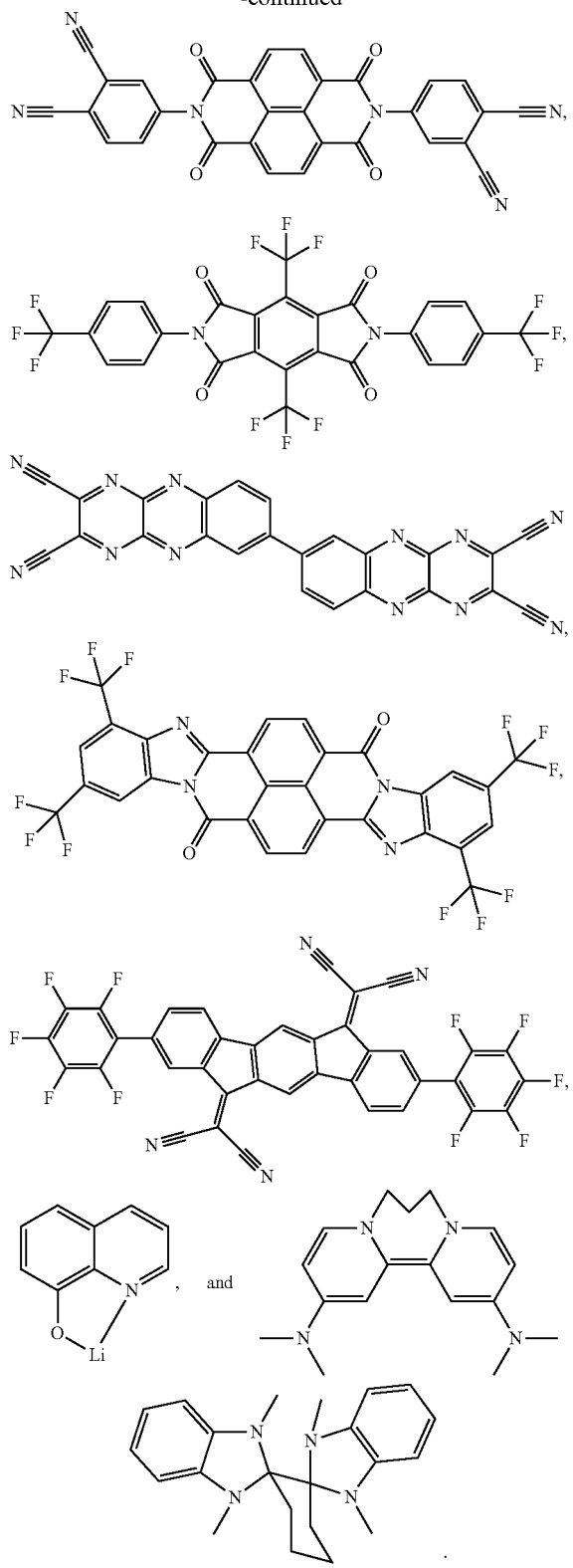

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to the following general structures:

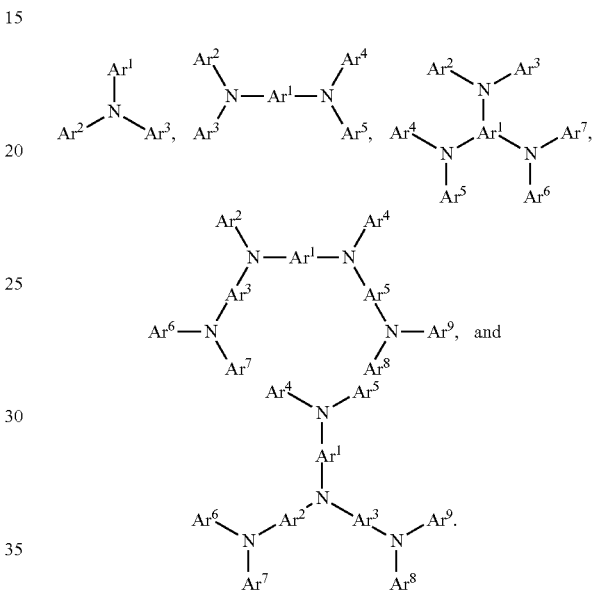

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

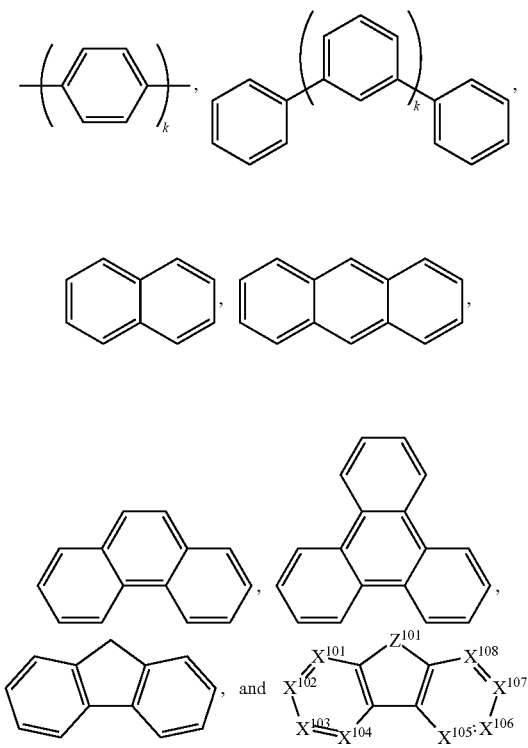

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

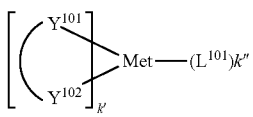

wherein Met is a metal, which can have an atomic weight greater than 40; $(Y^{101}-Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^{102})$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018,

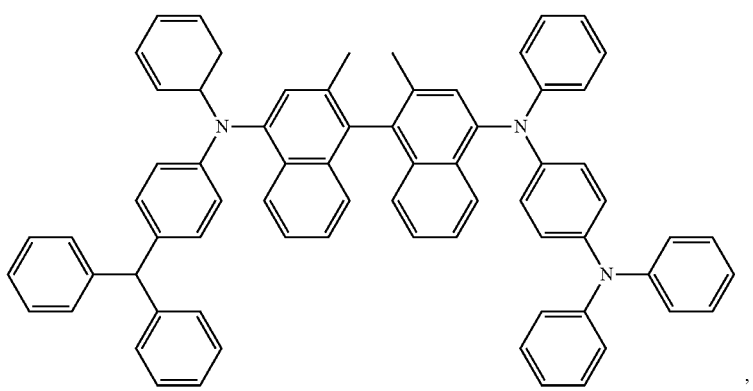

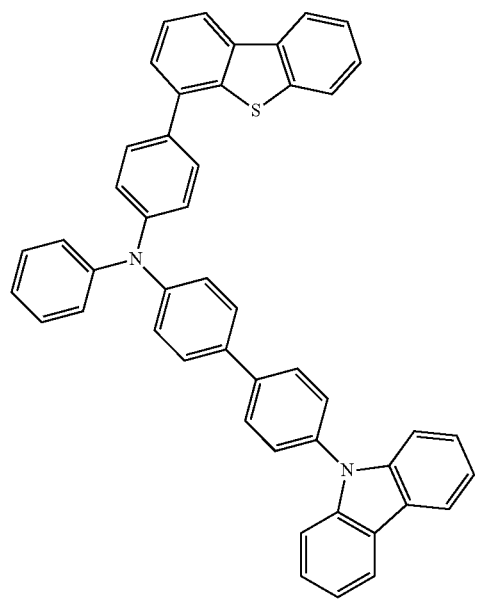
,
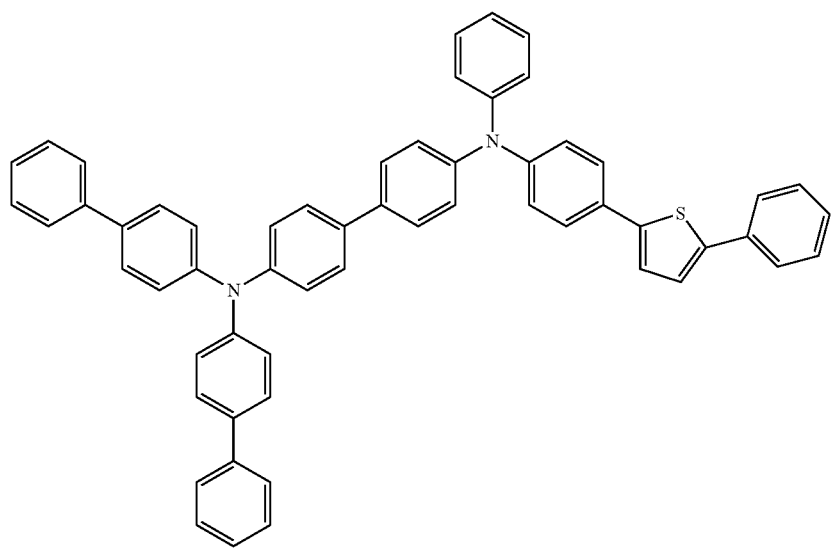
,
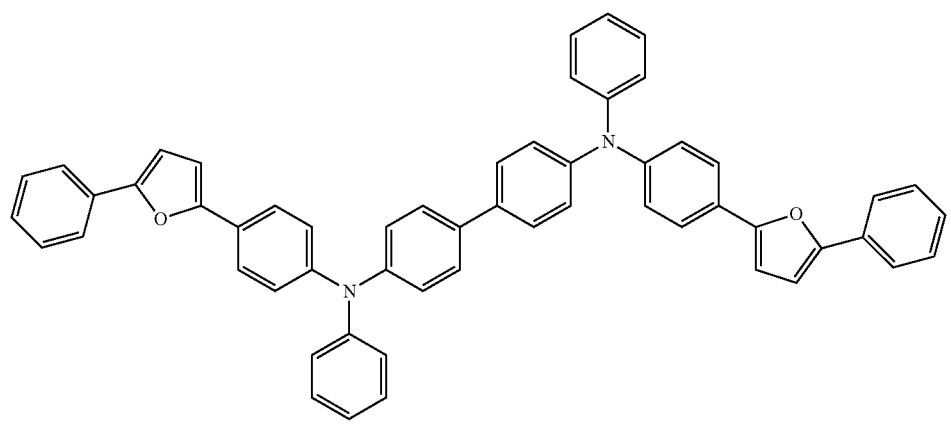
,

-continued
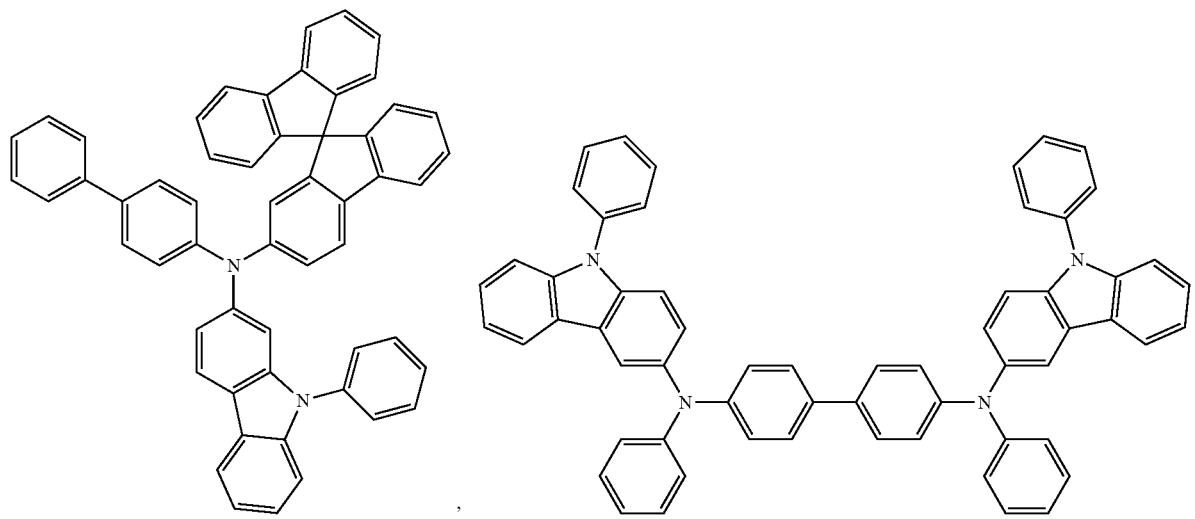
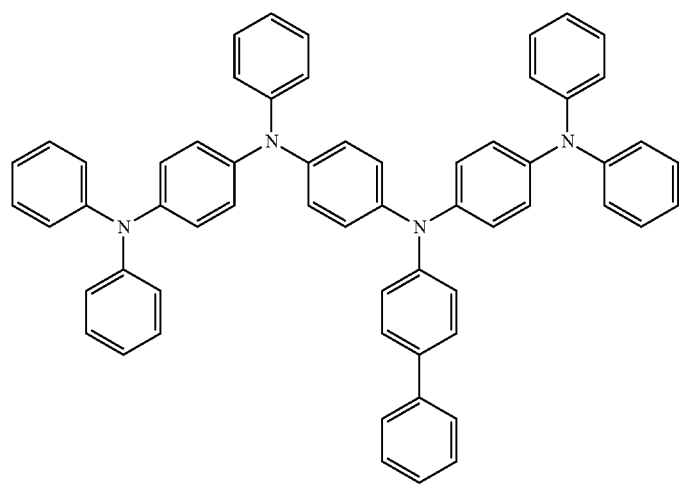
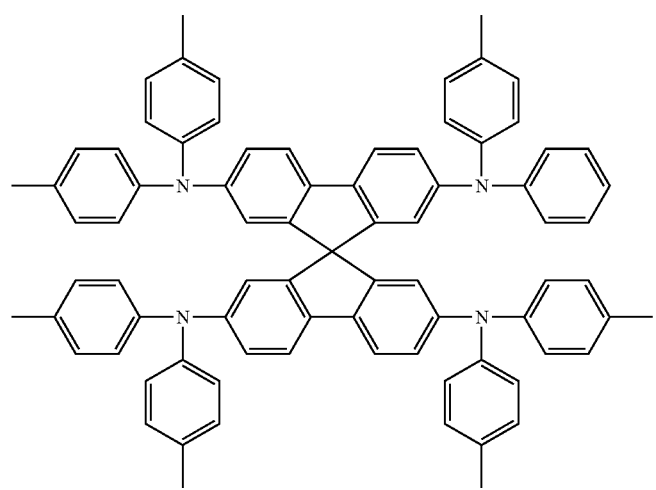

-continued
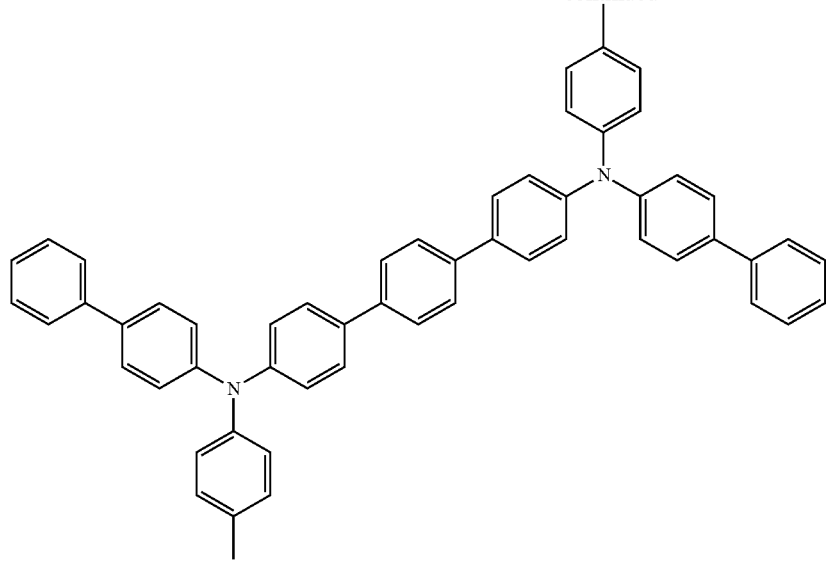
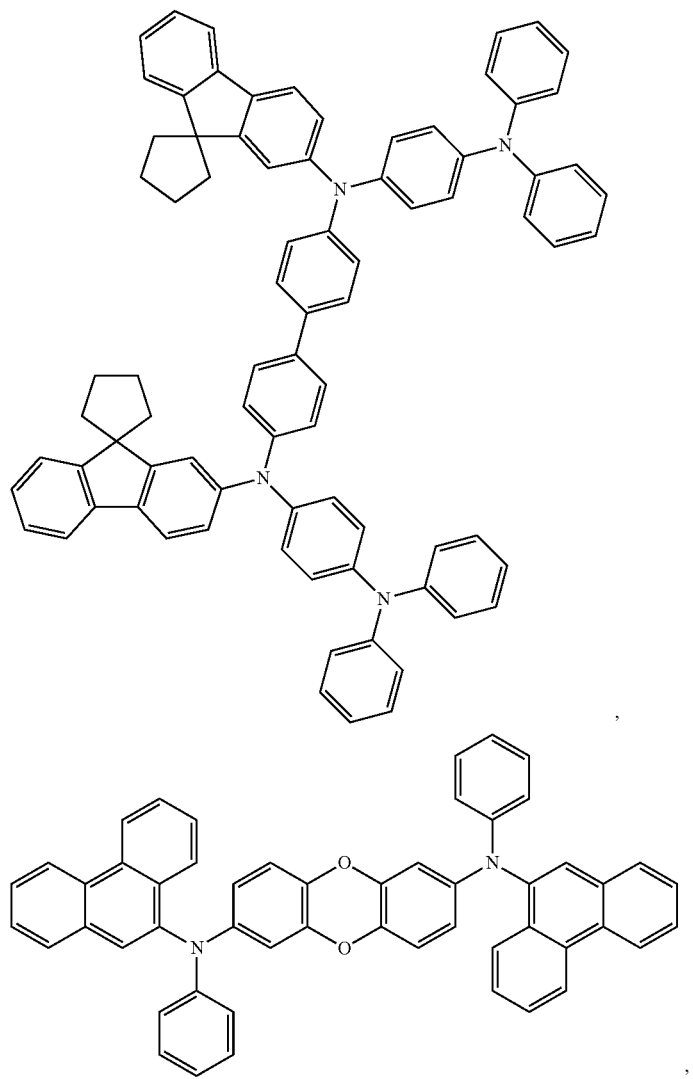

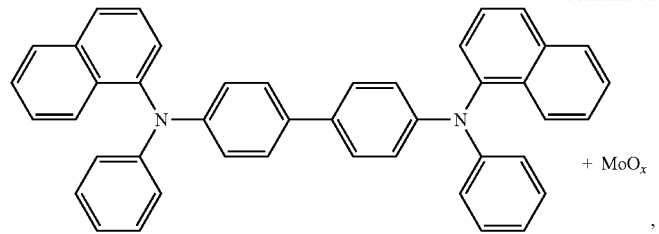
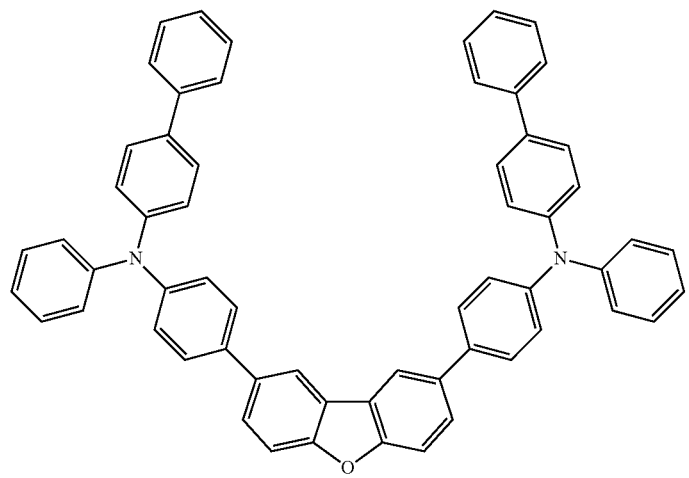
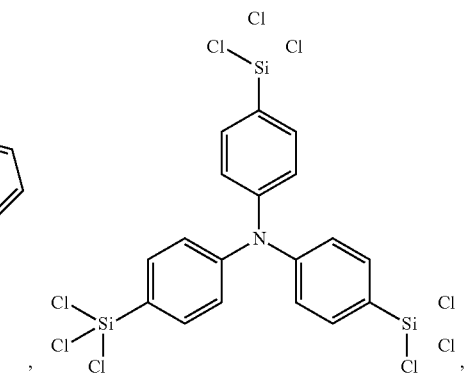
+ MoO$_x$
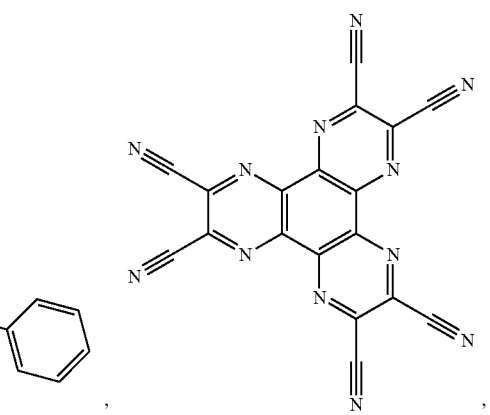
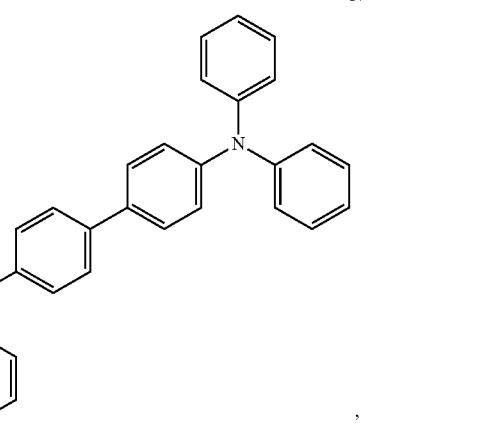

-continued
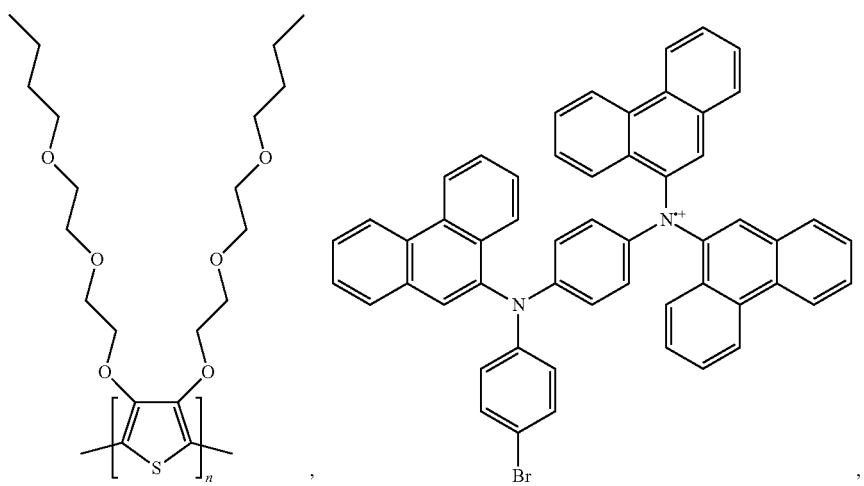
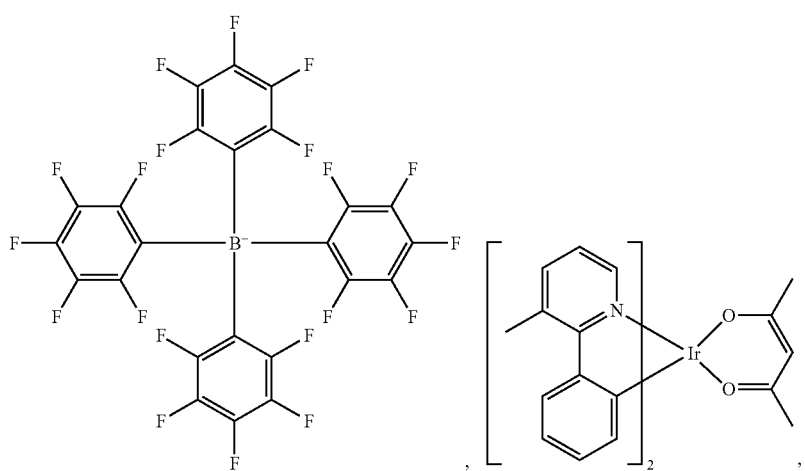
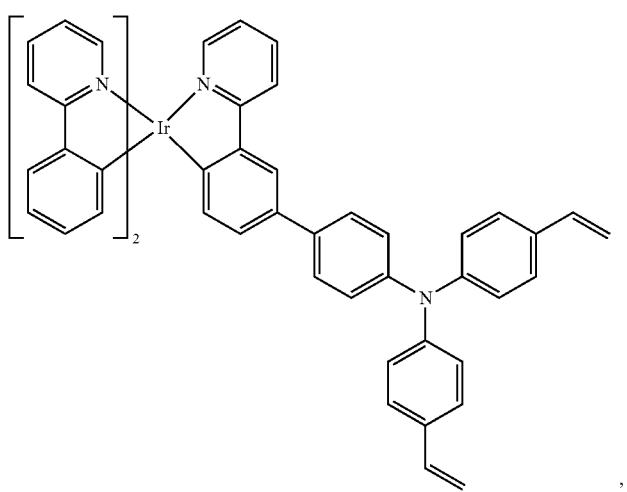

-continued
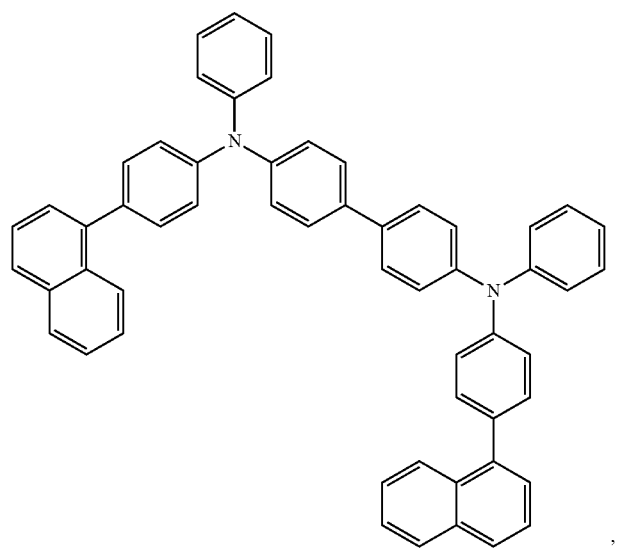
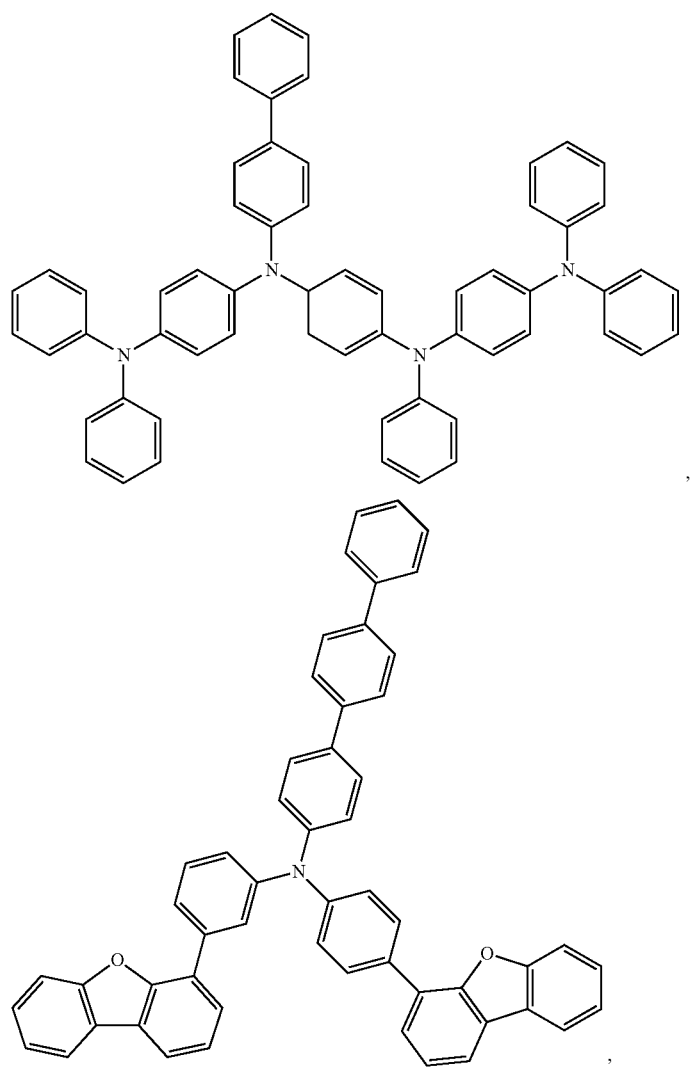

-continued
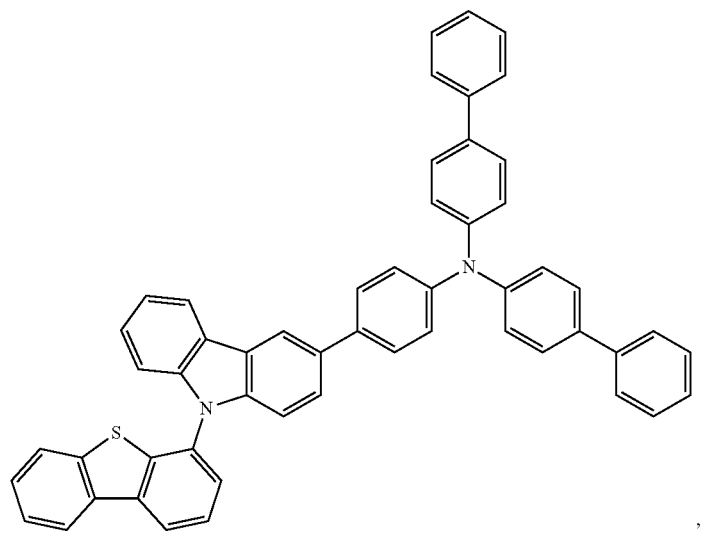
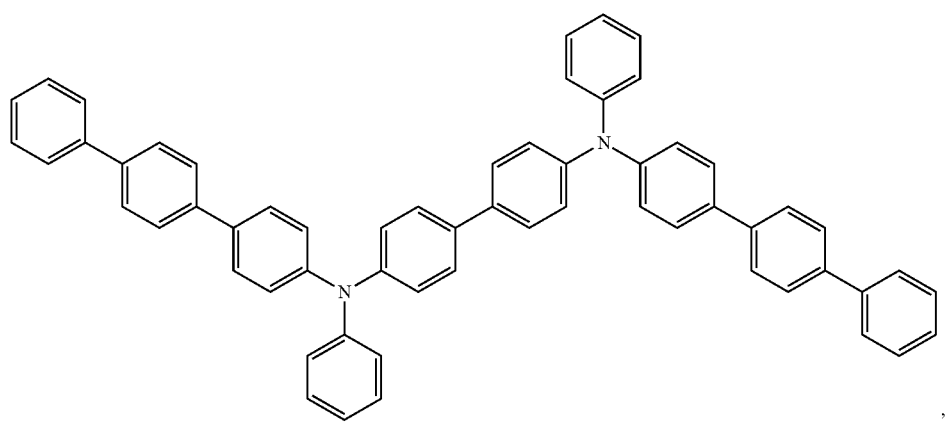
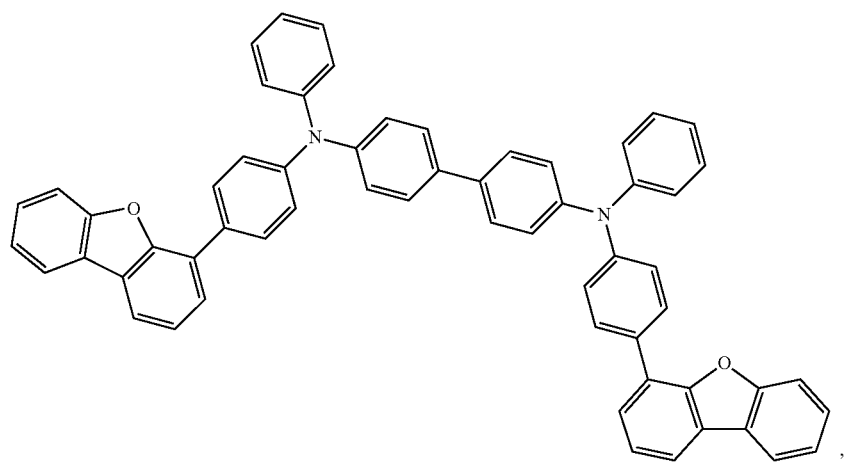

-continued
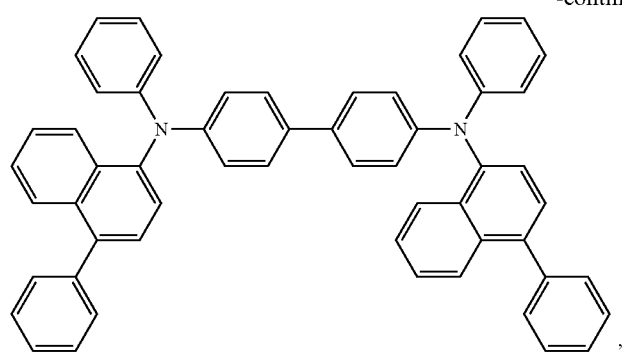
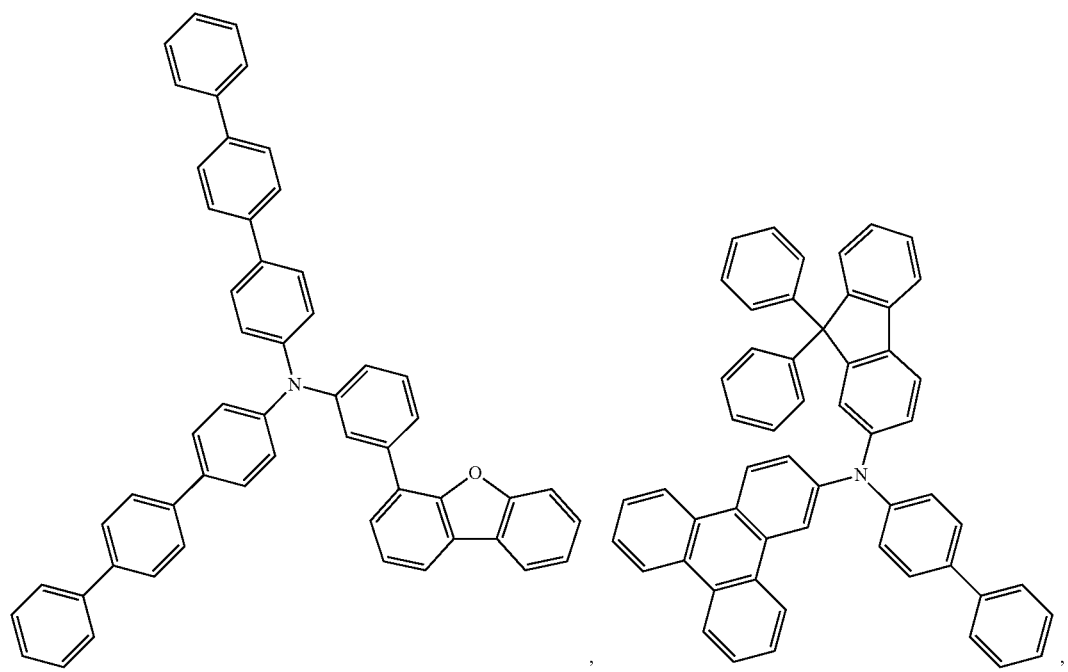
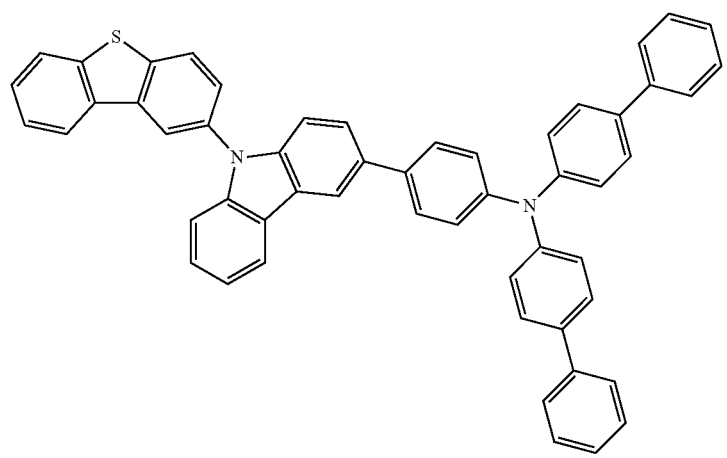

107
108
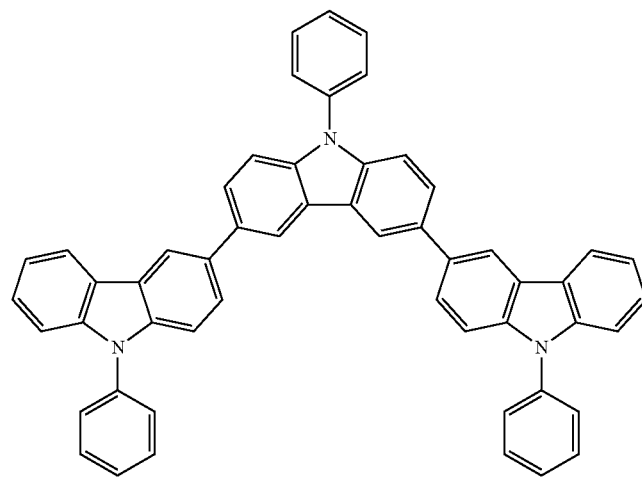
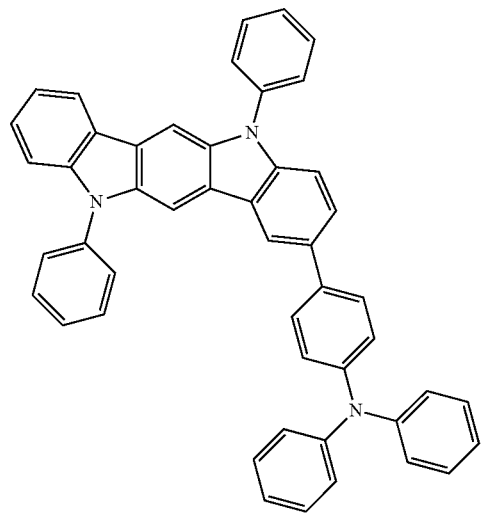
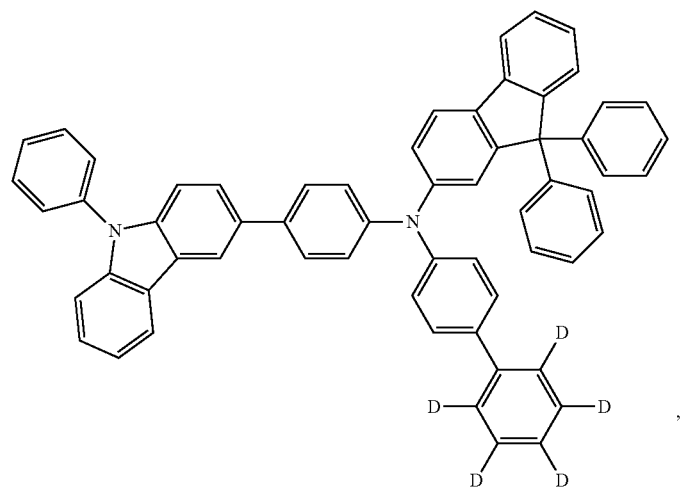
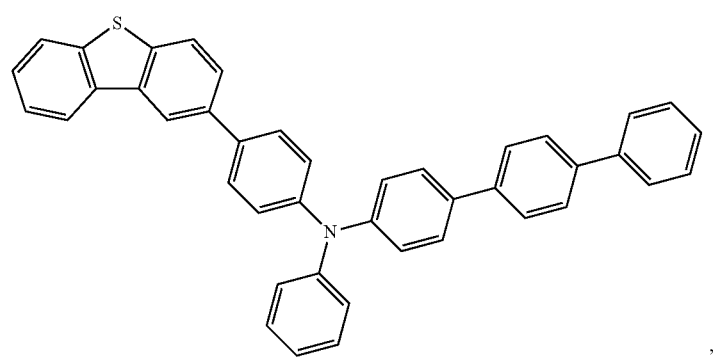

-continued
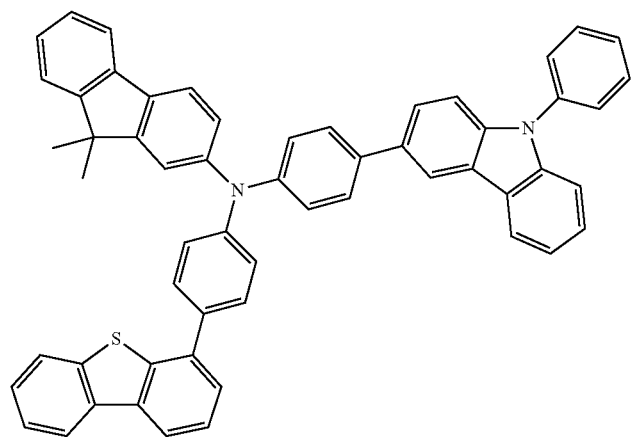
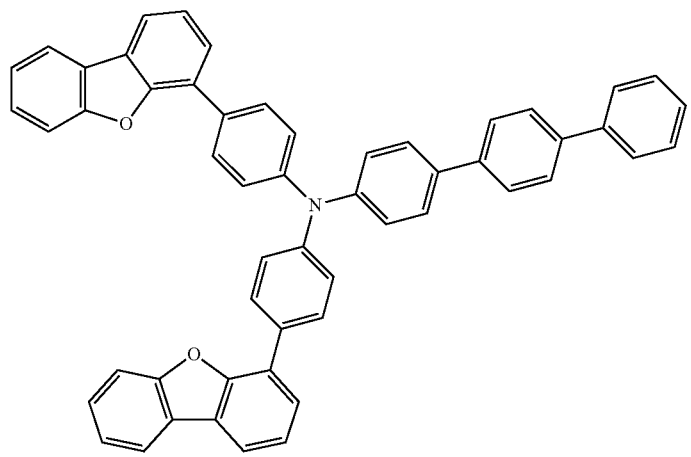
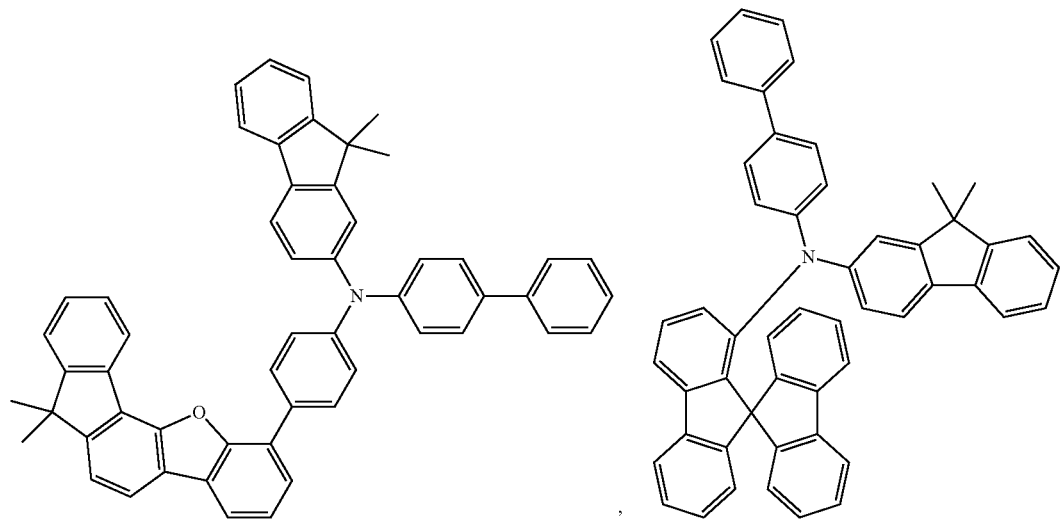

-continued
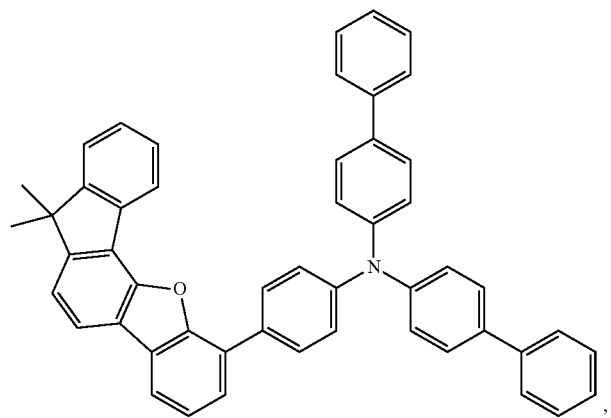
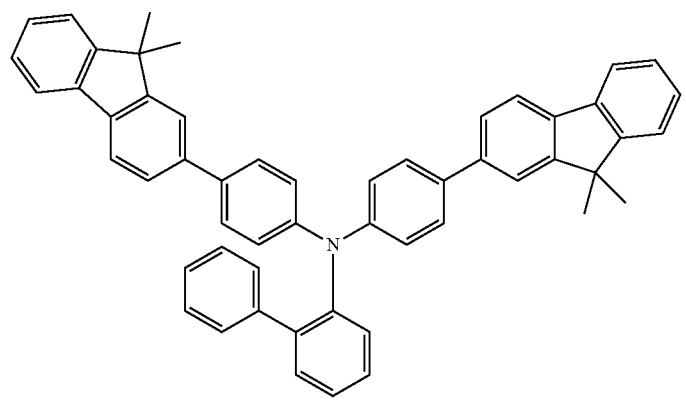
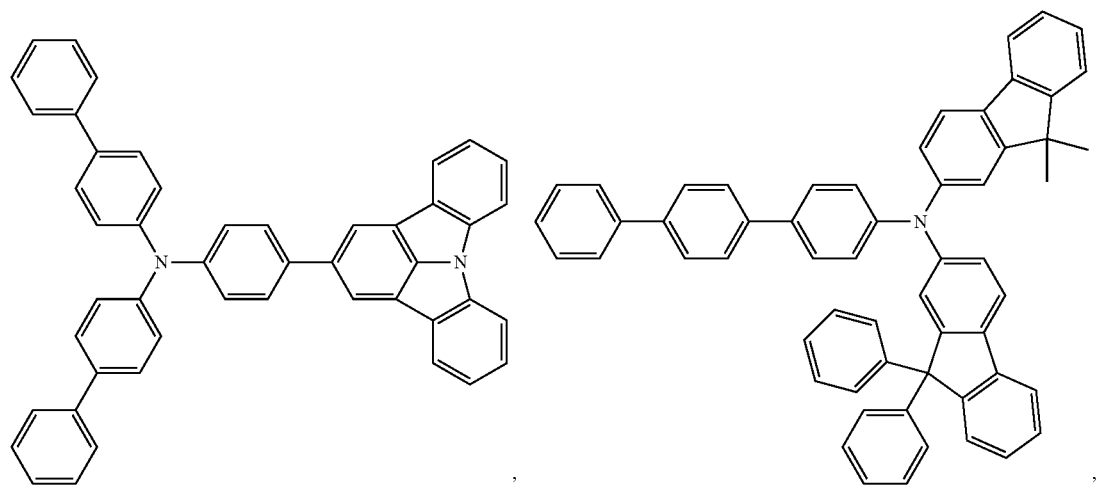

113 114
-continued
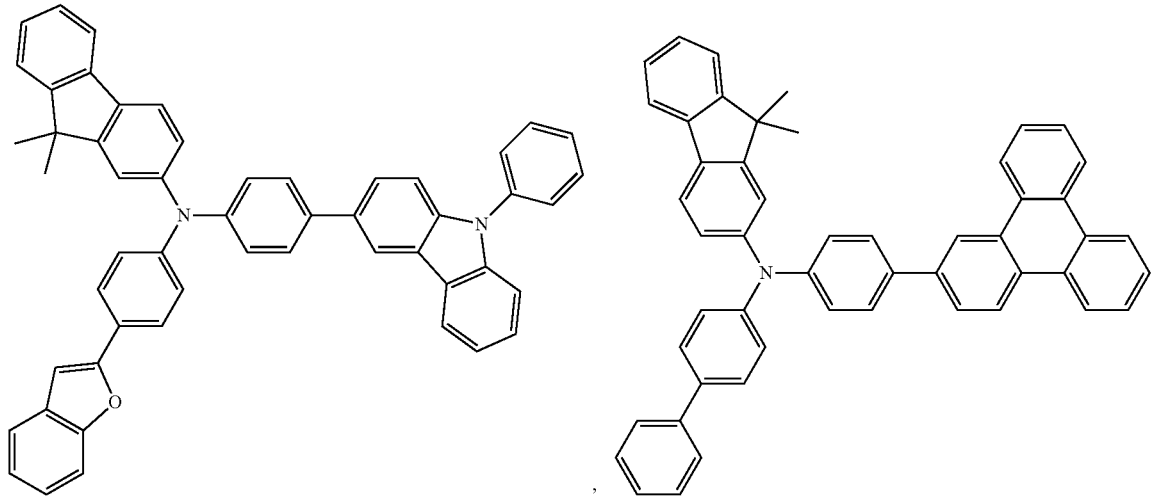
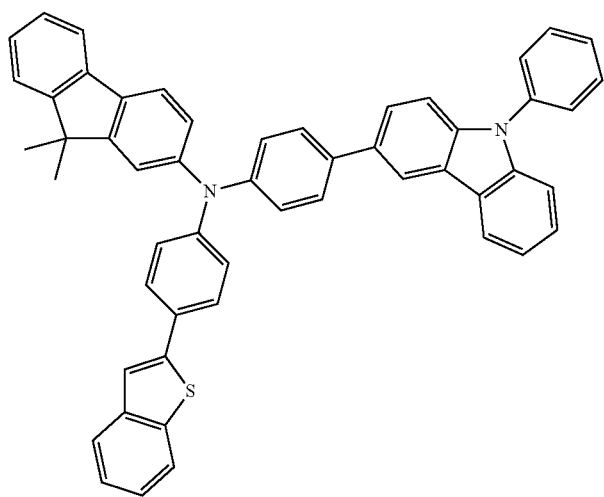
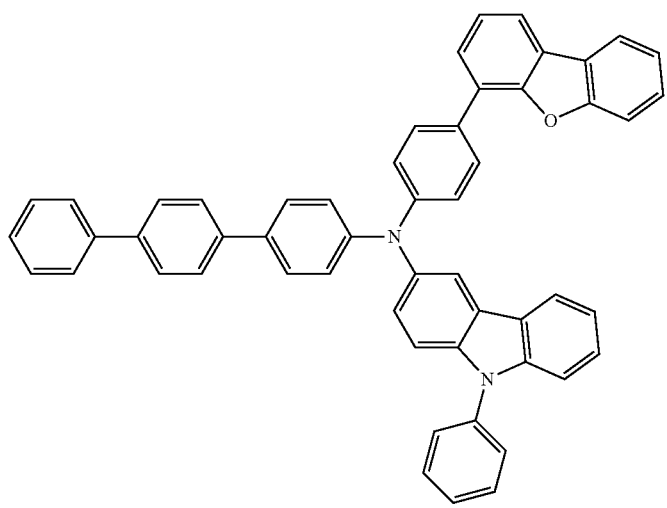

115
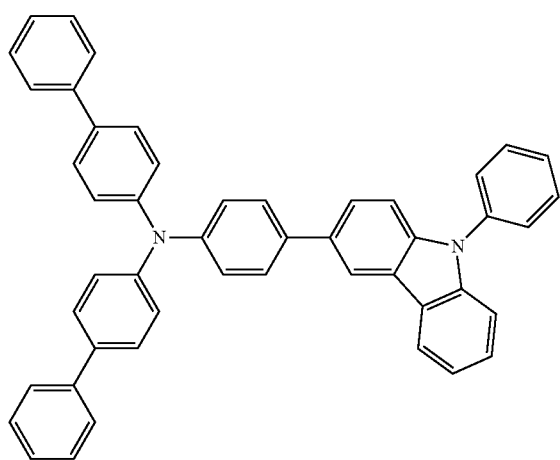
116
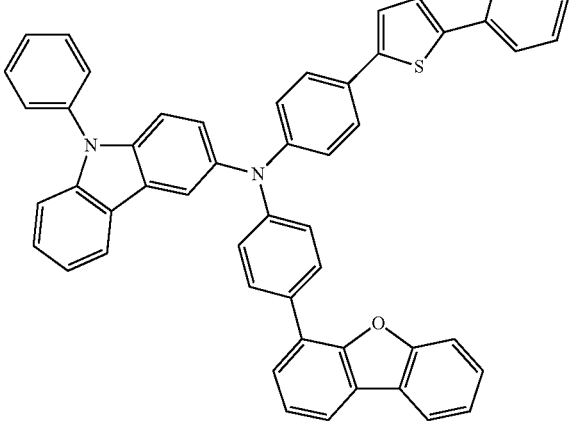
-continued
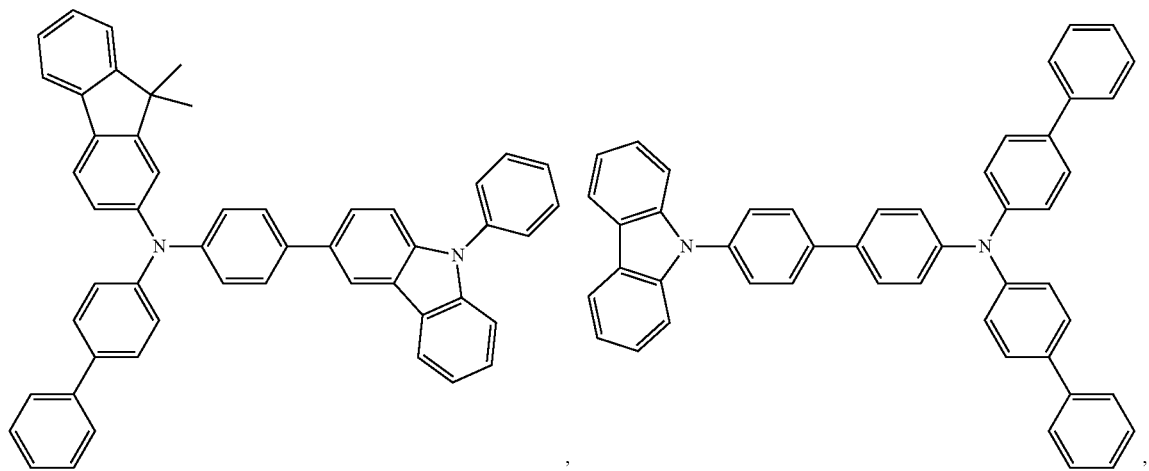
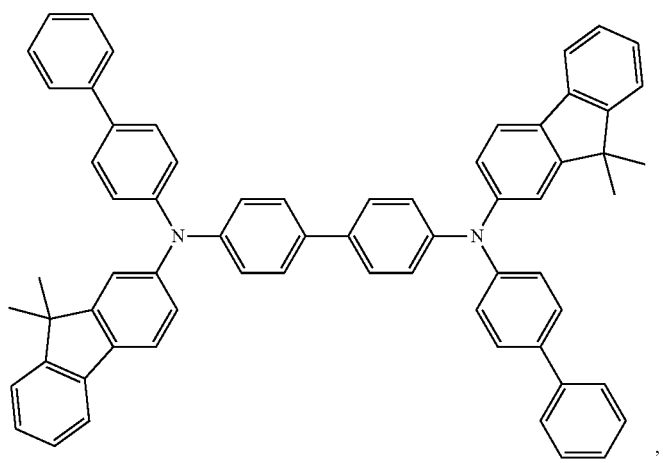

-continued
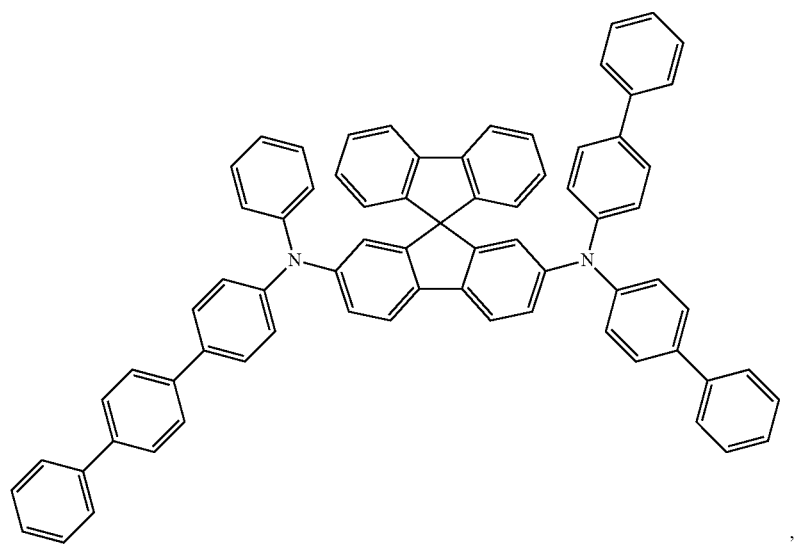
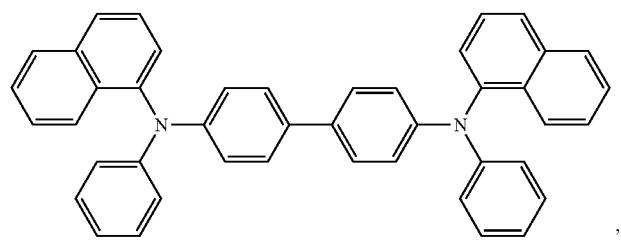
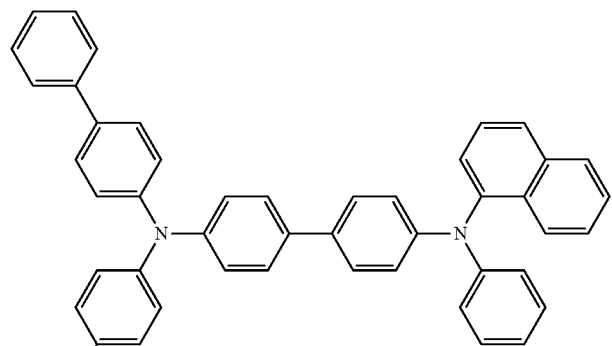
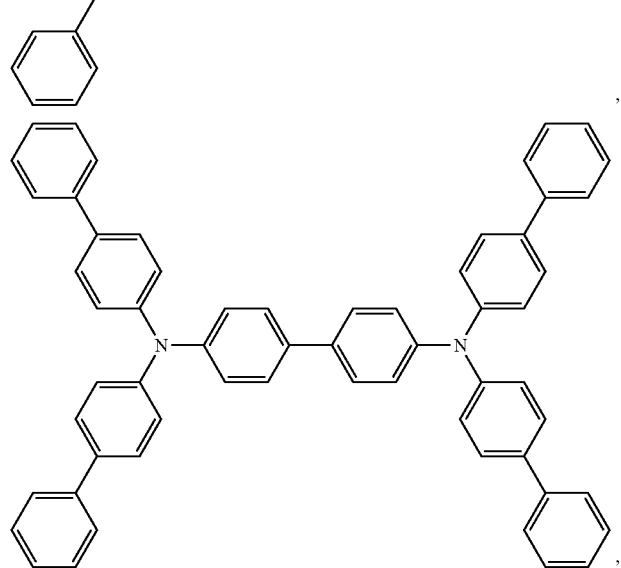

-continued
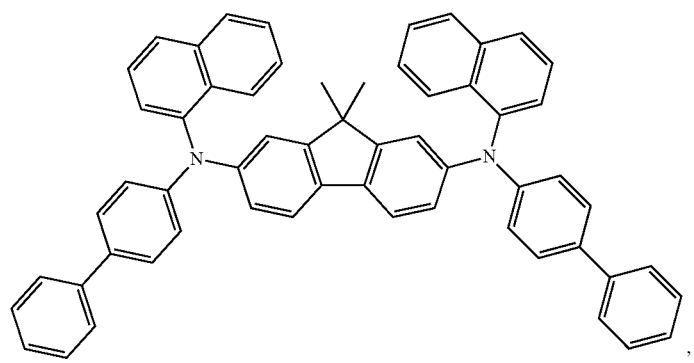
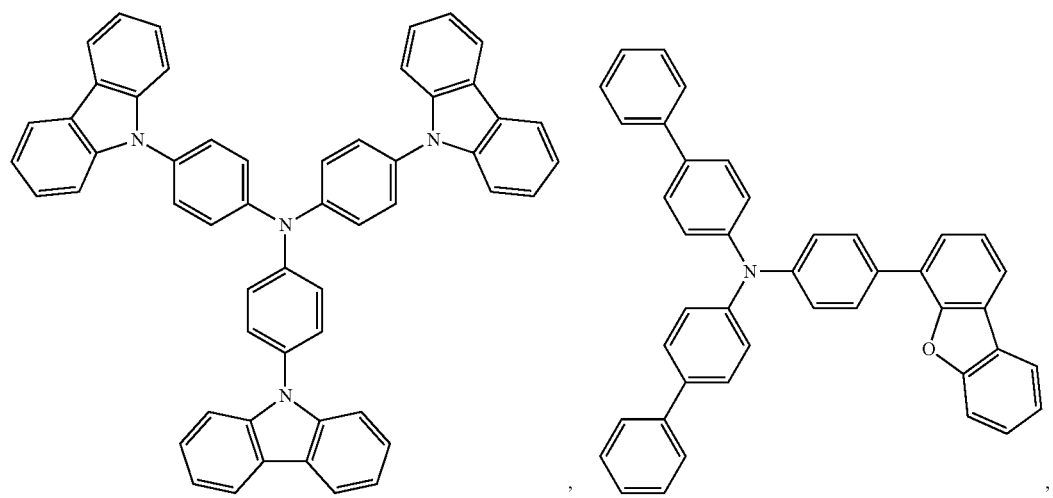
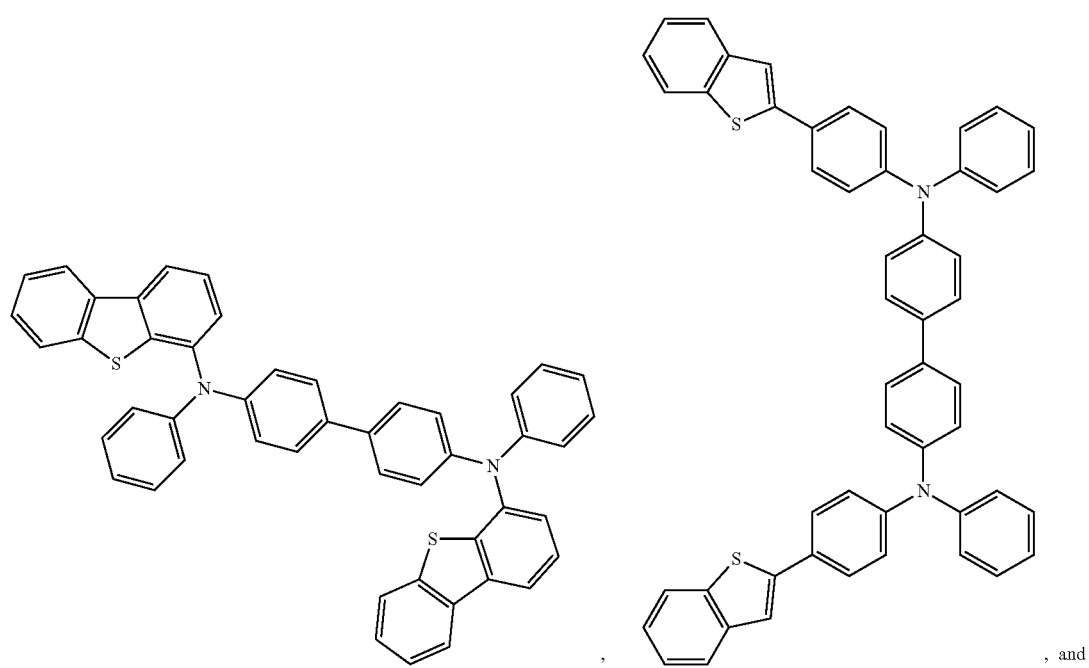
, and

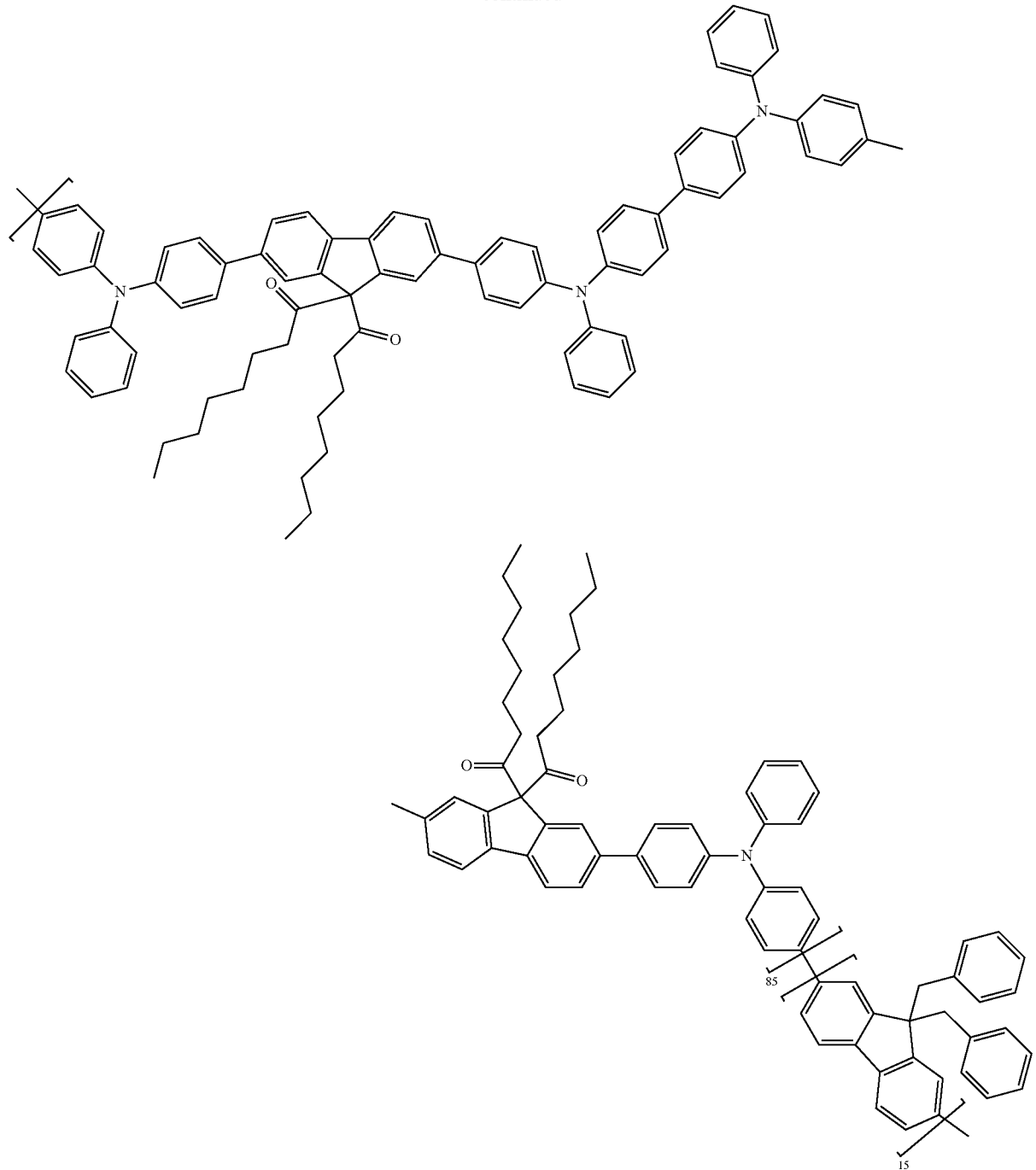

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Additional Hosts:

The light emitting layer of the organic EL device of the present invention preferably contains at least a metal complex as light emitting dopant material, and may contain one or more additional host materials using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

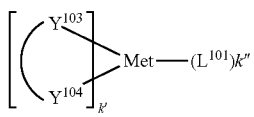

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k'' is the maximum number of ligands that may be attached to the metal.

In one aspect, the metal complexes are:

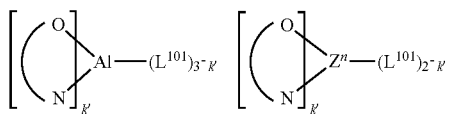

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of other organic compounds used as additional host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

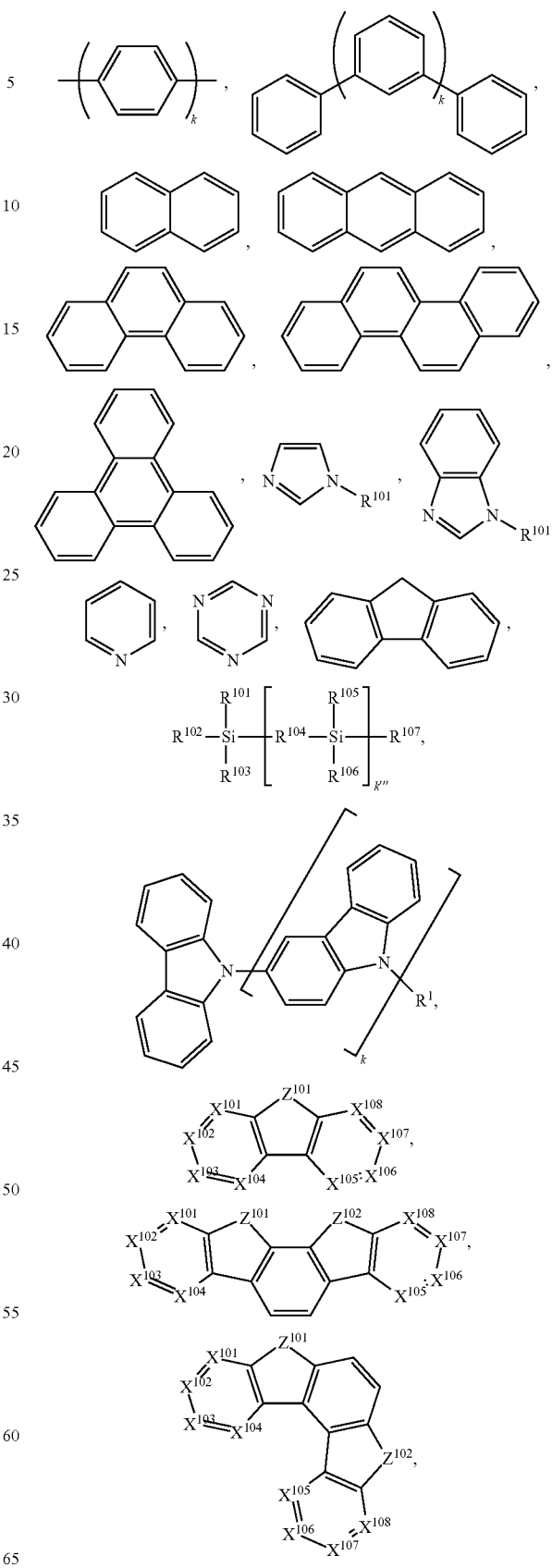

-continued

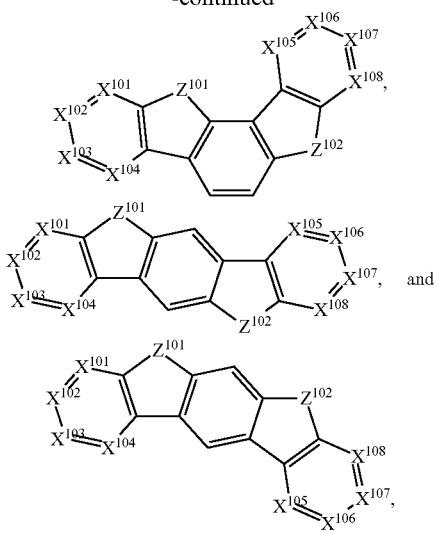

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

Non-limiting examples of the additional host materials that may be used in an OLED in combination with the host compound disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472,

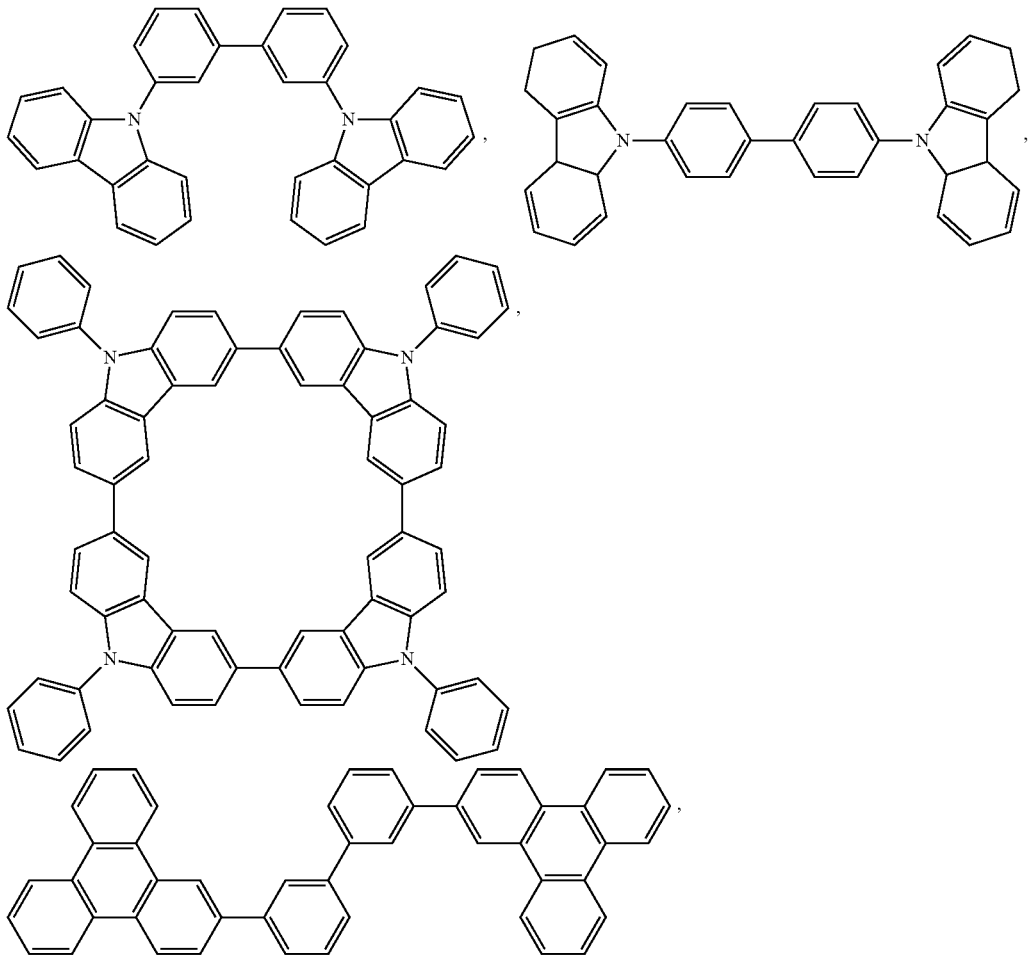

-continued
127
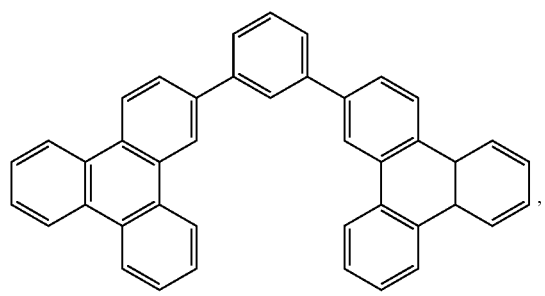
128
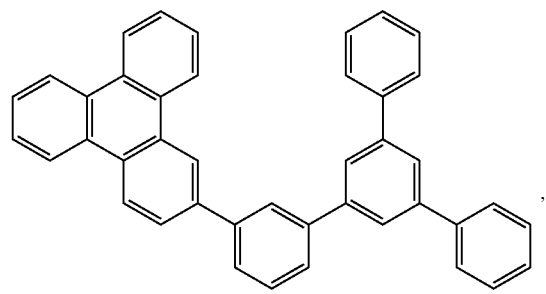
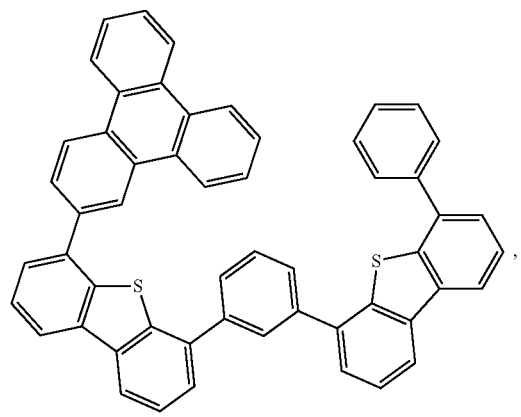
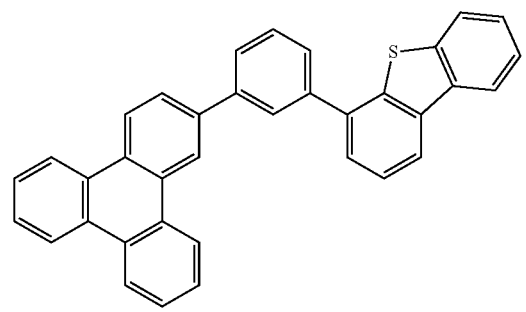
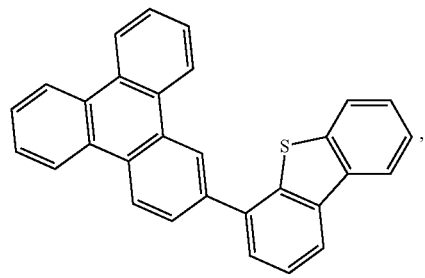
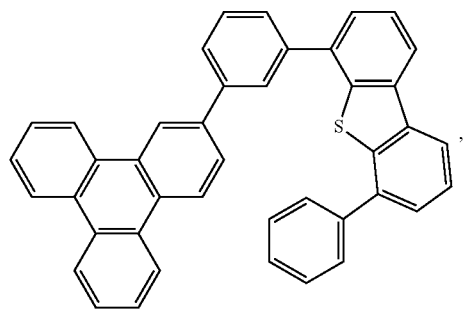
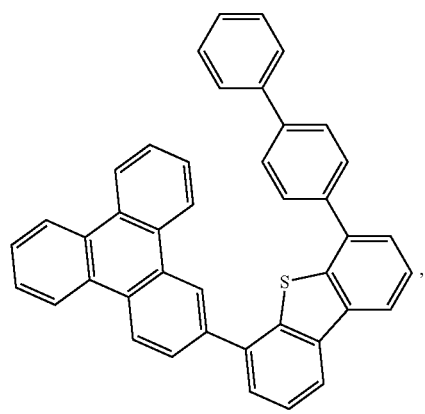
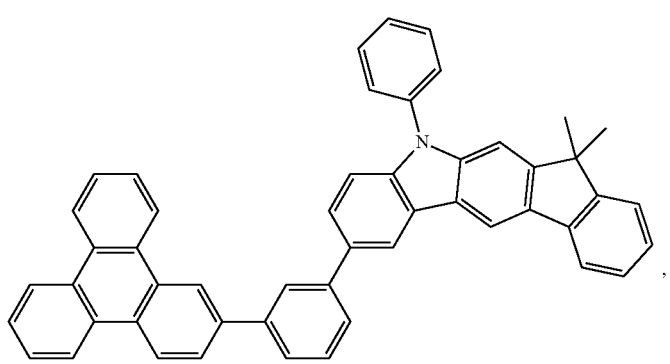

-continued
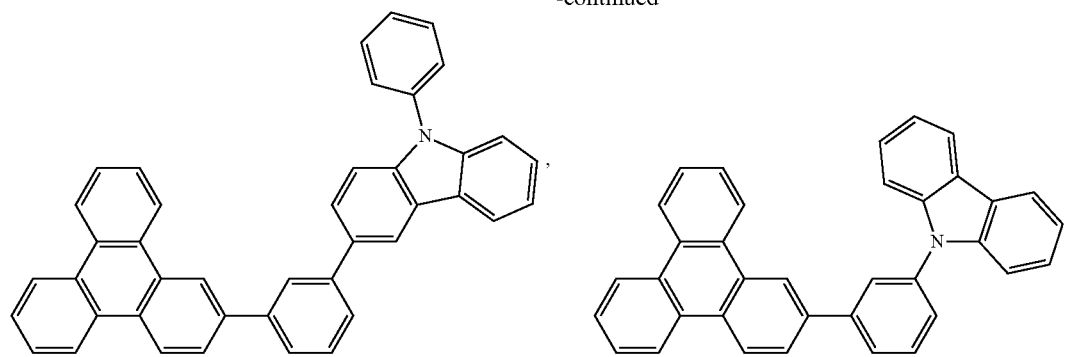
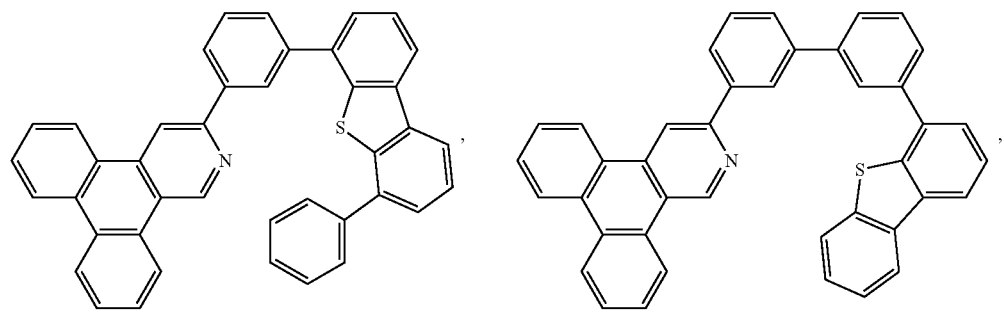
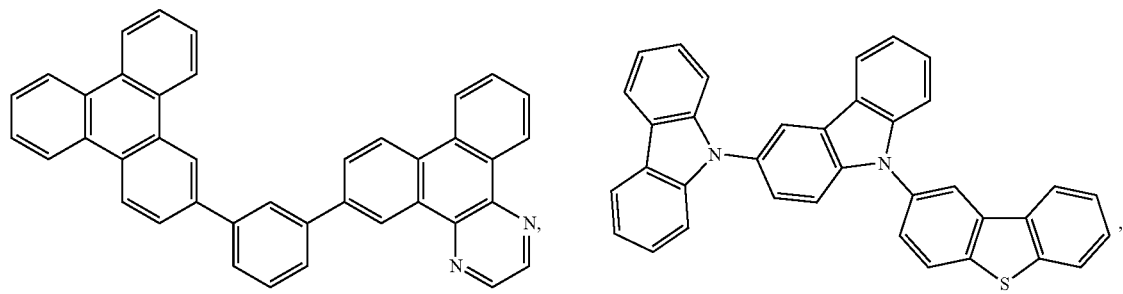
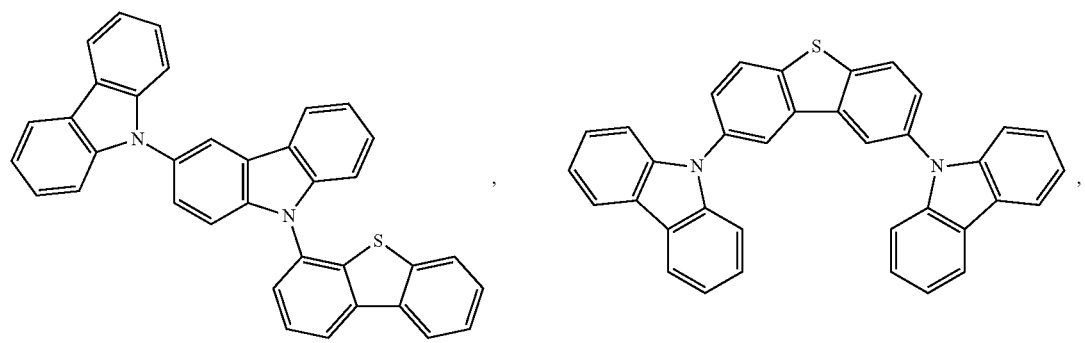
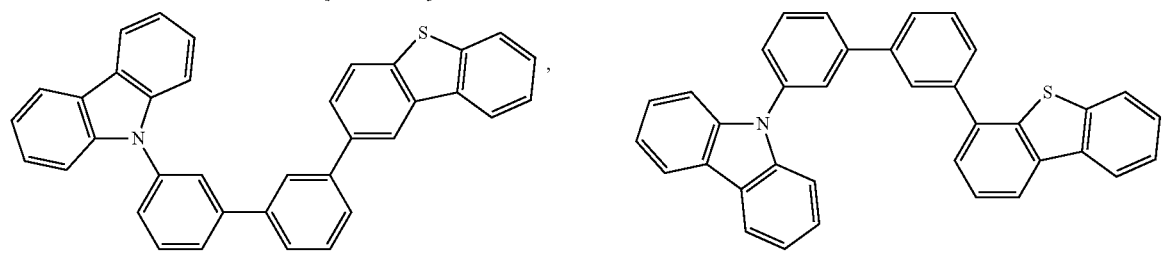

-continued
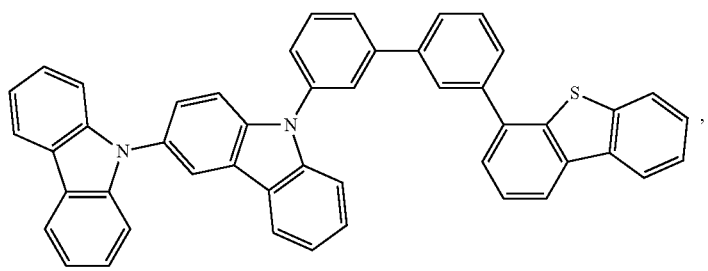
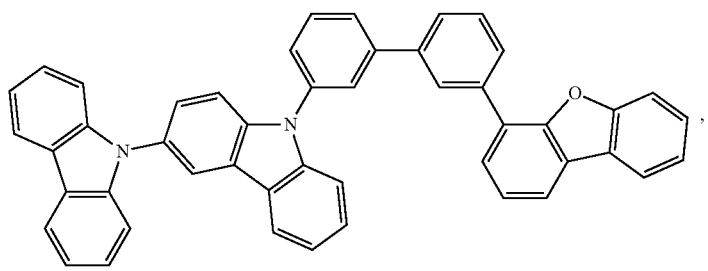
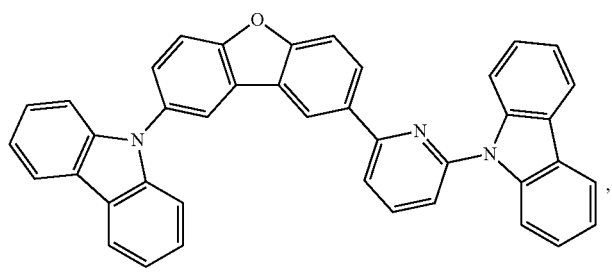
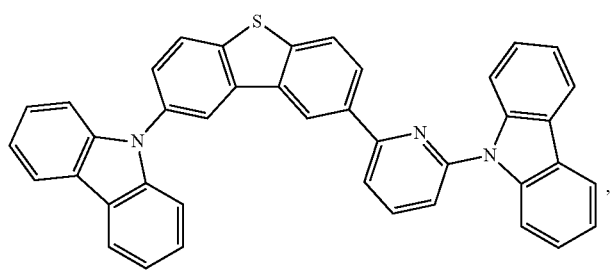
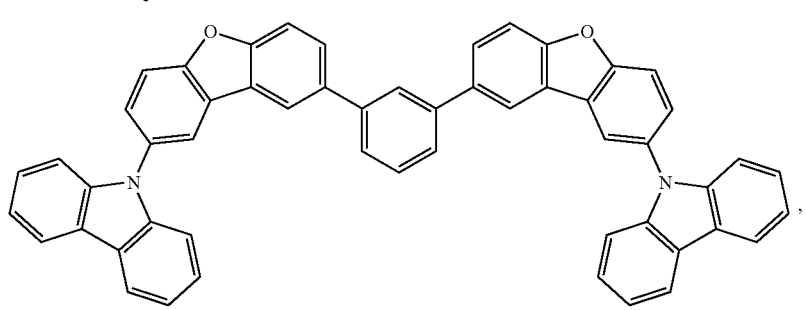
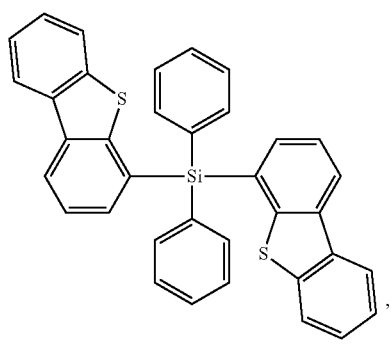
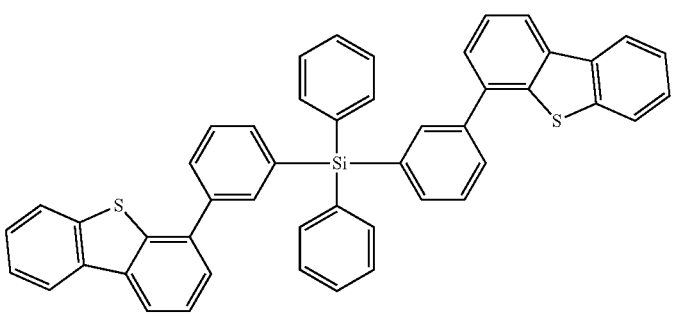

-continued
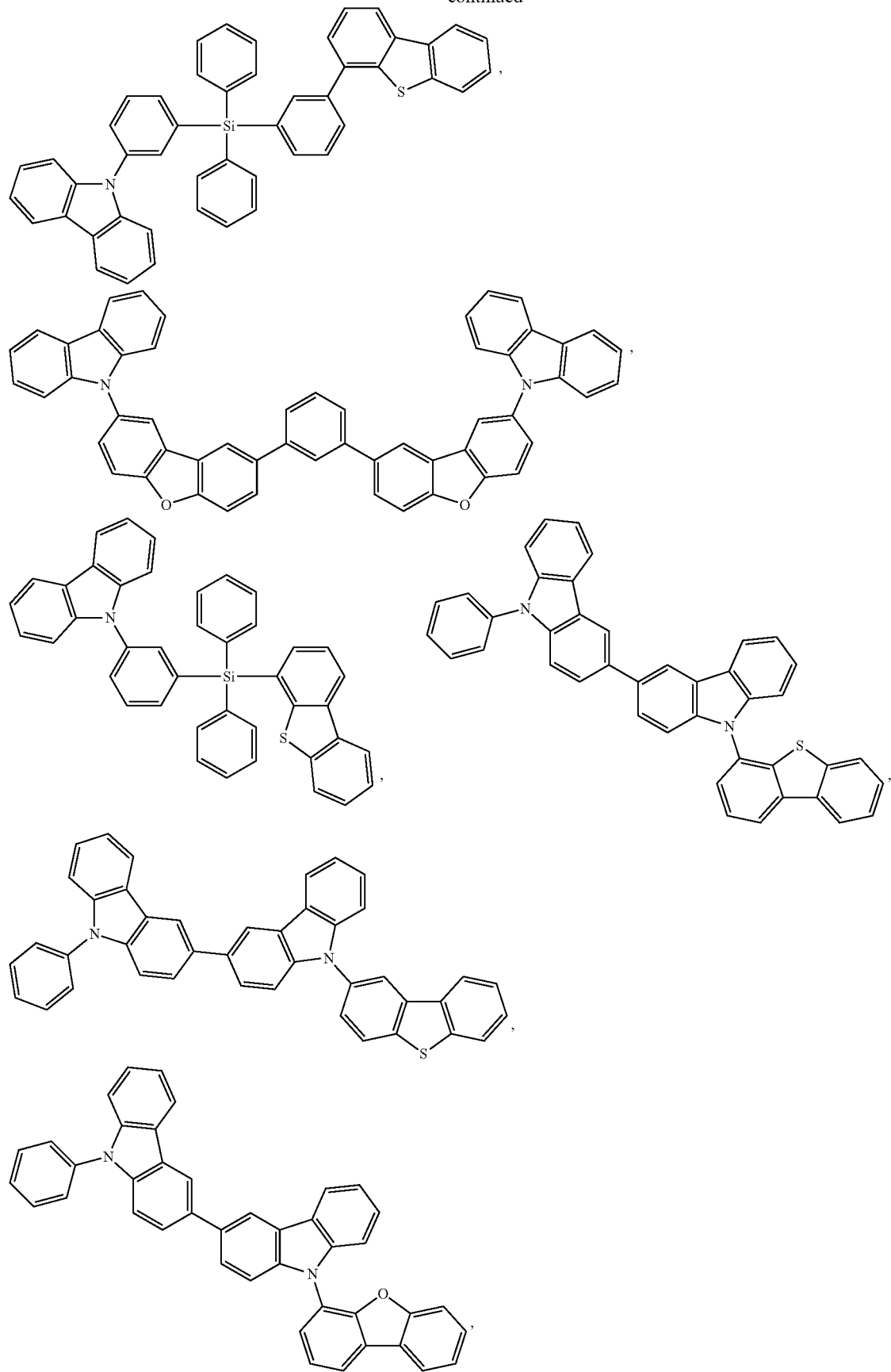

-continued
135
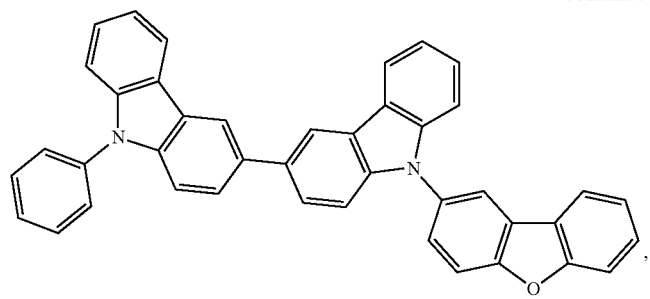
136
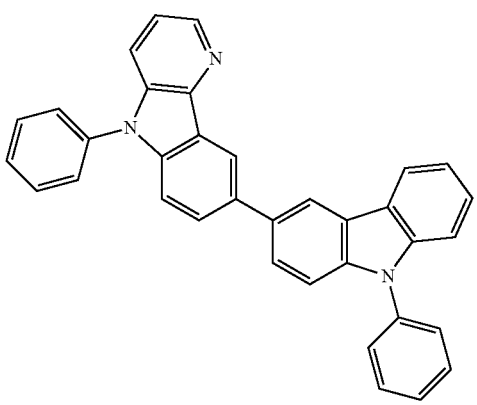
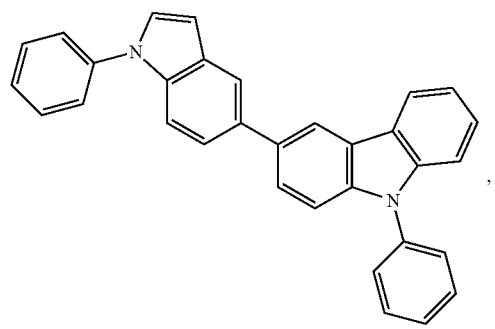
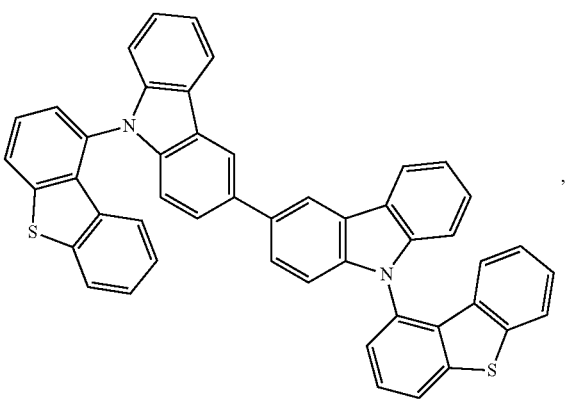
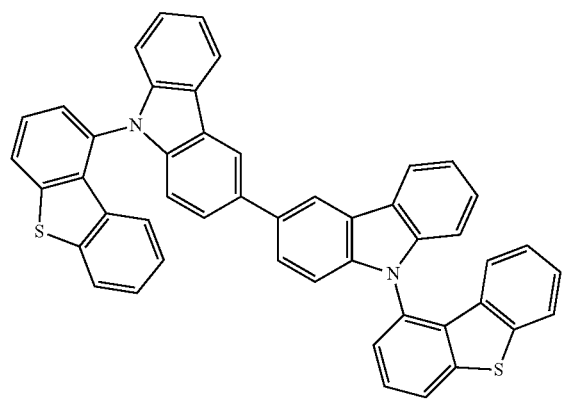
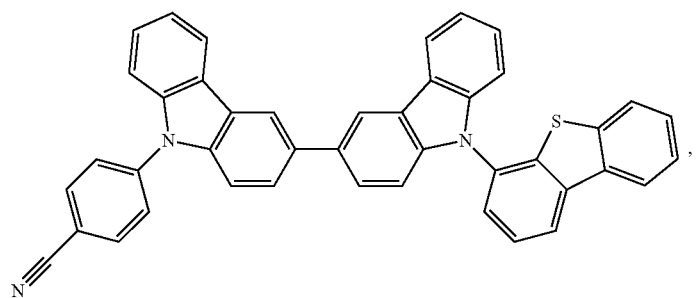

-continued
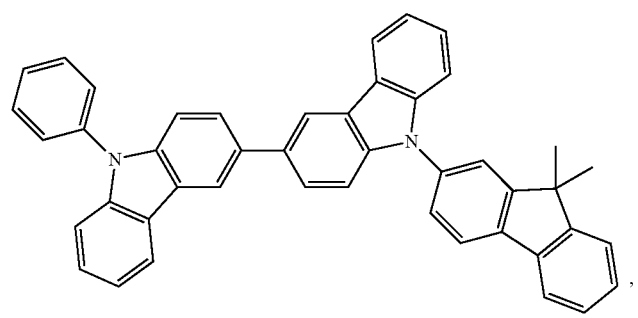
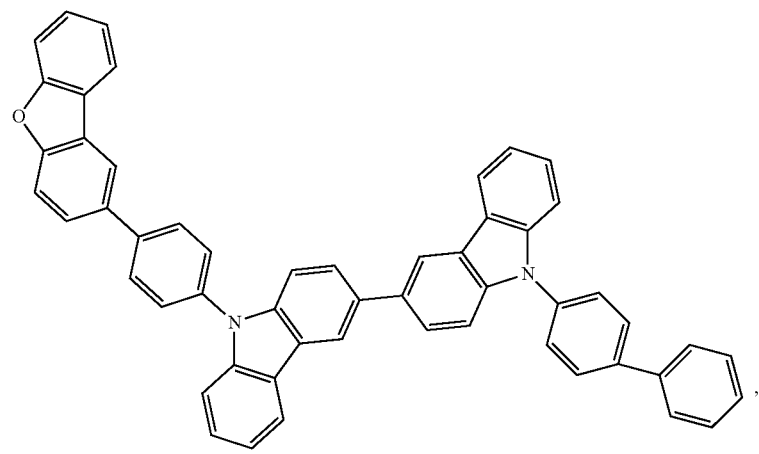
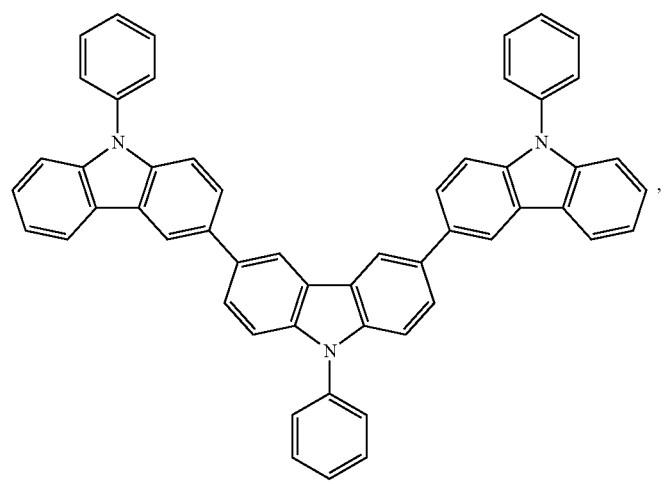
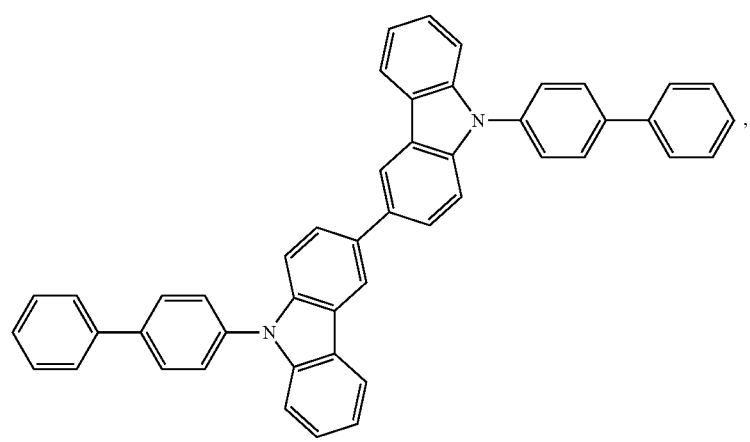

-continued
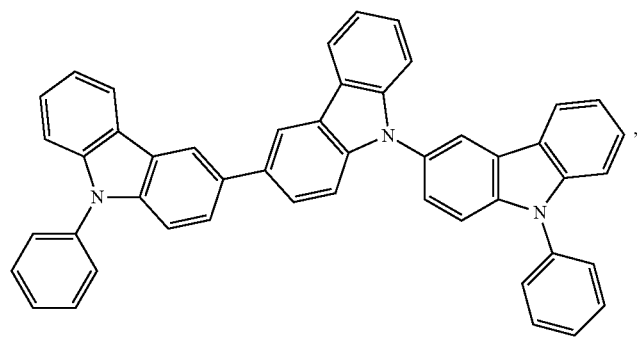
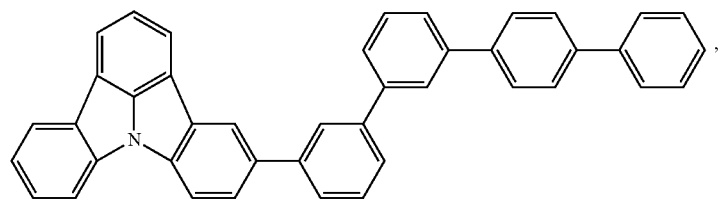
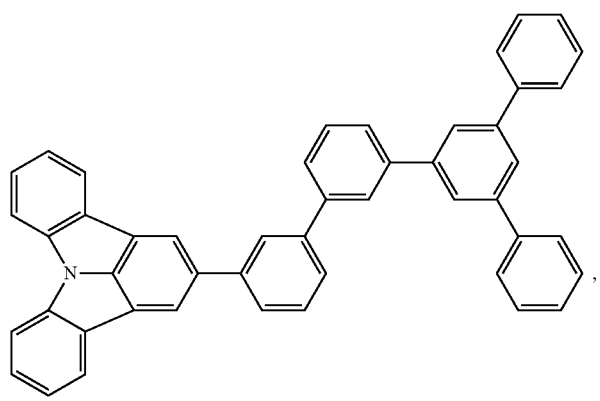
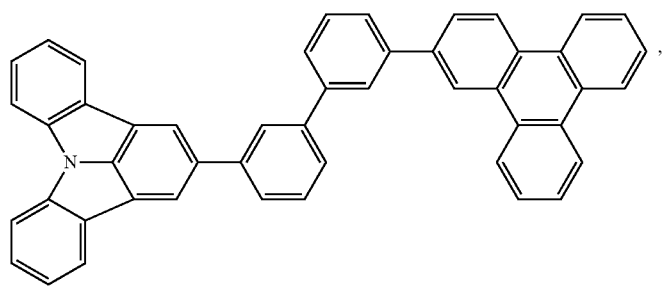
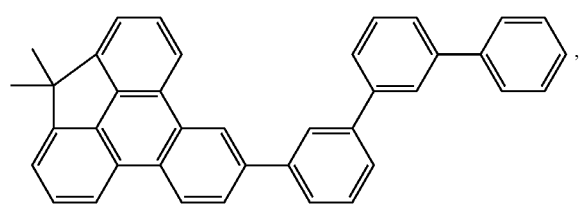
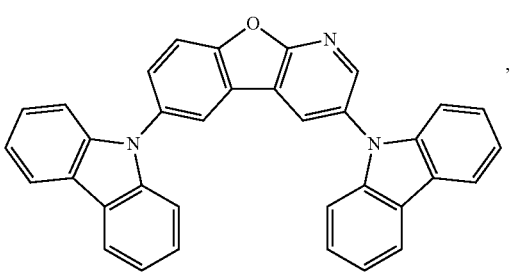

-continued
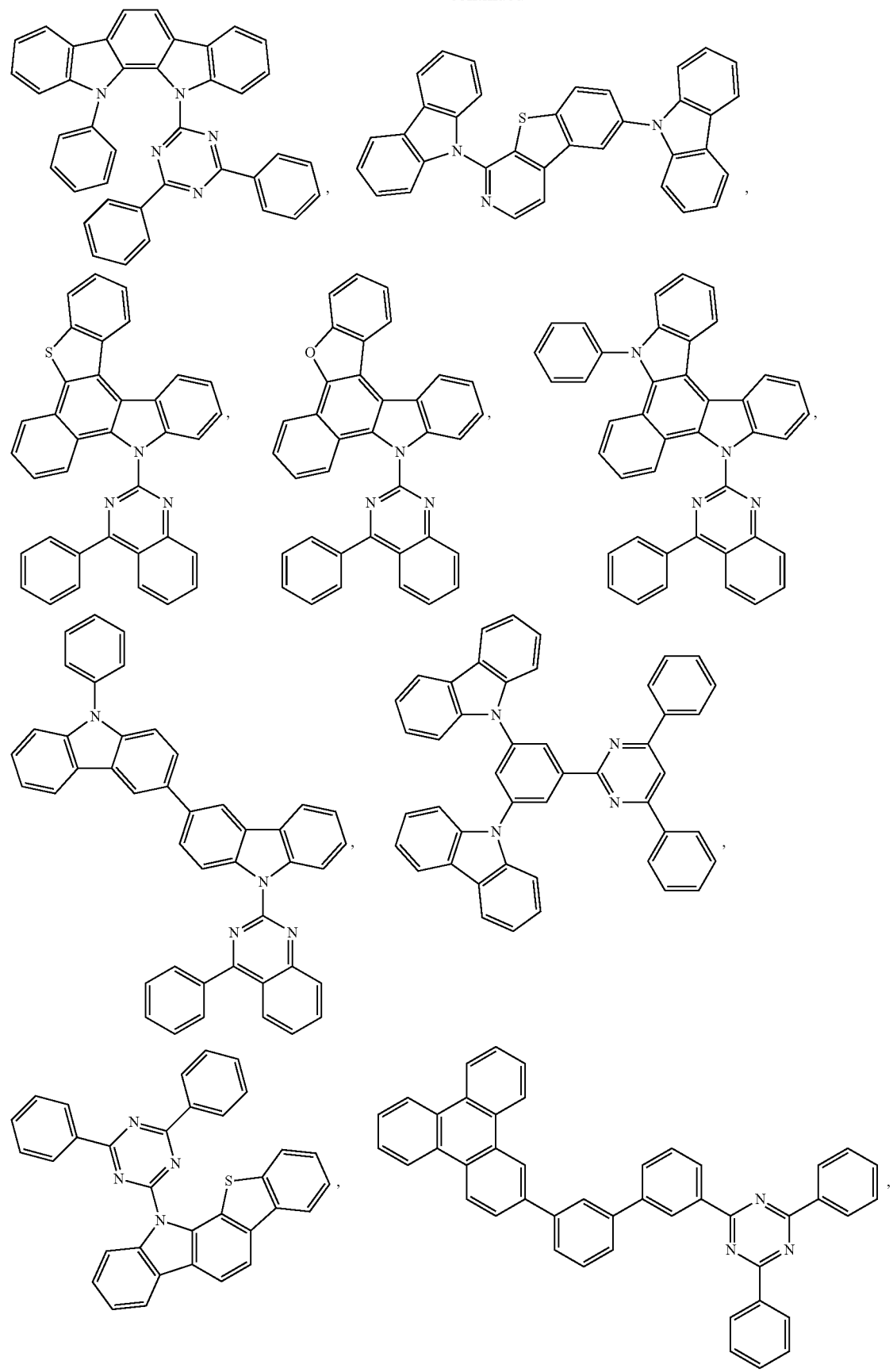

-continued
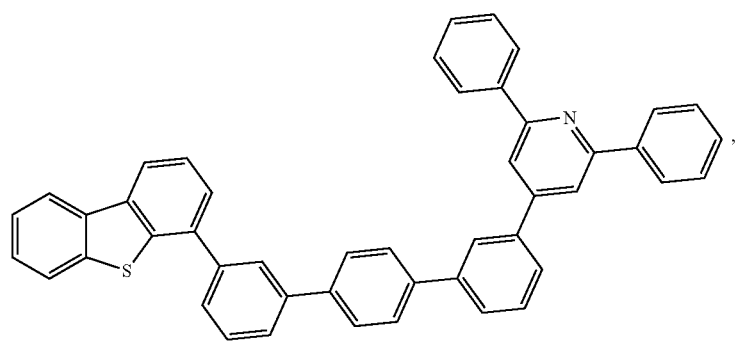
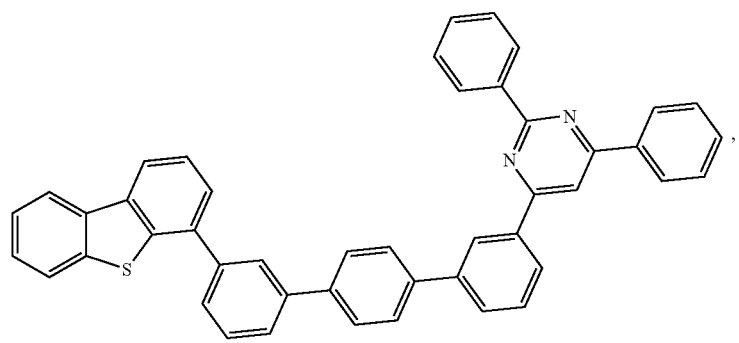
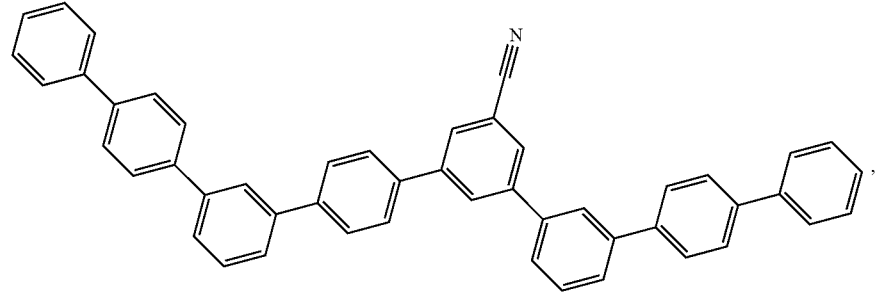
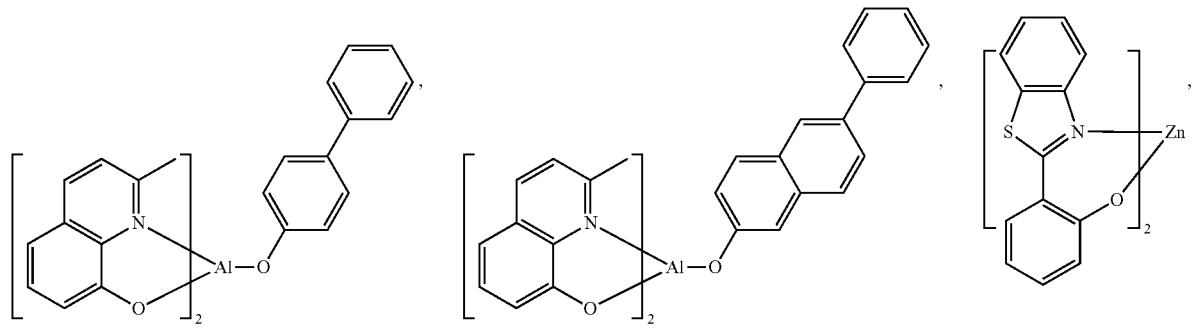
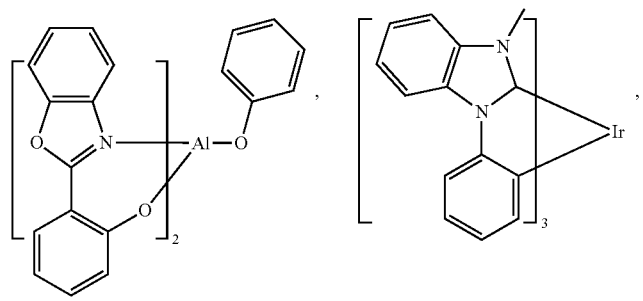

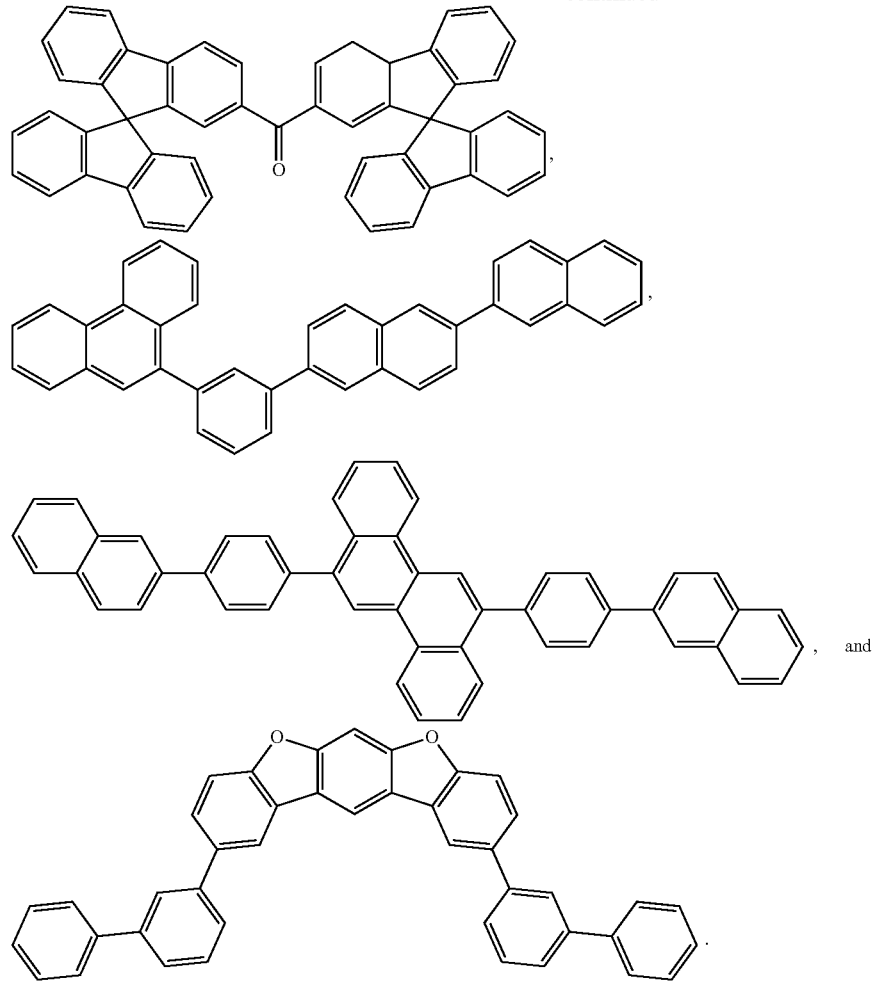

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450,
-continued
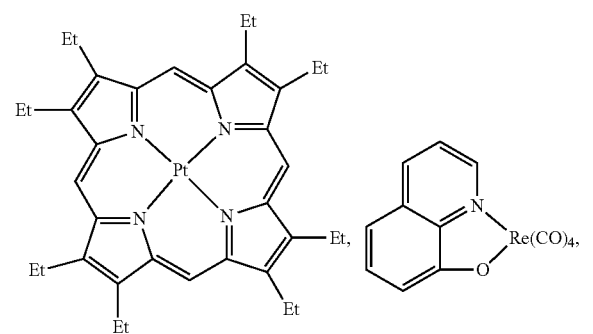
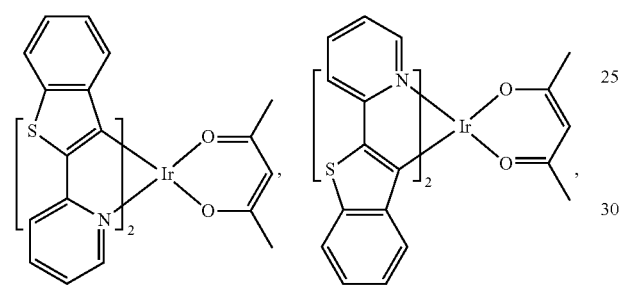
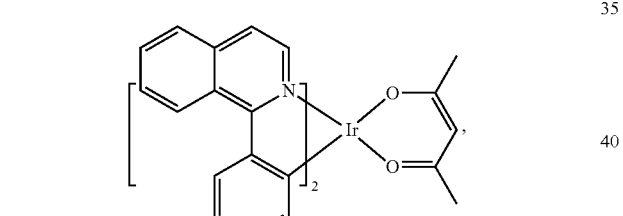
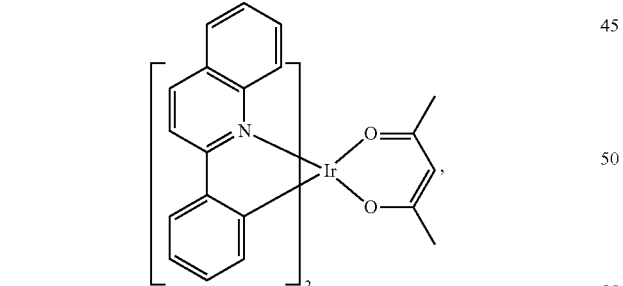
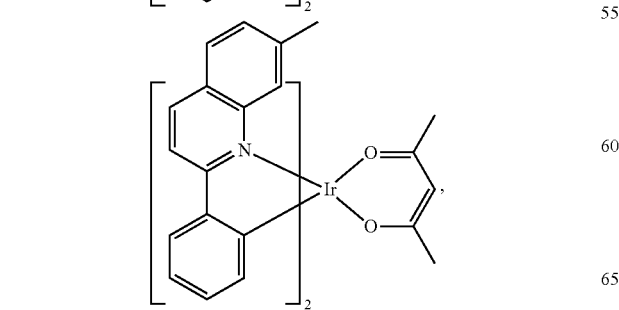
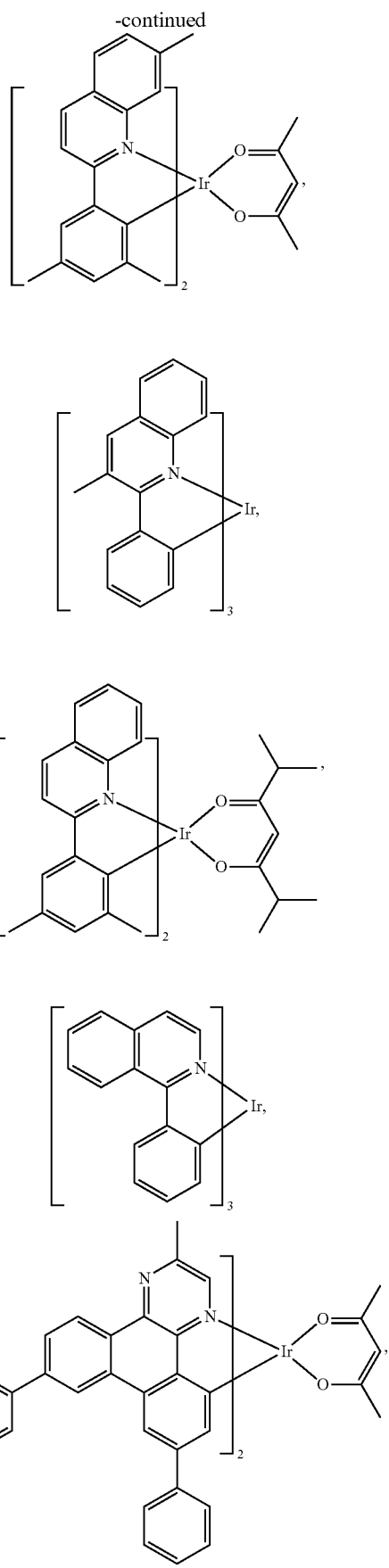

149
-continued
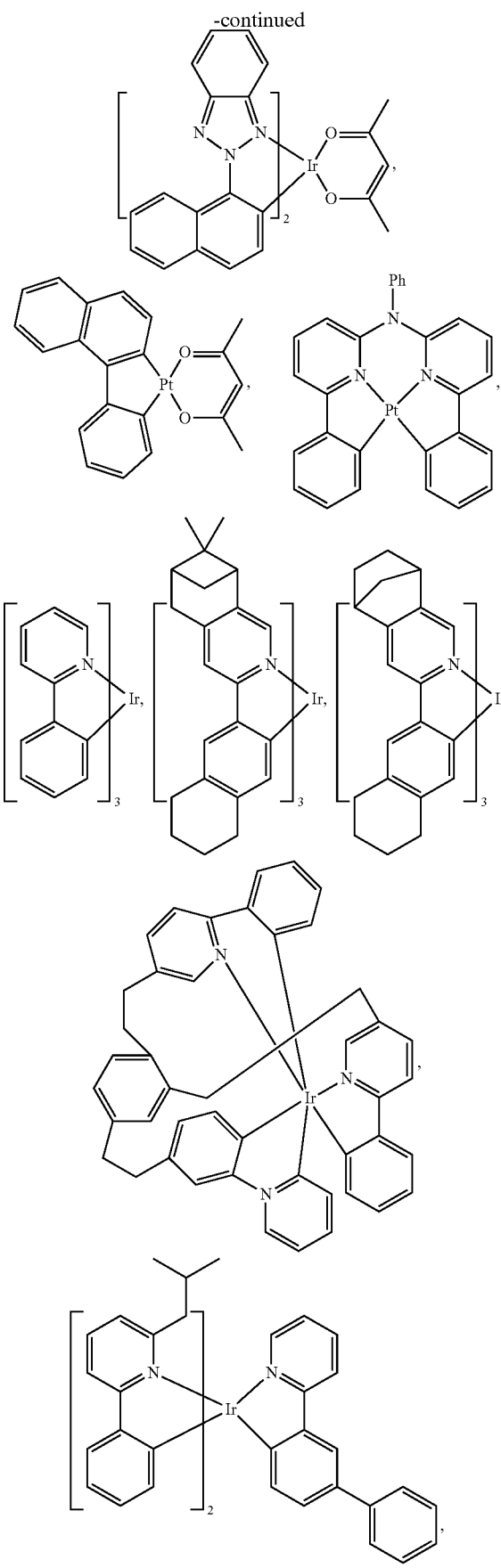
150
-continued
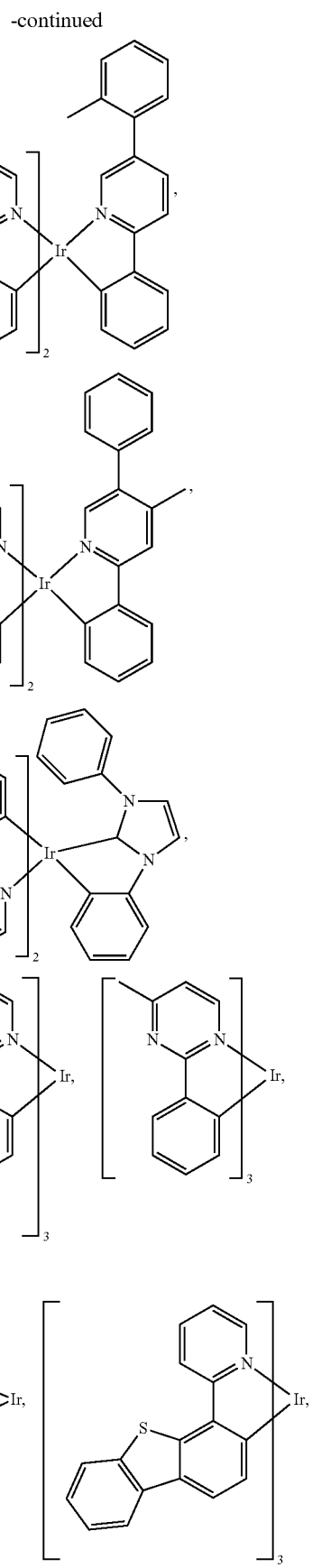

-continued
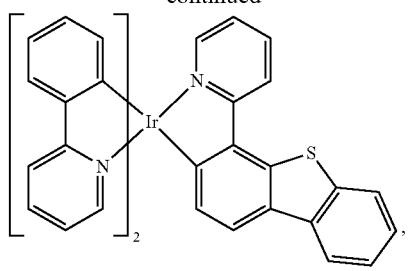
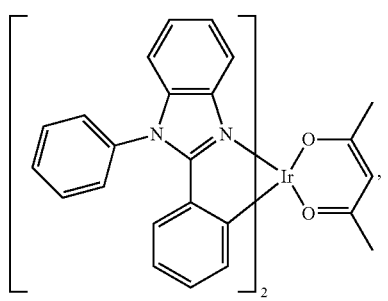
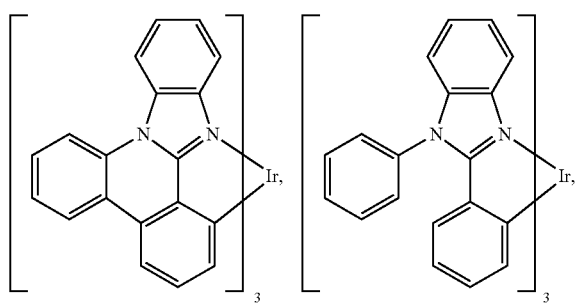
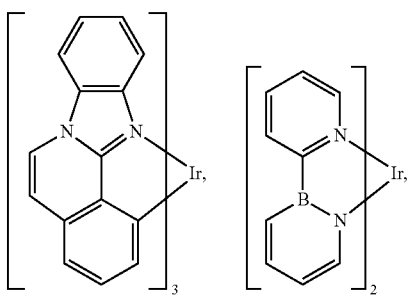
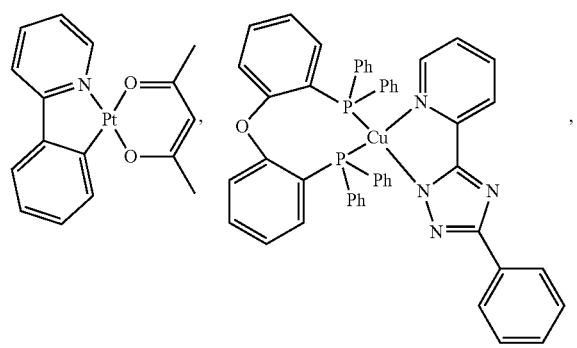
-continued
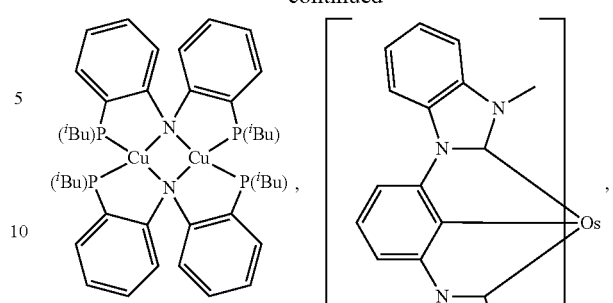
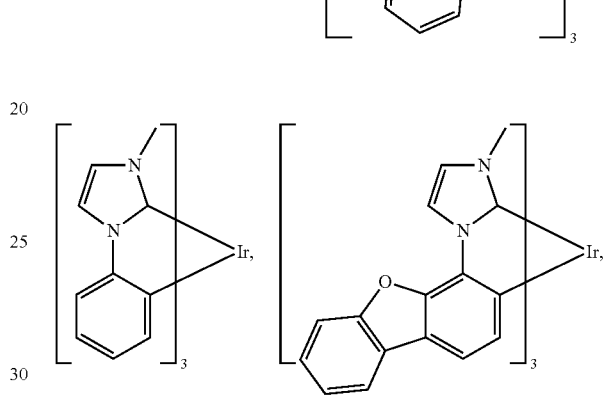
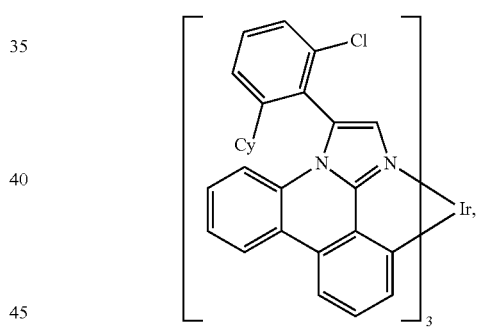
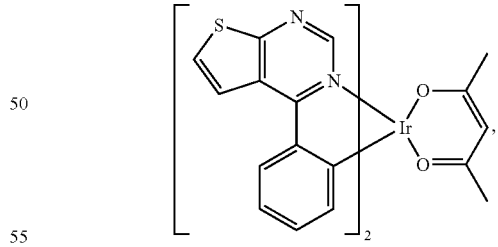
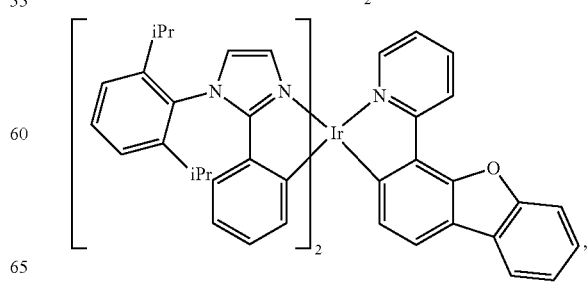

153
-continued
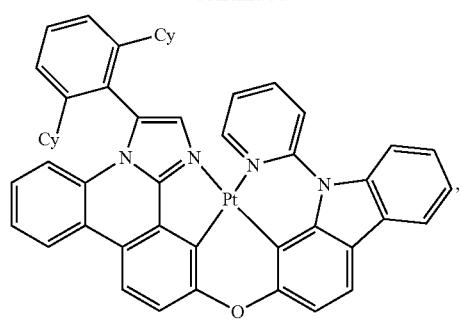
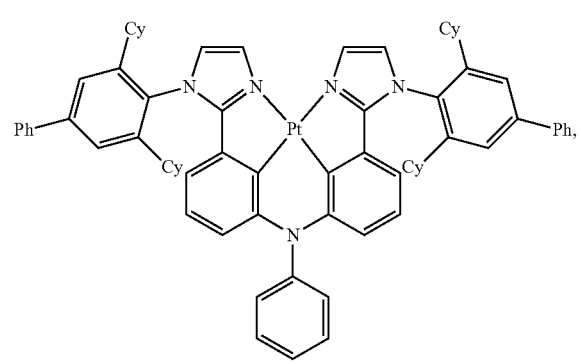
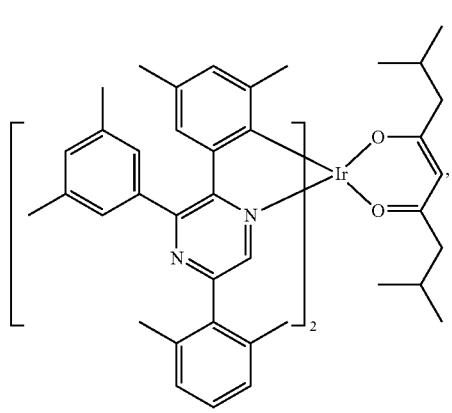
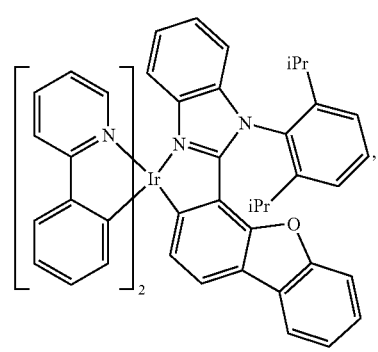
154
-continued
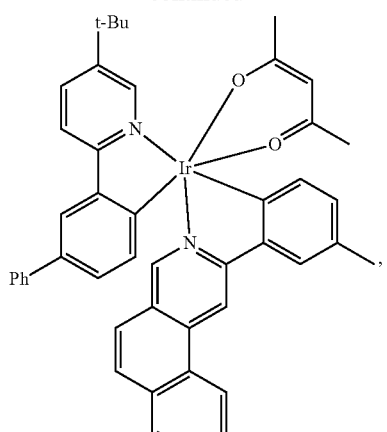
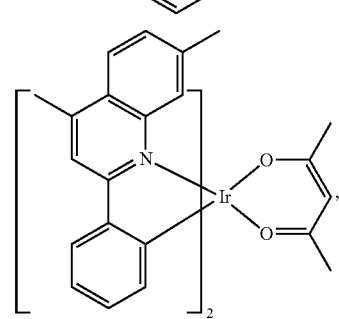
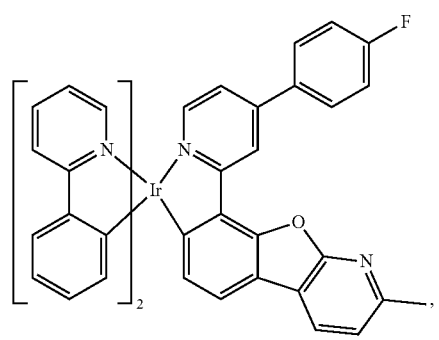
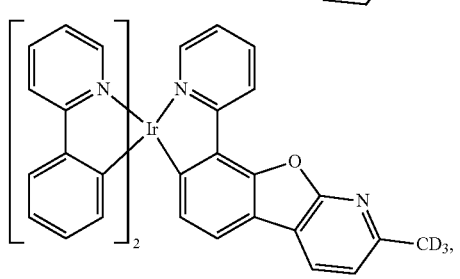
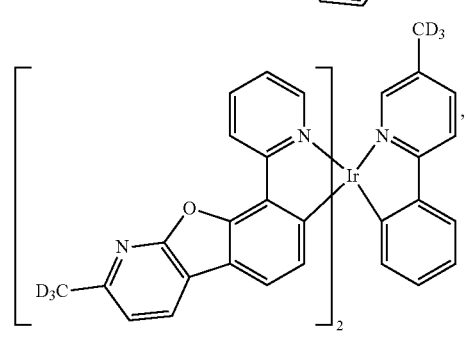

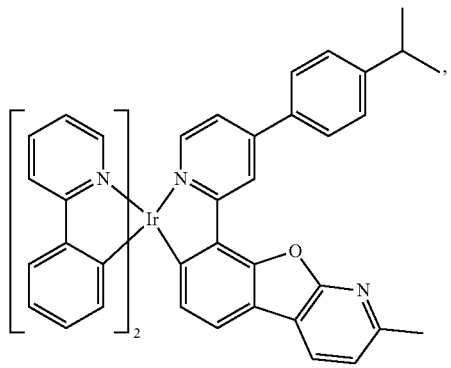
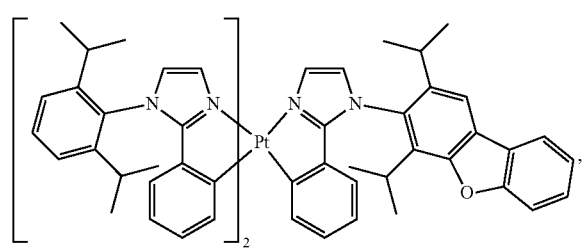
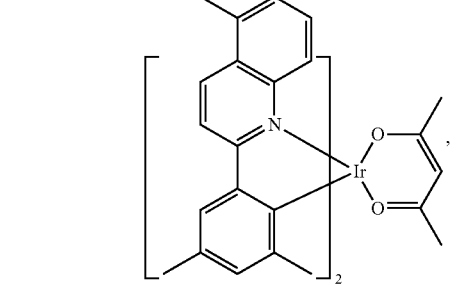
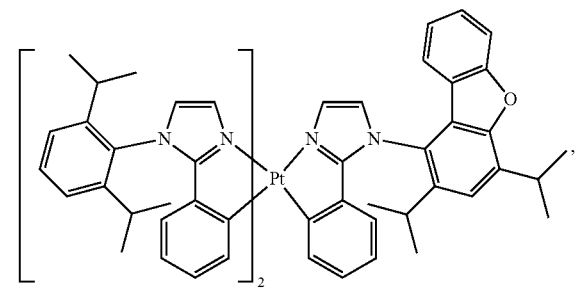
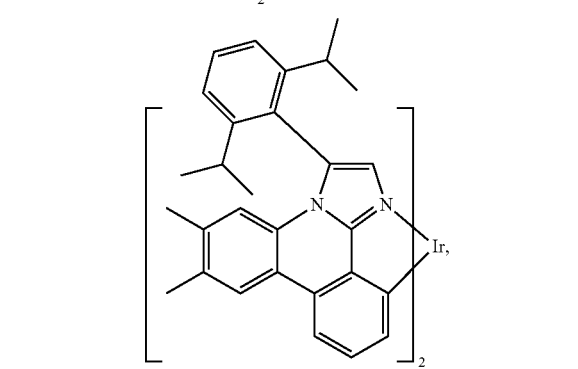
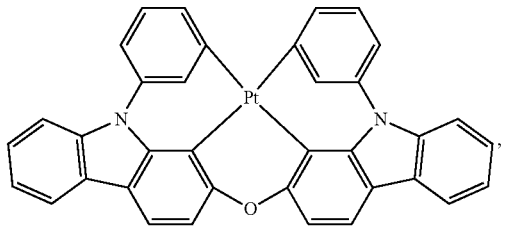
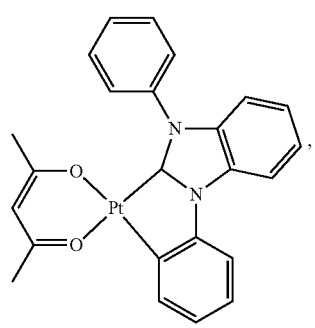
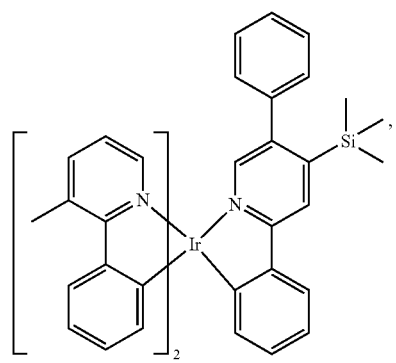
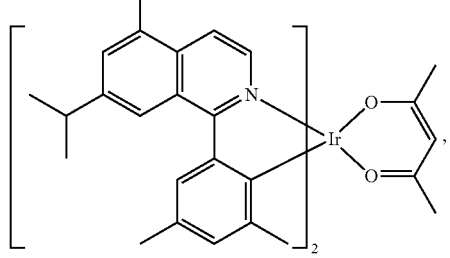
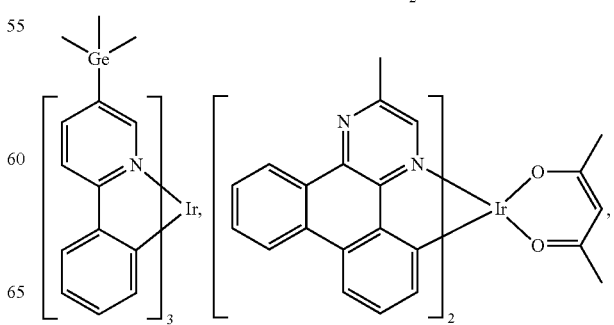

-continued
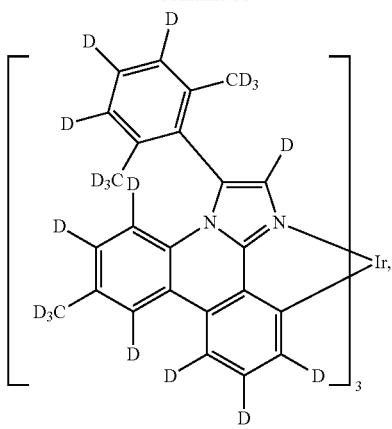
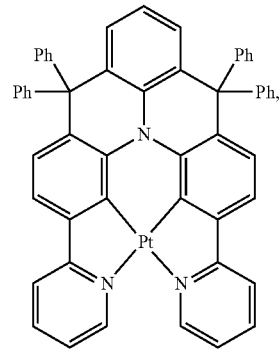
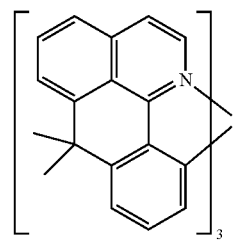
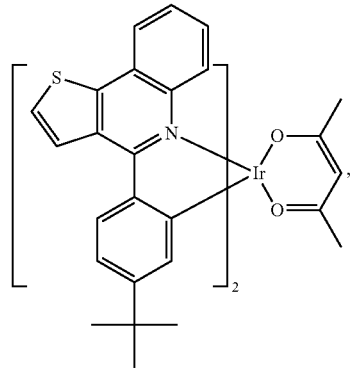
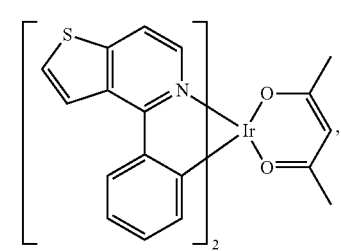
-continued
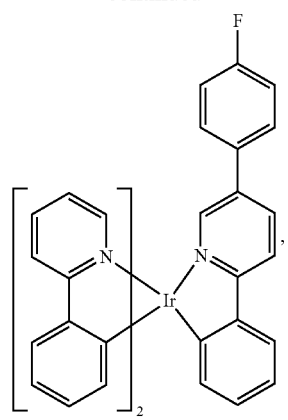
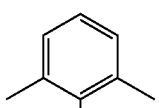
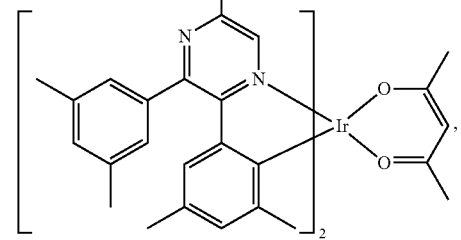
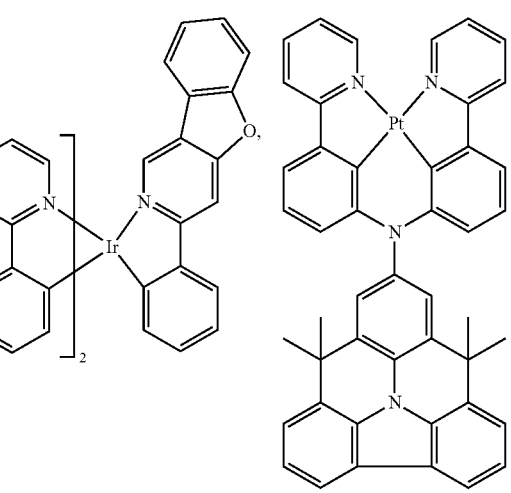
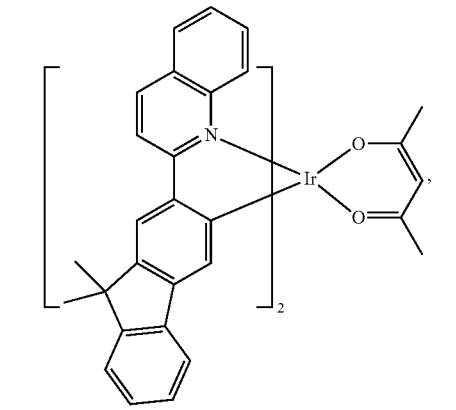

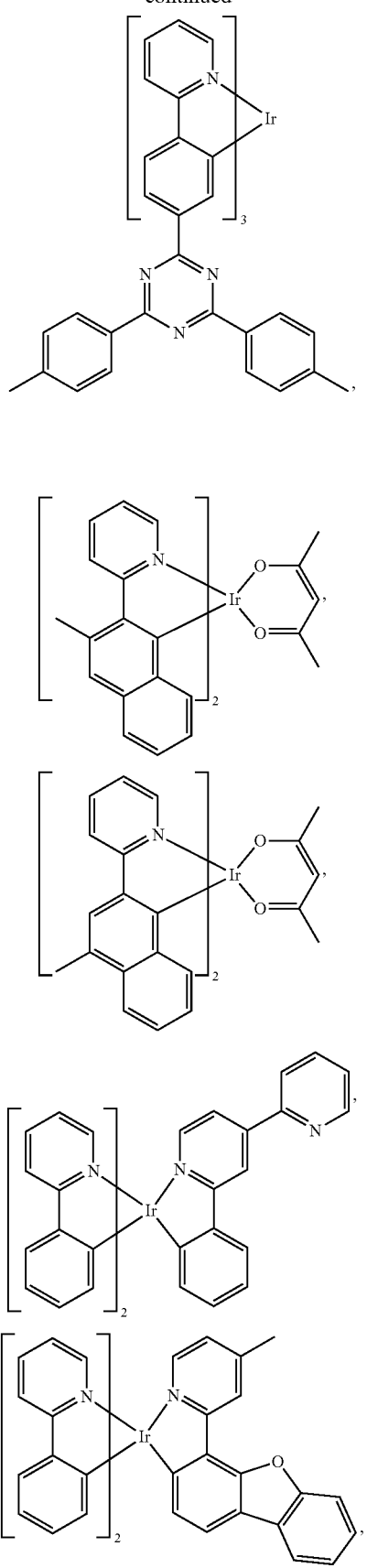
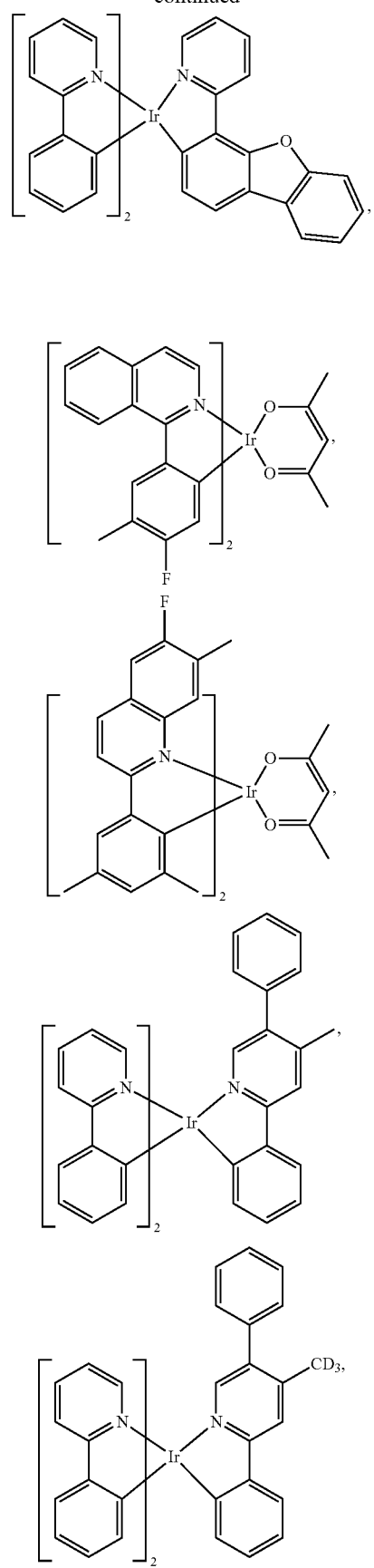

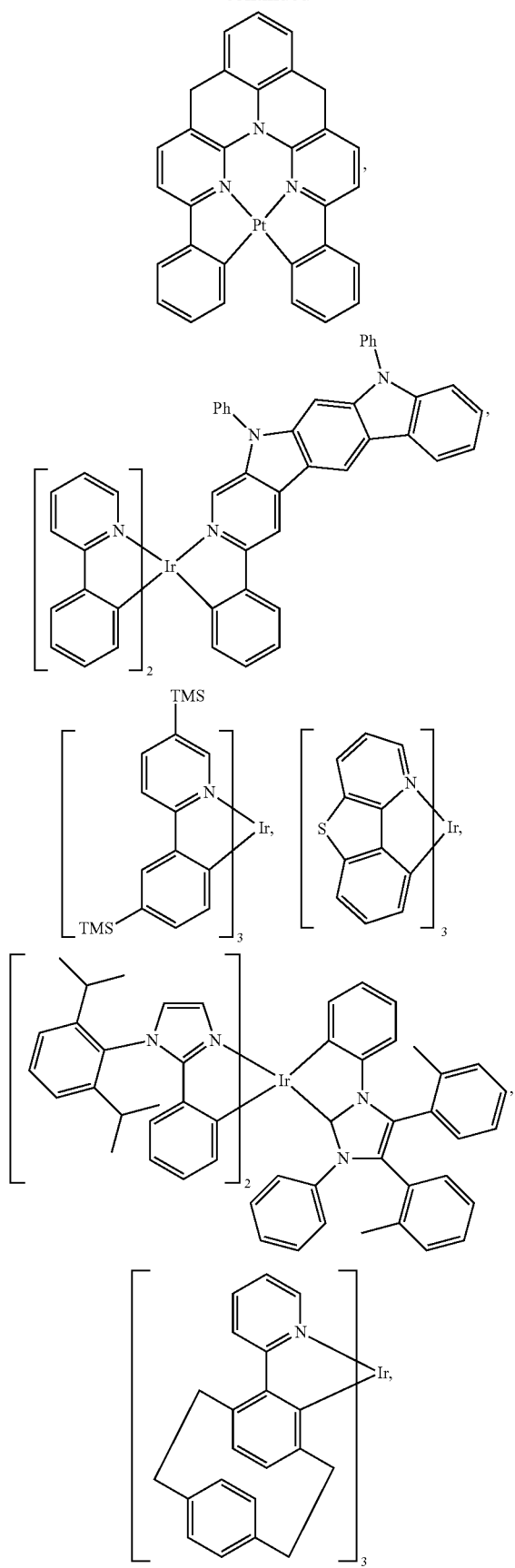

163
-continued
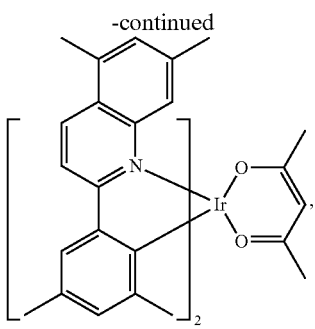
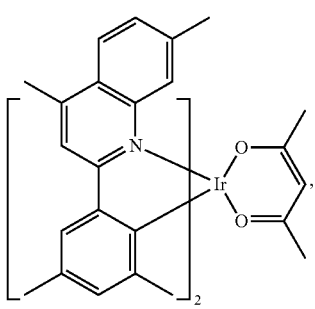
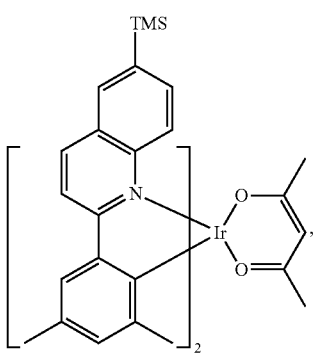
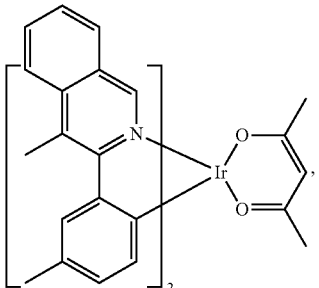
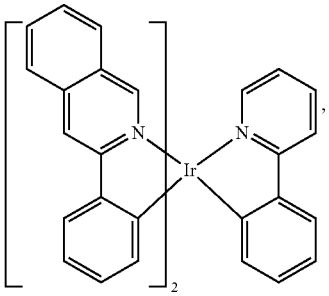
164
-continued
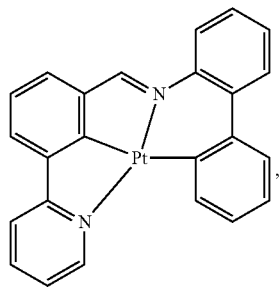
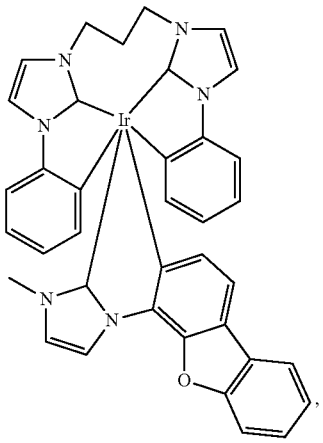
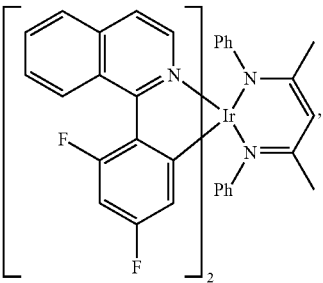

-continued
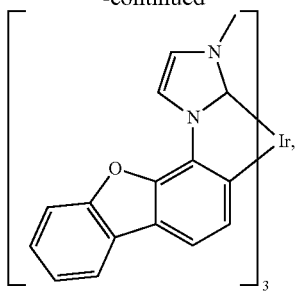
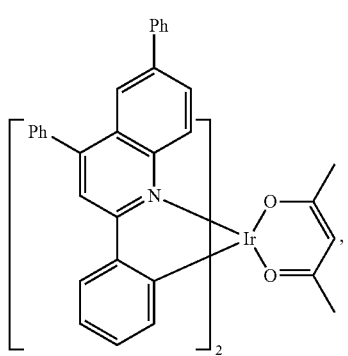
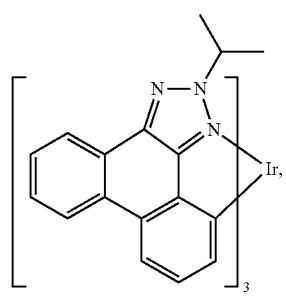
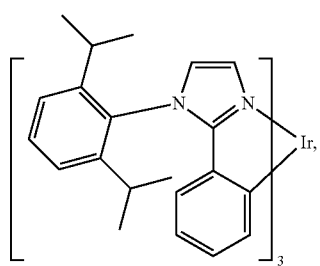
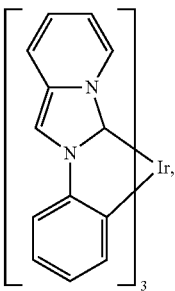
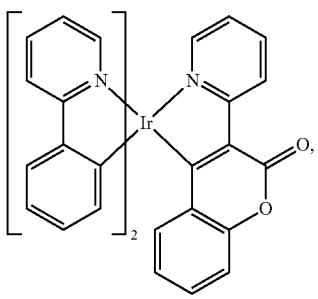
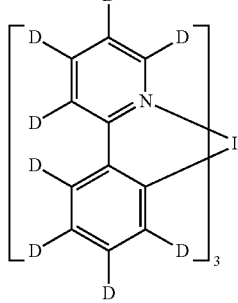
-continued
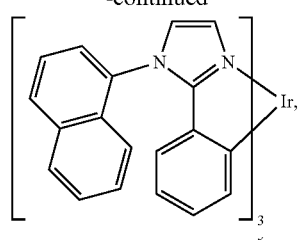
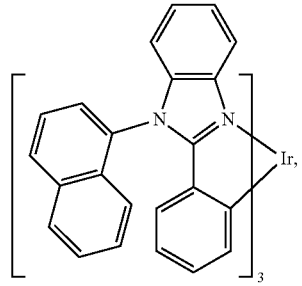
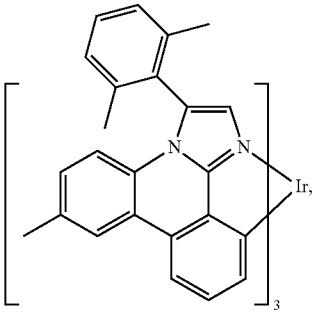
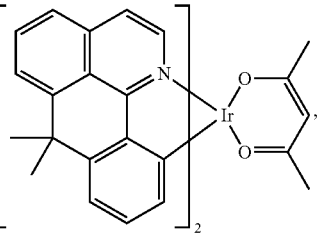
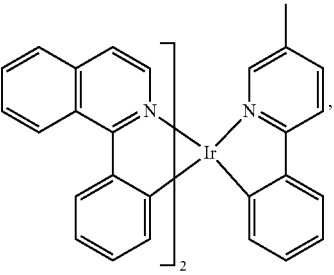
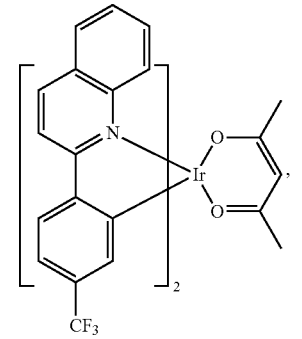

-continued

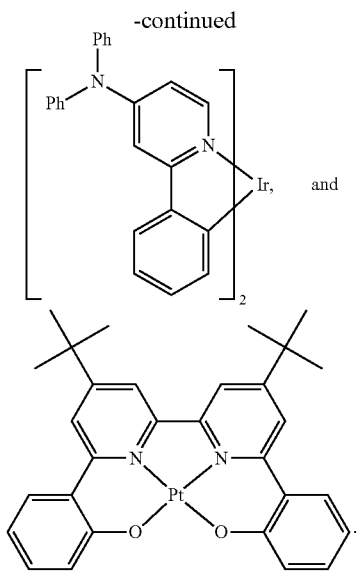

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

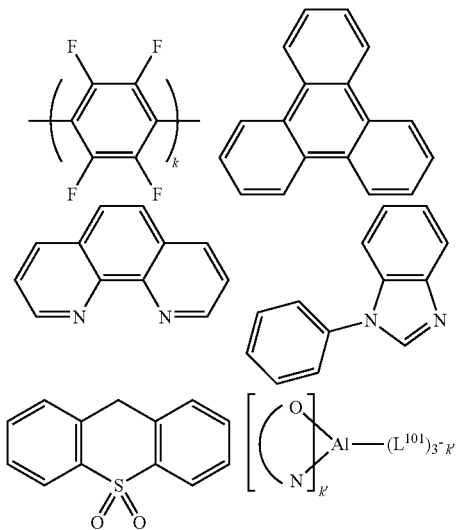

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

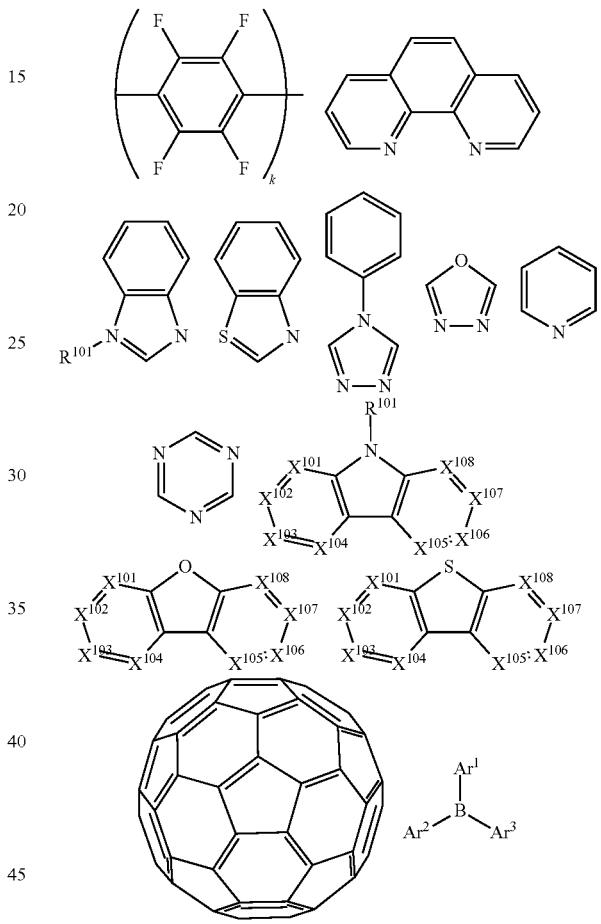

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

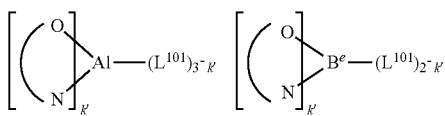

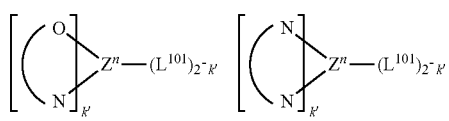

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

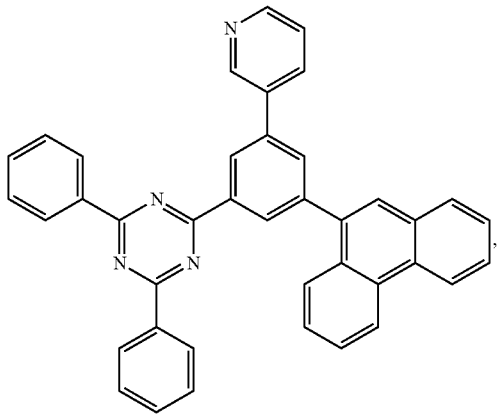

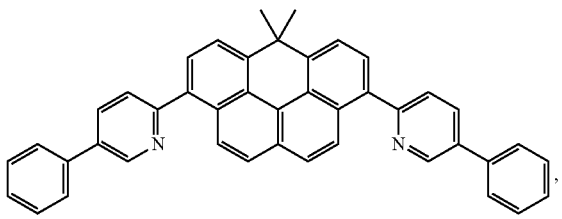

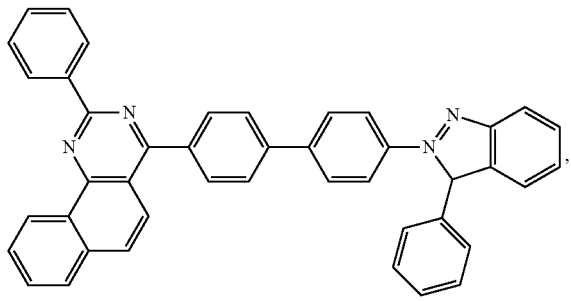

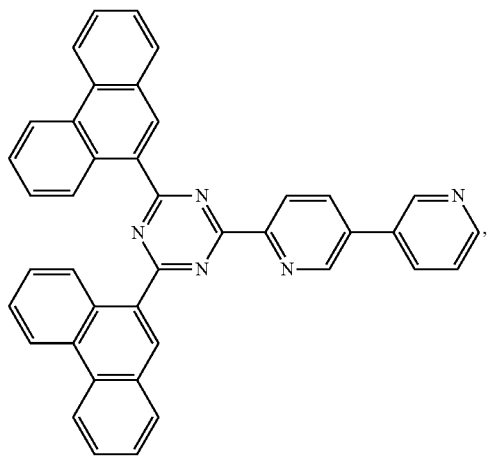

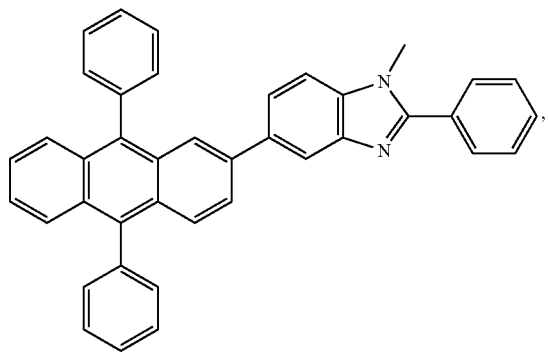

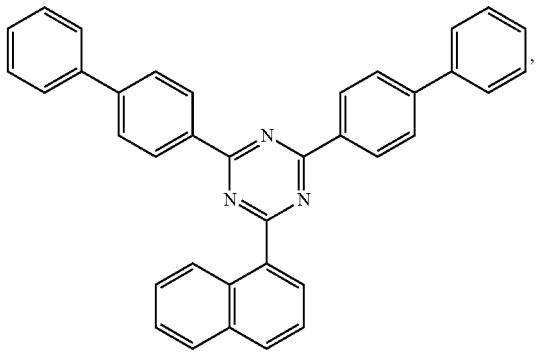

171
-continued
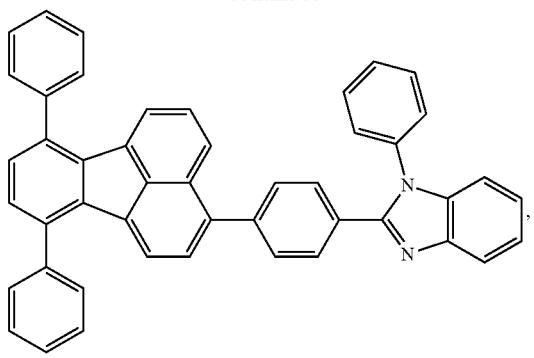
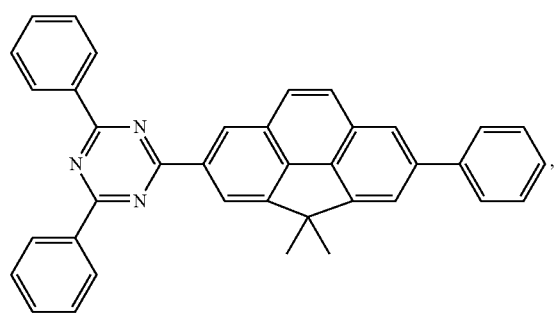
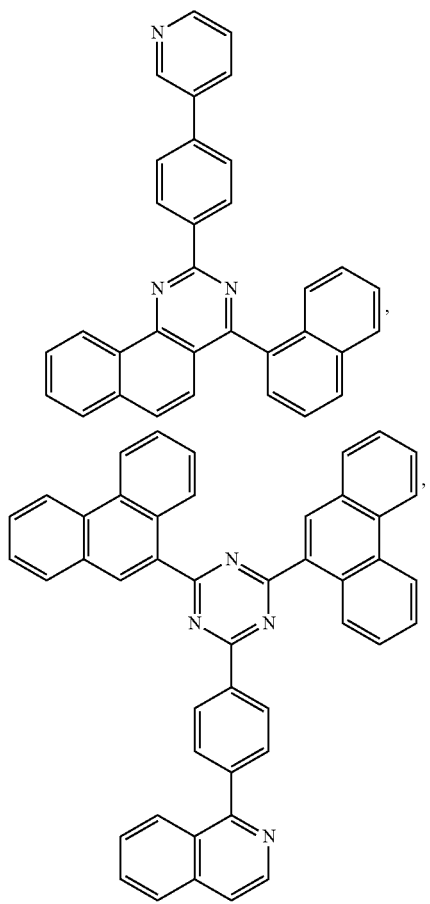
172
-continued
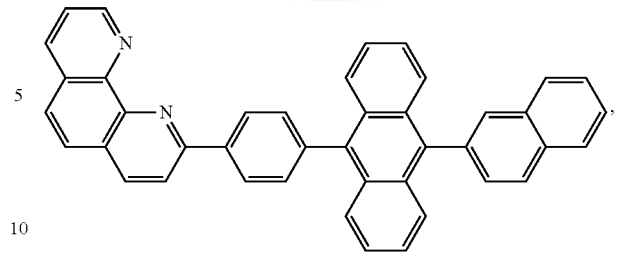
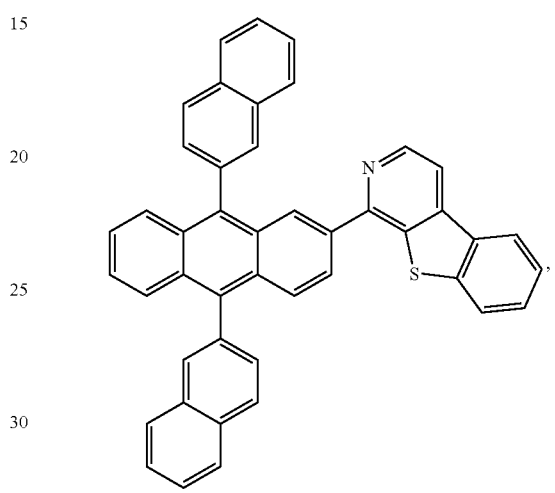
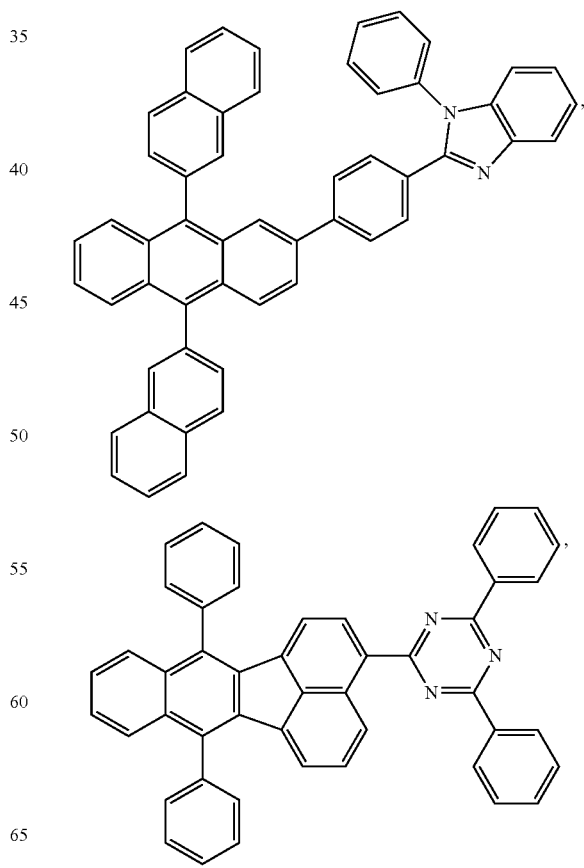

173
-continued
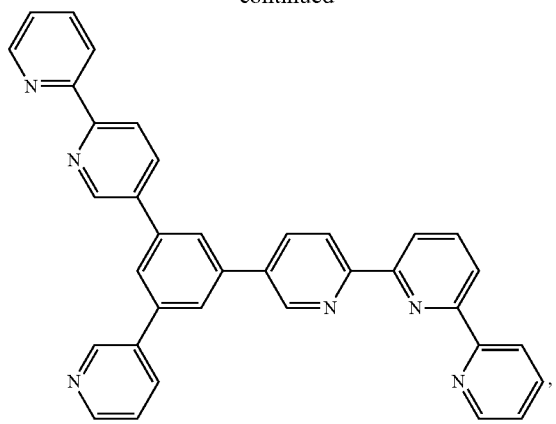
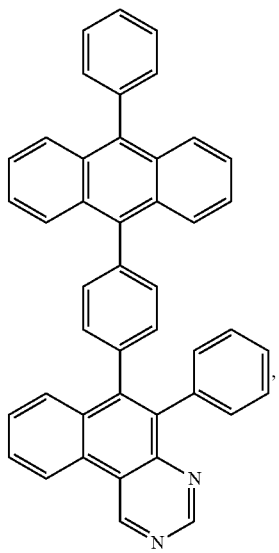
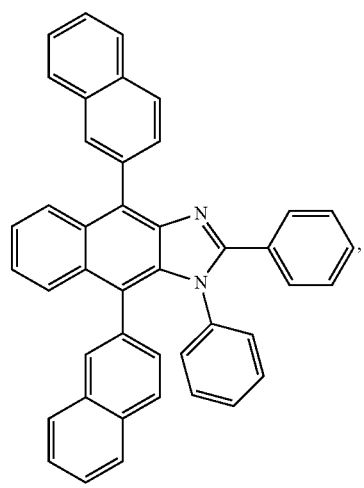
174
-continued
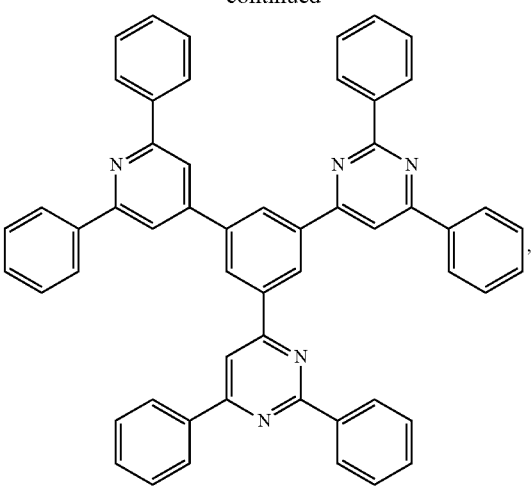
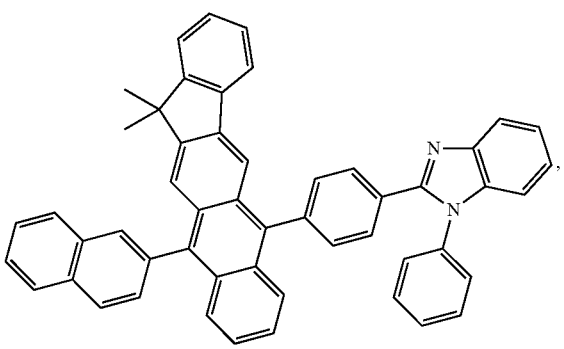

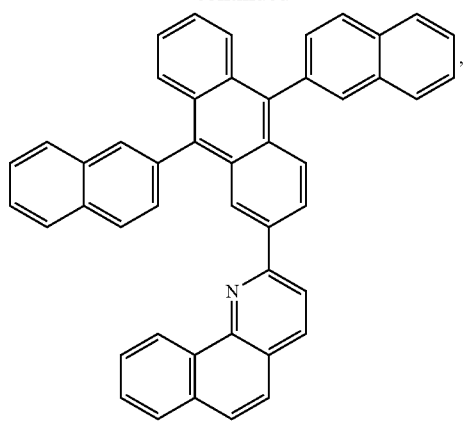
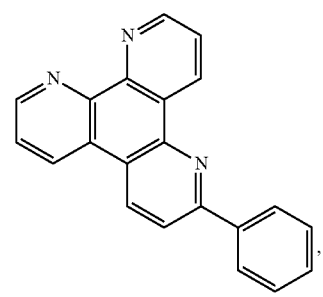
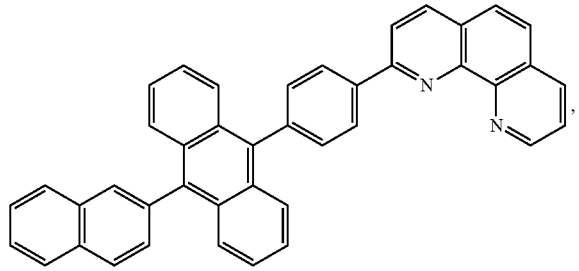
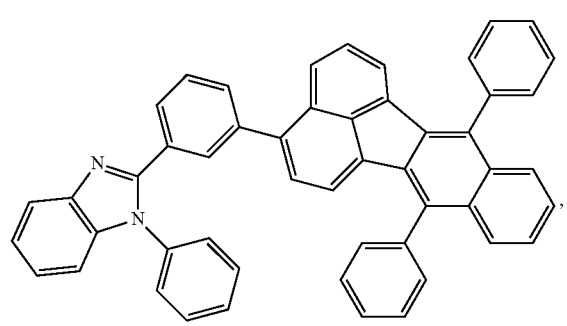
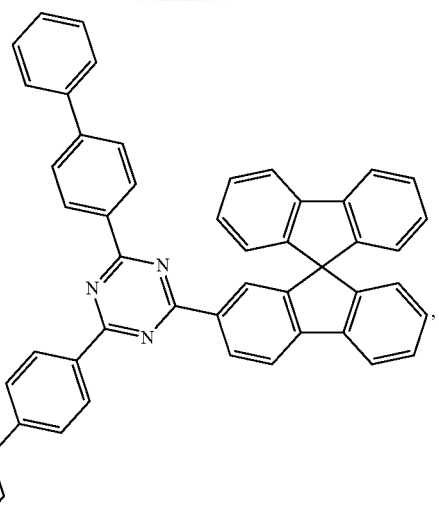
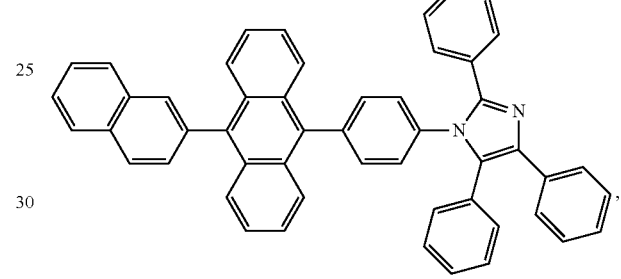
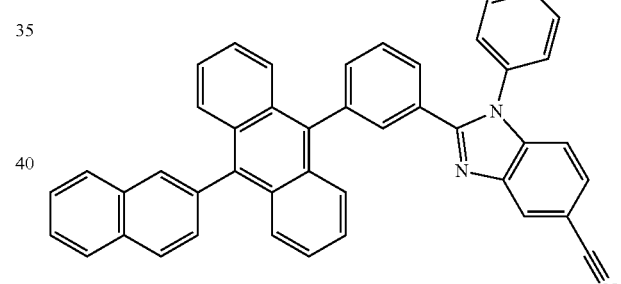
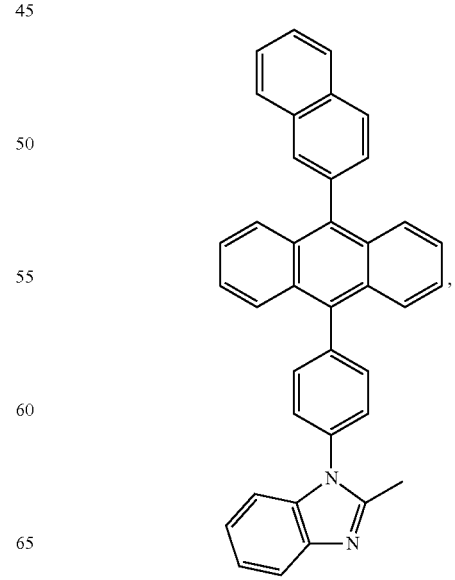

-continued

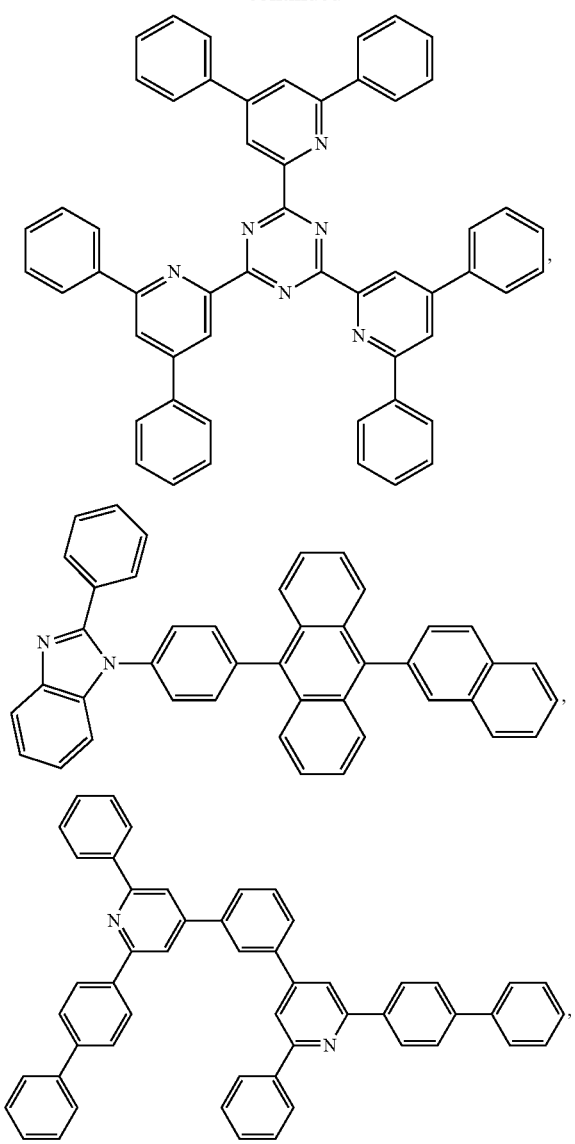

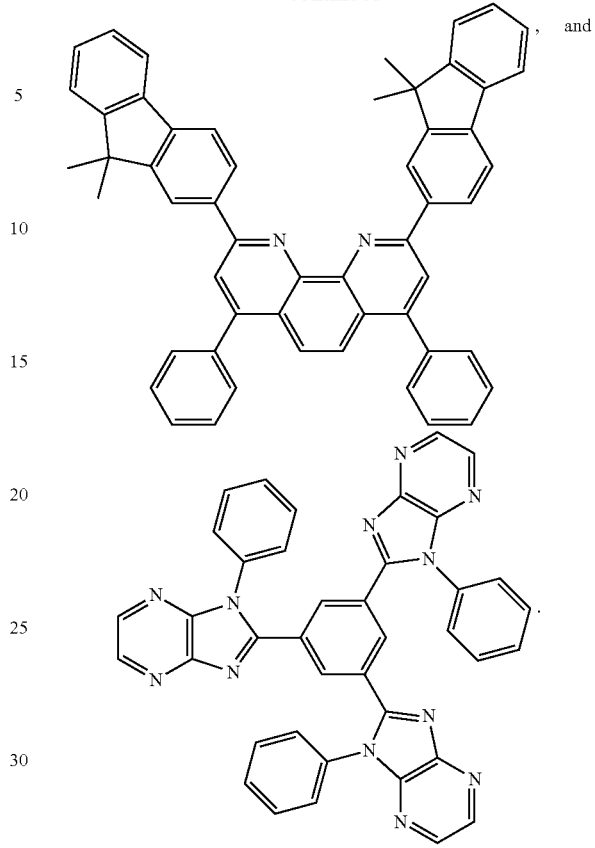

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

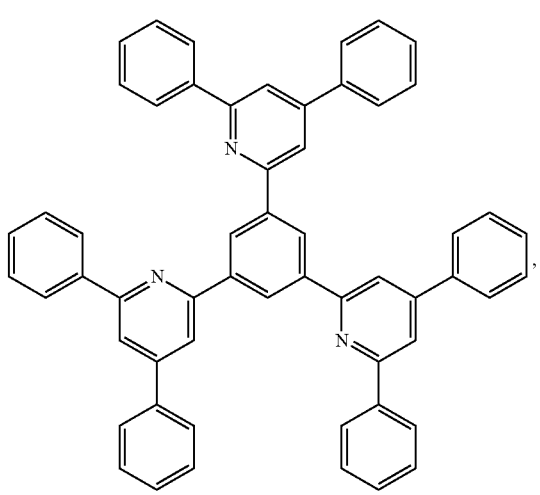

Synthesis of 2-(2'-bromo-[1,1'-biphenyl]-2-yl)-2,3-dihydrobenzo[2,3]benzofuro[6,5-d][1,3,2]oxazaborole

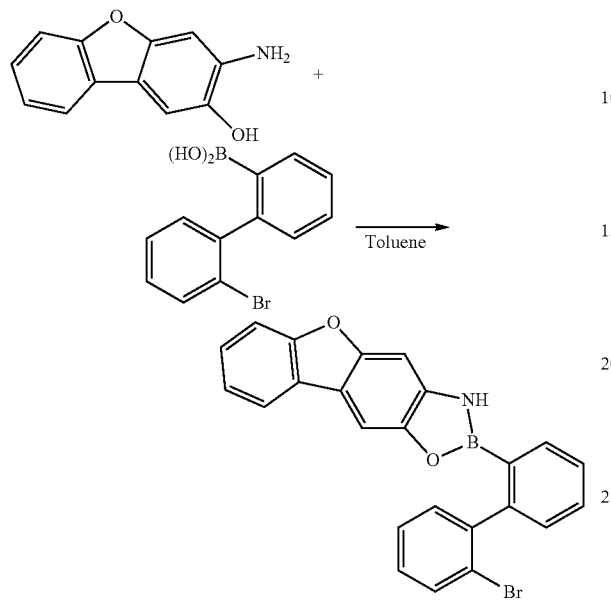

Toluene (36 mL) was bubbled with nitrogen for 10 min. 3-aminodibenzo[b,d]furan-2-ol (1.5 g, 7.53 mmol) and (2'-bromo-[1,1'-biphenyl]-2-yl)boronic acid (2.085 g, 7.53 mmol) were added and refluxed in a Dean-Stark apparatus for 24 h. The solution was concentrated under vacuum and used without further purification.

Synthesis of Compound 14

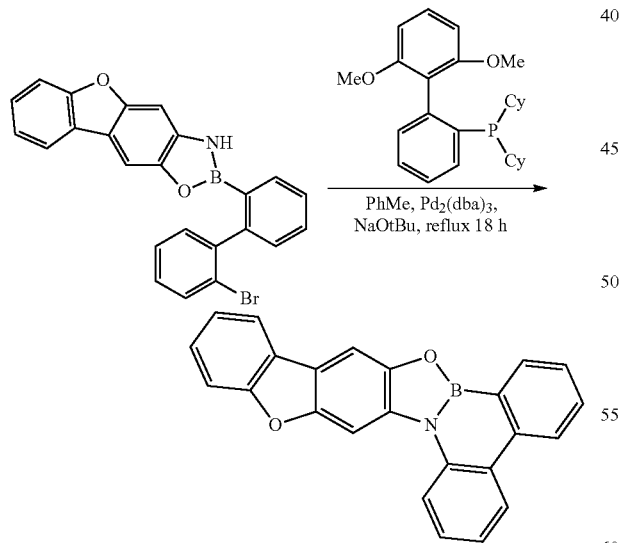

Toluene (20 mL) was bubbled with nitrogen for 10 min. 2-(2'-bromo-[1,1'-biphenyl]-2-yl)-2,3-dihydrobenzo[2,3]benzofuro[6,5-d][1,3,2]oxazaborole (3.2 g, 7.27 mmol), Pd$_2$(dba)$_3$ (0.666 g, 0.727 mmol), dicyclohexyl(2',6'-dimethoxy-[1,1'-biphenyl]-2-yl)phosphane (1.194 g, 2.91 mmol), sodium 2-methylpropan-2-olate (0.908 g, 9.45 mmol) were added. The mixture was bubbled with nitrogen for 15 min and refluxed for 18 h. After cooling (~22° C.), the reaction mixture was filtered through a silica pad and washed with toluene. The solvent was removed in vacuo and the residue was purified by flash column chromatography using hexane to 10% ethyl acetate in hexane to yield Compound 14 (1.2 g, 3.34 mmol, 45.9% yield) as a white solid.

Synthesis of 5-bromo-2-(2'-bromo-[1,1'-biphenyl]-2-yl)-2,3-dihydrobenzo[d][1,3,2]oxazaborole

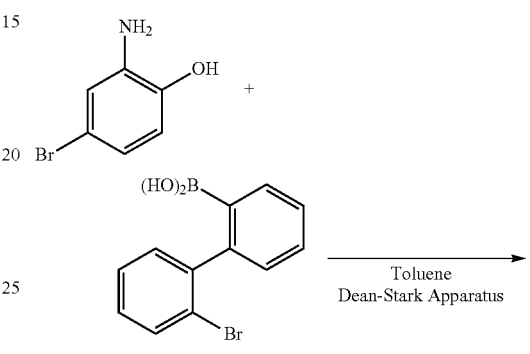

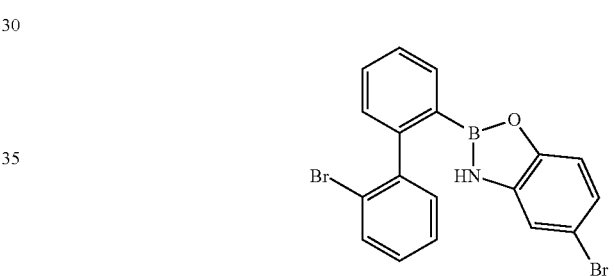

Toluene (40 mL) was bubbled with nitrogen for 10 min. 2-amino-4-bromophenol (5 g, 26.6 mmol) and (2'-bromo-[1,1'-biphenyl]-2-yl)boronic acid (7.36 g, 26.6 mmol) were added and refluxed in a Dean-Stark apparatus for 24 h. The solution was concentrated under vacuum and used without further purification.

Synthesis of 13-bromodibenzo[c,e]benzo[4,5][1,3,2]oxazaborolo[3,2-a][1,2]azaborinine

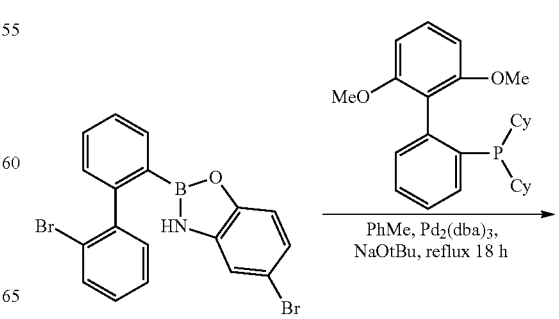

-continued

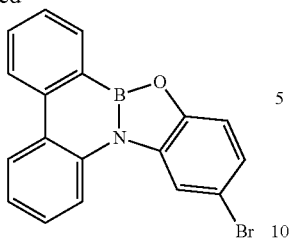

Toluene (20 ml) was bubbled with nitrogen for 10 min. 5-bromo-2-(2'-bromo-[1,1'-biphenyl]-2-yl)-2,3-dihydrobenzo[d][1,3,2]oxazaborole (11 g, 25.6 mmol), Pd$_2$(dba)$_3$ (2.348 g, 2.56 mmol), dicyclohexyl(2',6'-dimethoxy-[1,1'-biphenyl]-2-yl)phosphane (4.21 g, 10.26 mmol), sodium 2-methylpropan-2-olate (2.71 g, 28.2 mmol) were added. The mixture was bubbled with nitrogen for 15 min and refluxed for 18 h. After cooling (~22° C.), the reaction mixture was filtered through a silica pad and washed with toluene. The solvent was removed in vacuo and the residue was purified by flash column chromatography using hexane to 10% ethyl acetate in hexane to yield the product (2.0 g, 5.75 mmol, 22.4% yield) as a white solid.

Synthesis of Compound 4a

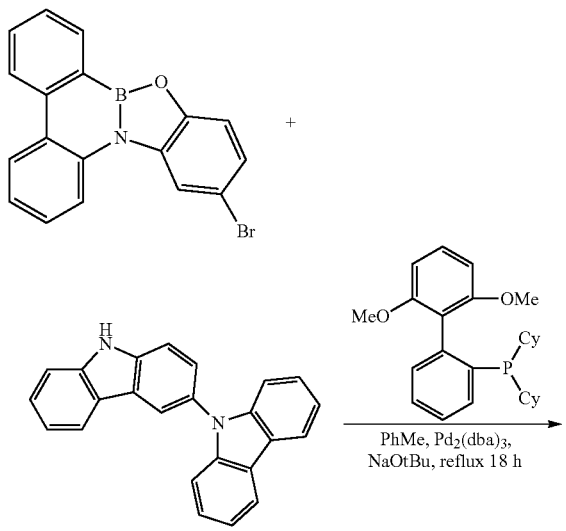

-continued

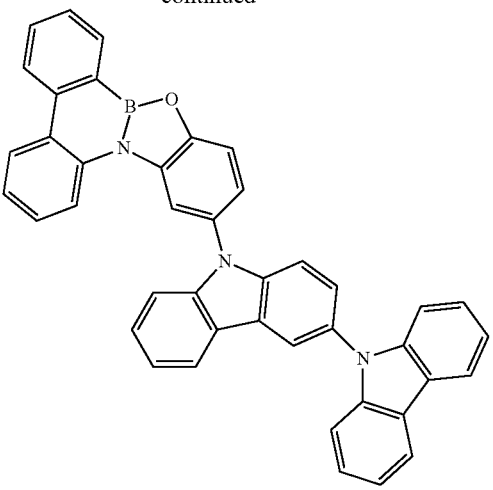

Toluene (20 mL) was bubbled with nitrogen for 10 min. 13-bromodibenzo[c,e]benzo[4,5][1,3,2]oxazaborolo[3,2-a][1,2]azaborinine (0.75 g, 2.155 mmol), 9H-3,9'-bicarbazole (0.716 g, 2.155 mmol), Pd$_2$(dba)$_3$ (0.395 g, 0.431 mmol), dicyclohexyl(2',6'-dimethoxy-[1,1'-biphenyl]-2-yl)phosphane (0.708 g, 1.724 mmol), sodium 2-methylpropan-2-olate (0.249 g, 2.59 mmol) were added. The mixture was bubbled with nitrogen gas for 15 min and refluxed for 18 h. After cooling (~22° C.), the reaction mixture was filtered through a silica pad and washed with toluene. The solvent was removed in vacuo and the residue was purified by flash column chromatography using hexane to 10% ethyl acetate in hexane to yield Compound 4a (0.126 g, 0.210 mmol, 9.8% yield) as a white solid.

The photophysical and electrochemical properties of some example compounds according to the present disclosure are provided in Table 1 below. The compounds show high triplet energy and are particularly useful as hosts for phosphorescent OLED.

TABLE 1

| Name | Structure | CV |
| --- | --- | --- |
| Compound 14 | 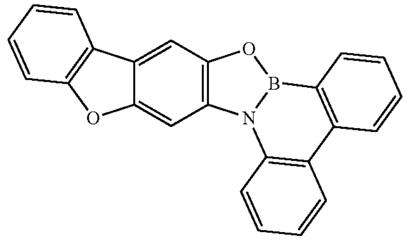 [SMILES: c1ccc2c(c1)B1Oc3cc4c(cc3N1c1ccccc1-2)oc1ccccc14] | R.T.: 382 nm  Red: −2.69 (IR) <br> 77K: 433 nm  Ox: 0.22 (IR) |

TABLE 1-continued

| Name | Structure | CV |
|---|---|---|
| Compound 4a | 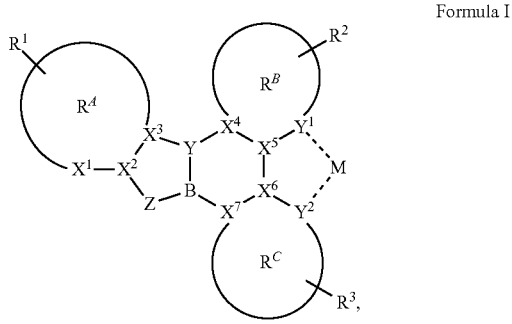 | R.T.: 386 nm  Red: −3.03 (IR)<br>77K: 414 nm  Ox: 0.46 (IR)<br>Tg = 163° C. |

We claim:

1. A compound having a structure or partial structure of Formula I:

Formula I

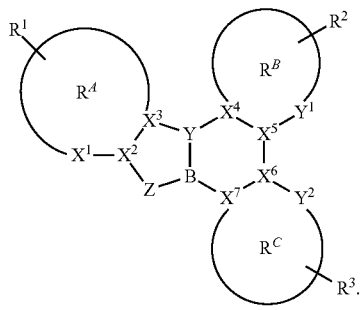

wherein $R^A$, $R^B$, and $R^C$ are each independently 5 or 6 membered aryl or heteroaryl rings;
wherein $R^1$, $R^2$, and $R^3$ each independently represent no substitutions or up to the maximum available substitutions;
wherein $R^1$, $R^2$, and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, sulfinyl, sulfonyl, phosphine, and combinations thereof;
wherein any adjacent $R^1$, $R^2$, and $R^3$ are optionally joined or fused to form a ring;
wherein $X^1$ and $X^7$ are C or N;
wherein $X^2$ to $X^6$ are independently C;
wherein Y is N or P;
wherein Z is CRR', O, PR, P(O)R, or S;
wherein $Y^1$ and $Y^2$ are each independently selected from the group consisting of carbon and nitrogen;
wherein R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, sulfinyl, sulfonyl, phosphine, and combinations thereof;
wherein R and/or R' are optionally joined or fused with $R^1$ or $R^3$ to form a ring;
wherein the dashed lines represent a metal M optionally coordinated to $R^B$ and $R^C$; and
wherein when M is coordinated to $R^B$ and $R^C$, M replaces $R^2$ and $R^3$ on $Y^1$ and $Y^2$ and bonds to $Y^1$ and $Y^2$.

2. The compound of claim 1, wherein the compound has the formula:

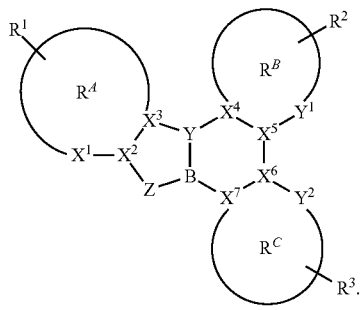

3. The compound of claim 1, wherein the compound is a dimer comprising two structures or partial structures of Formula I.

4. The compound of claim 1, wherein at least one of $R^1$, $R^2$, and $R^3$ substituents are joined or fused to form a 5- or 6-membered ring, which can be further substituted.

5. The compound of claim 1, wherein $X^1$-$X^6$ are C, and $X^7$ is C or N.

6. The compound of claim 1, wherein R and R' are independently aryl or heteroaryl.

7. The compound of claim 1, wherein the compound is selected from the group consisting of:

compound 1

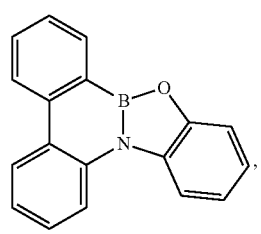

-continued
compound 2
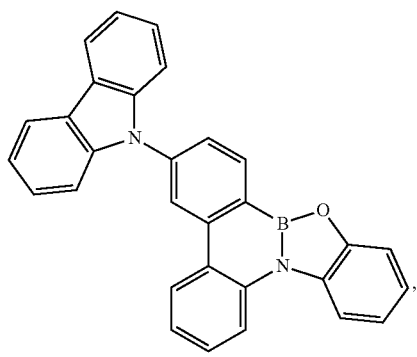
compound 3
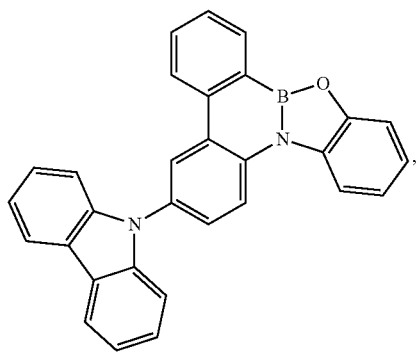
compound 4
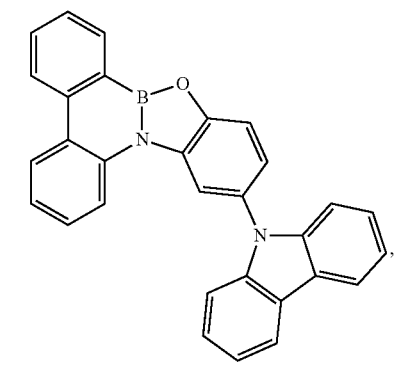
compound 4a
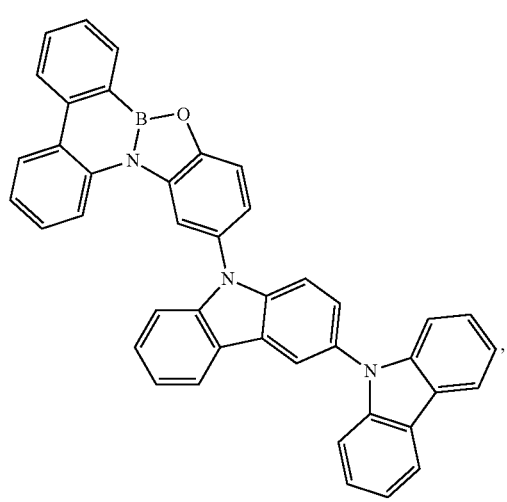
-continued
compound 5
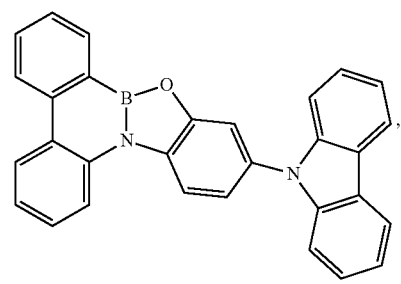
compound 6
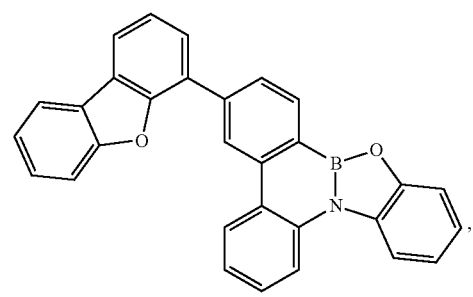
compound 7
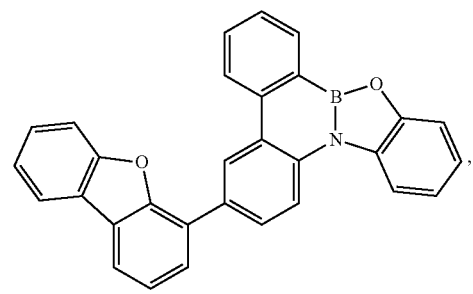
compound 8
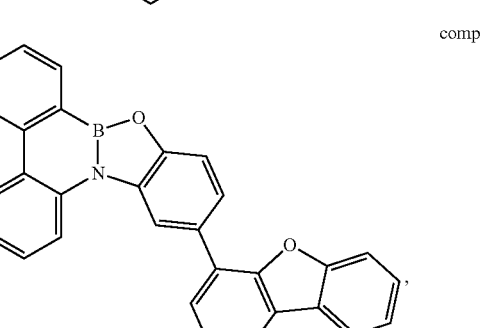
compound 9
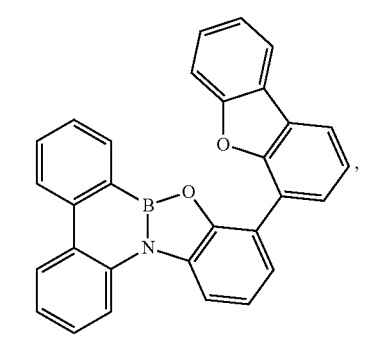

compound 10
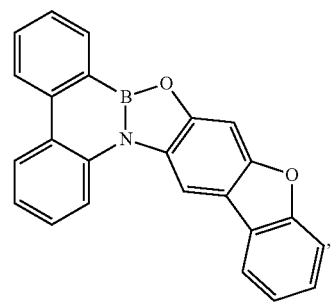
compound 11
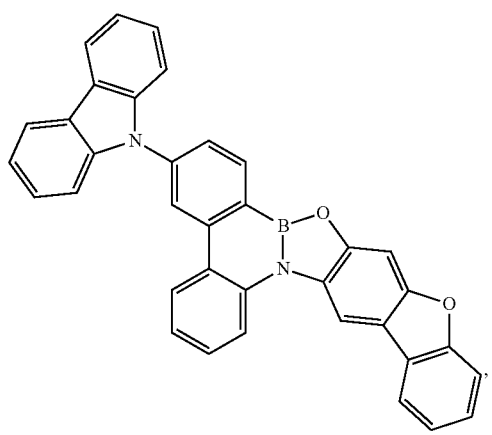
compound 12
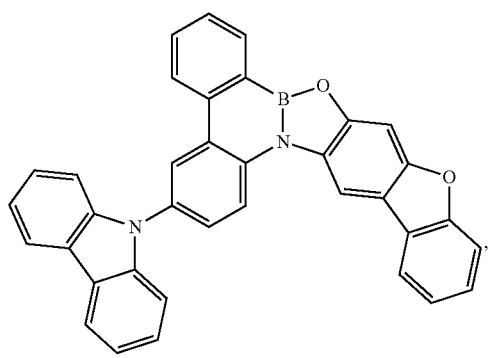
compound 13
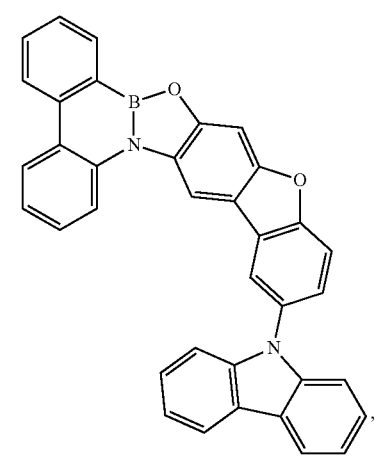
compound 14
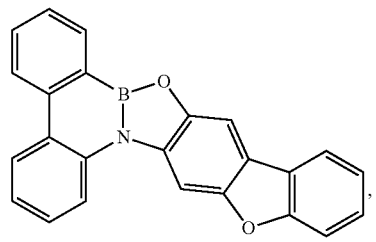
compound 15
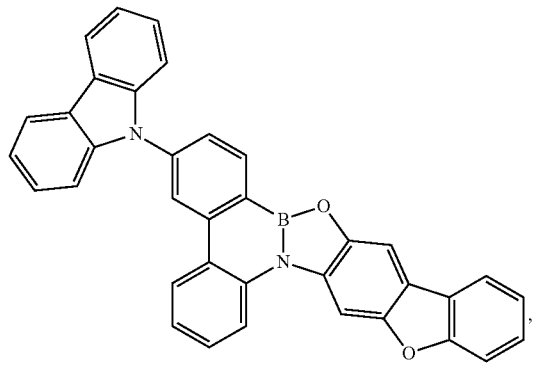
compound 16
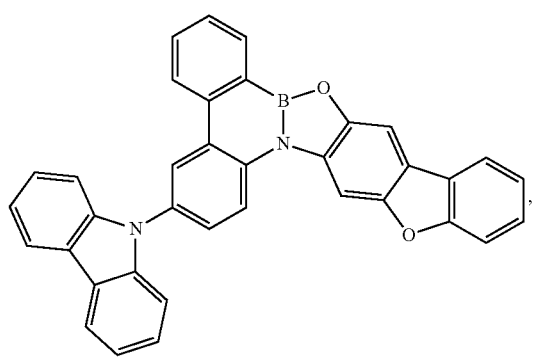
compound 17
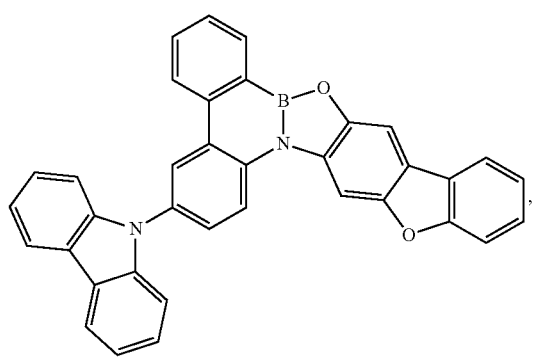
compound 18
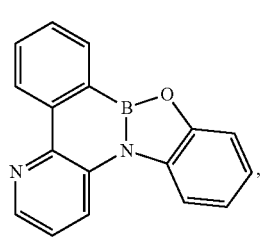

compound 19
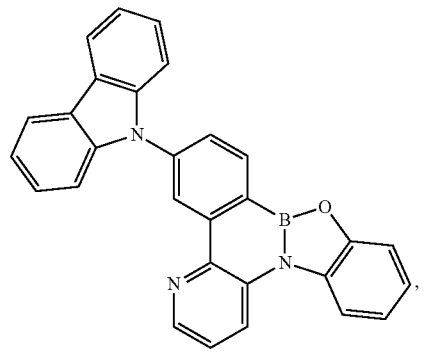
compound 20
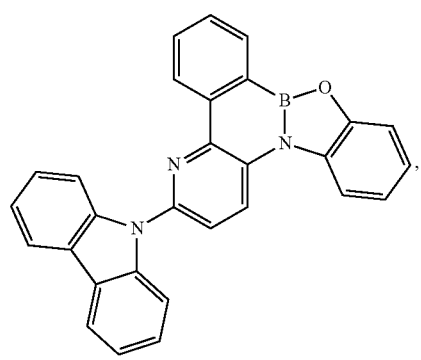
compound 21
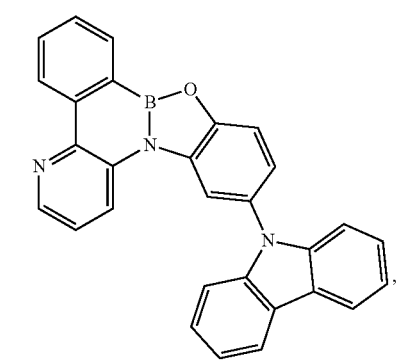
compound 22
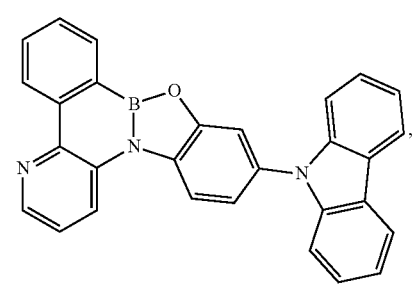
compound 23
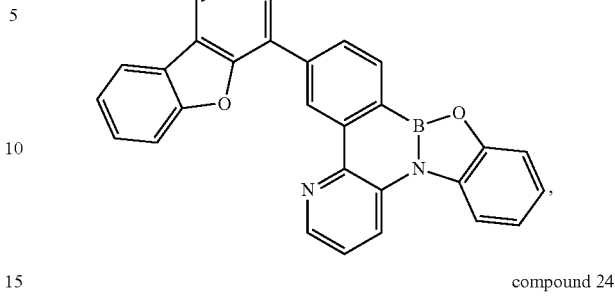
compound 24
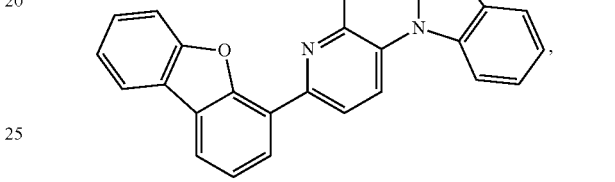
compound 25
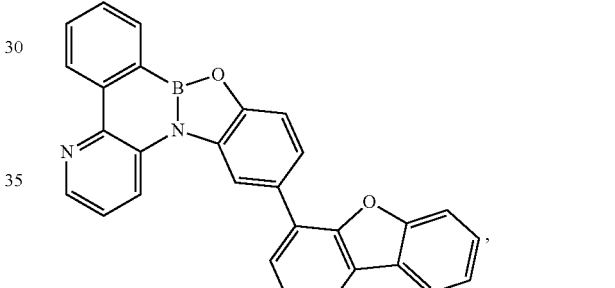
compound 26
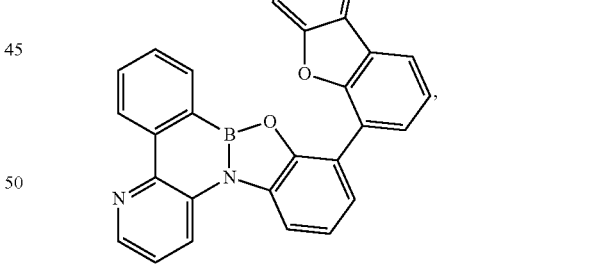
compound 27 compound 28
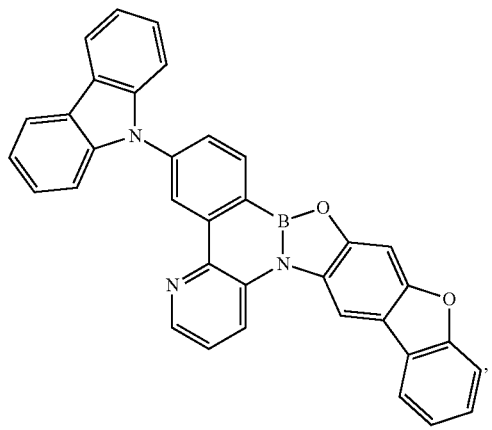
compound 29
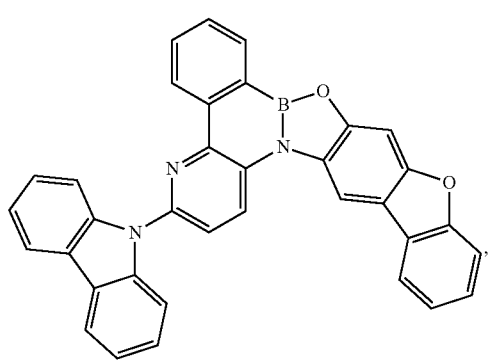
compound 30
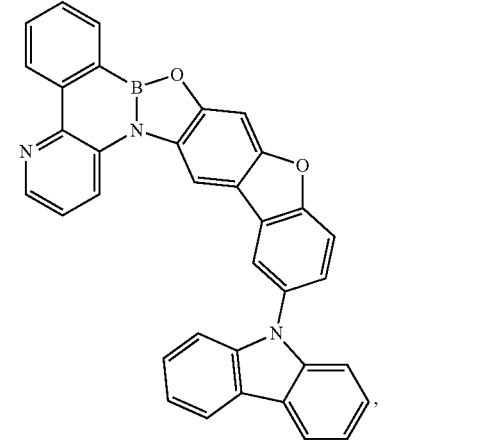
compound 31
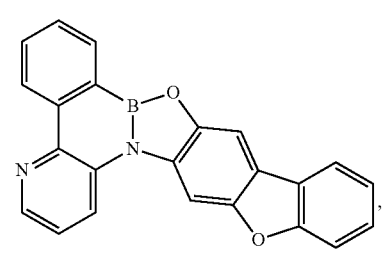
compound 32
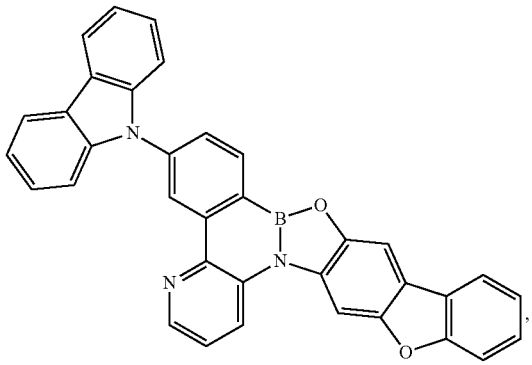
compound 33
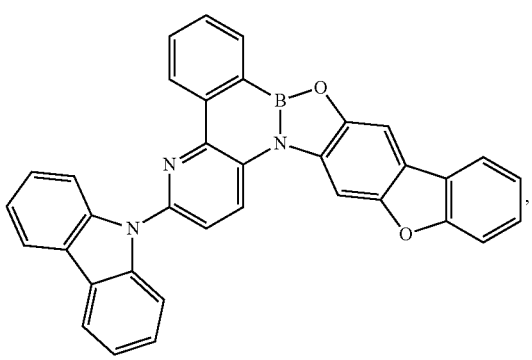
compound 34
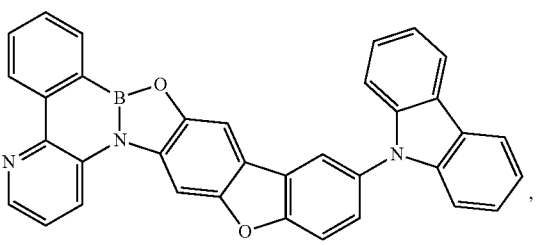
compound 35
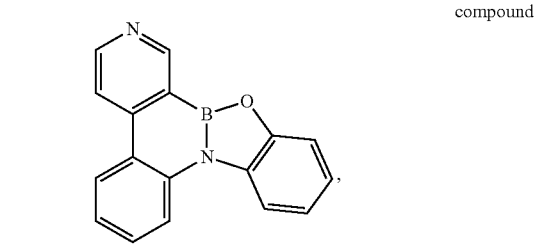
compound 36
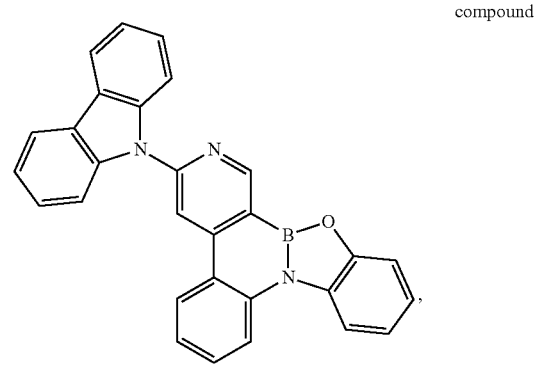

compound 37
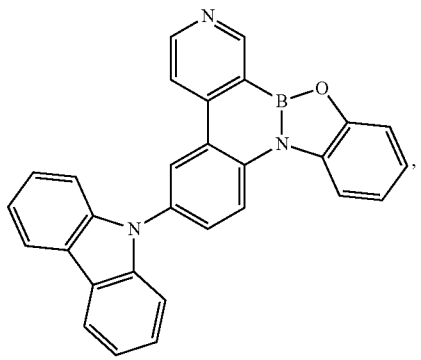
compound 38
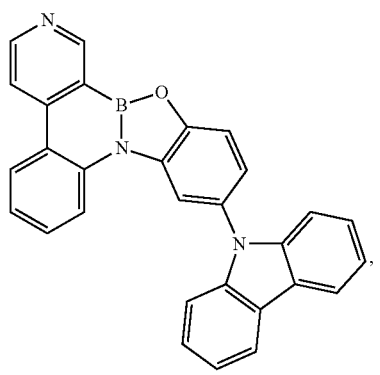
compound 39
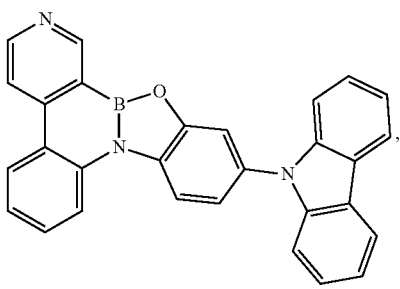
compound 40
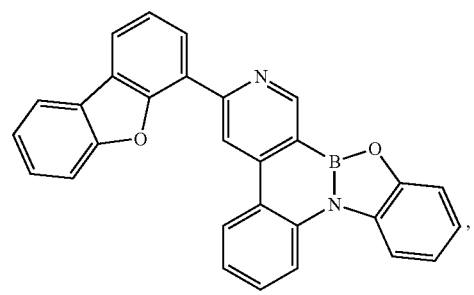
compound 41
compound 42
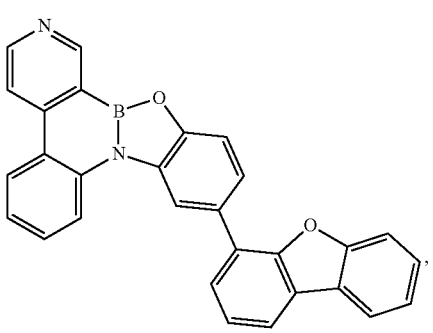
compound 43
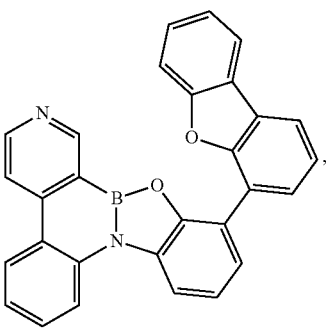
compound 44
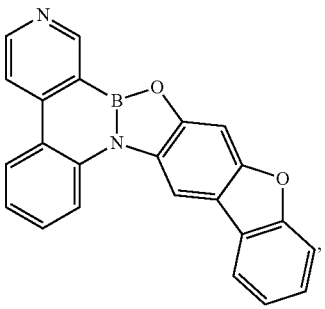
compound 45
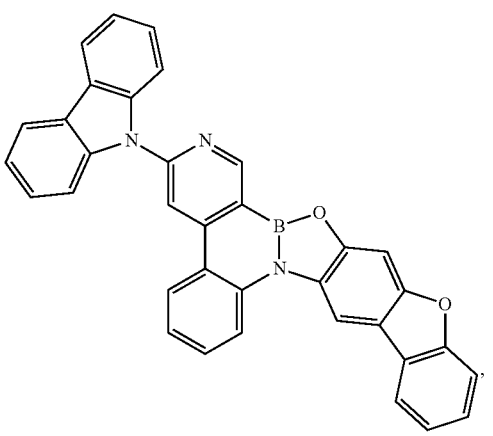

-continued
compound 46
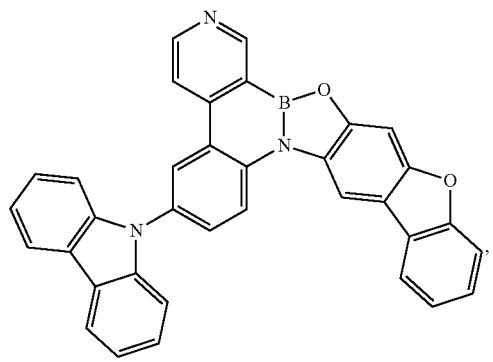
compound 47
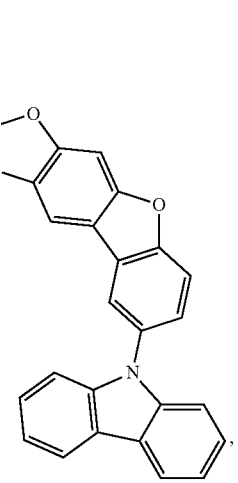
compound 48
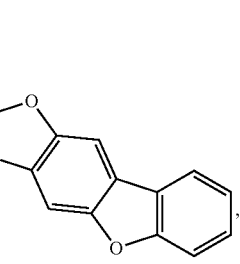
compound 49
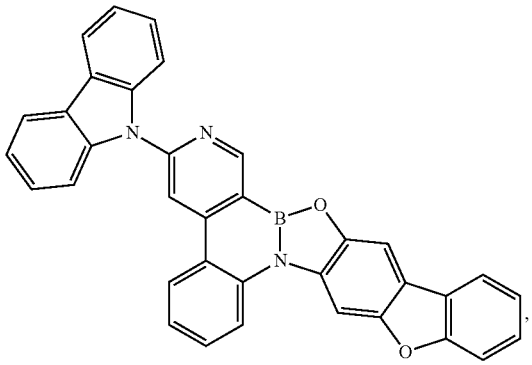
-continued
compound 50
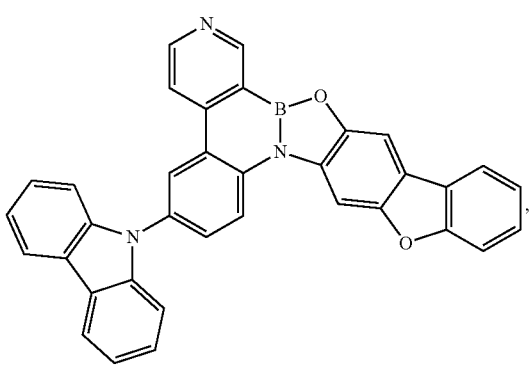
compound 51
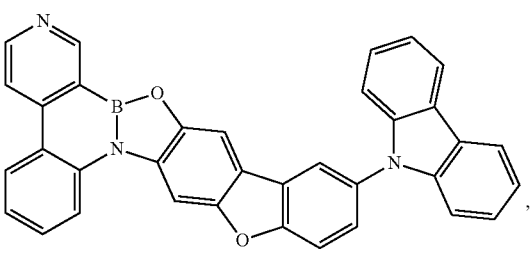
compound 52
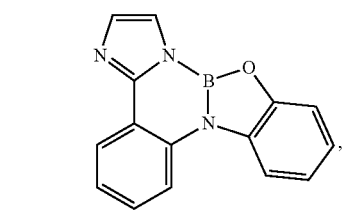
compound 53
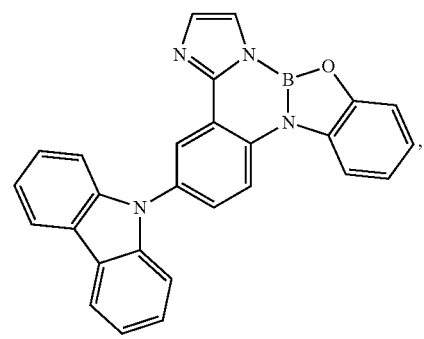
compound 54 compound 55
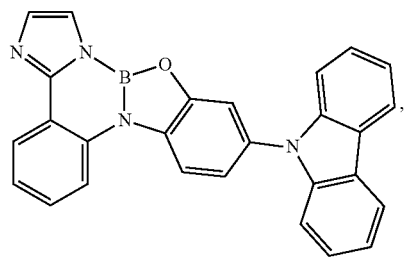
compound 56
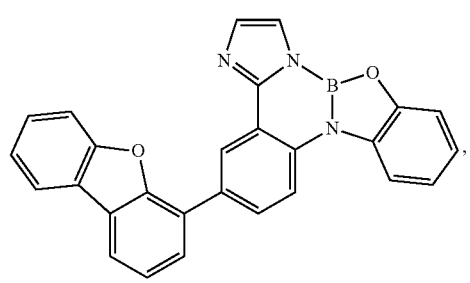
compound 57
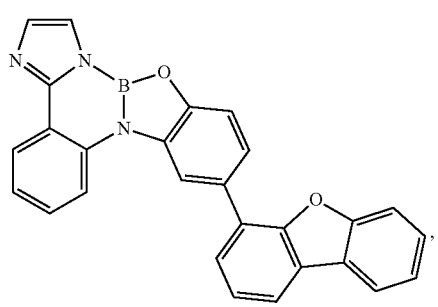
compound 58
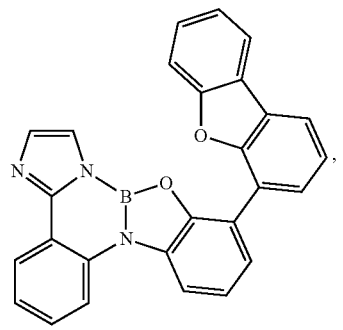
compound 59
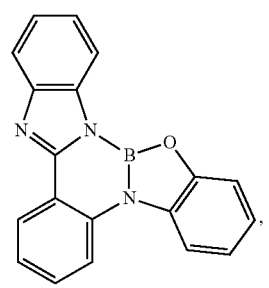
compound 60
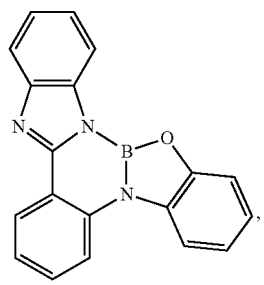
compound 61
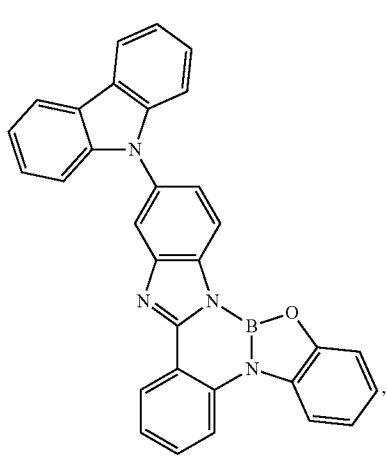
compound 62
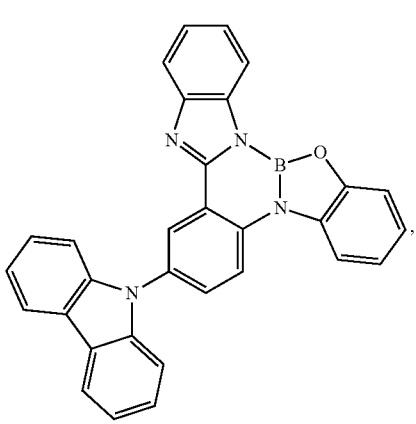
compound 63

-continued
compound 64
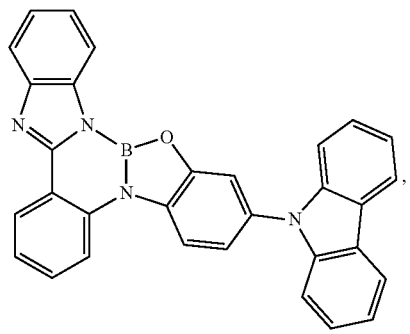
compound 65
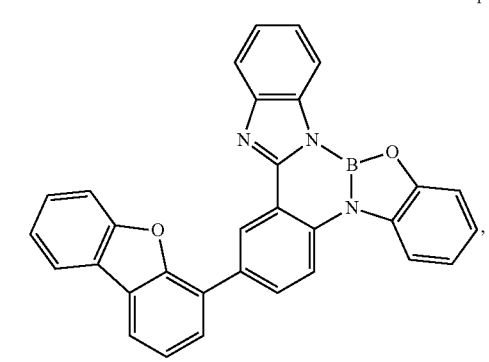
compound 66
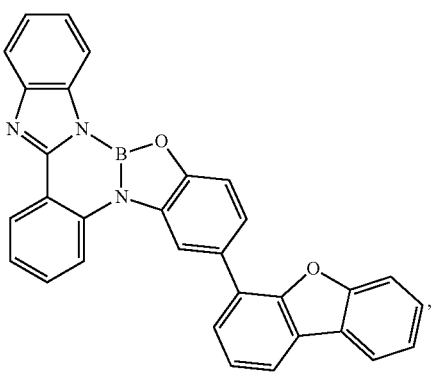
compound 67
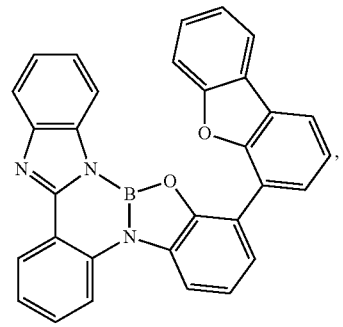
compound 68
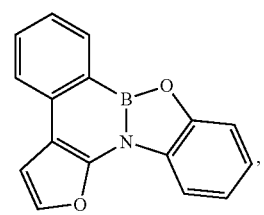
-continued
compound 69
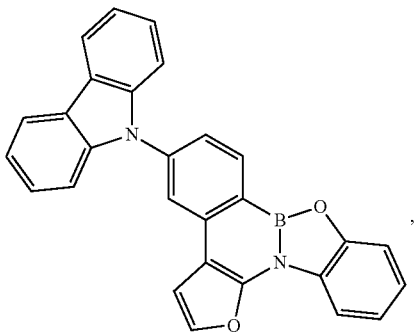
compound 70
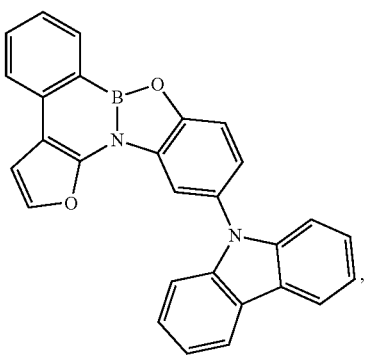
compound 71
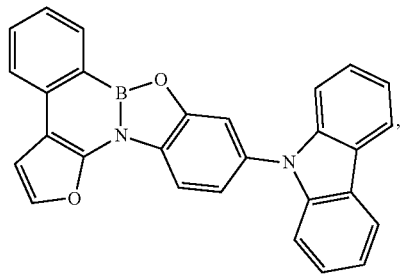
compound 72
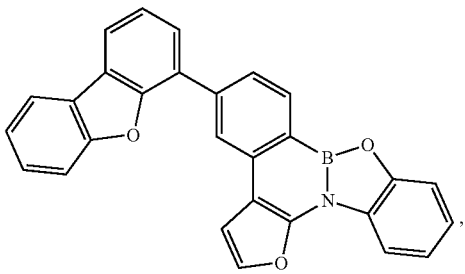
compound 73
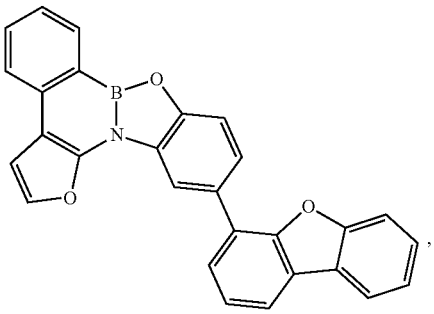

compound 74
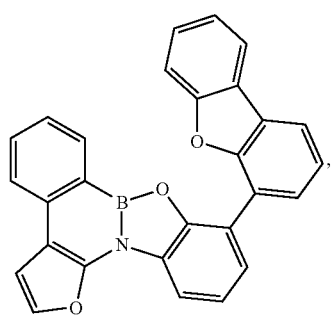
compound 79
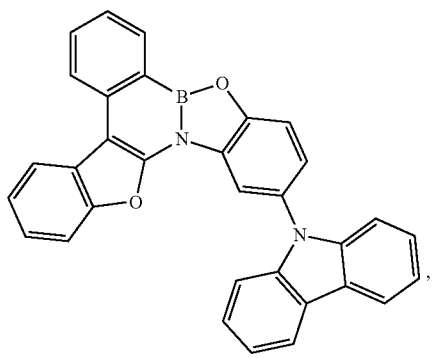
compound 75
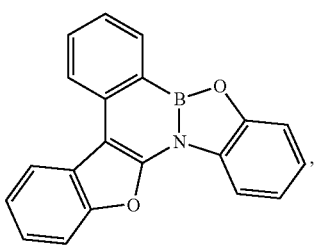
compound 76
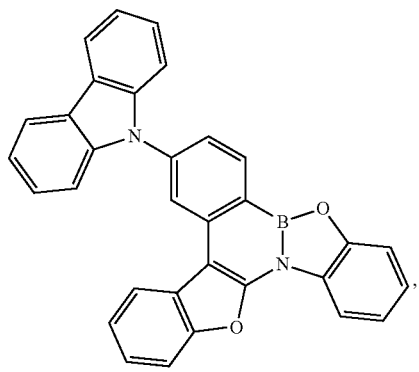
compound 80
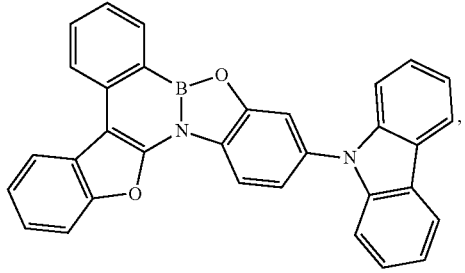
compound 77
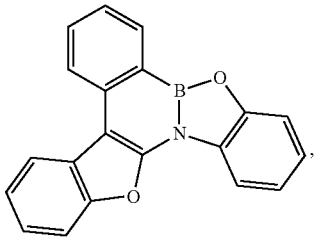
compound 81
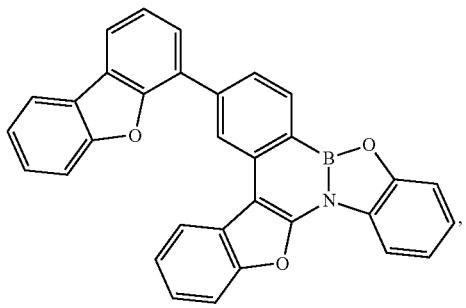
compound 78
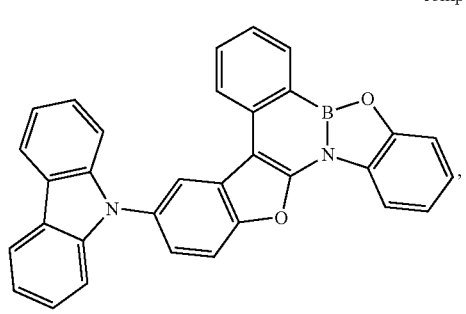
compound 82
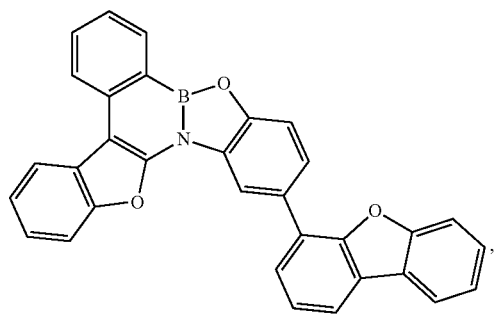

compound 83
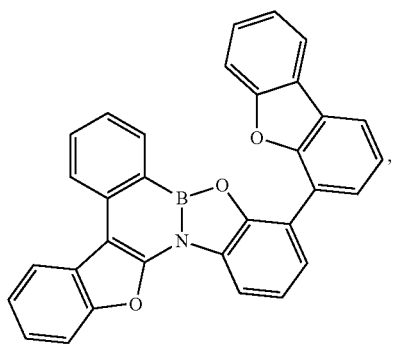
compound 87
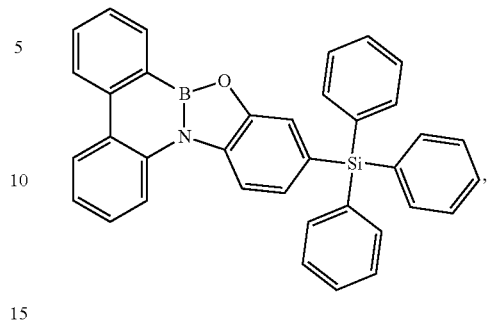
compound 84
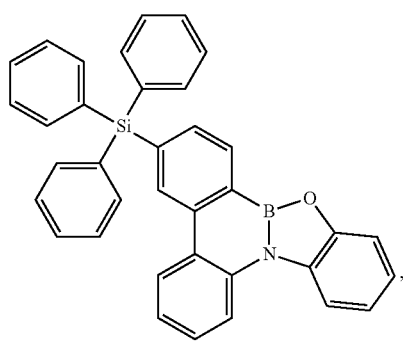
compound 88
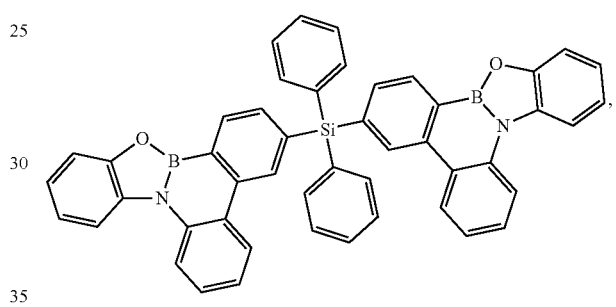
compound 85
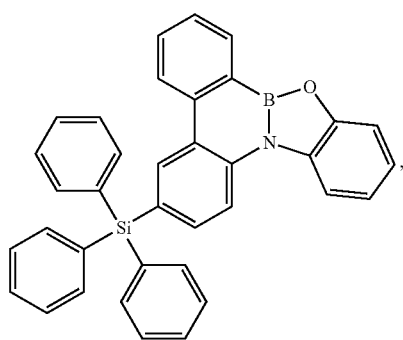
compound 89
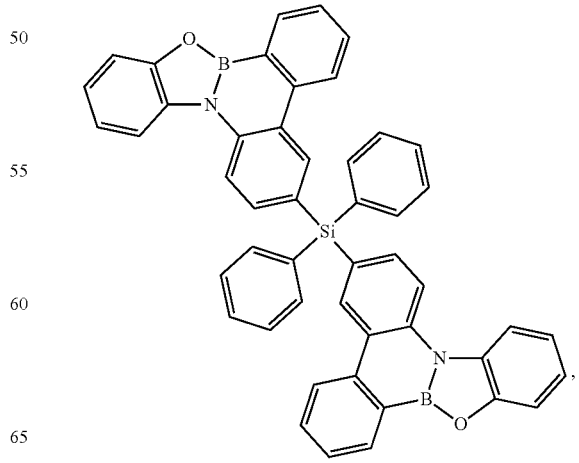
compound 86
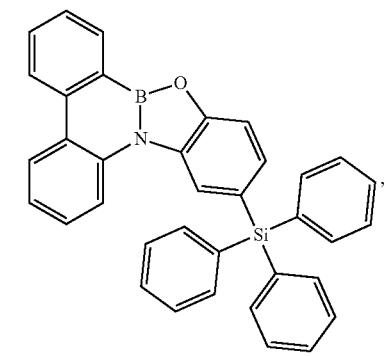

compound 90
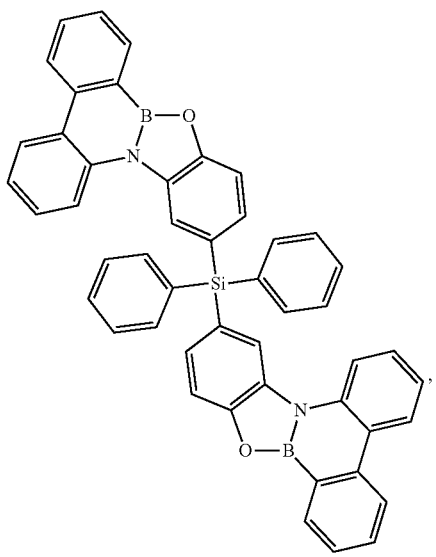
compound 93
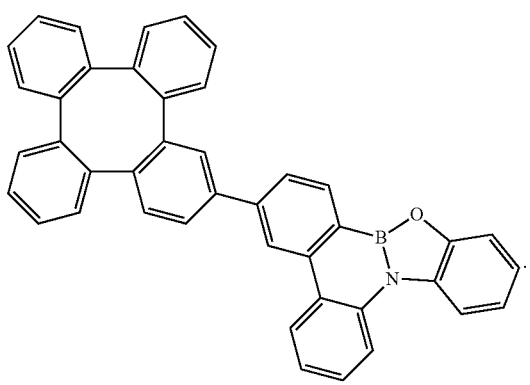
8. The compound of claim 1, wherein $X^1$ is C or N, $R^A$ is aryl or heteroaryl and $R^A$ is connected to $X^1$ to form a fused ring.
9. The compound of claim 1, wherein the compound is selected from the group consisting of:
compound 91
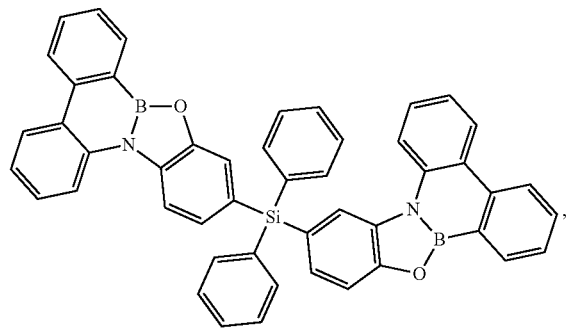
compound 94
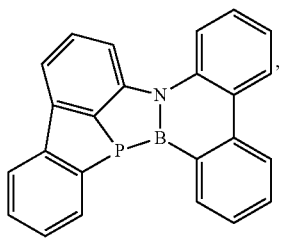
compound 95
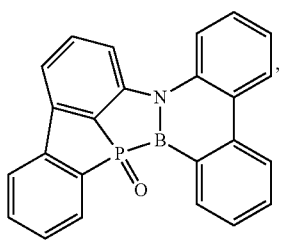
compound 92
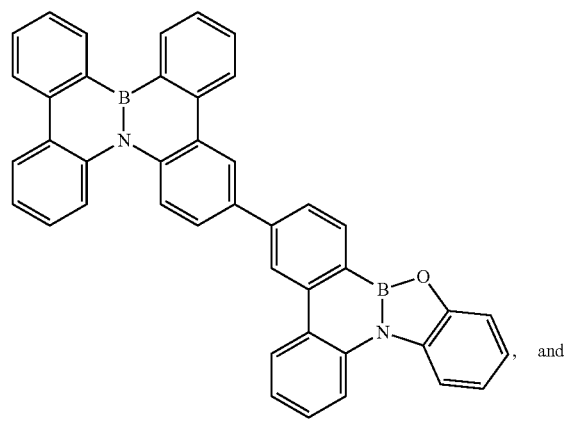, and
compound 96
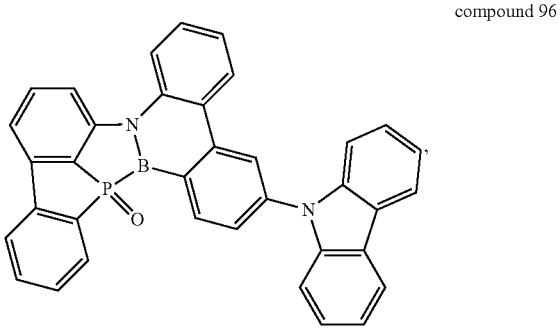, compound 97
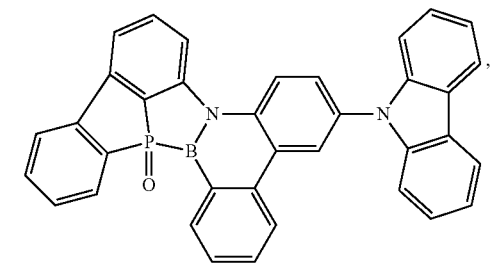
compound 98
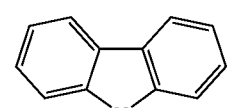
compound 99
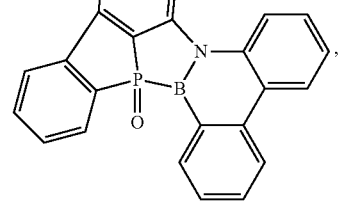
compound 100
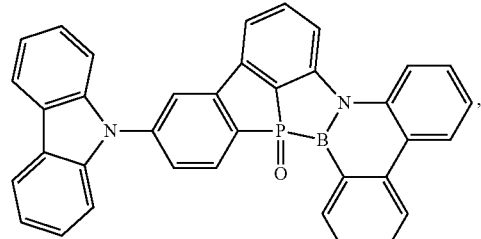
compound 101
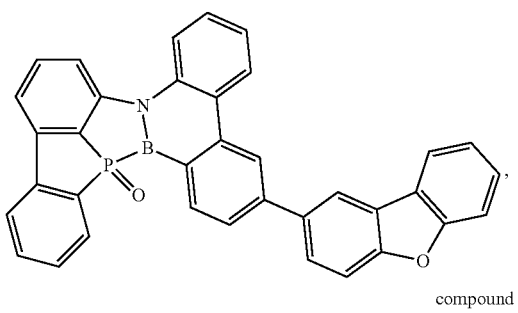
compound 102
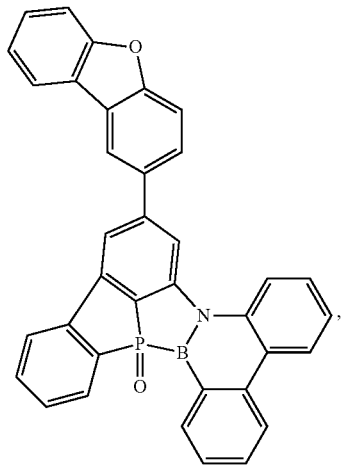
compound 103
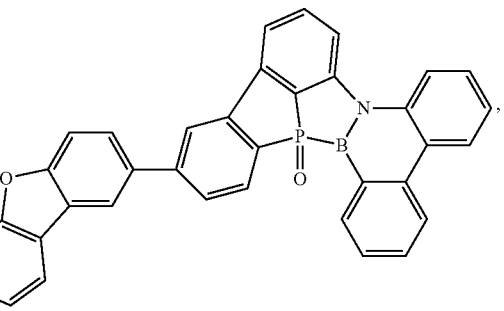
compound 104
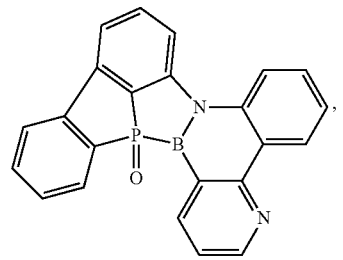
compound 105
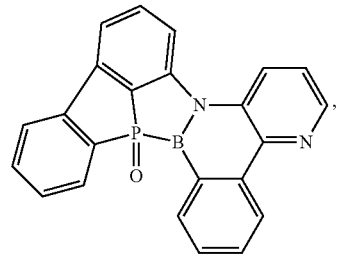
compound 106
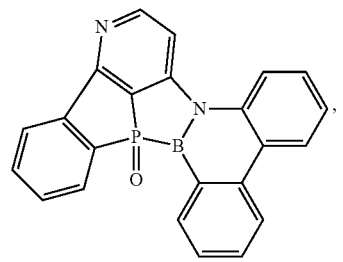

-continued
compound 107
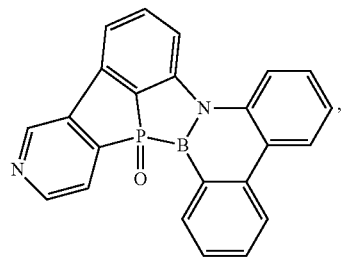
compound 108
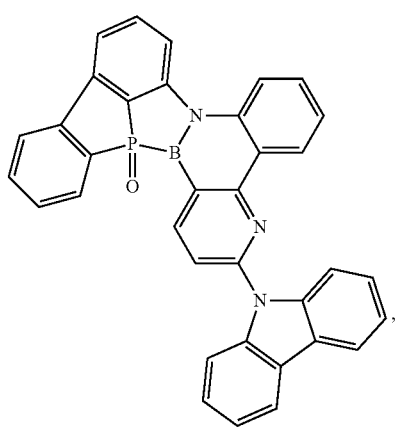
compound 109
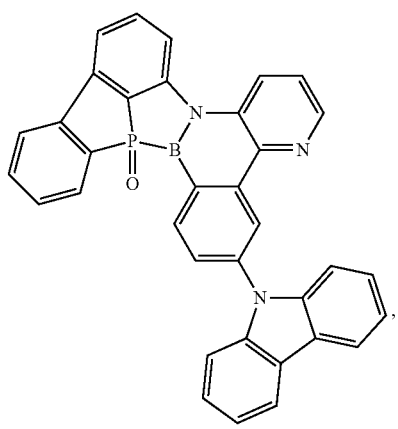
compound 110
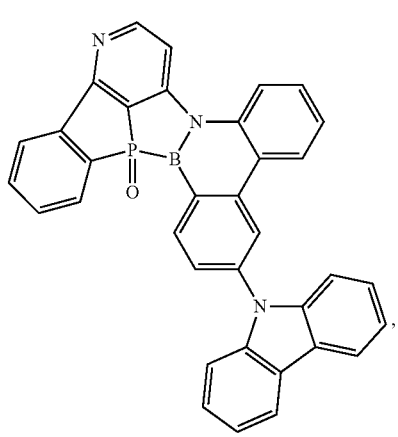
-continued
compound 111
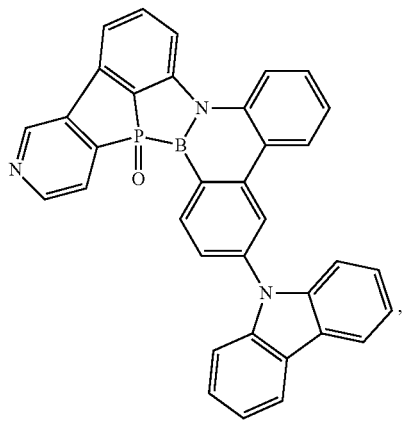
compound 112
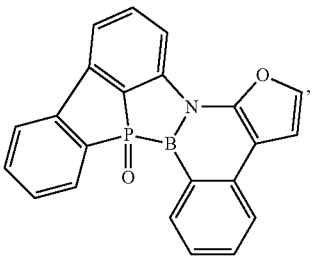
compound 113
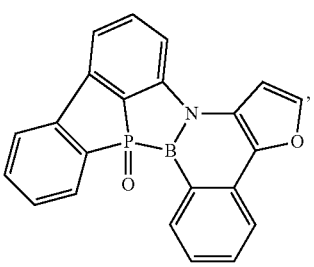
compound 114
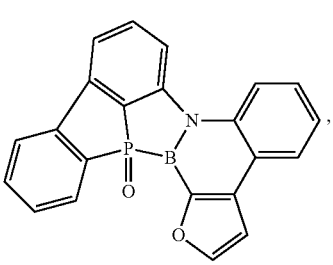
compound 115 compound 116
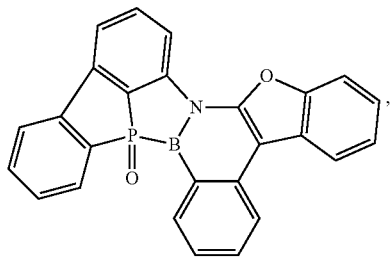
compound 117
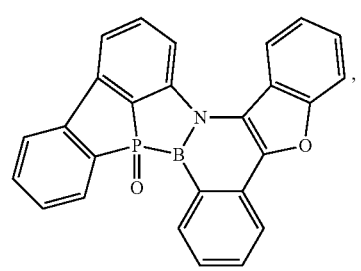
compound 118
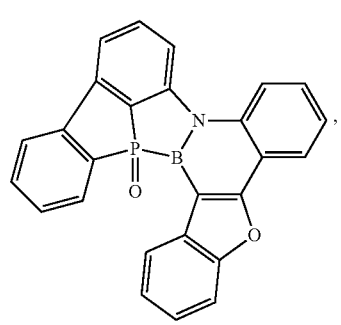
compound 119
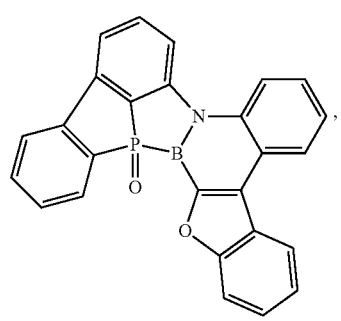
compound 120
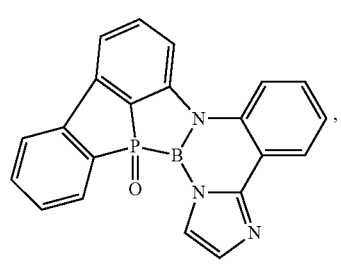
compound 121
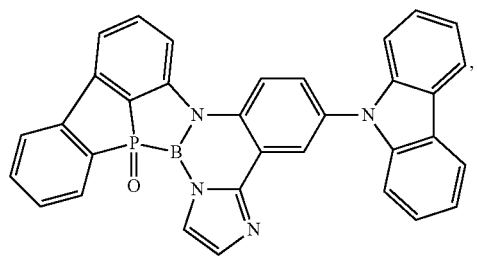
compound 122
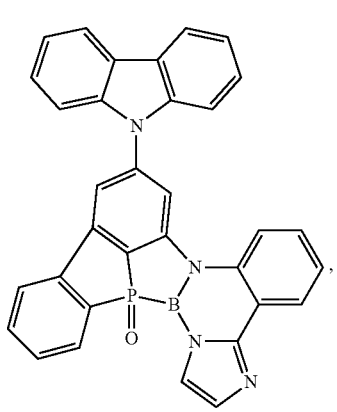
compound 123
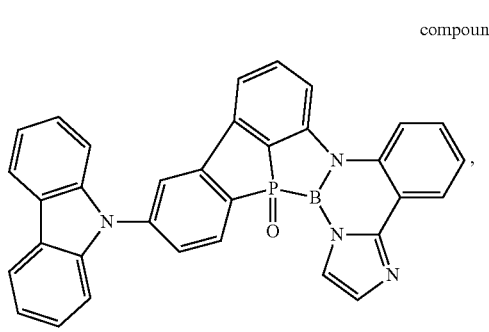
compound 124
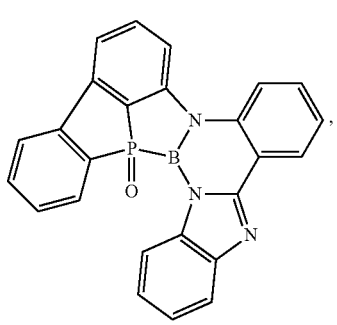

compound 125
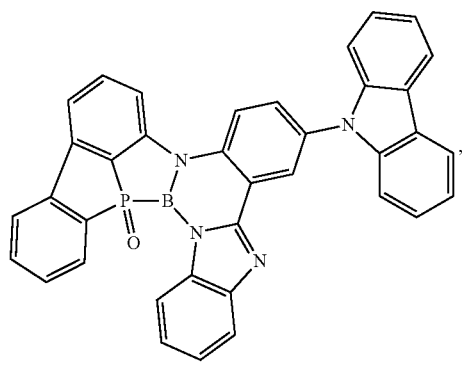
compound 128
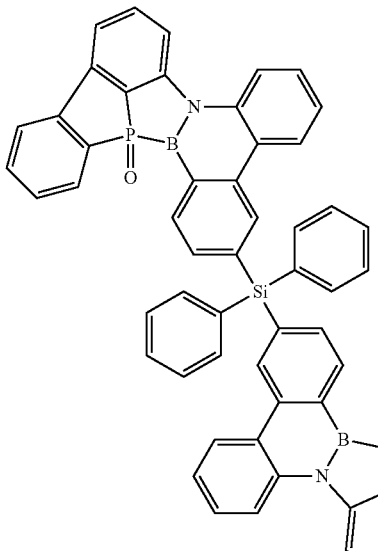
compound 126
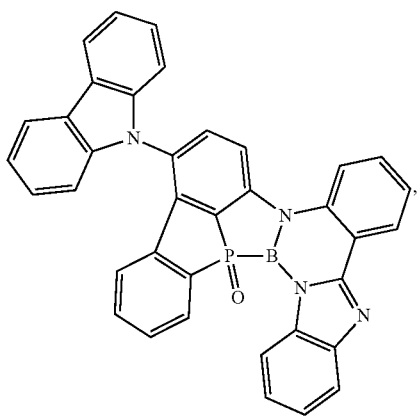
compound 129
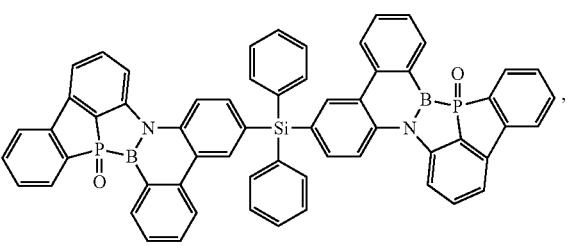
compound 130
compound 127
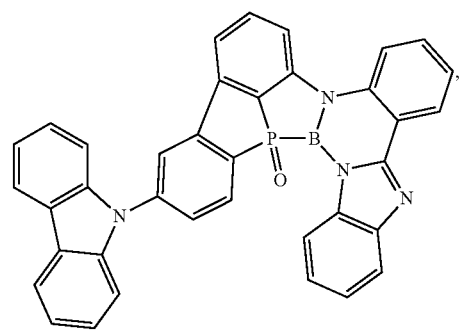
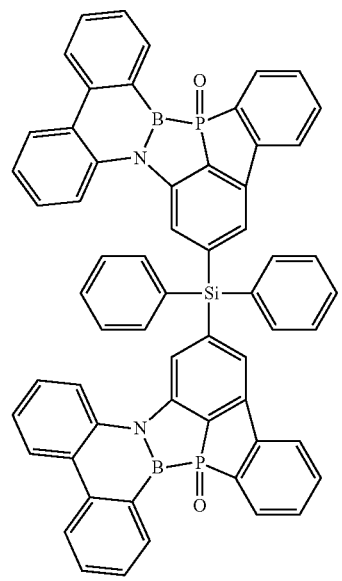
and -continued compound 131

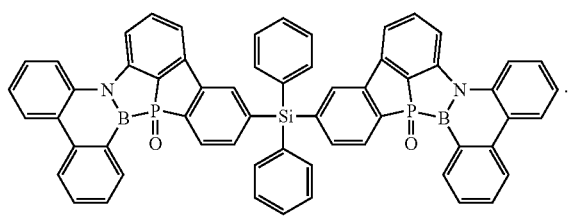

10. The compound of claim 1, wherein (a) at least one $R^1$, $R^2$, or $R^3$ comprises a substituent selected from the group consisting of carbazole, azacarbazole, dibenzofuran, azadibenzofuran, dibenzothiophene, azadibenzothiophene, dibenzoselenophene, azadibenzoselenophene, triphenylene, azatriphenylene, diphenylsilyl, triphenylsilyl, and tetraphenylsilyl;

(b) two adjacent substituents of $R^1$, $R^2$, or $R^3$ form a fused benzo substituent on $R^A$, $R^B$, or $R^C$, respectively; or (c) both (a) and (b) are true.

11. The compound of claim 1, wherein M is coordinated to $Y^1$ and $Y^2$, and the compound has the formula:

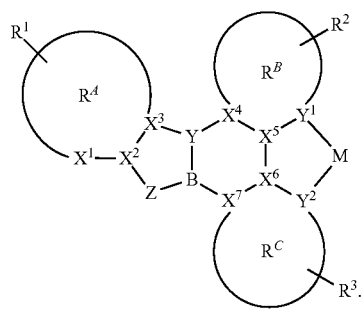

12. The compound of claim 11, wherein M is selected from the group consisting of Ir, Rh, Re, Ru, Os, Pt, Au, and Cu.

13. The compound of claim 11, wherein one of $Y^1$ and $Y^2$ is nitrogen and the other one of $Y^1$ and $Y^2$ is carbon; or one of $Y^1$ and $Y^2$ is neutral carbene carbon and the other one of $Y^1$ and $Y^2$ is anionic carbon.

14. The compound of claim 11, wherein the compound is selected from the group consisting of:

Compound M1

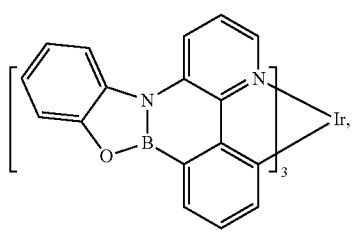

Compound M2

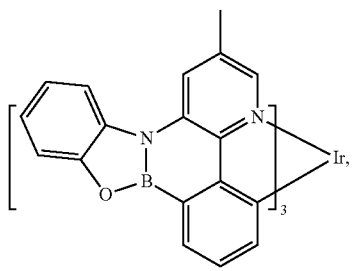

Compound M3

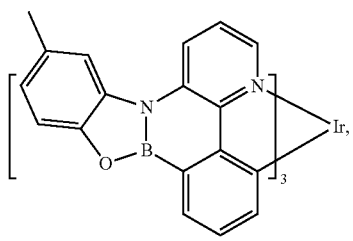

Compound M4

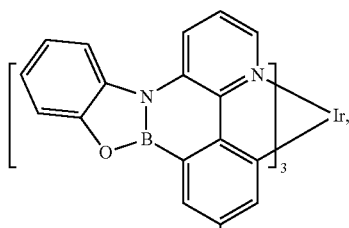

Compound M5

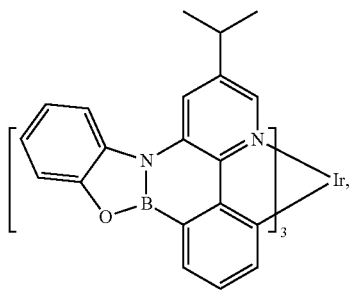

Compound M6

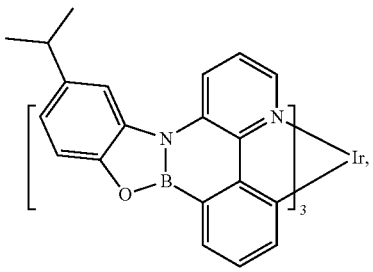

Compound M7

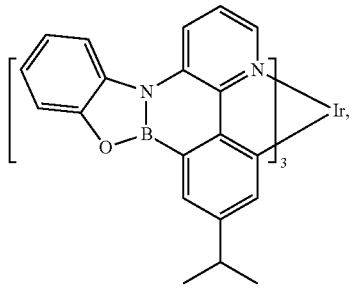

Compound M8
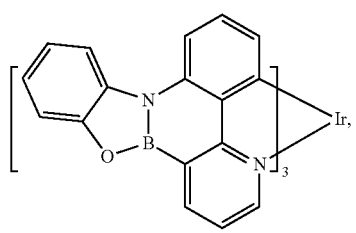
Compound M9
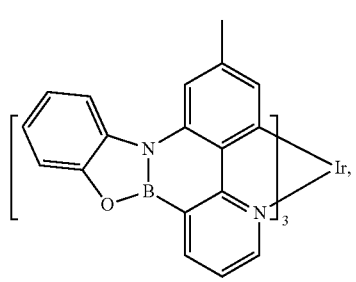
Compound M10
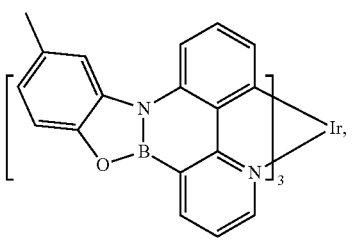
Compound M11
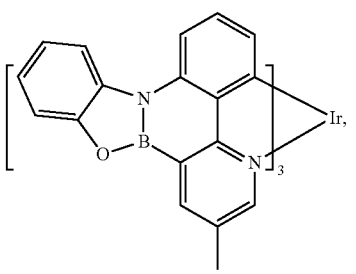
Compound M12
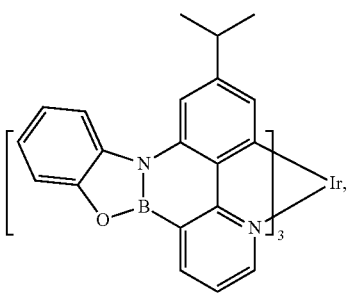
Compound M13
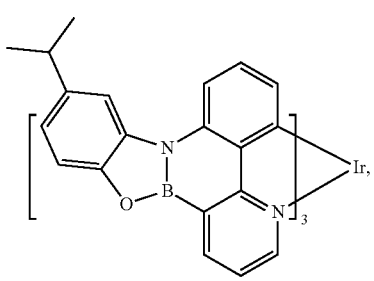
Compound M14
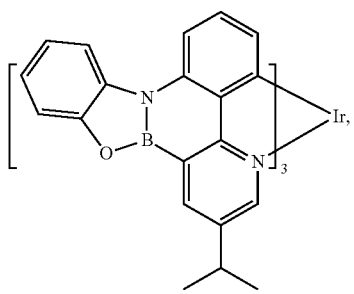
Compound M15
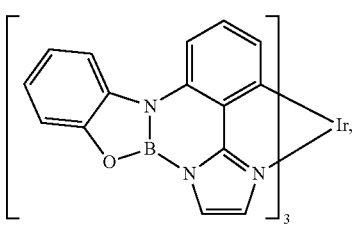
Compound M16
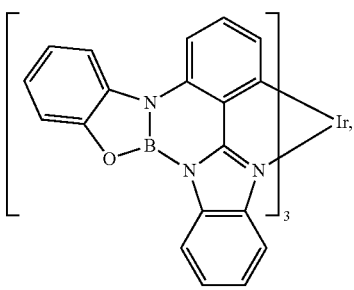
Compound M17
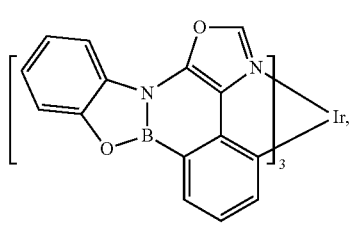
Compound M18
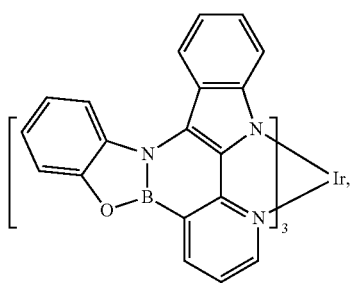
Compound M19
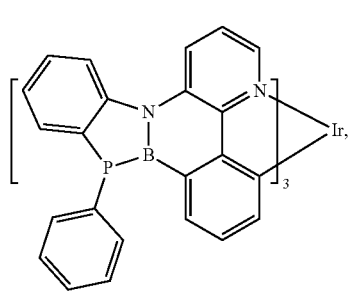

Compound M20
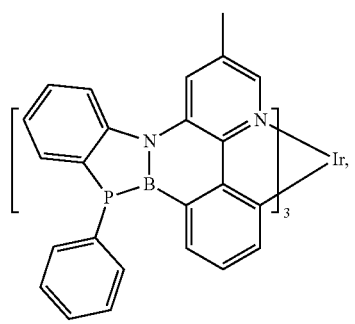
Compound M21
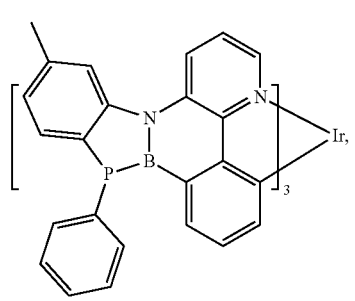
Compound M22
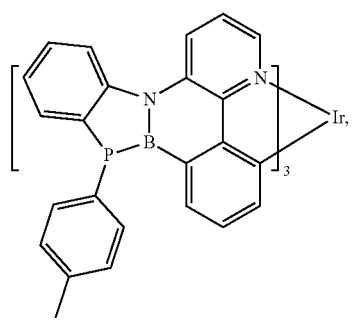
Compound M23
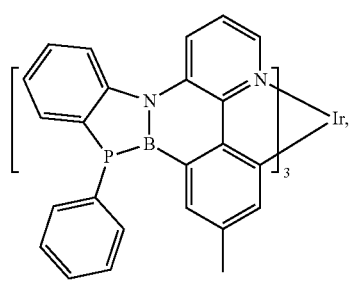
Compound M24
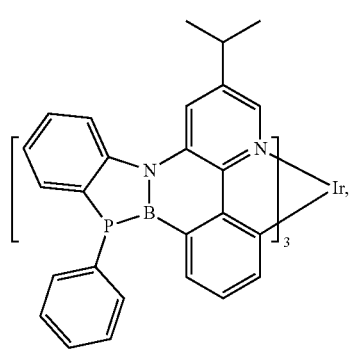
Compound M25
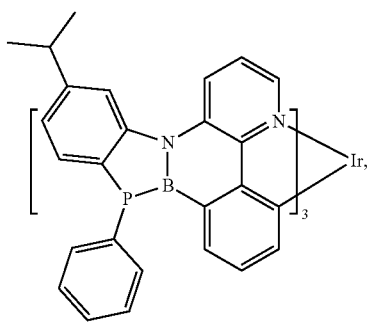
Compound M26
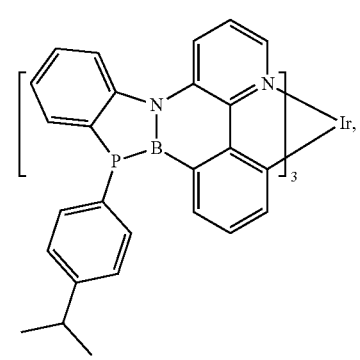
Compound M27
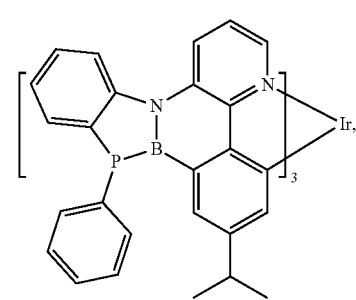
Compound M28
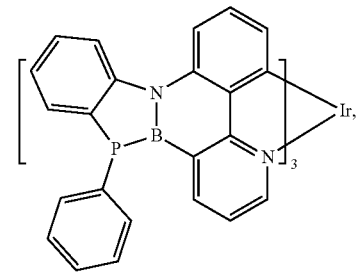

Compound M29
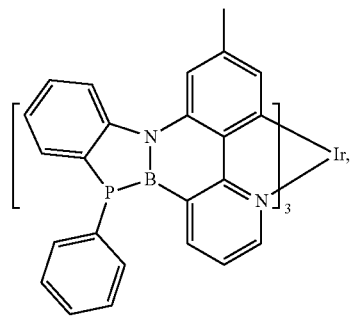
Compound M30
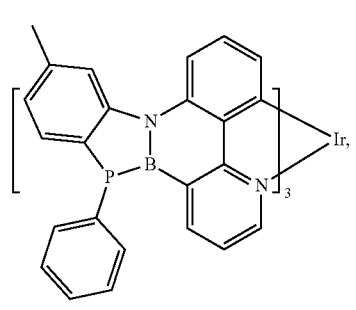
Compound M31
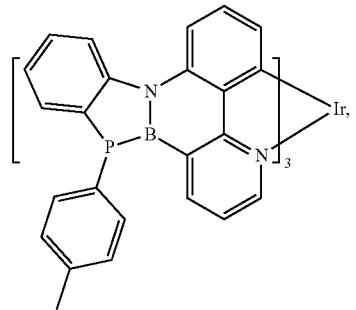
Compound M32
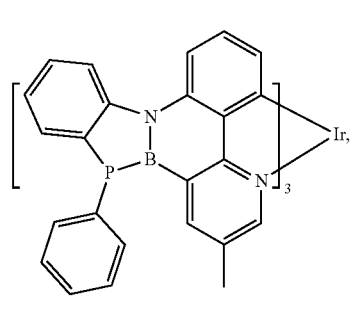
Compound M33
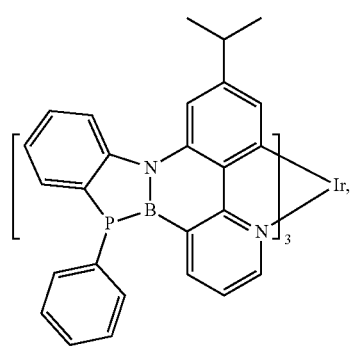
Compound M34
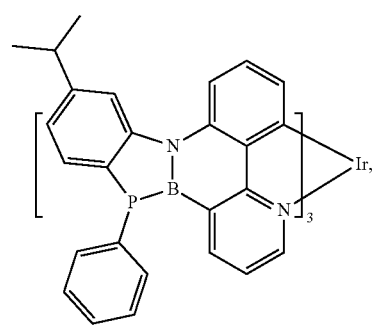
Compound M35
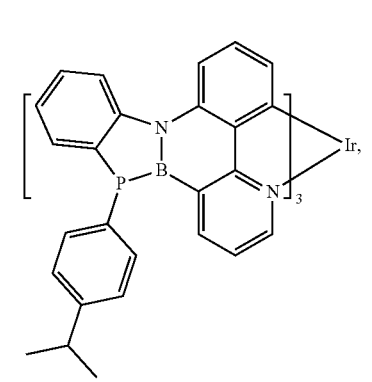
Compound M36
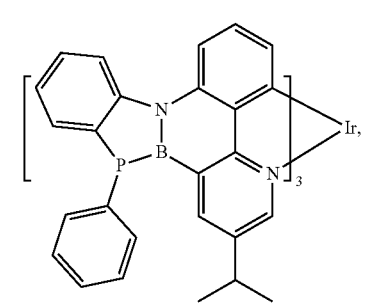
Compound M37
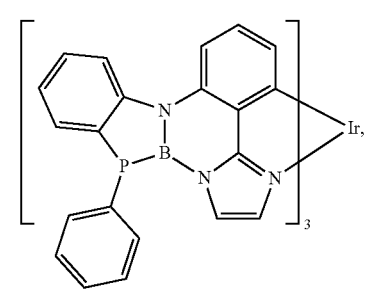
Compound M38
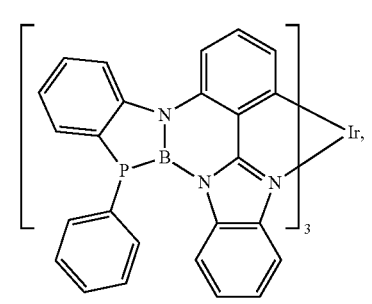

-continued
Compound M39
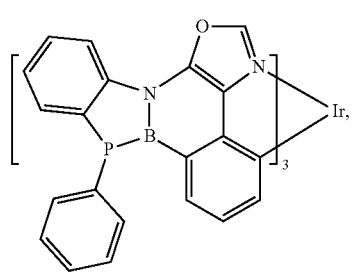
Compound M40
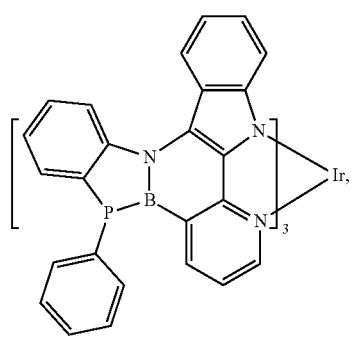
Compound M41
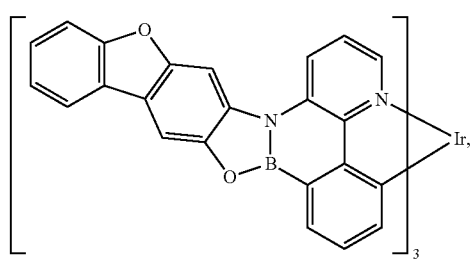
Compound M42
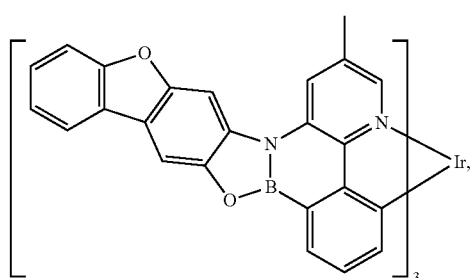
Compound M43
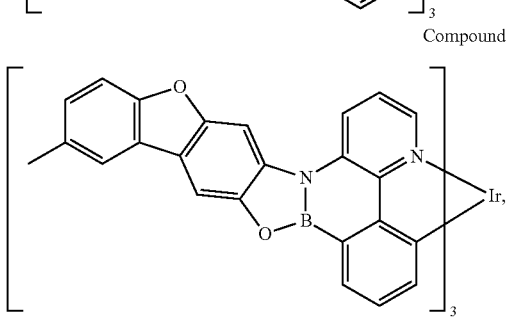
-continued
Compound M44
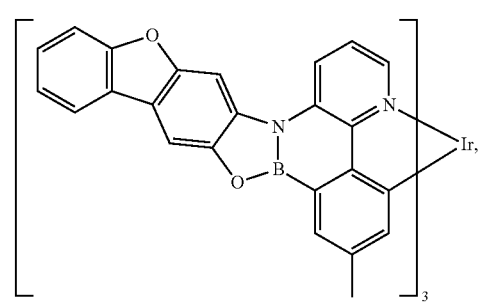
Compound M45
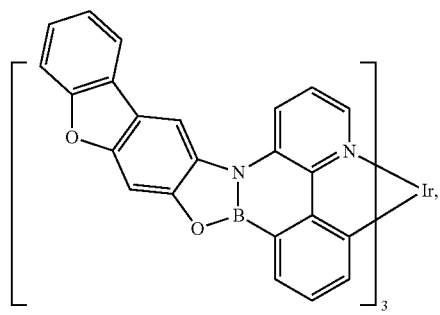
Compound M46
Compound M47
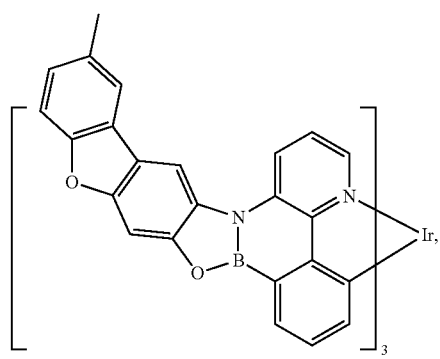

Compound M48
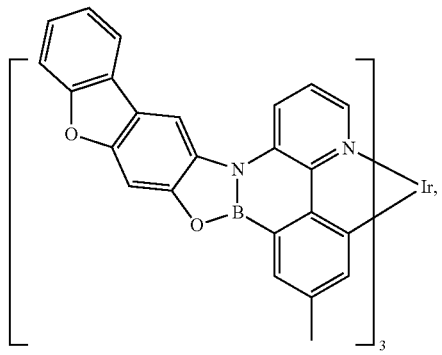
Compound M49
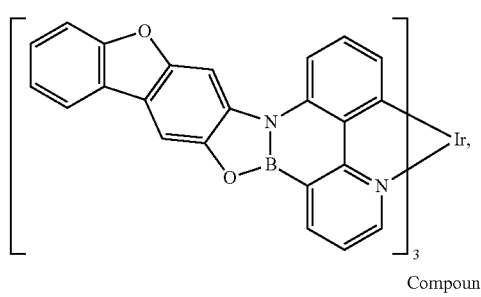
Compound M50
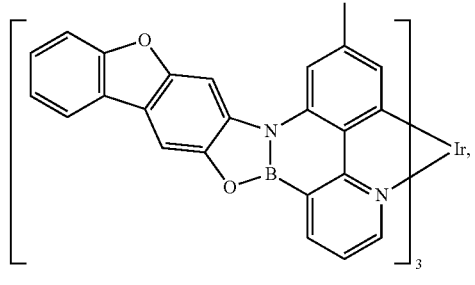
Compound M51
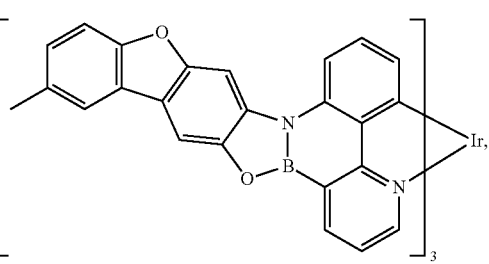
Compound M52
Compound M53
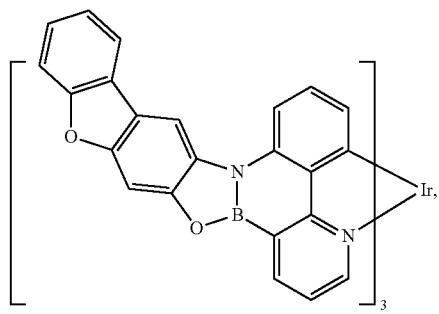
Compound M54
Compound M55
Compound M56
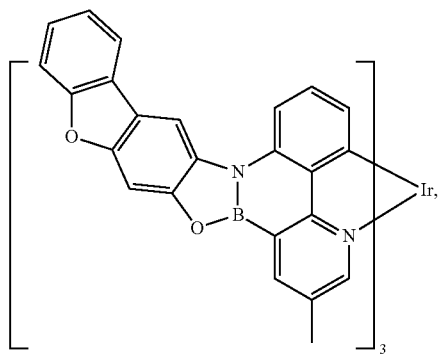

Compound M57
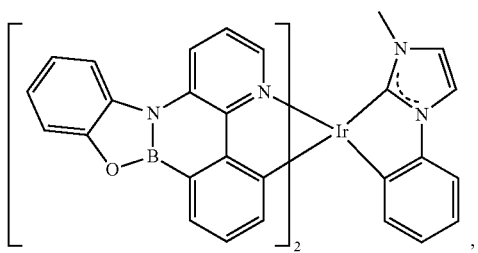
Compound M58
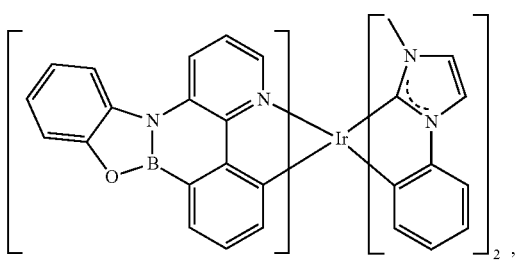
Compound M59
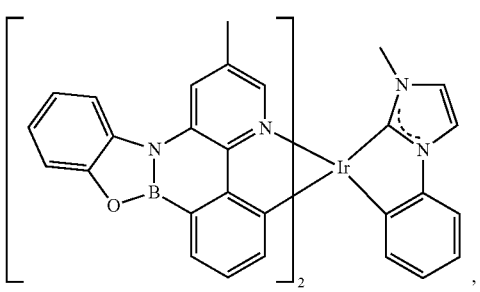
Compound M60
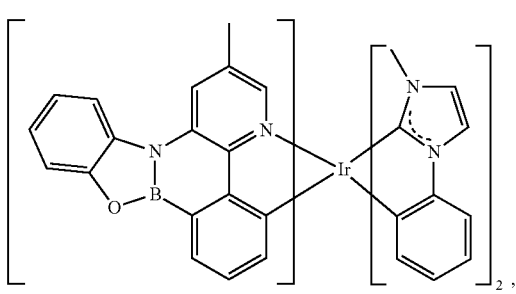
Compound M61
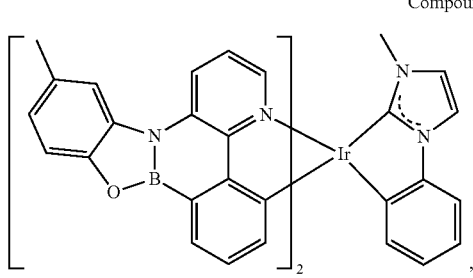
Compound M62
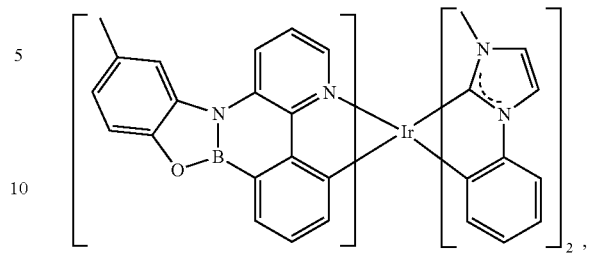
Compound M63
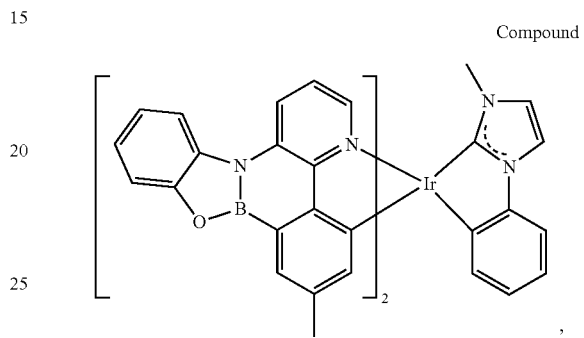
Compound M64
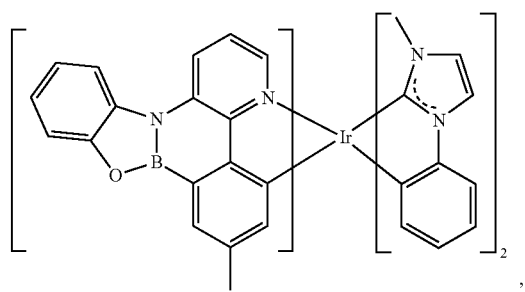
Compound M65
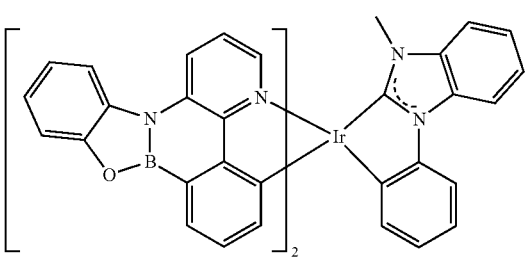
Compound M66
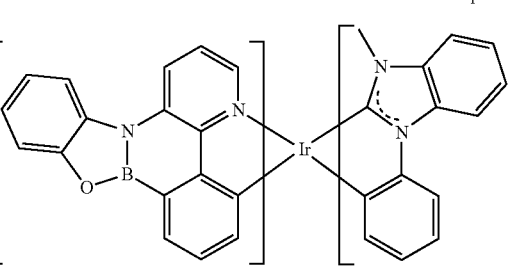

-continued
Compound M67
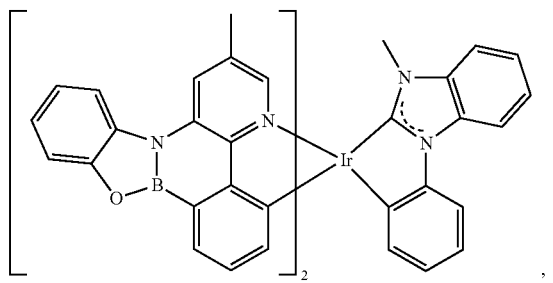
Compound M68
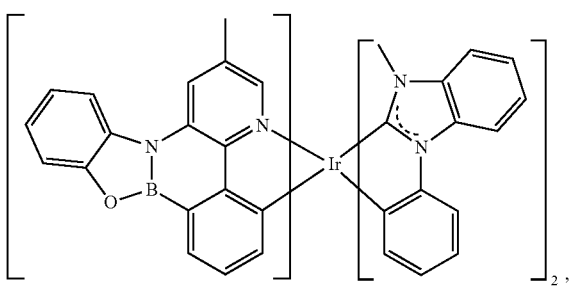
Compound M69
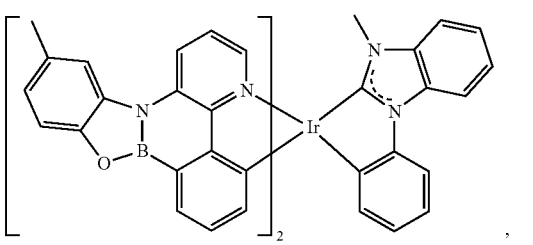
Compound M70
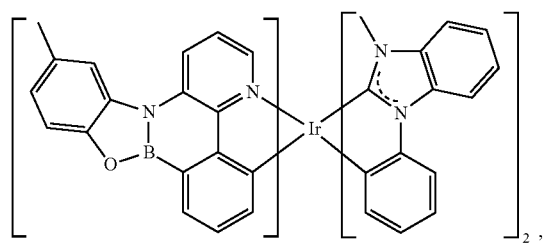
Compound M71
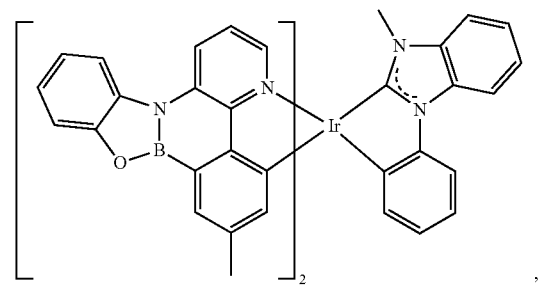
-continued
Compound M72
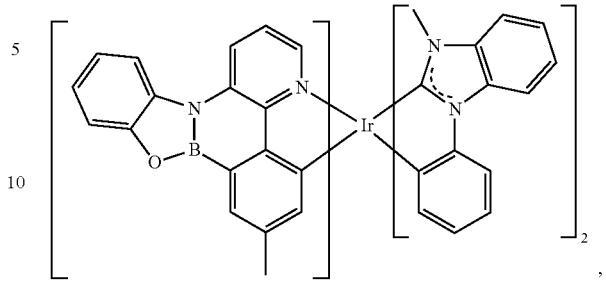
Compound M73
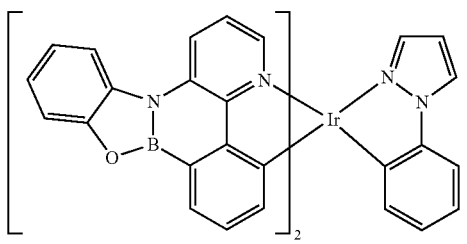
Compound M74
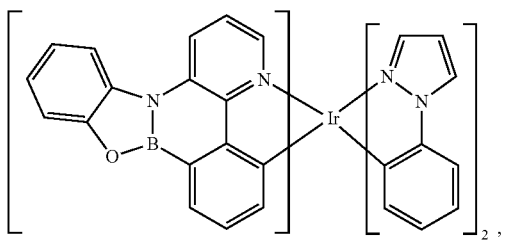
Compound M75
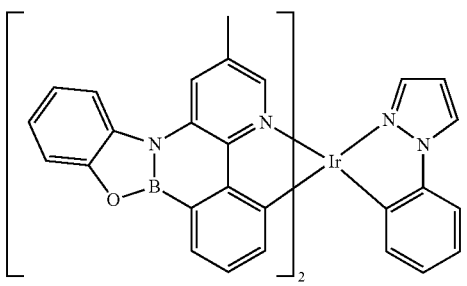
Compound M76
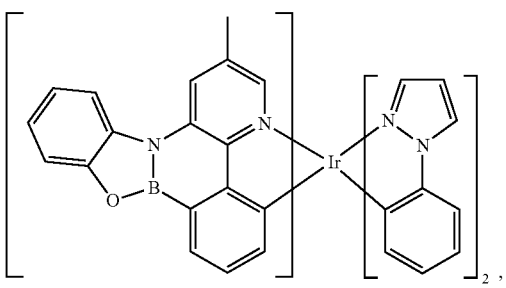

Compound M77
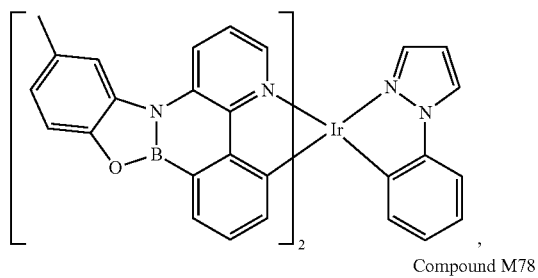
Compound M78
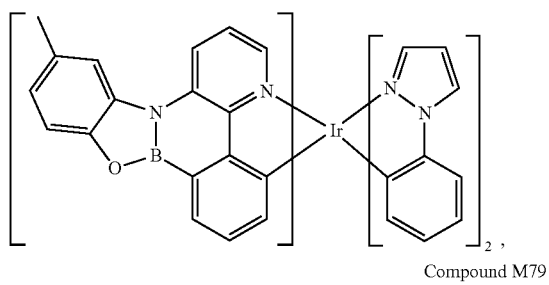
Compound M79
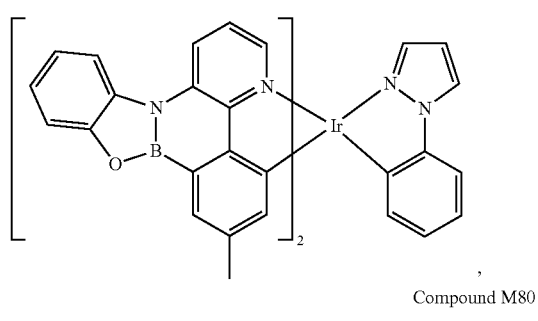
Compound M80
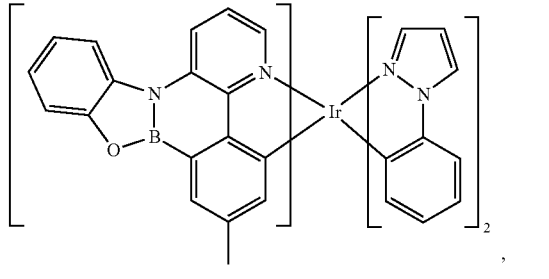
Compound M81
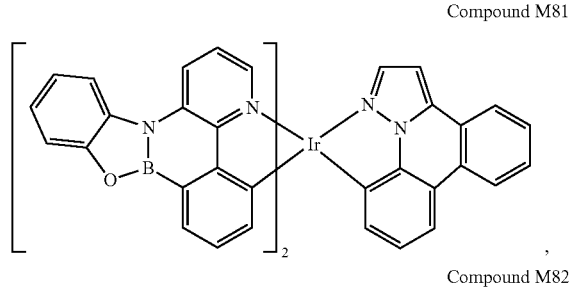
Compound M82
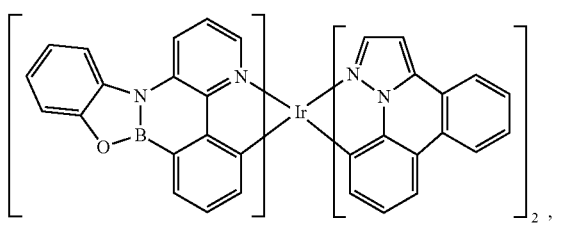
Compound M83
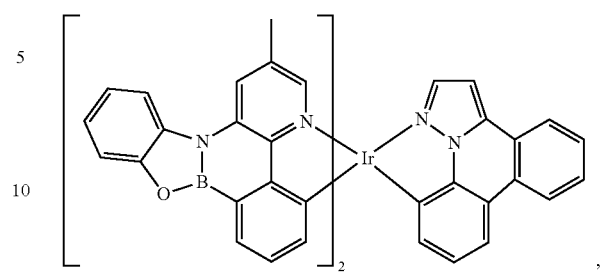
Compound M84
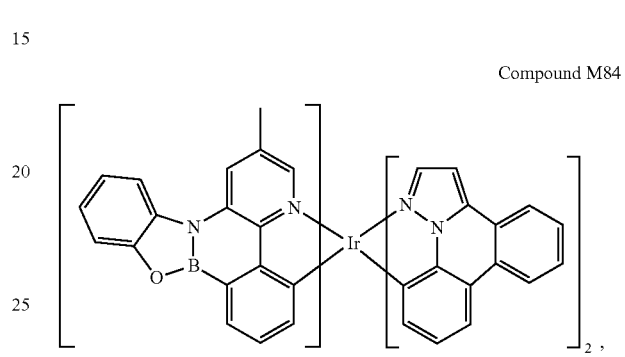
Compound M85
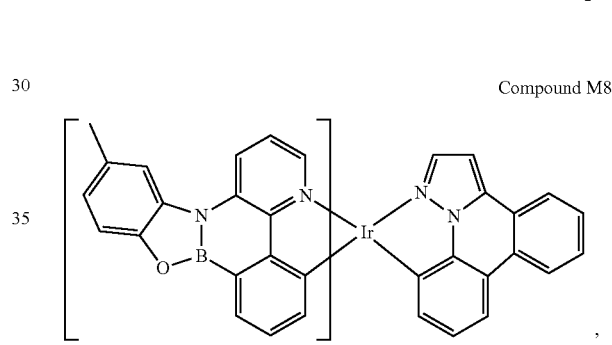
Compound M86
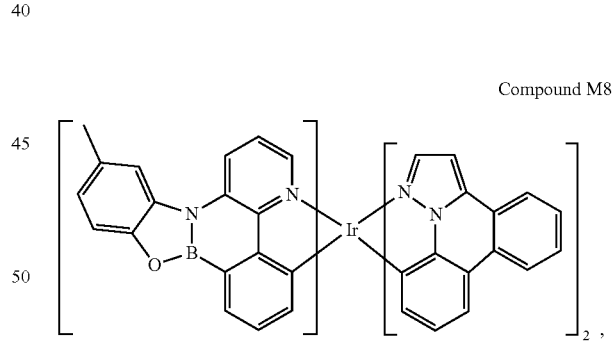
Compound M87
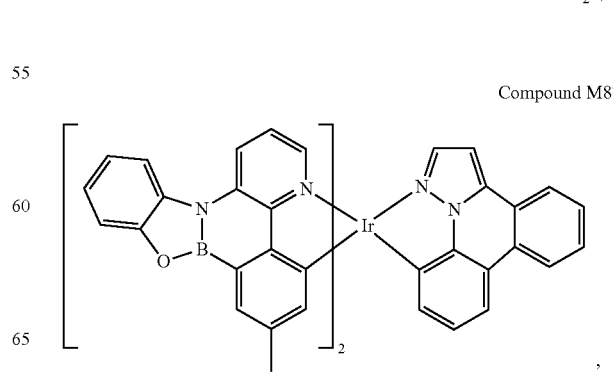

Compound M88
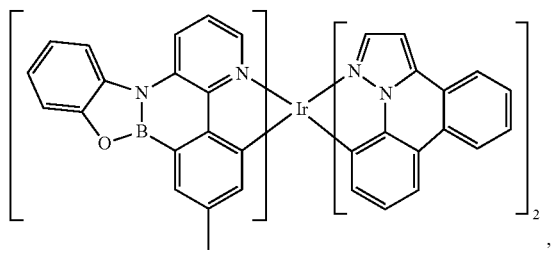
Compound M93
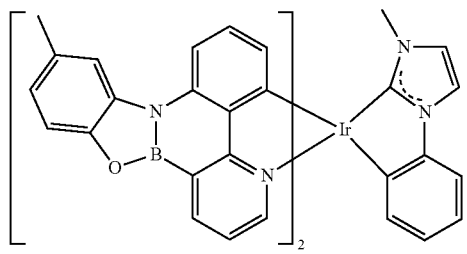
Compound M89
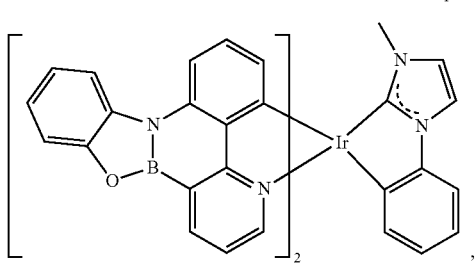
Compound M94
Compound M90
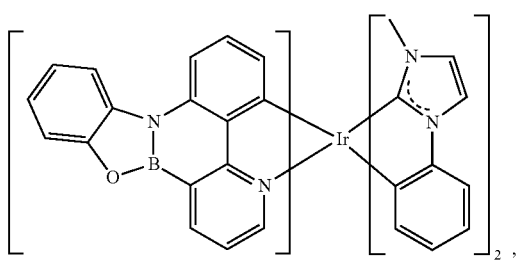
Compound M95
Compound M91
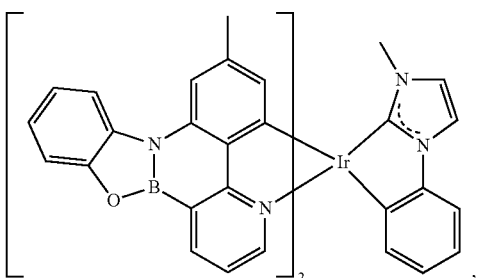
Compound M96
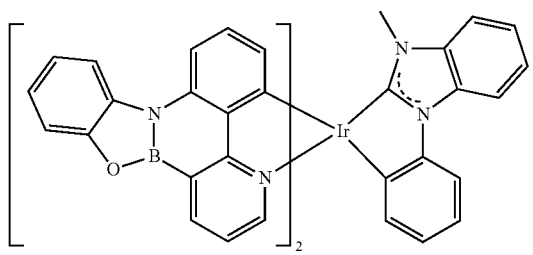
Compound M92
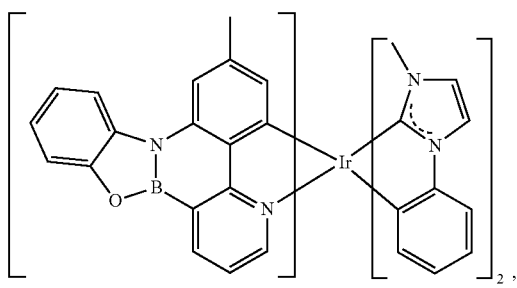
Compound M97

Compound M98
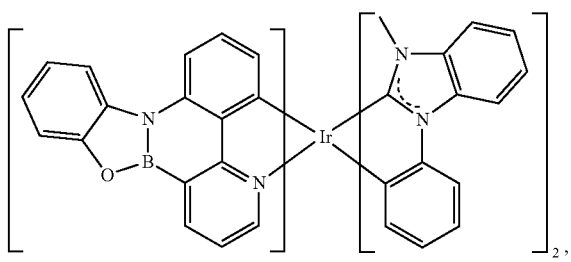
Compound M103
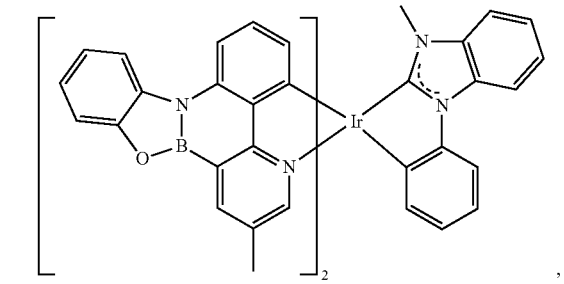
Compound M99
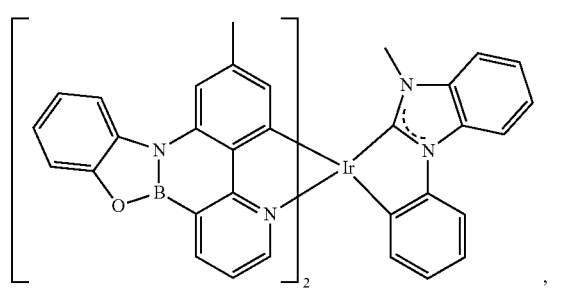
Compound M104
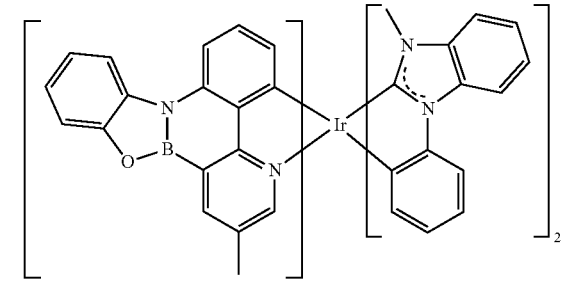
Compound M100
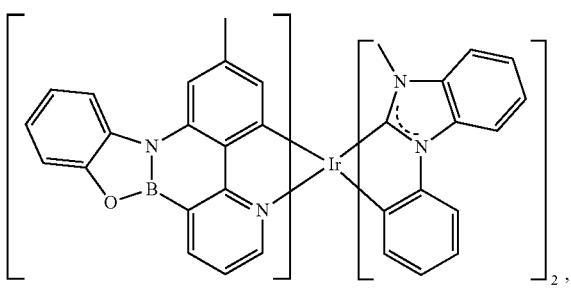
Compound M105
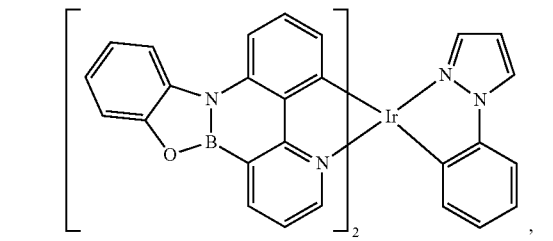
Compound M101
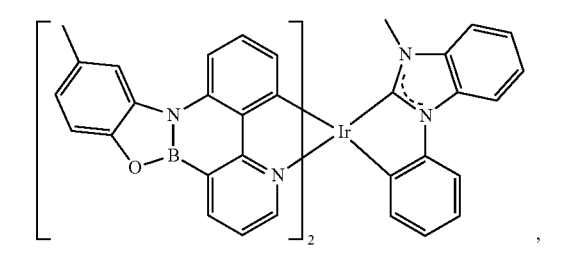
Compound M106
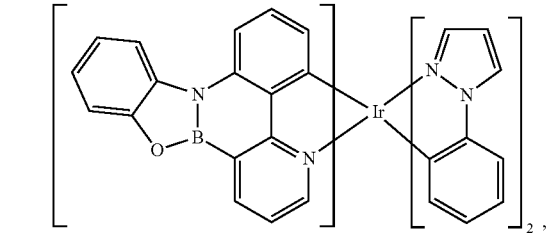
Compound M102
Compound M107
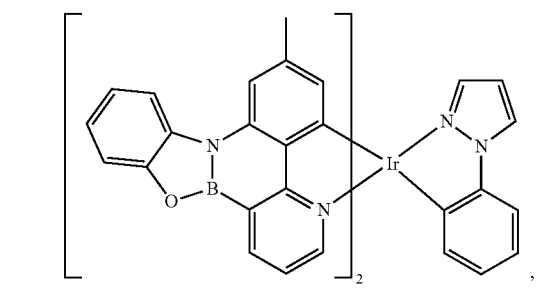

Compound M108
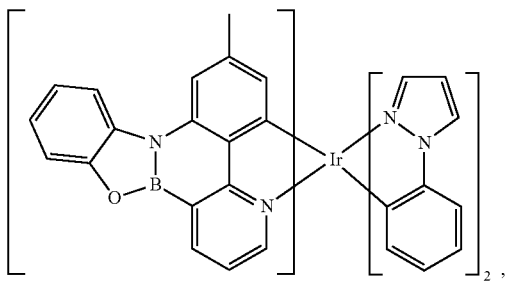
Compound M109
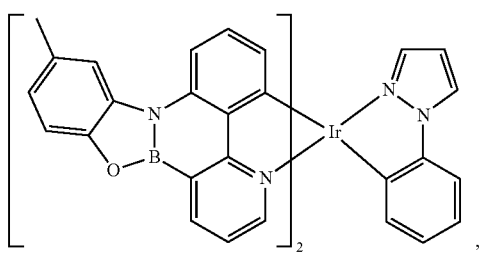
Compound M110
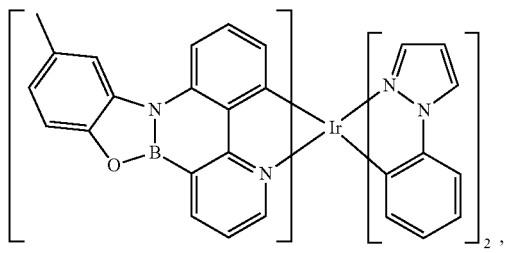
Compound M111
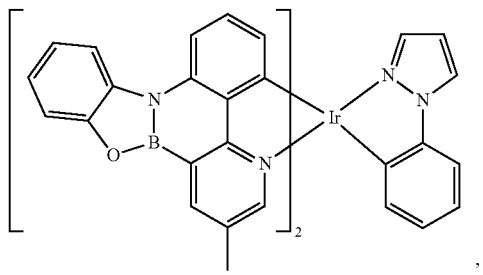
Compound M112
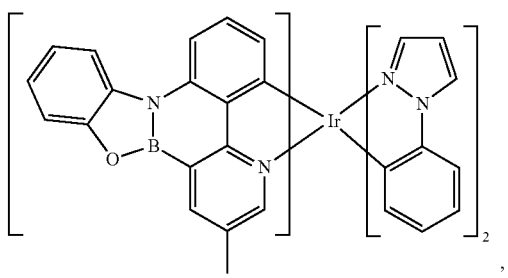
Compound M113
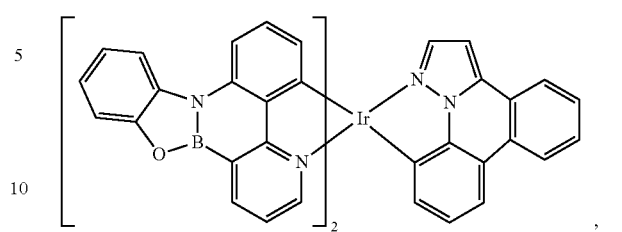
Compound M114
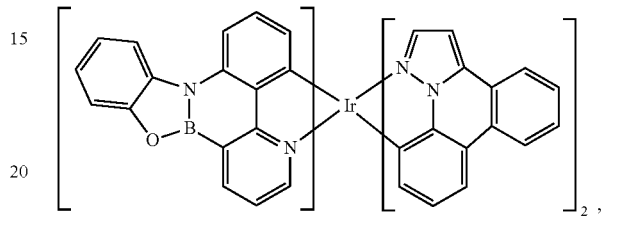
Compound M115
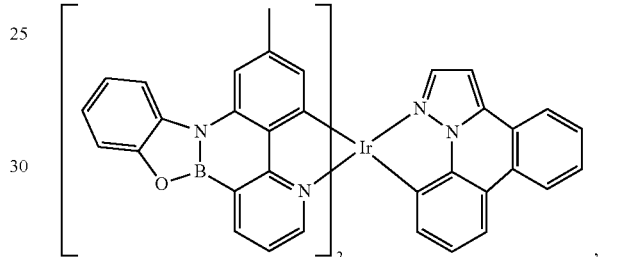
Compound M116
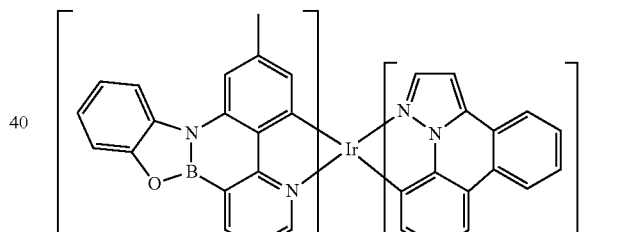
Compound M117
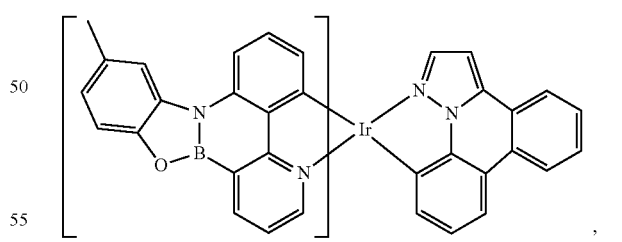
Compound M118
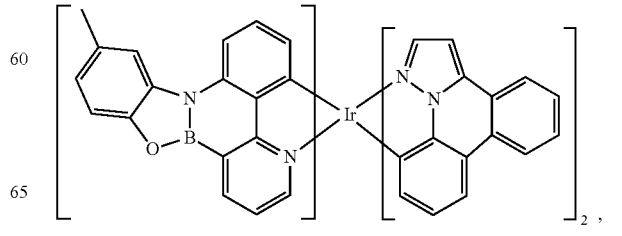

Compound M119
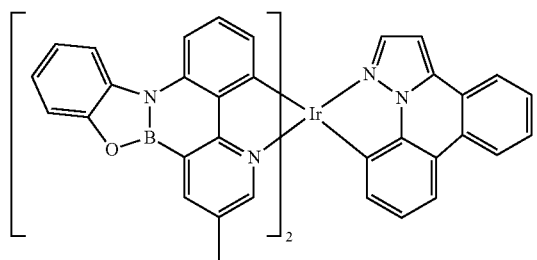
Compound M120
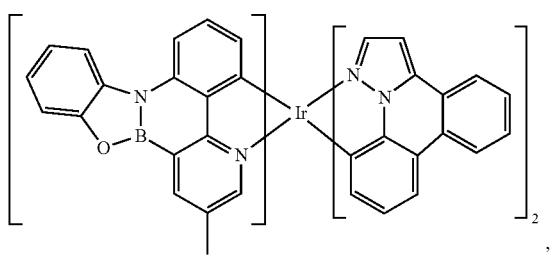
Compound M121
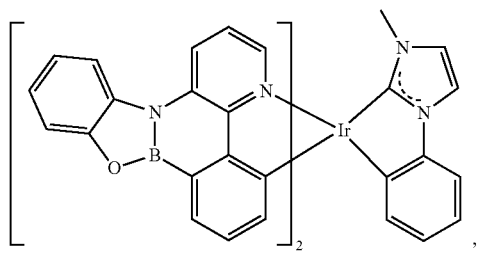
Compound M122
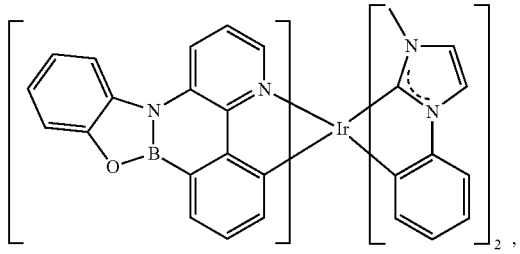
Compound M123
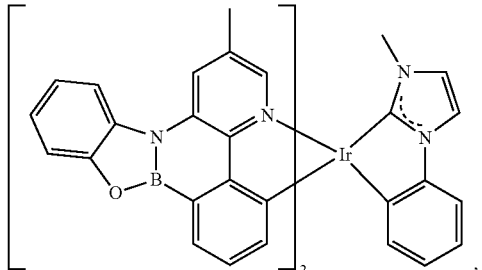
Compound M124
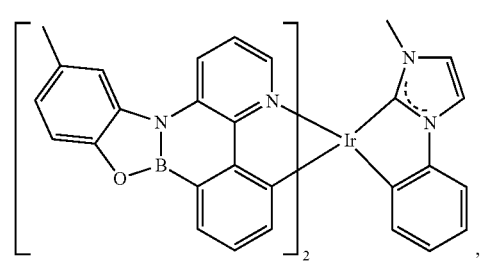
Compound M125
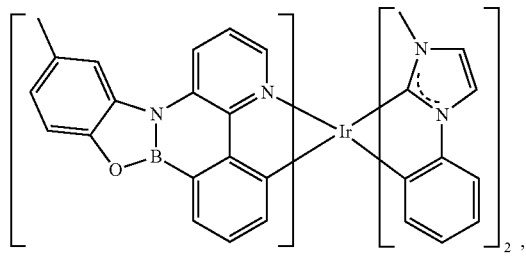
Compound M126
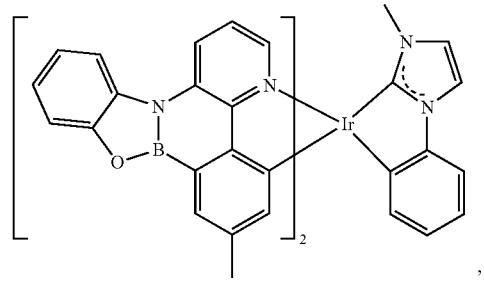
Compound M127
Compound M128
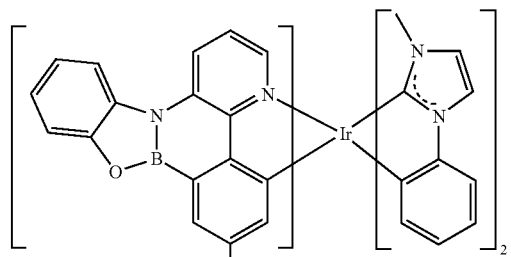

Compound M129
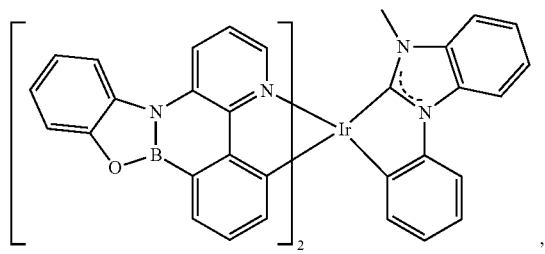
Compound M130
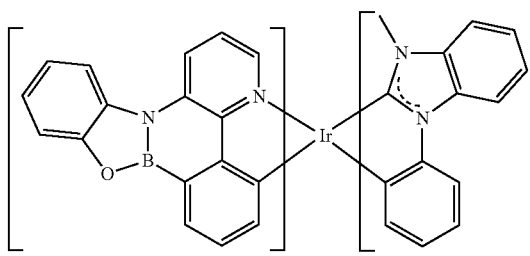
Compound M131
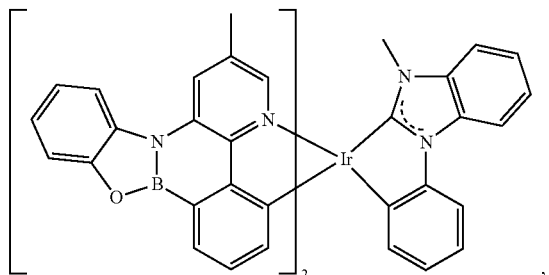
Compound M132
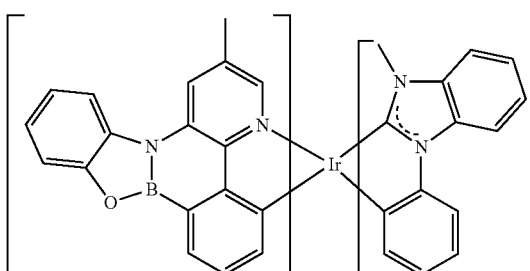
Compound M133
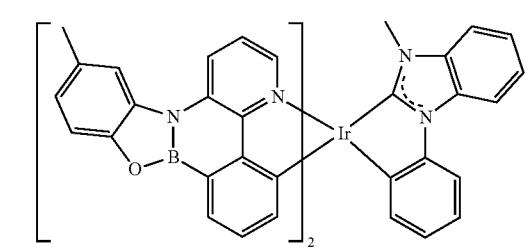
Compound M134
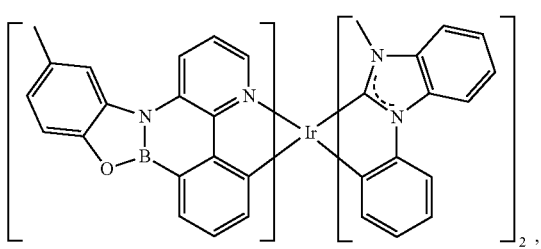
Compound M135
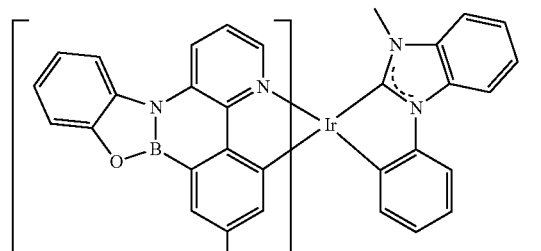
Compound M136
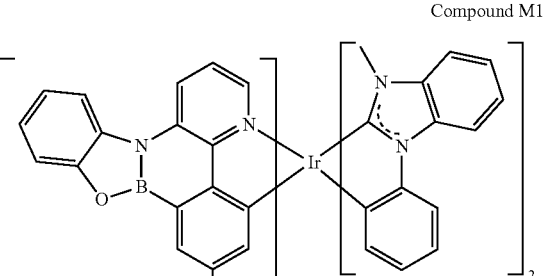
Compound M137
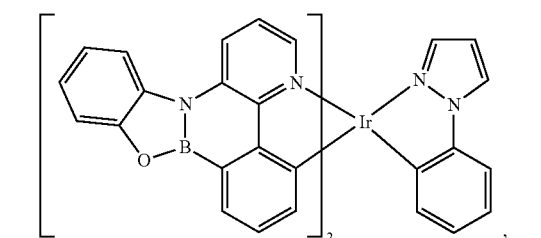
Compound M138
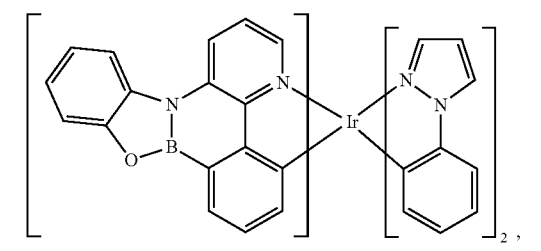

Compound M139
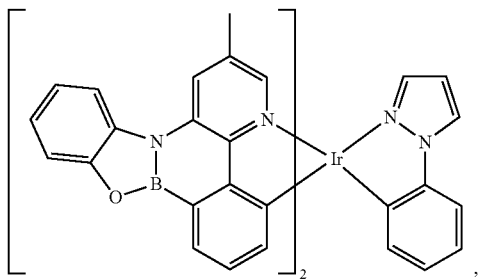
Compound M140
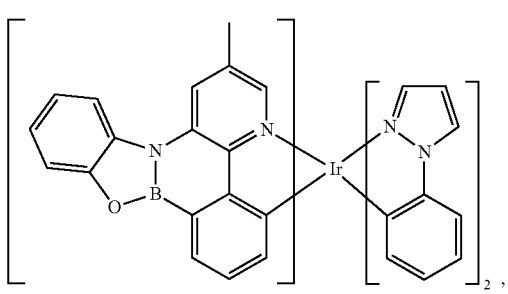
Compound M141
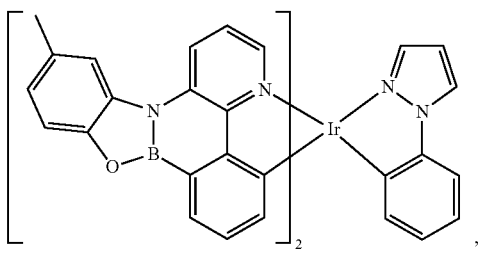
Compound M142
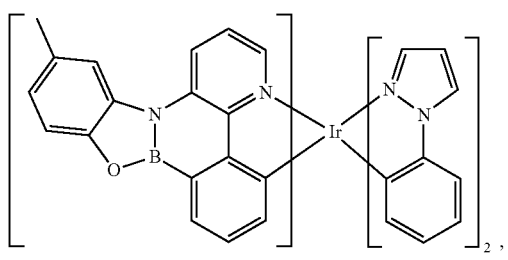
Compound M143
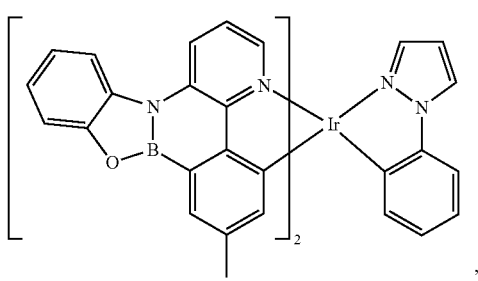
Compound M144
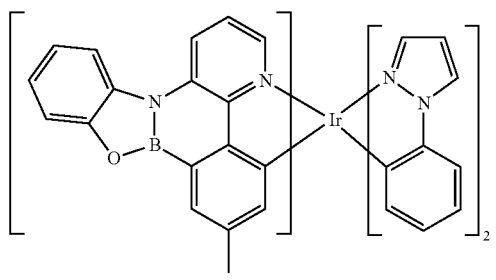
Compound M145
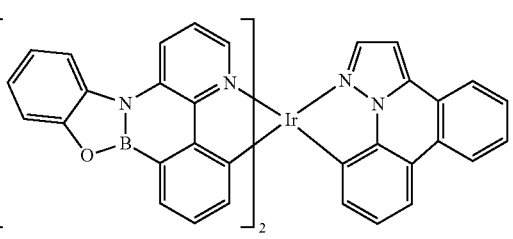
Compound M146
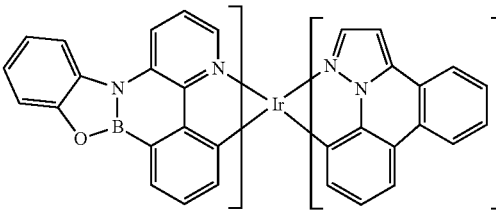
Compound M147
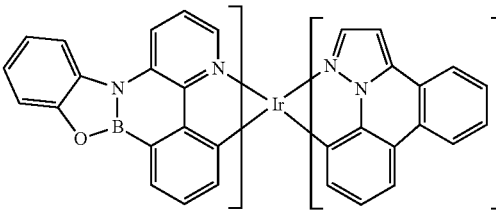
Compound M148
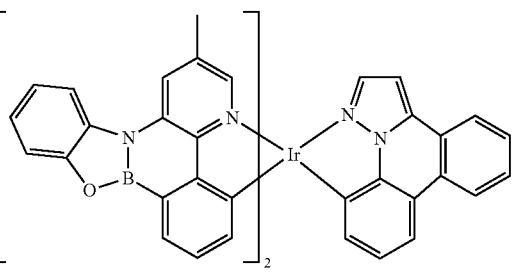
Compound M149
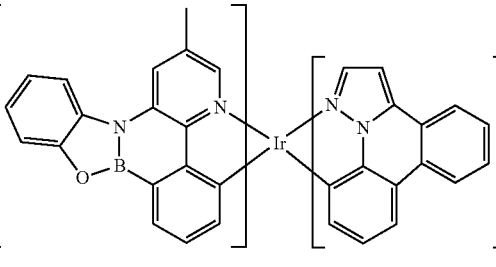

Compound M150
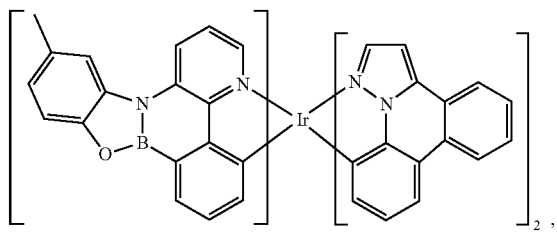
Compound M151
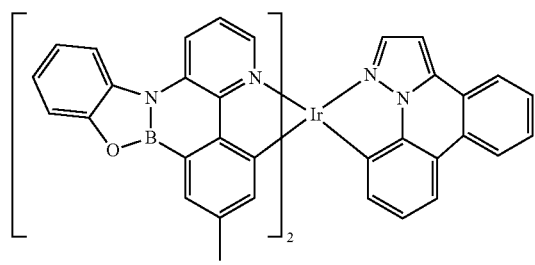
Compound M152
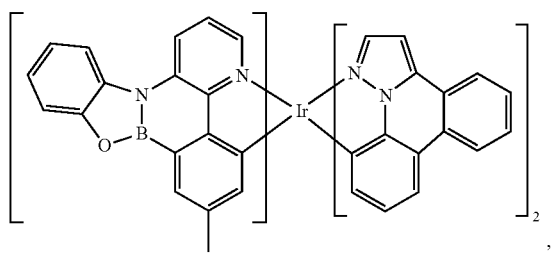
Compound M153
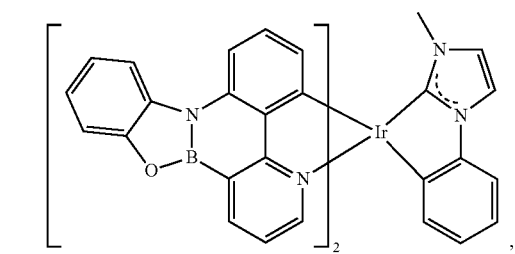
Compound M154
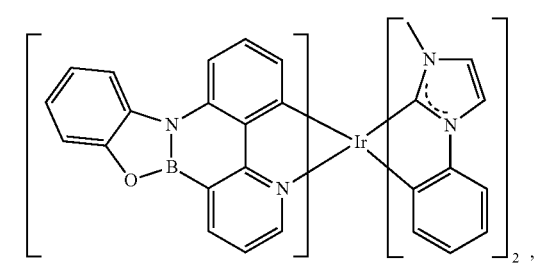
Compound M155
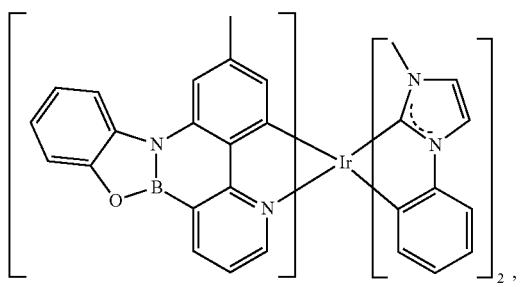
Compound M156
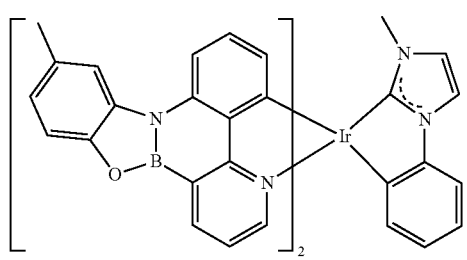
Compound M157
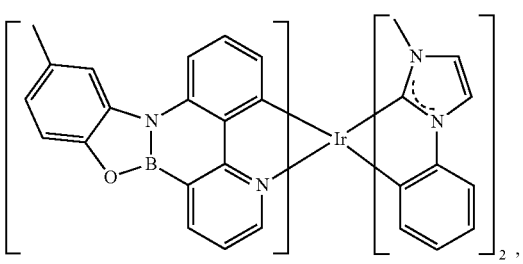
Compound M158
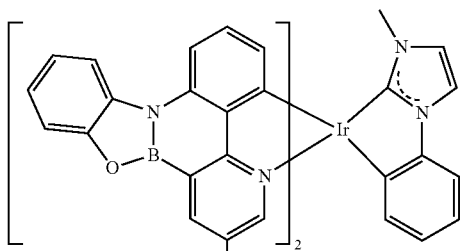
Compound M159

Compound M160
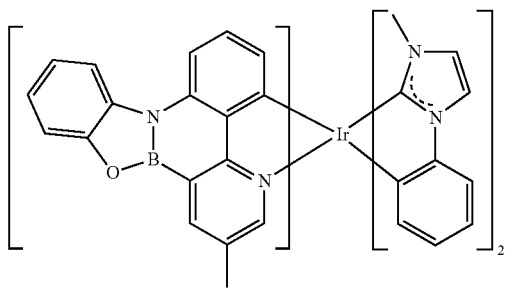
Compound M165
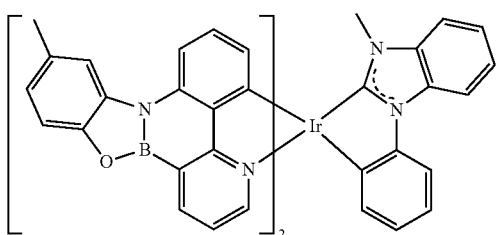
Compound M161
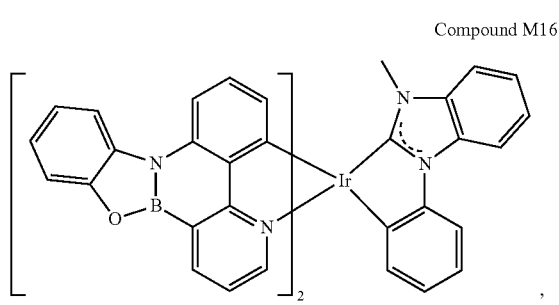
Compound M166
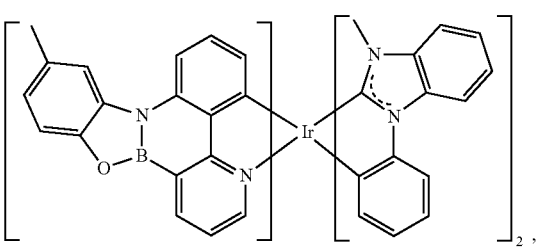
Compound M162
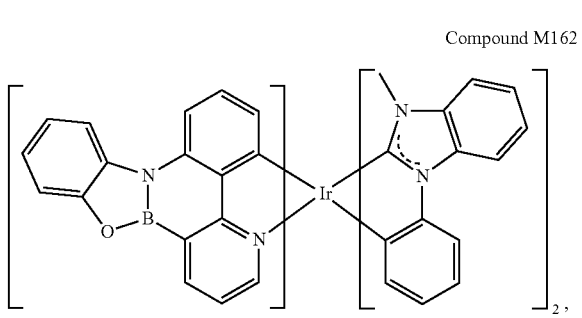
Compound M167
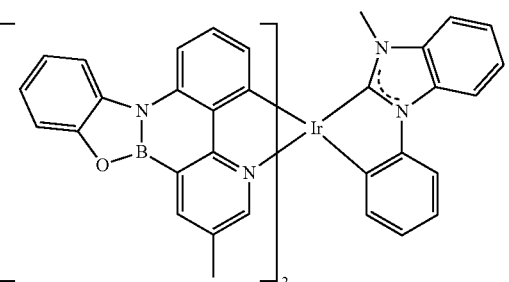
Compound M163
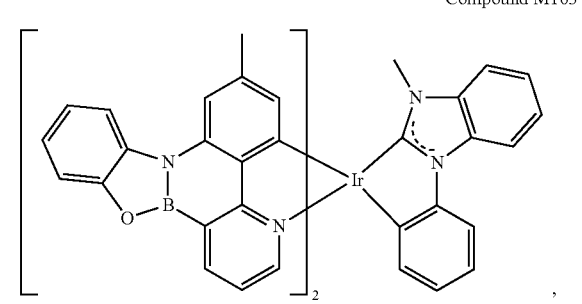
Compound M168
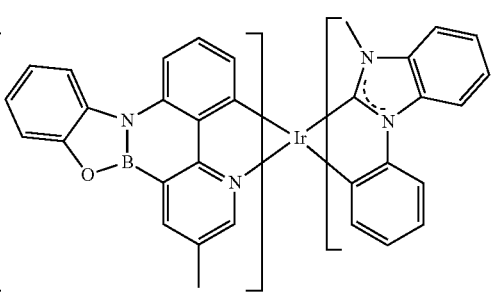
Compound M164
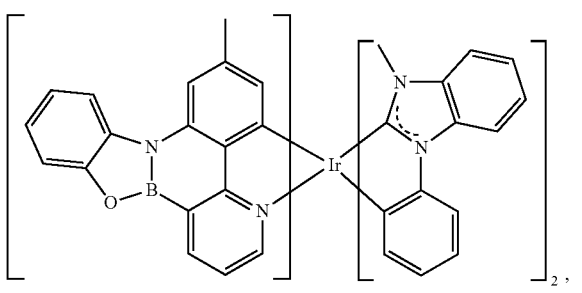
Compound M169
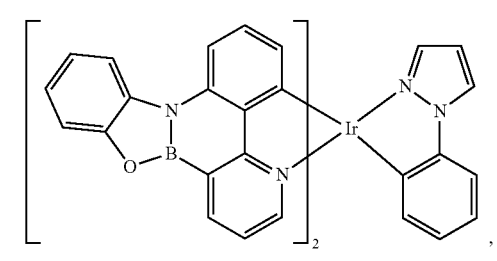

-continued
Compound M170
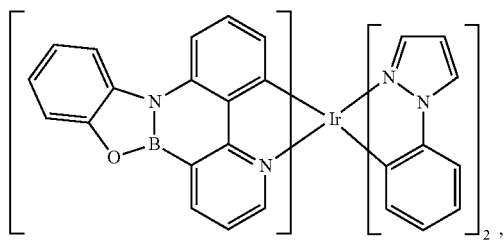
Compound M171
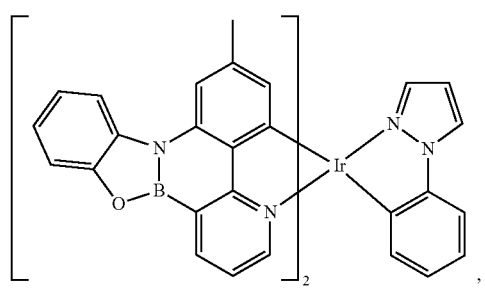
Compound M172
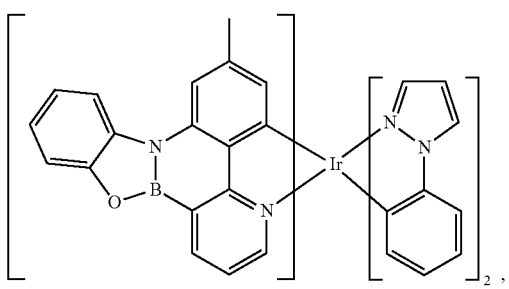
Compound M173
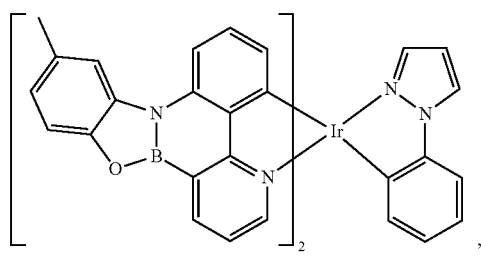
Compound M174
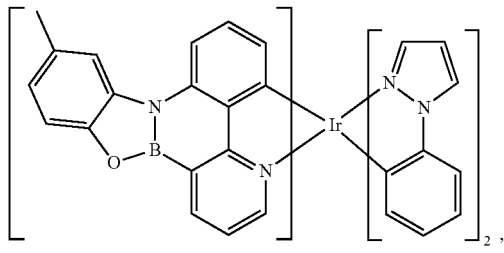
-continued
Compound M175
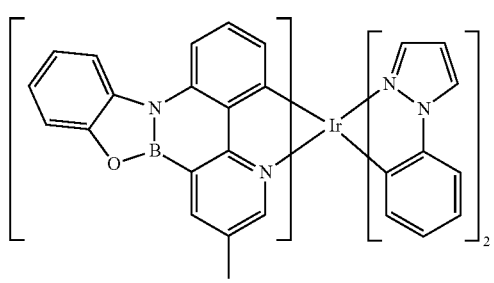
Compound M176
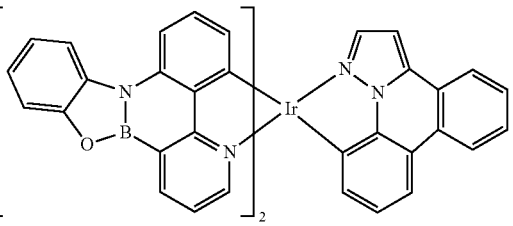
Compound M177
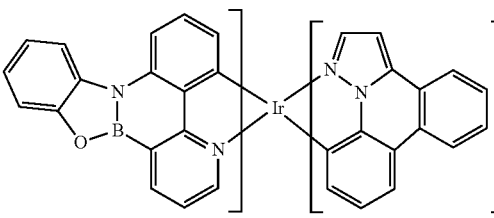
Compound M178
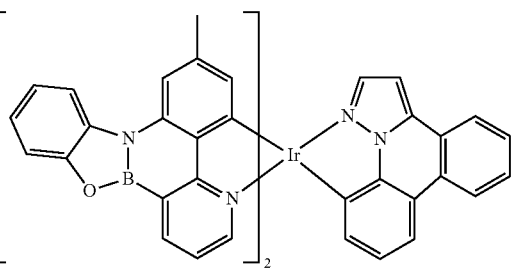
Compound M179

-continued
Compound M180
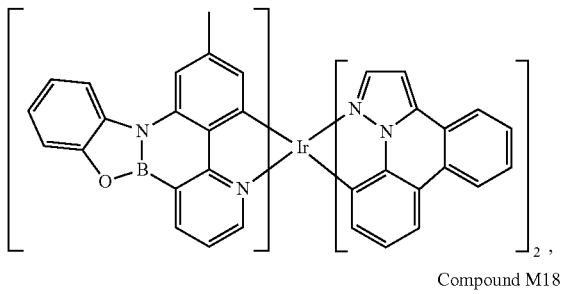
Compound M181
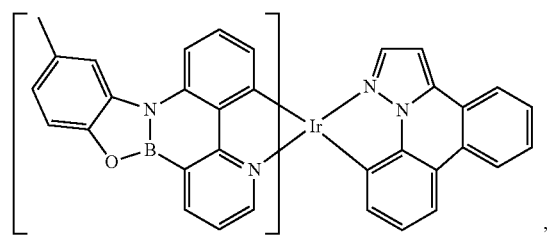
Compound M182
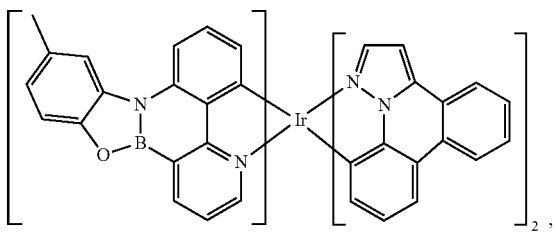
Compound M183
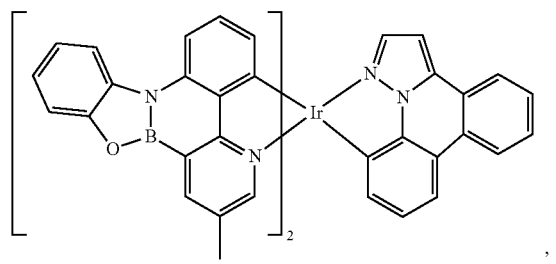
Compound M184
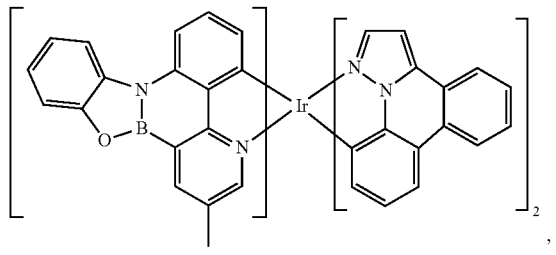
Compound M185
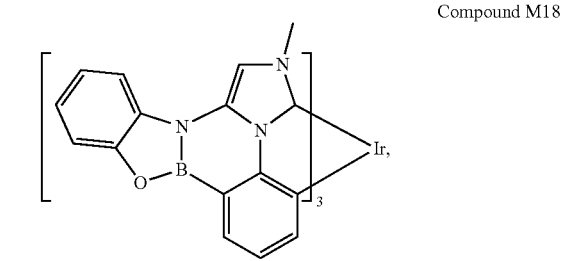
-continued
Compound M186
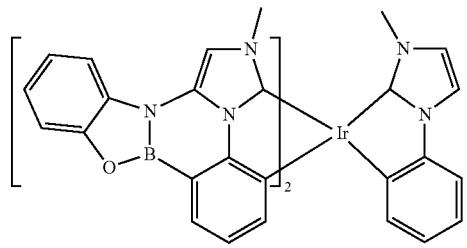
Compound M187
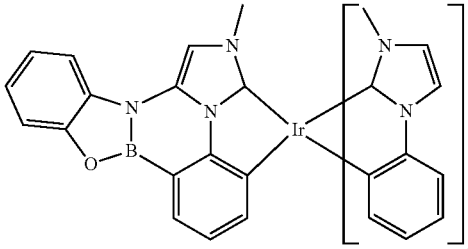
Compound M188
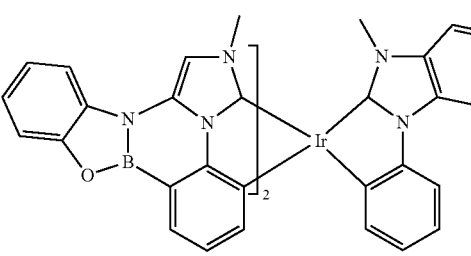
Compound M189
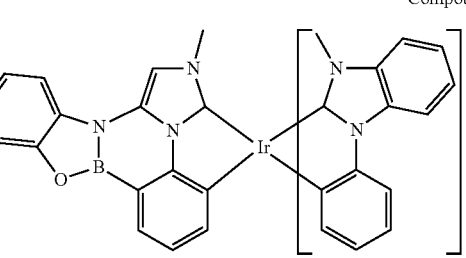
and
Compound M190
15. An organic light-emitting device (OLED) comprising:
an anode;
a cathode; and
an organic layer, disposed between the anode and the cathode, comprising a compound having a structure or partial structure of Formula I:

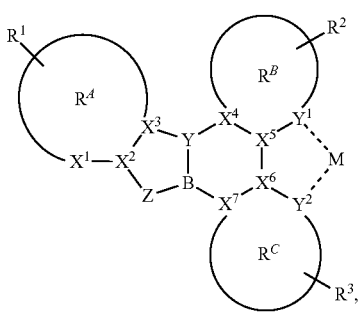

Formula I wherein $R^A$, $R^B$, and $R^C$ are each independently 5 or 6 membered aryl or heteroaryl rings;
  wherein $R^1$, $R^2$, and $R^3$ each independently represent no substitutions or up to the maximum available substitutions;
  wherein $R^1$, $R^2$, and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, sulfinyl, sulfonyl, phosphine, and combinations thereof;
  wherein any adjacent $R^1$, $R^2$, and $R^3$ are optionally joined or fused to form a ring;
  wherein $X^1$ and $X^7$ are C or N;
  wherein $X^2$ to $X^6$ are independently C;
  wherein Y is N or P;
  wherein Z is CRR', O, PR, P(O)R, or S;
  wherein $Y^1$ and $Y^2$ are each independently selected from the group consisting of carbon and nitrogen;
  wherein R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, sulfinyl, sulfonyl, phosphine, and combinations thereof;
  wherein R and/or R' are optionally joined or fused with $R^1$ or $R^3$ to form a ring;
  wherein the dashed lines represent a metal M optionally coordinated to $R^B$ and $R^C$; and
  wherein when M is coordinated to $R^B$ and $R^C$, M replaces $R^2$ and $R^3$ on $Y^1$ and $Y^2$ and bonds to $Y^1$ and $Y^2$.

16. The OLED of claim 15, wherein the organic layer is an emissive layer and the compound of Formula I is a host.

17. The OLED of claim 15, wherein the organic layer further comprises a phosphorescent emissive dopant that is a transition metal complex having at least one ligand or part of the ligand if the ligand is more than bidentate, selected from the group consisting of:

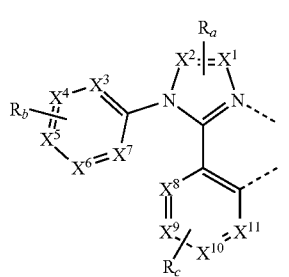

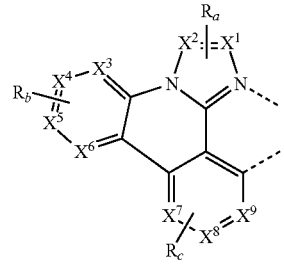

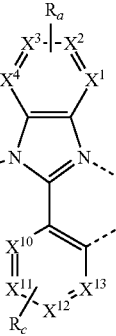

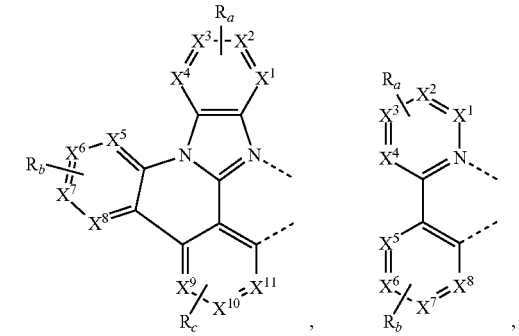

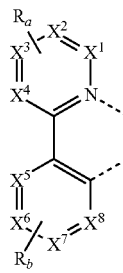

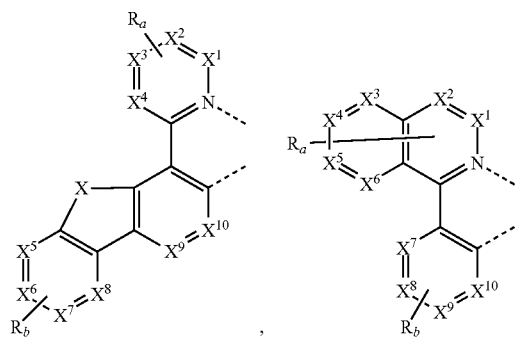

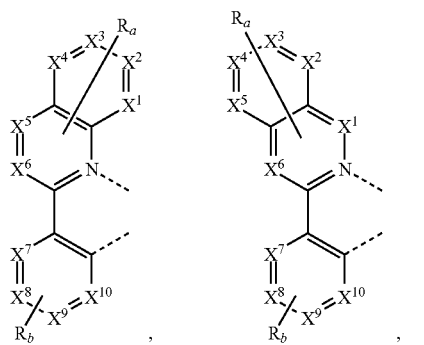

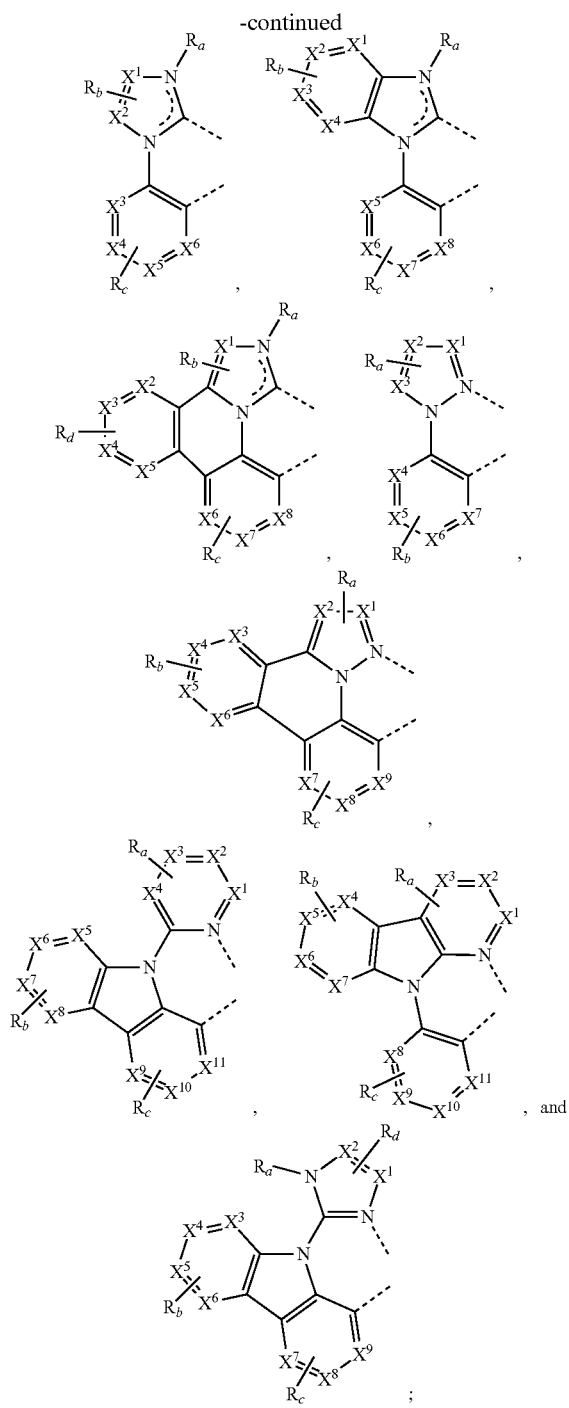

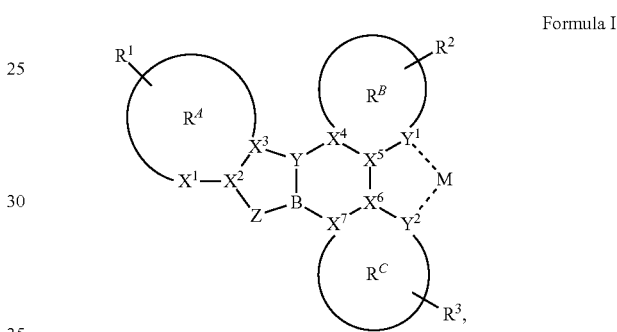

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

18. The OLED of claim 15, wherein the organic layer is a charge carrier blocking layer and the compound having Formula I is a charge carrier blocking material in the organic layer or the organic layer is a charge carrier transporting layer and the compound having Formula I is a charge carrier transporting material in the organic layer.

19. A consumer product comprising an organic light-emitting device comprising:
an anode;
a cathode; and
an organic layer, disposed between the anode and the cathode, comprising a compound having a structure or partial structure of Formula I:

Formula I wherein $R^A$, $R^B$, and $R^C$ are each independently 5 or 6 membered aryl or heteroaryl rings;

wherein $R^1$, $R^2$, and $R^3$ each independently represent no substitutions or up to the maximum available substitutions;

wherein $R^1$, $R^2$, and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, sulfinyl, sulfonyl, phosphine, and combinations thereof;

wherein any adjacent $R^1$, $R^2$, and $R^3$ are optionally joined or fused to form a ring;

wherein $X^1$ and $X^7$ are C or N;

wherein $X^2$ to $X^6$ are independently C;

wherein Y is N or P;

wherein Z is CRR', O, PR, P(O)R, or S;

wherein $Y^1$ and $Y^2$ are each independently selected from the group consisting of carbon and nitrogen;

wherein R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, sulfinyl, sulfonyl, phosphine, and combinations thereof;

wherein R and/or R' are optionally joined or fused with $R^1$ or $R^3$ to form a ring;

wherein the dashed lines represent a metal M optionally coordinated to $R^B$ and $R^C$; and wherein when M is coordinated to $R^B$ and $R^C$, M replaces $R^2$ and $R^3$ on $Y^1$ and $Y^2$ and bonds to $Y^1$ and $Y^2$.

20. The consumer product of claim 19, wherein the consumer product is selected from the group consisting of flat panel displays, computer monitors, medical monitors, televisions, billboards, lights for interior or exterior illumination and/or signaling, heads-up displays, fully or partially transparent displays, flexible displays, laser printers, telephones, mobile phones, tablets, phablets, personal digital assistants (PDAs), wearable devices, laptop computers, digital cameras, camcorders, viewfinders, micro-displays, 3-D displays, virtual reality or augmented reality displays, vehicles, video walls comprising multiple displays tiled together, theater or stadium screen, and a sign.

* * * * *